(12) United States Patent
Richelle et al.

(10) Patent No.: US 11,192,918 B2
(45) Date of Patent: Dec. 7, 2021

(54) MULTICYCLIC PEPTIDES AND METHODS FOR THEIR PREPARATION

(71) Applicants: Universiteit van Amsterdam, Amsterdam (NL); Stichting voor de Technische Wetenschappen, Utrecht (NL)

(72) Inventors: Gaston Julia Johannes Richelle, Amsterdam (NL); Dieuwertje Emma Streefkerk, Amsterdam (NL); Jan Herman van Maarseveen, Amsterdam (NL); Peter Timmerman, Amsterdam (NL)

(73) Assignees: Stichting voor de Technische Wetenschappen, Utrecht (NL); Universiteit van Amsterdam, Amsterdam (NL)

( * ) Notice: Subject to any disclaimer, the term of this patent is extended or adjusted under 35 U.S.C. 154(b) by 0 days.

(21) Appl. No.: 16/467,138

(22) PCT Filed: Dec. 6, 2017

(86) PCT No.: PCT/NL2017/050820
§ 371 (c)(1),
(2) Date: Jun. 6, 2019

(87) PCT Pub. No.: WO2018/106112
PCT Pub. Date: Jun. 14, 2018

(65) Prior Publication Data
US 2020/0239516 A1 Jul. 30, 2020

(30) Foreign Application Priority Data

Dec. 6, 2016 (EP) ..................................... 16202466
Sep. 1, 2017 (EP) ..................................... 17189088

(51) Int. Cl.
| | | |
|---|---|---|
| *C07K 1/107* | (2006.01) |
| *C07K 1/04* | (2006.01) |
| *C07K 7/56* | (2006.01) |
| *C07K 7/64* | (2006.01) |
| *C40B 30/04* | (2006.01) |
| *G01N 33/543* | (2006.01) |

(52) U.S. Cl.
CPC ............ *C07K 1/047* (2013.01); *C07K 1/1077* (2013.01); *C07K 7/56* (2013.01); *C07K 7/64* (2013.01); *C40B 30/04* (2013.01); *G01N 33/54353* (2013.01); *G01N 2500/04* (2013.01)

(58) Field of Classification Search
None
See application file for complete search history.

(56) References Cited

PUBLICATIONS

Houseman et al (Langmuir 19:1522-31) (Year: 2003).*
Sato et al (Tetrahedron Letters 53:3585-89) (Year: 2012).*
El-Gendy et al (Egyptian J. Chem. 32:335-49) (Year: 1989).*
Bashiruddin et al.: "Synthesis of fused tricyclic peptides using a reprogrammed translation system and chemical modification" Bioorganic Chemistry., vol. 61, No. I, Aug. 1, 2015 (Aug. 1, 2015), pp. 45-50, XP55356360, Academic Press Inc., New York, NY. ISSN: 0045-2068 the whole document.
Chua et al.: "Small cyclic agonists of iron regulatory hormone hepcidin" Bioorganic & Medicinal Chemistry Letters, vol. 25, No. 21, Dec. 3, 2015 (Dec. 3, 2015), pp. 4961-4969, XP002778701, Pergamon ISSN: 0960-894X the whole document.
Smeenk et al.: "Reconstructing the discontinuous and conformational betal/beta3 loop binding site of hFSH/hCG by using highly constrained multicyclic peptides" Chembiochem—A European Journal of Chemical Biology., vol. 16, No. I, Jan. 1, 2015 (Jan. 1, 2015), pp. 91-99, XP2770376, Wiley VCH, Weinheim. ISSN: 1439-4227 the whole document.
Smeenk et al.: "Synthesis of Water-Soluble Scaffolds for Peptide Cyclization, Labeling, and Ligation" Organic Letters, vol. 14, No. 5, Feb. 3, 2012 (Feb. 3, 2012), pp. 1194-1197, XP55165712, American Chemical Society the whole document.
Becker et al. "An Efficient Route to 1,3,5-Triazido-2,4,6-tricyanobenzene". Z. Naturforsch. 2012, 67b, 643-649 / DOI: 10.5560/MB .2012-0092.

* cited by examiner

*Primary Examiner* — Christopher M Gross
(74) *Attorney, Agent, or Firm* — Banner & Witcoff, Ltd.

(57) ABSTRACT

The invention relates to methods for preparing a compound comprising a peptide attached to a molecular scaffold whereby multiple peptide loops are formed, to compounds that can be obtained with such methods and uses thereof.

16 Claims, 55 Drawing Sheets

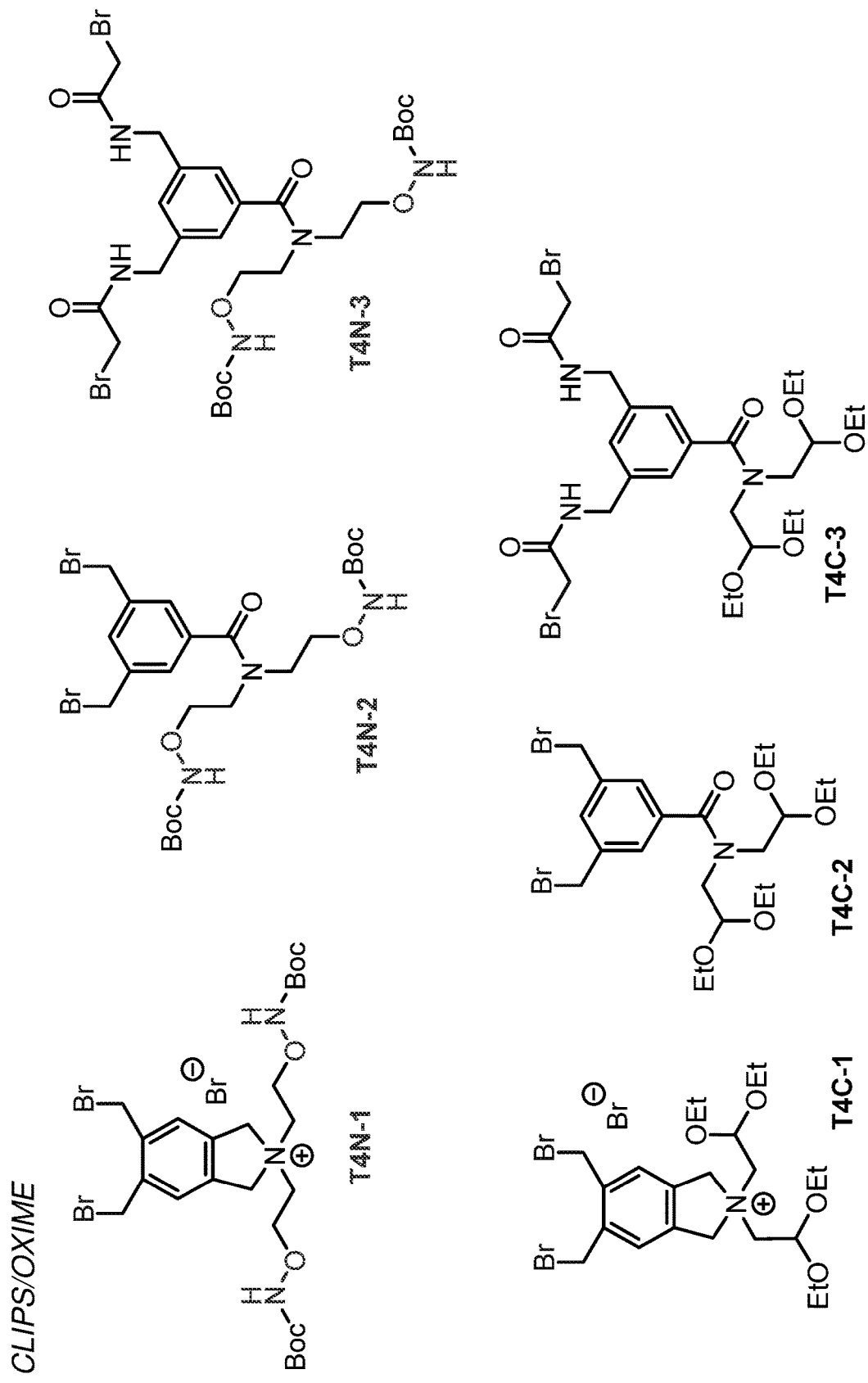
Fig. 5, Cont'd

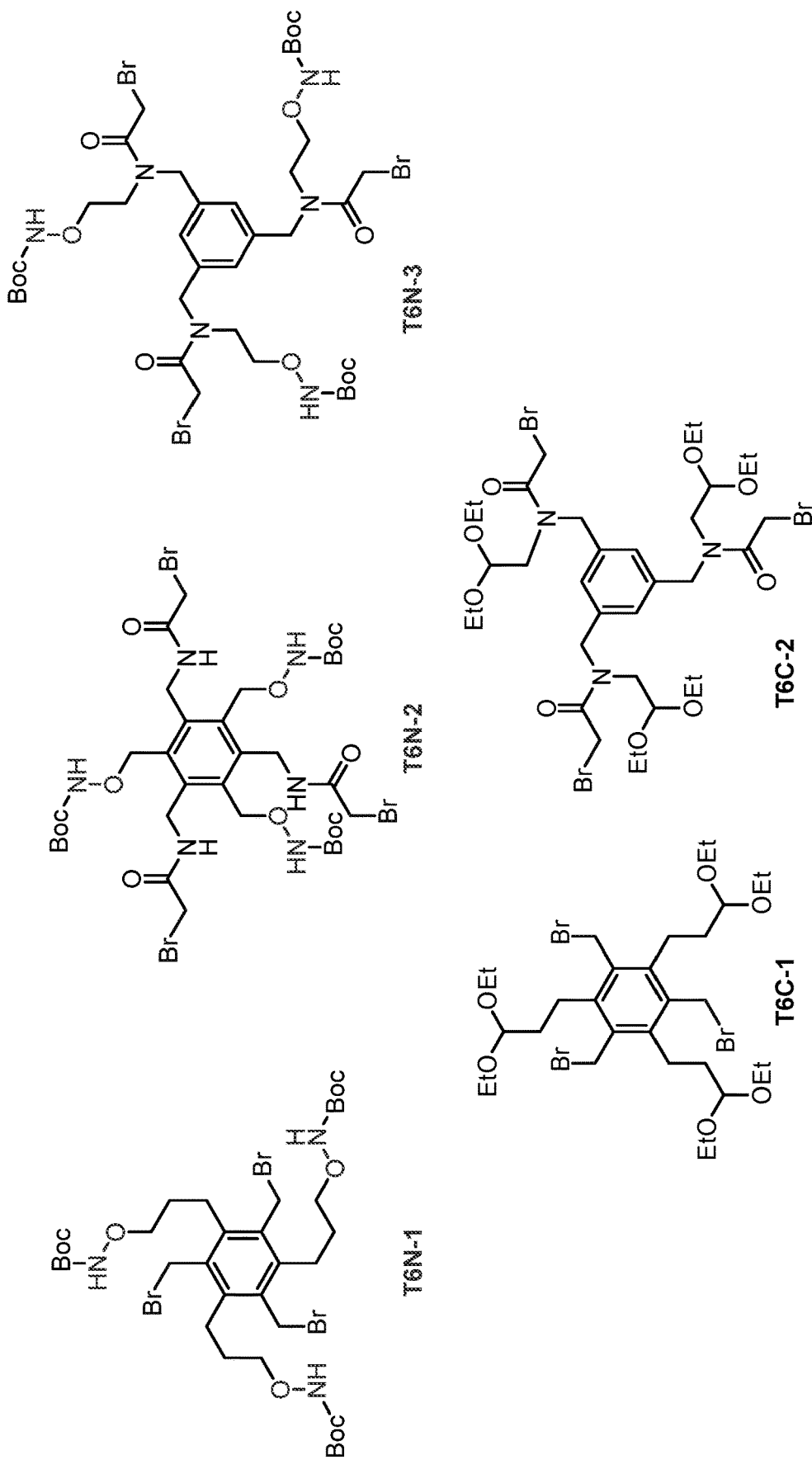
Fig. 6, Cont'd

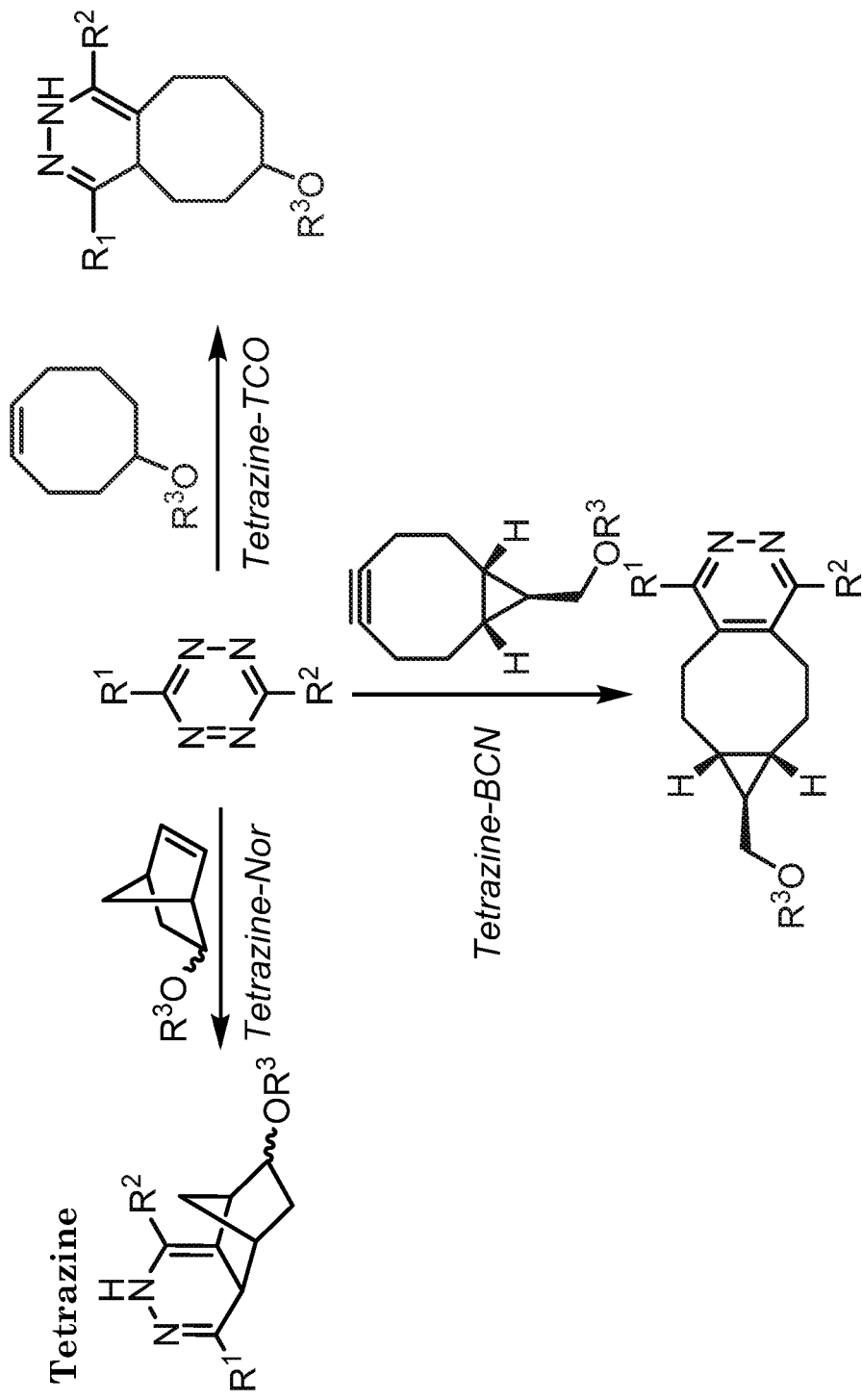
Fig. 7, Cont'd

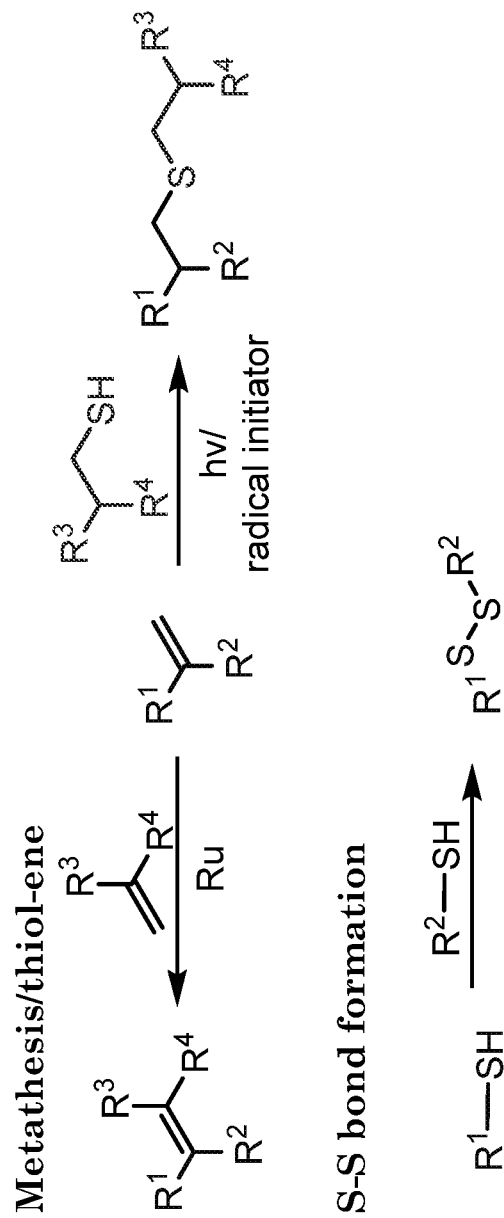
Fig. 7, Cont'd

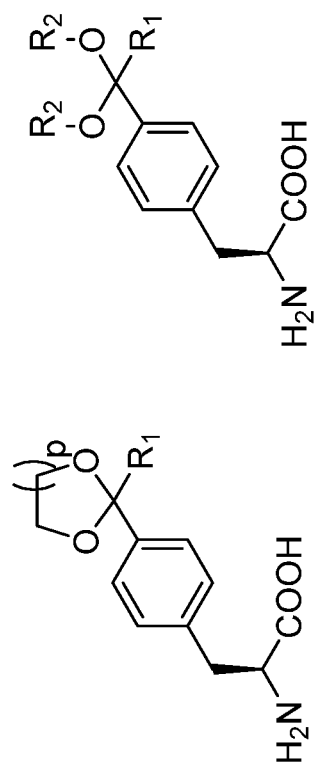
Fig. 9A, Cont'd

Lysine derivatives

Aspartic acid derivatives

Where n = 1 - 10
Where $R_1$ is:

Where m = 1 - 10
Where $R_2$ = H, Me, Et, Pr, Ph, etc
Where p = 1 or 2
Where PG = protecting group, such as Boc, Phthalimide, isopropylidene (pictured right), Fmoc, Cbz, Trt, Mmt, Mtt

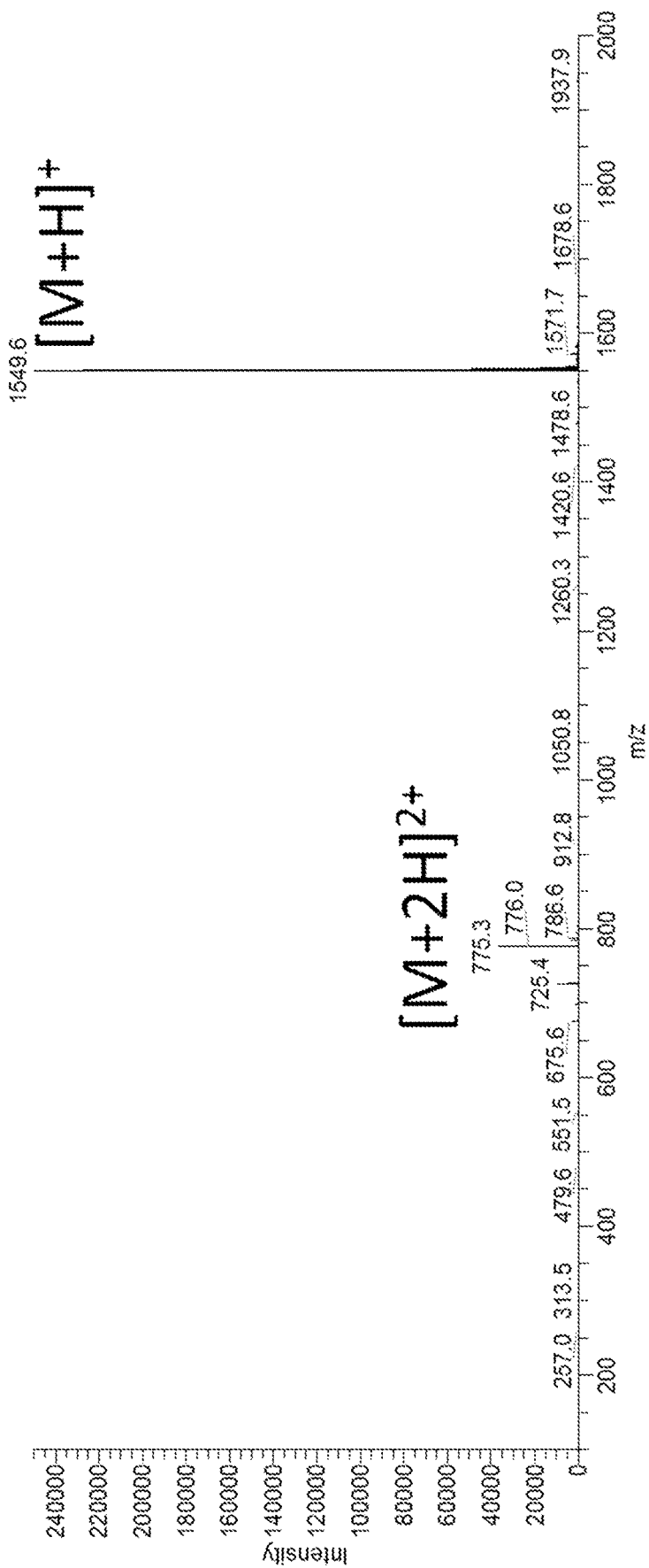
Fig. 10, Cont'd

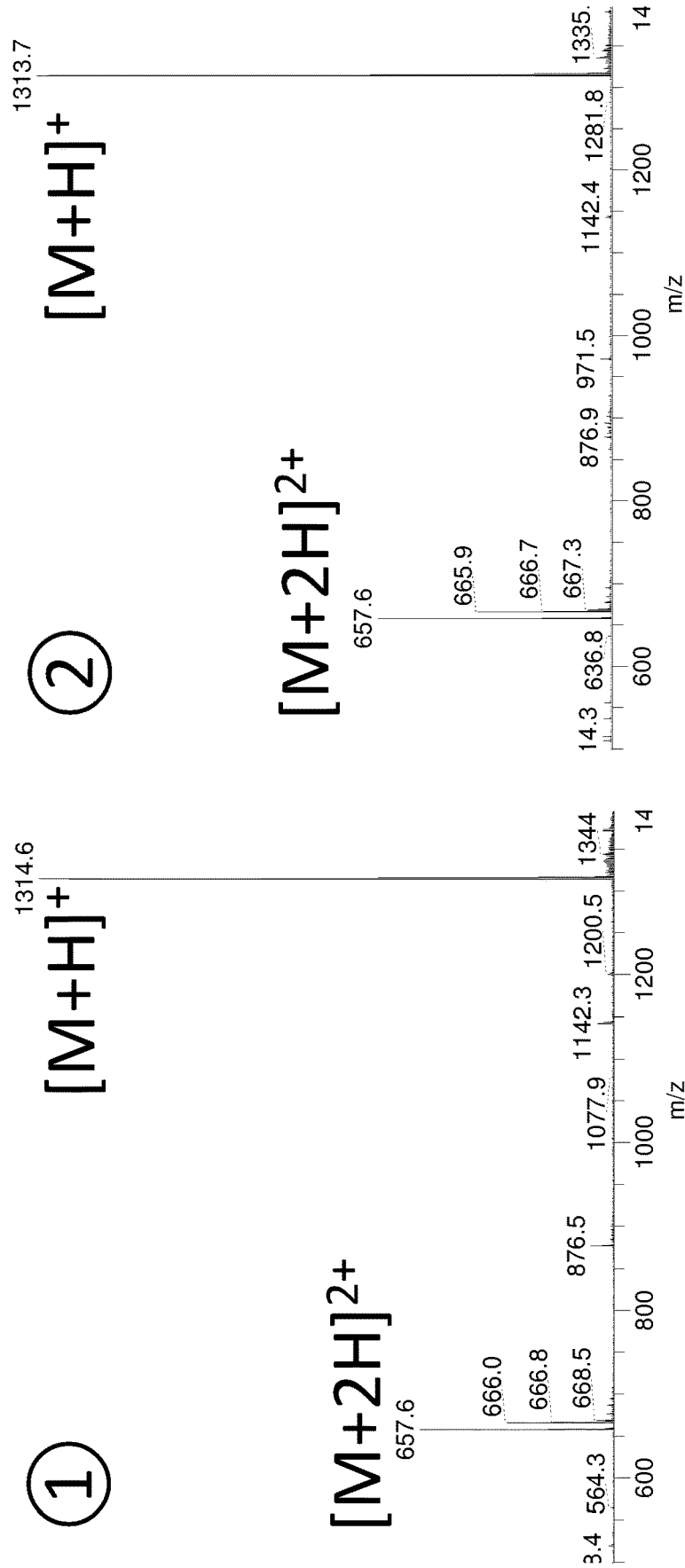
Fig. 11, Cont'd

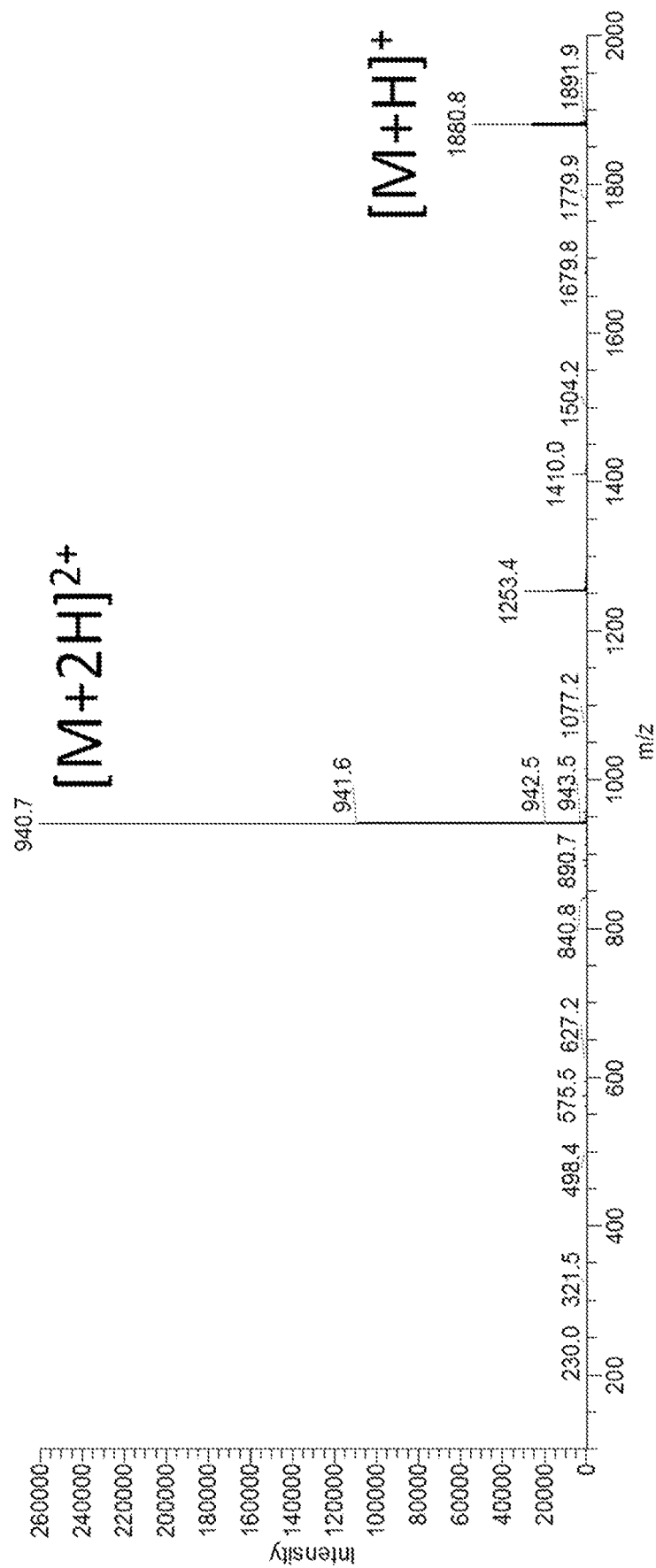
Fig. 12, Cont'd

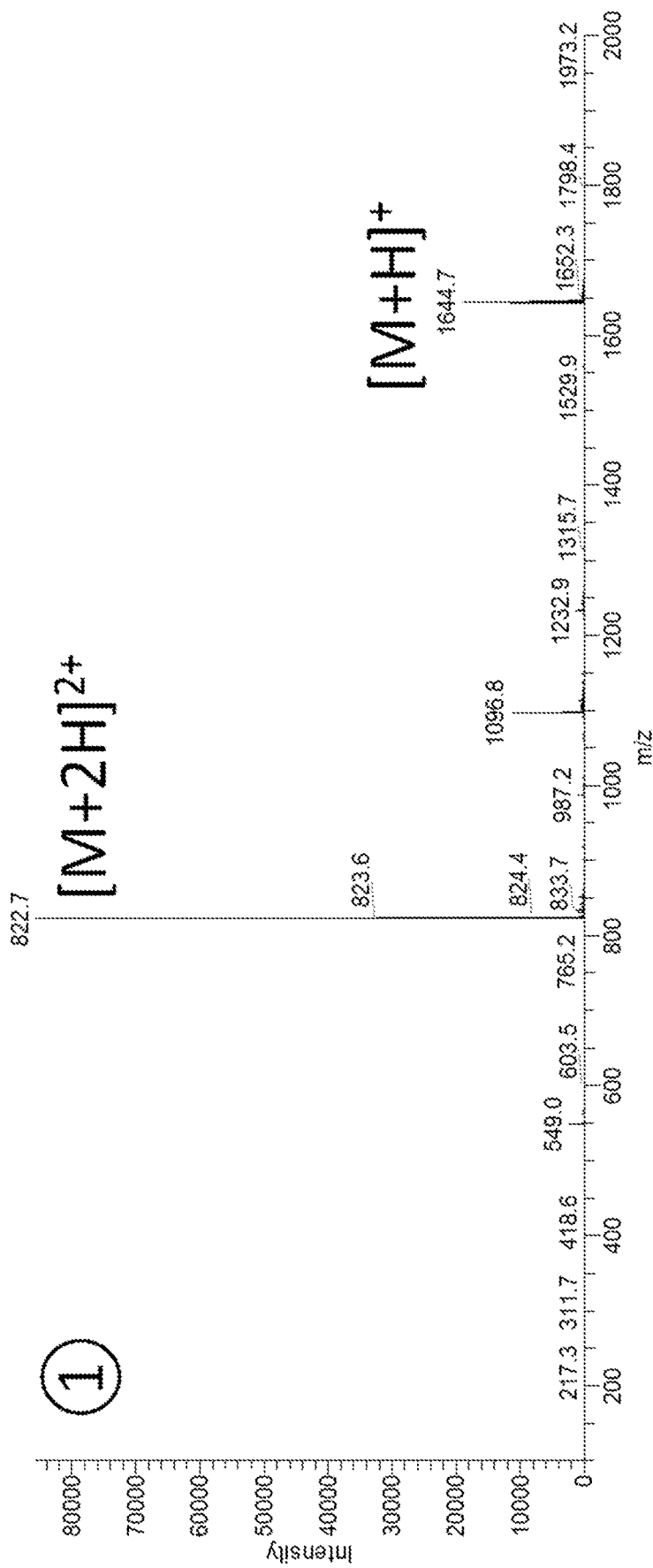
Fig. 13, Cont'd

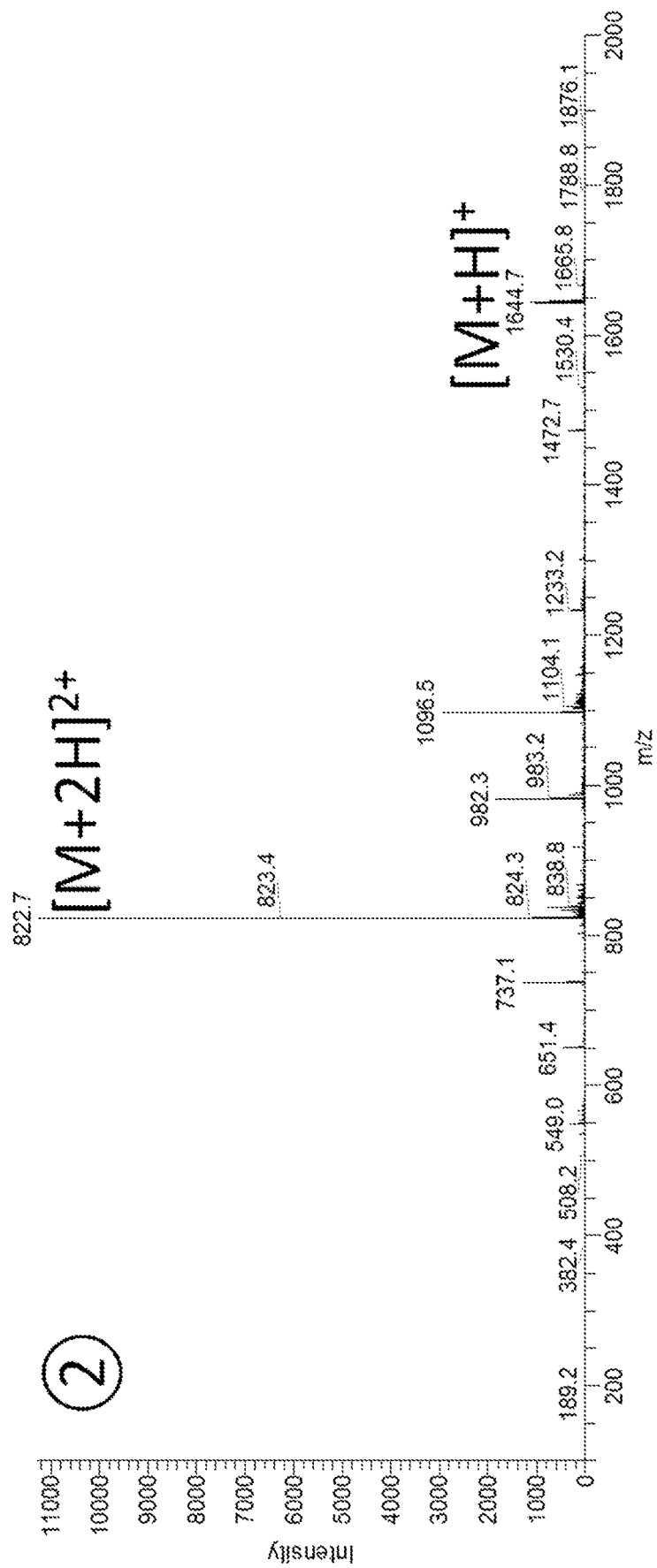
Fig. 13, Cont'd

A.

B.

C.

A.

B.

C.

Linear Peptide: Ac-CQ[Aha]KCF[Aha]ACK[Aha]-NH$_2$: 22$_{11111}$

CLIPS: 22$_{11111}$ + T6(-≡)$_3$-1

Linear peptide: Ac-CQW[Aha]KACFS[Aha]ATCKN[Aha]-NH$_2$: 23$_{22222}$

CLIPS: 23$_{22222}$ + T6-($\equiv$)$_3$-1

CuAAC: 23$_{22222}$ + T6-(≡)$_3$-1

Linear peptide: H-CQWGA[Aha]KASECFSEK[Aha]ATKGCGNKG[Aha]-NH$_2$: 24$_{44444}$ CLIPS: $24_{44444}$ + T6-($\equiv$)$_3$-1

CuAAC: $24_{44444}$ + T6-($\equiv$)$_3$-1

Linear peptide: H-CQWGAS[Aha]KASEVCFSEKG[Aha]ATKGKCGNKGE[Aha]-NH$_2$: 25$_{55555}$

CLIPS: 25$_{55555}$ + T6-(≡)$_3$-1

B.

MULTICYCLIC PEPTIDES AND METHODS FOR THEIR PREPARATION

RELATED APPLICATIONS

This application is a National Stage Application under 35 U.S.C. 371 of co-pending PCT application PCT/NL2017/050820 designating the United States and filed Dec. 6, 2017; which claims the benefit of EP application number 17189088.2 filed on Sep. 1, 2017 and EP application number 16202466.5 filed on Dec. 6, 2016 each of which are hereby incorporated by reference in their entireties.

FIELD OF THE INVENTION

The invention relates to the field of proteinmimetics. In particular, the invention relates to methods for preparing compounds comprising a peptide covalently attached to a scaffold via several bonds resulting in multiple peptide loops. The invention also relates to cyclized peptides or peptidomimetics obtainable with such methods and uses thereof.

BACKGROUND OF THE INVENTION

Multicyclic peptide frameworks constitute a promising new class of peptide therapeutics. Their widespread occurrence in nature has kept the search for novel and innovative synthetic procedures ongoing for decades. Cyclized peptides commonly have much better characteristics than their linear analogues for use in drug development, generally thanks to their fixed secondary structures, and increased proteolytic stabilities towards a variety of exo-peptidases.

The next level of structural complexity involves the synthesis of multicyclic pseudopeptide frameworks. The fact that a number of clinically approved candidate drugs are based on such multicyclic frameworks is particularly interesting. The major problem associated with these drugs, of which vancomycin is the most striking example, is the challenging and labor-intensive synthetic routes for making them. Amongst others, attempts have been made to overcome this hurdle by synthesizing constrained 'vancomycin' mimetics, making use of the so-called "rolling-loop scan" for limited diversity generation (ten Brink 2006). A different approach is to mimic antibody-like properties using rationally-designed peptide loops on top of a calix[4]arene framework (Hamura 1997; Blaskovich 2000; Sun 2004). Despite their fascinating architectures, the general limitation of these methods is the inability to routinely generate 'antibody-like' structural diversity, which makes it extremely difficult to fine-tune binding affinities and/or selectivities.

In 2005, the synthesis of mono-, bi- and tricycle peptides via tandem-cyclization of linear di-, tri- and tetra-SH peptides with 1,2-; 1,3-; or 1,4-dibromo-xylene, 1,3,5-tribromomesitylene or 1,2,4,5-tetrabromodurene was reported (Timmerman 2005; Timmerman 2009, WO 2004/077062). WO 2004/077062 describes a method for restricting the three dimensional structure of a compound by attaching the compound to a (hetero)aromatic molecule, for instance a halomethylarene. Coupling of a compound, for instance a peptide, to a (hetero)aromatic molecule as described in WO 2004/077062 will lead to formation of a peptide loop. Such peptide loop resembles for instance a loop in a native protein for which the compound may be used as a mimic. The technology, that was named "CLIPS", is unique in synthetic simplicity and mildness: the multi-cyclizations run to completion in <30 min. at room temperature, without the help of a catalyst and even without side-chain protective groups. Moreover, the cyclizations proceed under aqueous conditions at neutral pH (~7.8) and are compatible with sensitive biological systems, like phage-display libraries (PDLs).

The existing CLIPS peptide cyclization technology, that was developed by the present inventors and described in for instance WO 2004/077062, have their limitations in terms of i) structural rigidity, ii) structural diversity, hi) binding selectivity, and iv) binding/inhibition potency. It was recently discovered that affinity optimizations (<50 nM) get seriously hampered for certain target proteins (Heinis, 2011), maybe due to the structural limitations of the CLIPS-bicycles. However, expanding the CLIPS chemistry towards the generation of tricyclic peptides leads to the formation of a complex mixture of up to six regioisomers as shown in FIG. 1, which prevents the strategy for straightforward usage in screening processes.

Ruchala et al. (2015) describes the use of a pentaerythritol-based scaffold that could lead up to tricyclic peptides without regioisomer formation. However, still two diastereoisomers are formed and there is no straightforward way of expanding this methodology towards the formation of more functionalized multicyclic peptides (e.g. tetracycles).

Suga et al. (2015) describes the synthesis of fused tricyclic peptides by synthesis of a peptide containing four cysteine residues and an N-terminal chloroacetyl group. The authors state that by selective placement of the second cysteine group, the first monocycle can be formed by selective reaction with the N-terminal chloromethyl group. The remaining three cysteine residues can be reacted with a T3-scaffold leading to tricyclic peptides. Accurate installation of orthogonally protected cysteine residues is necessary in this technology as otherwise mixtures of products will be formed. This methodology also does not provide for the formation of more functionalized multicyclic peptides such as tetracycles.

Smeenk et al. (2012) and Smeenk et al. (2015) form bicyclic compounds consisting of two separate monocyclic peptides in a process wherein first two monocyclic peptides (peptides 1 and 2) are prepared by attaching a single peptide to a scaffold via two thioether linkages in a CLIPS reaction. The scaffolds attached to peptide 1 contain one reactive group for participating in an orthogonal ligation reaction and the scaffolds attached to peptide 2 contain the complementary reactive group. Subsequently, two of such peptide-containing scaffolds can be attached to each other via a single bond in the orthogonal ligation reaction. With such approach only bicyclic compounds can be formed. Further loops to obtain tricyclic or tetracyclic compounds need to be introduced by forming intrapeptide disulfide bonds.

Hence, there exists a need in the art to increase the structural diversity of scaffold-cyclized peptides and to provide improved multicyclic peptides, in particular for those having at least three peptide loops.

SUMMARY OF THE INVENTION

The present invention aims to overcome disadvantages, such as those described above, of existing methodologies for preparing multicyclic peptides and to increase the structural diversity of scaffold-cyclized peptides. The present inventors developed novel methods using a specific approach wherein CLIPS chemistry and an additional orthogonal ligation reaction are combined in a specific two-step reaction protocol. While with previous technologies only bicyclic peptides could be obtained in pure form, this new approach leads to the generation of cyclized peptides wherein two to six, and in particular three to six, peptide loops are formed. The cyclized peptides are preferably formed in mainly one or two regioisomeric forms, more preferably in essentially one or two regioisomeric forms.

In a first aspect the invention therefore provides a method for preparing a compound comprising a peptide attached to a molecular scaffold, the method comprising:

1) performing a thiolate nucleophilic substitution reaction between a peptide and a molecular scaffold to form two or three thioether linkages between said peptide and said molecular scaffold; and 2) performing a reaction between said peptide and said molecular scaffold selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction to form two or three further linkages between said peptide and said molecular scaffold, thereby forming three to six peptide loops; whereby:

said peptide and said molecular scaffold comprise two or three reactive groups capable of participating in said thiolate nucleophilic substitution reaction and two or three reactive groups capable of participating in said reaction in step 2) prior to performing said reactions, said molecular scaffold comprises an aromatic or heteroaromatic cyclic moiety, a 6-membered cycloalkyl or a 6-membered cycloalkylene and possesses twofold or threefold symmetry. The reactions in 1) and 2) are performed in the indicated order. In a preferred embodiment said compound comprises three to six peptide loops.

In a further aspect the invention provides a method for preparing a compound comprising a peptide attached to a molecular scaffold, the method comprising:

1) performing a thiolate nucleophilic substitution reaction between a peptide and a molecular scaffold to form two or three thioether linkages between said peptide and said molecular scaffold; and 2) performing a reaction between said peptide and said molecular scaffold selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction to form one, two or three further linkages between said peptide and said molecular scaffold, thereby forming two to six peptide loops; whereby:

said peptide and said molecular scaffold comprise two or three reactive groups capable of participating in said thiolate nucleophilic substitution reaction and one, two or three reactive groups capable of participating in said reaction in step 2) prior to performing said reactions, said molecular scaffold comprises an aromatic or heteroaromatic cyclic moiety, a 6-membered cycloalkyl or a 6-membered cycloalkylene and possesses twofold or threefold symmetry. The reactions in 1) and 2) are performed in the indicated order.

The invention further provides a compound obtainable by a method according to the invention.

In a further aspect, the invention provides a compound comprising a peptide and a molecular scaffold, wherein:

i. said peptide is attached to said molecular scaffold by four to six linkages;

ii. said molecular scaffold comprises an aromatic or heteroaromatic cyclic moiety or a 6-membered cycloalkyl or cycloalkylene and possesses twofold or threefold symmetry;

iii. said compound comprises three to six peptide loops formed as a result of attachment of said peptide to said molecular scaffold;

iv. two or three of said linkages are thioether linkages; and v. two or three of said linkages result from a reaction selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction.

In a further aspect, the invention provides a library comprising a plurality of compounds according to the invention.

In a further aspect, the invention provides a compound comprising a peptide and a molecular scaffold, wherein:

i. said peptide is attached to said molecular scaffold by two to six linkages;

ii. said molecular scaffold comprises an aromatic or heteroaromatic cyclic moiety or a 6-membered cycloalkyl or cycloalkylene and possesses twofold or threefold symmetry;

iii. said compound comprises two to six peptide loops formed as a result of attachment of said peptide to said molecular scaffold;

iv. two or three of said linkages are thioether linkages; and v. one, two or three of said linkages result from a reaction selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction.

In a further aspect, the invention provides a library comprising a plurality of compounds according to the invention.

In a further aspect, the invention provides a molecular scaffold comprising:

an aromatic or heteroaromatic cyclic moiety, a 6-membered cycloalkyl or a 6-membered cycloalkylene, two or three reactive groups capable of participating in a thiolate nucleophilic substitution reaction, two or three reactive groups capable of participating in a reaction selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction whereby said molecular scaffold possesses twofold or threefold symmetry with the proviso that the scaffold is not 1,3,5-tris(bromomethyl)-2,4,6-tris(trimethylsilylethynyl) benzene.

In a further aspect, the invention provides a method for identifying a compound capable of binding to a target of interest, comprising contacting a library of compounds according to the invention with the target of interest, determining binding of said compounds to said target and selecting a compound that binds to said target.

In a further aspect, the invention provides a use of a compound according to the invention or a library according to the invention in a method for selecting a candidate drug compound.

In a further aspect, the invention provides a compound according to the invention for use in medicine.

DETAILED DESCRIPTION

The methods of the invention allow the preparation of multicyclic peptides and at the same time prevent or limit the formation of undesired regioisomers. While with previous technologies only bicyclic peptides in a single regioisomeric form could be obtained, the methods of the invention allows the generation of multicyclic peptides in a essentially a single regioisomeric form. In addition, whereas in the previous technology using a single step coupling method whereby peptides are coupled to a scaffold via two or more thioether linkages, the two-step method of the present invention increases the structural diversity of scaffold-cyclized peptides. By using a different scaffold equipped with two different functionalities for attachment of the peptide, structurally different loops and therefore products can be formed. Hence, the utilization of the thiolate nucleophilic ligation and the orthogonal ligation technique is essential and both the scaffold and the starting peptide have to be equipped with the proper functionalities. Another advantage of this combination of different ligation techniques over previously methods, is the relative fast and easy manner in which large libraries of multicyclic peptides can be prepared. This allows for a straightforward approach to screening against biologically relevant targets.

In an example of a method of the invention, a peptide is attached to a molecular scaffold by four linkages thereby forming three peptide loops or four peptide loops if the starting peptide is for instance a backbone-cyclized peptide. In a first step two thioether linkages are formed between the peptide and scaffold in a first reaction. In a second step two further linkages of the same type, e.g. two 1,2,3-triazole linkages or two oxime conjugate linkages, are formed between the peptide and the scaffold in a second reaction. The synthesis of such cyclized peptide is schematically shown in FIG. 2A, and FIGS. 2B and 2C where each shows an example of specific reactions. In this compound, further peptide loops can optionally be formed by introducing additional linkages in the peptide, for instance by coupling of the N-terminus and the C-terminus of the peptide or formation of a disulfide bridge between two amino acid residues in the peptide.

In a further example of a method of the invention, a peptide is attached to a molecular scaffold by five linkages to form a compound having four peptides loops, or five peptide loops if the starting peptide is for instance a backbone-cyclized peptide. In a first step three thioether linkages are formed between the peptide and scaffold in a first reaction. In a second step two further linkages of the same type, e.g. two 1,2,3-triazole linkages or two oxime conjugate linkages, are formed between the peptide and the scaffold in a second reaction. The synthesis of such cyclized peptide is schematically shown in FIG. 3A, and FIGS. 3B and 3C and each shows an example of specific reactions. In this compound, further peptide loops can optionally be formed by introducing additional linkages in the peptide, for instance by coupling of the N-terminus and the C-terminus of the peptide or formation of a disulfide bridge between two amino acid residues in the peptide.

In yet another example of a method of the invention, a peptide is attached to a molecular scaffold by six linkages to form a compound having five peptides loops, or six peptide loops if the starting peptide is for instance backbone-cyclized. In a first step three thioether linkages are formed between the peptide and scaffold in a first reaction. In a second step three further linkages of the same type, e.g. three 1,2,3-triazole linkages or three oxime conjugate linkage, are formed between the peptide and the scaffold in a second reaction. The synthesis of such cyclized peptide is schematically shown in FIG. 4A. FIGS. 4B and 4C each show an example of specific reactions. In this compound, further peptide loops can be introduced by making additional linkages in the peptide, for instance by coupling of the N-terminus and the C-terminus of the peptide.

In all these examples, as a result of i) the use of two different types of reactions and linkages formed between peptide and scaffold and ii) the selection of the typical alternating presence of two or three reactive groups for each of the two different reactions in the peptide and in a molecular scaffold that possesses threefold rotational symmetry, the peptide is forced into a preferred conformational structure, or even a single possible conformational structure, limiting the formation of undesired regioisomers.

In yet another example of a method of the invention, a peptide is attached to a molecular scaffold by three linkages to form a compound having two peptides loops, or three peptide loops if the starting peptide is for instance backbone-cyclized. In a first step two thioether linkages are formed between the peptide and scaffold in a first reaction. In a second step one further linkage, e.g. a 1,2,3-triazole linkages or an oxime conjugate linkage, is formed between the peptide and the scaffold in a second reaction. In this compound, further peptide loops can be introduced by making additional linkages in the peptide, for instance by coupling of the N-terminus and the C-terminus of the peptide.

The term "molecular scaffold" as used herein refers to a molecule serving as a scaffold for a peptide and that is provided with multiple functional groups to which the peptide can be attached. In a molecular scaffold present in a compound according to the invention the reactive groups are no longer present as these groups have reacted to result in linkages between the peptide and scaffold. The terms "molecular scaffold" and "scaffold" are used herein interchangeably.

The molecular scaffold according to the invention, used in accordance with the invention or present in a compound of the invention comprises an aromatic or heteroaromatic cyclic moiety, a 6-membered cycloalkyl or a 6-membered cycloalkylene and possesses twofold or threefold symmetry. The cyclic structure and symmetry present in the scaffold ensure that the coupling of the peptide result in a compound in essentially a single regioisomer or essentially two regioisomers, depending to the specific scaffold that is selected. In a preferred embodiment, a scaffold comprises an aromatic or hetero-aromatic moiety. An "aromatic or hetero-aromatic cyclic moiety" is herein also referred to as a "(hetero) aromatic moiety". Heteroatoms optionally present in the aromatic moiety are preferably N, S or O. It is further preferred that the aromatic moiety contains 0, 1 or 2 heteroatoms. Preferred (hetero)aromatic moieties are phenyl, biphenyl, naphthyl and isoindoline. In a particularly preferred embodiment, a molecular scaffold used in accordance with the invention or present in a compound of the invention comprises a phenyl, optionally forming a fused bicyclic ring structure, a Spiro-bicyclic ring structure with a second cyclic group, or a tricyclic ring structure comprising a fused bicyclic ring whereby one of the rings is attached to a third ring structure. If the molecular scaffold possesses threefold symmetry as defined herein, the scaffold preferably comprises a 6-membered (hetero)aromatic moiety, preferably phenyl. If the molecular scaffold possesses twofold symmetry as defined herein, the scaffold preferably comprises a 6-membered (hetero)aromatic moiety, preferably phenyl, optionally forming a fused bicyclic ring structure, a spirobicyclic ring structure with a second cyclic group, or a tricyclic ring structure comprising a fused bicyclic ring whereby one of the rings is attached to a third ring structure.

A molecular scaffold according to the invention, used in accordance with the invention or present in a compound of the invention possesses twofold or threefold symmetry. In particular, a molecular scaffold possesses twofold symmetry, preferably twofold rotational symmetry, if it has two reactive groups capable of participating in the thiolate nucleophilic substitution reaction and two reactive groups capable of participating in the second reaction, or if it is attached to the peptide via four linkages. A molecular scaffold possesses threefold molecular symmetry, preferably threefold rotational symmetry, if it has three reactive groups capable of participating in the thiolate nucleophilic substitution reaction and three reactive groups capable of participating in the second reaction, or if it is attached to the peptide via five or six linkages. Most preferably a molecular scaffold has $C_{2v}$ symmetry or $D_{3h}$ symmetry. In particular, a scaffold having two reactive groups capable of participating in the thiolate nucleophilic substitution reaction and two reactive groups capable of participating in the second reaction, or attached to the peptide by four linkages, preferably has $C_{2v}$ symmetry. A molecular scaffold having three reactive groups capable of participating in the thiolate nucleophilic substitution reaction and three reactive groups capable of participating in the second reaction, or attached to the peptide by five or six linkages, preferably has $D_{3h}$ symmetry. These symmetry groups are commonly used in the art. A skilled person is therefore well capable of determining whether a particular molecular scaffold belongs to a $C_{2v}$ or $D_{3h}$ symmetry group and/or construct a molecular scaffold belonging to such symmetry group for use in the methods and compounds of the invention. In brief, a $C_{2v}$ symmetry group has a twofold rotational symmetry axis ($C_2$) and two mirror planes (called $\sigma_v$ and $\sigma_{v'}$) that coincide with the twofold rotational symmetry axis. A $D_{3h}$ symmetry group has a threefold rotational symmetry axis ($C_3$), three twofold axes ($C_2$) perpendicular to the threefold rotational symmetry axis and three vertical planes of symmetry ($\sigma_v$) that coincide with the twofold rotational symmetry axes. A skilled person is well capable of selecting a molecular scaffold that has a cyclic group as defined herein, preferably a (hetero)aromatic moiety that fulfils the symmetry requirements as defined herein.

Examples of suitable and preferred molecular scaffolds are provided in FIGS. 5 and 6. Hence, in a preferred embodiment, a scaffold is selected from the scaffolds depicted in FIGS. 5 and 6. Of course, if the scaffold is present in a compound of the invention, the reactive groups shown in FIGS. 5 and 6 have been replaced by linkages to the peptide, optionally leaving one reactive group in the scaffolds comprising six reactive groups in total if the peptide is attached to the scaffold by five linkages.

A molecular scaffold according to the invention or used in the methods of the invention further comprises two or three reactive groups capable of participating in the thiolate nucleophilic substitution reaction and one, two or three reactive groups capable of participating in the second reaction prior to performing said reactions. In a preferred embodiment, a molecular scaffold according to the invention or used in the methods of the invention comprises two or three reactive groups capable of participating in the thiolate nucleophilic substitution reaction and two or three reactive groups capable of participating in the second reaction prior to performing said reactions so that compounds having at least three peptide loops are formed. Suitable and preferred reactive groups are discussed below. Preferably a scaffold comprises either four reactive groups, i.e. two reactive groups of each type, or six reactive groups, i.e. three reactive groups of each type. Preferably, a molecular scaffold prior to performing the first and second reactions comprises either:
i) two reactive groups capable of participating in the thiolate nucleophilic substitution reaction (first reaction) and two reactive groups capable of participating in the second reaction, preferably an oxime-ligation reaction or an alkyne-azide cycloaddition, or
ii) three reactive groups capable of participating in the thiolate nucleophilic substitution reaction (first reaction) and three reactive groups capable of participating in the second reaction, preferably an oxime-ligation reaction or an alkyne-azide cycloaddition. Said two or three reactive groups capable of participating in an oxime ligation reaction are preferably the same, more preferably two or three ketones, two of three aldehydes or two or three aminoxy groups. Said two or three reactive groups capable of participating in an alkyne-azide cycloaddition reaction are preferably the same, more preferably two or three azides or two or three alkynes.

The combination of reactive groups in i) is preferred for preparing a compound according to the invention comprising three or four peptide loops formed as a result of attachment of the peptide to the scaffold. The combination of reactive groups in i) is preferred for preparing a compound according to the invention comprising four, five or six peptide loops formed as a result of attachment of the peptide to the scaffold.

The molecular scaffold provided by the invention preferably is not 1,3,5-tris(bromomethyl)-2,4,6-tris(trimethylsilylethynyl)benzene (the first structure in FIG. 6). The molecular scaffold provided by the invention is also not 1,3,5-tris(acetoxymethyl)-2,4,6-triethynylbenzene. These scaffolds are, however, suitable for use in the methods and compounds provided by the invention.

In a particularly preferred embodiment, a scaffold according to the invention or used in accordance with the invention possesses $C_{2v}$ symmetry or $D_{3h}$ symmetry and comprises:
   an aromatic or heteroaromatic cyclic moiety,
   two or three halides, each attached to an activated methylene group, and
   two or three reactive groups capable of participating in a reaction selected from the group consisting of an oxime-ligation reaction, an alkyne-azide cycloaddition and a thiol-ene reaction, preferably in an oxime-ligation reaction or an alkyne-azide cycloaddition. Preferably said scaffold comprises two halides, each attached to an activated methylene group, and two reactive groups capable of participating in a reaction selected from the group consisting of an oxime-ligation reaction, an alkyne-azide cycloaddition and a thiol-ene reaction, preferably in an oxime-ligation reaction or an alkyne-azide cycloaddition, or three halides, each attached to an activated methylene group, and three reactive groups capable of participating in a reaction selected from the group consisting of an oxime-ligation reaction, an alkyne-azide cycloaddition and a thiol-ene reaction, preferably in an oxime-ligation reaction or an alkyne-azide cycloaddition.
Said two or three reactive groups capable of participating in an oxime ligation reaction are preferably the same, more preferably two or three ketones, two of three aldehydes or two or three aminoxy groups. Said two or three reactive groups capable of participating in an alkyne-azide cycloaddition reaction are preferably the same, more preferably two or three azides or two or three alkynes.

A further preferred molecular scaffold comprises a free rotatable bond located between a part of the scaffold that contains said two or three reactive groups capable of participating in a thiolate nucleophilic substitution reaction and a part of the scaffold that contains said two or three reactive groups capable of participating in a reaction selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction. Said molecular scaffold further preferably comprises two of each type of reactive groups and possess $C_{2v}$ symmetry. Hence, a further preferred molecular scaffold comprises:

two halides, each attached to an activated methylene group;

two reactive groups capable of participating in a reaction selected from the group consisting of an oxime-ligation reaction, an alkyne-azide cycloaddition and a thiol-ene reaction, preferably in an oxime-ligation reaction or an alkyne-azide cycloaddition, and a free rotatable bond located between a part of the scaffold that contains said two halides and a part of the scaffold that contains said two reactive groups whereby said molecular scaffold possesses $C_{2v}$ symmetry.

In another embodiment, a molecular scaffold prior to performing the first and second reactions comprises two reactive groups capable of participating in the thiolate nucleophilic substitution reaction (first reaction) and one reactive group capable of participating in the second reaction, preferably an oxime-ligation reaction or an alkyne-azide cycloaddition. Said reactive group capable of participating in an oxime ligation reaction is preferably a ketone, an aldehyde or an aminoxy group. Said reactive group capable of participating in an alkyne-azide cycloaddition reaction is preferably an azide or an alkyne.

The term "peptide" as used herein refers to a peptide or polypeptide that comprise multiple amino acids. The terms "peptide" and "polypeptide" are used interchangeably. "A peptide" as used herein refers to a single peptide. I.e. a method for preparing a compound comprising a peptide attached to a molecular scaffold via four to six linkages comprise the attached of a single peptide to a molecular scaffold via said four to six linkages. This means that the amino acids that are used to form said four to six linkages are present in a single peptide. The same applies to a compound comprising a peptide attached to a molecular scaffold according to the invention. The peptide may contain both natural amino acids and non-natural or non-ribosomal amino acids, or any combination thereof. "Non-natural amino acids" and "non-ribosomal amino acids" as used herein refers to non-genetically encoded amino acids, irrespective of whether they appear in nature or not. For instance, non-natural amino acids comprising reactive groups are for instance present to participate in the first and second reaction of a method of the invention. A peptide used in accordance with the invention or present in a compound of the invention may comprise non-peptidic structural elements. Such non-peptidic structural elements may be present in the amino acid sequence of a polypeptide of the invention as a result of substitution of modification of one or more amino acids of said sequence. Alternatively, or additionally, the peptide may comprise non-peptidic structural elements outside the amino acid sequence, e.g. in optional N- and/or C-terminal elongating groups. Examples of modifications include acetylation, amidation, acylation, phosphorylation and methylation.

In a compound according to the invention, the peptide is attached to the molecular scaffold by three, four, five or six linkages. The compound according to the invention, or prepared in accordance with the invention comprises two to six peptide loops or looped peptide segments formed as a result of the three to six linkages between peptide and said molecular scaffold. Preferably the compound according to the invention, or prepared in accordance with the invention comprises three to six peptide loops or looped peptide segments formed as a result of four to six linkages between peptide and said molecular scaffold. In a preferred embodiment, the compound contains three to six peptide loops. In a preferred embodiment, the compound contains three to six peptide loops. As used herein the term "peptide loop" is defined as a structure formed after coupling two different amino acids in the peptide with two linkages to a molecular scaffold as defined herein. The formation of these loops and thus the looped or cyclic peptide structure is a result of the attachment of the peptide to the scaffold via the four to six linkages between separate amino acids and the scaffold, which forces the peptide into such specific conformation. Attachment of the peptide via four, five or six linkages to the scaffold results in the formation of three, four or five peptide loops, respectively, if the starting peptide is for instance a linear peptide. Attachment of the peptide via four, five or six linkages to the scaffold results in the formation of four, five or six peptide loops, respectively, if the starting peptide is for instance a backbone cyclized peptide, i.e. the peptide backbone of the N- and C-terminal amino acids are coupled. Such peptide loop for instance resembles a peptide loop present in a proteinaceous molecule for which the compound is used as a mimic.

Each of the linkages between peptide and scaffold is preferably between a separate amino acid of the peptide and the scaffold. Hence, the peptide is preferably attached to the scaffold via linkages with three, four, five or six different amino acids, more preferably via linkages with four, five or six different amino acids. A peptide used in a method of the invention or present in a compound of the invention has preferably at least 7 amino acids. However, there are preferably at least two amino acids located between each of the amino acids that are attached to the scaffold, i.e. each peptide loop consists of at least two amino acids, excluding the amino acids that are attached to the scaffold via the four to six linkages formed as a result of the first and second reaction. As a result, the peptide preferably comprises or contains at least 10 amino acids, e.g. if the peptide is attached to the scaffold by four linkages. If the peptide is attached to the scaffold by five linkages, the peptide preferably has at least 13 amino acids and if the peptide is attached to the scaffold by six linkages, the peptide preferably has at least 16 amino acids. More preferably each linkage is formed between a different amino acid of the peptide and at least three amino acids are located between each of these amino acids that attached to the scaffold, i.e. each peptide loop preferably consists of at least three amino acids, excluding the amino acids that are linked to the scaffold. For instance, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 20 amino acids or 25 amino acids. It is to be understood that the number of amino acids of each loop, i.e. the number of amino acids located between each set of two amino acids that are linked to the scaffold, does not have to be the same within a single compound of the invention. I.e. the number of amino acids in each peptide loop in a compound of the invention is independent of the number of amino acids in the other peptide loops. Hence, preferably each peptide loop independently comprise at least two amino acids, preferably at least three amino acids, more preferably at least four amino acids, excluding the amino acids that are linked to the scaffold. In addition, a peptide used in a method of the invention may have one or more amino acids located N-terminally and/or C-terminally of the outer amino acids that are linked to the scaffold. The upper limit of the number of amino acids in the peptide loops and the length of the entire peptide is less critical and may be up to e.g. 200 amino acids, or even more, preferably up to 200 amino acids for the entire peptide. Preferably, in order to e.g. minimize costs of production of the peptide, the length of the total peptide is for instance up to 70 amino acids. Hence, a peptide used according to the invention or present in a compound according to the invention preferably has a length of 7-200 amino acids, more preferably of 10-200 amino acids, more preferably 13-200, preferably such as 10-70, 13-70, 16-70, 20-70 amino acids. Preferably, each peptide loop independently consists of 2-100 amino acids, more preferably of 2-75 amino acids, more preferably of 2-50 amino acids, more preferably of 2-25 amino acids, more preferably of 2-15 amino acids. "Independently" as used in this context means that the number of amino acids in each peptide loop in a compound of the invention is independent of the number of amino acids in the other peptide loops.

In a preferred embodiment, a peptide used in a method of the invention is a linear peptide prior to attachment to the scaffold. Alternatively, the peptide used in a method of the invention contains one or more linkages in the peptide prior to attachment to the scaffold, i.e. in addition to the linkages of the peptide backbone, such as a disulfide bond between two amino acid residues, e.g. cysteines, or a coupling between the N- and C-terminal amino acids so that the peptide is backbone-cyclized.

A peptide used in the methods of the invention further comprise two or three reactive groups capable of participating in the thiolate nucleophilic substitution reaction and one, two or three reactive groups capable of participating in the second reaction prior to performing said reactions. Suitable and preferred reactive groups are discussed below. In one embodiment the peptide comprises two or three reactive groups capable of participating in the thiolate nucleophilic substitution reaction and two or three reactive groups capable of participating in the second reaction prior to performing said reactions. Preferably, such peptide prior to performing the first and second reactions comprises either:
i) two reactive groups capable of participating in the thiolate nucleophilic substitution reaction (first reaction) and two reactive groups capable of participating in the second reaction, preferably an oxime-ligation reaction or an alkyne-azide cycloaddition, or
ii) three reactive groups capable of participating in the thiolate nucleophilic substitution reaction (first reaction) and three reactive groups capable of participating in the second reaction, preferably an oxime-ligation reaction or an alkyne-azide cycloaddition. Said two or three reactive groups capable of participating in the thiolate nucleophilic substitution reaction are preferably the same, more preferably two or three thiols. Said two or three reactive groups capable of participating in an oxime ligation reaction are preferably the same, more preferably two or three ketones, two of three aldehydes or two or three aminoxy groups. Said two or three reactive groups capable of participating in an alkyne-azide cycloaddition reaction are preferably the same, more preferably two or three azides or two or three alkenes.

In another embodiment, the peptide comprises two or three reactive groups capable of participating in the thiolate nucleophilic substitution reaction and one reactive group capable of participating in the second reaction prior to performing said reactions. Said two reactive groups capable of participating in the thiolate nucleophilic substitution reaction are preferably the same, more preferably two or three thiols. Said reactive group capable of participating in an oxime ligation reaction is preferably a ketone, an aldehyde or an aminoxy. Said reactive group capable of participating in an alkyne-azide cycloaddition reaction is preferably an azide or an alkyne.

A method of the invention for preparing a compound comprising a peptide attached to a molecular scaffold comprises a two-step reaction for coupling the peptide to the scaffold. First a thiolate nucleophilic substitution reaction is performed to form two or three thioether linkages between the peptide and the scaffold. This reaction is herein also referred to as the first reaction. Subsequently, a second reaction, which is selected from an oxime-ligation reaction, an alkyne-azide cycloaddition, a thiol-ene reaction, a hydrazone ligation reaction, a Diels Alder type reaction, a disulfide bridge formation and a ring-closing metathesis reaction is carried out to form a further one, two or three linkages between the peptide and scaffold, preferably a further two or three linkages between the peptide and scaffold. This reaction is herein also referred to as the second reaction. These reactions are examples of orthogonal ligation reactions. The resulting type of linkage is dependent on the specific reaction that is selected as the second reaction.

Hence, a total of three, four, five or six linkages between peptide and scaffold are formed in the methods of the invention. in one preferred embodiment, four, five or six linkages between peptide and scaffold are formed in the methods of the invention. These linkages are preferably covalent linkages, also referred to as covalent bonds. The term "covalent linkage" or "covalent bond" refers to a form of chemical bonding that is characterized by the sharing of pairs of electrons between atoms. The methods of the invention use two different types of reactions as the first and second reaction. As a result thereof the peptide is attached to the scaffold via a first set of two or three thioether linkages a second set of, two or three linkages of the same type. For instance, the peptide is attached to the scaffold by two or three thioether linkages and by two or three linkages resulting from an oxime-ligation reaction. As another example, the peptide is attached to the scaffold by two or three thioether linkages and by two or three linkages resulting from an alkyne-azide cycloaddition.

The reaction performed in the first step of a method of the invention is a thiolate nucleophilic substitution reaction. This reaction results in the formation of two or three thioether linkages between the peptide and the molecular scaffold. Hence, in essence two or three separate thiolate nucleophilic substitution reactions are performed between each single peptide and scaffold. Nucleophilic substitution reactions are commonly known in the art and are reactions whereby an electron rich nucleophile selectively bonds with a positive or partially positive charge of an atom or a group of atoms to replace a leaving group. In the first reaction of a method of the invention, a thiolate anion, which is a strong nucleophile, reacts with an electrophilic carbon atom connected to a leaving group. Preferably, two or three thiolate reactive groups are present in the peptide, and two or three leaving group are present in the molecular scaffold. The thiolate nucleophilic substitution reaction is preferably a reaction of the SN2-type. In a SN2-type mechanism the formation of a carbocation in the scaffold is so slow that is does not effectively take place, thereby avoiding hydrolysis of the scaffold by reaction with water. The thiolate nucleophilic reaction is described in detail in Timmerman 2005; Timmerman 2009 and WO 2004/077062, which are incorporated herein by reference.

The reaction used in the second step of a method of the invention are well known in the art and a person skilled in the art is well capable of selecting appropriate reactive groups to perform such reactions. The reactions are often collectively indicated as "click reactions". "Click Chemistry" is a term that was introduced by K. B. Sharpless in 2001 to describe reactions that are high yielding, wide in scope, create only byproducts that can be removed without chromatography, are stereospecific, simple to perform, and can be conducted in easily removable or benign solvents. FIG. 7 schematically shows examples of oxime ligation, hydrazone ligation, copper-catalyzed alkyne-azide cycloaddition, copper-free (strain promoted) alkyne-azide cycloaddition and tetrazine ligations. The reaction in step 2) of a method of the invention results in the formation of two or three additional linkages between the peptide and the molecular scaffold. Each reaction takes place between a reactive group in an amino acid residue of the peptide and a reactive group in the scaffold molecule. Hence, in essence two or three separate reactions are performed between each single peptide and scaffold. It is preferred that the two or three separate reactions are the same, e.g. two or three separate oxime-ligation reactions or two or three separate alkyne-azide cycloadditions.

An oxime-ligation reaction is a chemical reaction between a substituted aminoxy group (R1-O—NH$_2$) and an aldehyde group [R2-(C=O)H] or ketone [R2-C(=O)R3] group, resulting in the formation of an oxime conjugate (R1-O—N=CH—R2 or R1-O—N=C—R2R3). R1 and R2 are typically independently —(C=O)-alkyl- or —(C=O)-aryl-, wherein 'alkyl' refers to any linear or branched, e.g. C1-4, carbon fragment and 'aryl' refers to any 5- or 6-membered (substituted) (hetero)aryl linking unit, and R3 is any linear or branched, e.g. C1-4, alkyl or any, e.g. 5- or 6-membered, (optionally substituted) (hetero)aryl group. This reaction is chemoselective and can be performed in the presence of peptides with fully unprotected side chains. The reaction can be carried out under aqueous conditions, preferably at a slightly acid pH, of ~4-6, although the reaction will also proceed under slightly basic conditions (Advanced Organic Chemistry, J. March, 4th edition, pg 906-907).

A hydrazone-ligation reaction is a chemical reaction between a substituted hydrazine (R1-NH—NH$_2$) and an aldehyde group [R2-(C=O)H] or ketone [R2-C(=O)—R3] group, resulting in the formation of a hydrazone conjugate (R1-NH—N=CH—R2 or R1-NH—N=C(—R2)-R3), wherein R1 and R2 are typically independently —(C=O)-alkyl- or —(C=O)-aryl-, wherein 'alkyl' refers to any linear or branched, e.g. C1-4, carbon fragment and 'aryl' refers to any 5- or 6-membered (substituted) (hetero)aryl linking unit, and R3 is any linear or branched, e.g. C1.4, alkyl or any, e.g. 5- or 6-membered, (optionally substituted) (hetero)aryl group. This reaction is chemoselective and can be performed in the presence of peptides with fully unprotected side chains. The reaction can be carried out under aqueous conditions, preferably at a pH of ~4-6 (Advanced Organic Chemistry, J. March, 4th edition, pg 904-905).

An alkyne-azide cycloaddition (also referred to as 'CLICK' reaction) is a chemical reaction between a substituted alkyne (R1-C≡CH) and an azide (R2-N=N$^+$=N$^-$, or simply R2-N$_3$), resulting in the formation of a 1,2,3 triazole, wherein R1 and R2 are typically independently (C=O) alkyl- or —(C=O)-aryl-, wherein 'alkyl' refers to any linear or branched, e.g. C1-4, carbon fragment, and 'aryl' refers to any, e.g. 5- or 6-membered (optionally substituted) (hetero) aryl group. The reaction is fully chemo-selective and is usually catalyzed by Cu(I). The reaction can be performed in the absence of Cu(I) for some alkynes that are part of a strained (hetero)cycle (e.g.) and therefore react spontaneously with azides. The Cu(I) catalyzed reaction exclusively forms the 1,4-isomer, while a mixture of the 1,4- and 1,5-isomer is being formed in the thermal reaction.

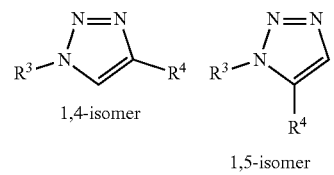

1,4-isomer 1,5-isomer

The reaction can be carried out under aqueous conditions in the presence of peptides with fully unprotected side chains (Bock et al. 2006).

A thiol-ene reaction is a reaction involving the (radical) addition of a thiol (R3SH) to an unsaturated or double bond (R10CH=CHR7), resulting in the formation of a thioether.

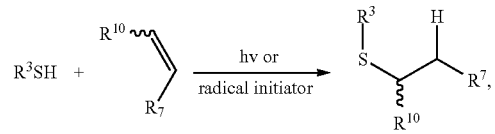

wherein R3 is —(C=O)-alkyl- or —(C=O)-aryl-, and R10 is C(=O)-alkyl-O—, C(=O)-alkyl-NH—, C(=O)-alkyl-O—C(=O)—, C(=O)-alkyl-NH—C(=O)—, C(=O)-aryl-O—, C(=O)-aryl-NH—, C(=O)-aryl-O—C(=O)—, C(=O)-aryl-NH—C(=O)—, wherein 'alkyl' refers to any linear or branched, e.g. C1-4, carbon fragment and 'aryl' refers to any, e.g. 5- or 6-membered, (optionally substituted) (hetero)aryl group, and R7 is any linear or branched, e.g. C1-4, alkyl, or any, e.g. 5- or 6-membered, (optionally substituted) (hetero)aryl group or hydrogen. This reaction is not metal-catalyst dependent and that is compatible with O$_2$ and water (Advanced Organic Chemistry, J. March, 4th edition, pg 766-767; Dondoni et al. 2009).

A Diels-Alder type reaction includes both a Diels-Alder reaction and a tetrazine ligation reaction.

With a Diels-Alder reaction is meant a [4+2] cycloaddition reaction between a dienophile (any compound containing a double bond) and a conjugated diene, resulting in the formation of a six-membered ring (typically a cyclohexene ring).

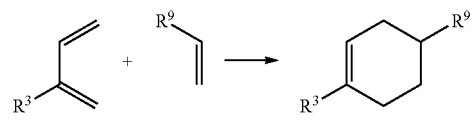

wherein R³ is —(C=O)-alkyl- or —(C=O)-aryl- and R⁹ is —(C=O)-alkyl-C(=O)—, —C(=O)-alkyl-O—C(=O)—, —C(=O)-alkyl-NH—C(=O)—, —C(=O)-alkyl-S(=O)—, —C(=O)-alkyl-O—S(=O)—, —(C=O)-aryl-C(=O)—, —C(=O)-aryl-O—C(=O)—, —C(=O)-aryl-NH—C(=O)—, —C(=O)-aryl-S(=O)—, or —C(=O)-aryl-O—S(=O)—, wherein 'alkyl' refers to any linear or branched, e.g. C1-4, carbon fragment, and 'aryl' refers to any, e.g. 5- or 6-membered, (optionally substituted) (hetero)aryl linking unit. Normal alkenes react slowly, but alkenes substituted with electron-withdrawing groups rapidly react with dienes in a Diels-Alder reaction. The reaction is fully chemoselective and can be carried out under aqueous conditions in the presence of peptides with fully unprotected side chains (Advanced Organic Chemistry, J. March, 4th edition, pg 839-852).

A tetrazine ligation reaction is an inverse electron demand Diels-Alder reaction between tetrazine and strained alkenes, such as norbornene, forming dihydropyrazine products. Strained alkynes can also be used, yielding pyrazine products. These reactions generally occur under ambient conditions, in aqueous media under micromolar dilution, using no catalyst, additive, or external stimulus. The reaction is very fast and selective, as well as equimolar, forming no byproducts. The reaction can be carried out with fully unprotected peptides, and can be performed in the presence of cell lysate and live cells. (Devaraj N K, et al. 2008.)

A ring-closing metathesis reaction is a ruthenium catalyzed reaction between two alkenes. In a ring-closing metathesis, two terminal alkenes are required to form cyclic products. The formation of the cyclic product is entropically favoured by the release of ethylene. The development of highly functional-group tolerant ruthenium catalysts has greatly facilitated the incorporation of ring-closing ring-closing metathesis in the realm of peptides and other biological systems. (White C J, Yudin, A K. 2011).

A disulfide bridge formation is a reaction between two thiols, resulting in a linkage of the general structure R—S—S—R', also referred to as disulfide bond. The reaction is fully chemoselective and can be carried out under aqueous conditions in the presence of peptides with fully unprotected side chains, with the exception of thiol containing residues that are not intended to participate in the disulfide bridge formation.

The first reaction whereby two or three linkages are formed between the peptide and the molecular scaffold is a thiolate nucleophilic substitution reaction. The second reaction whereby a further one, two or three linkages, preferably two or three linkages, are formed between the peptide and the molecular scaffold is selected from group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction. More preferably the second reaction is selected from the group consisting of an oxime-ligation reaction, an alkyne-azide cycloaddition and a thiol-ene reaction, even more preferably from an oxime-ligation reaction and an alkyne-azide cycloaddition. The thiolate nucleophilic substitution reaction is performed as the first reaction, i.e. for the formation of the initial two or three thioether linkages between the peptide and scaffold, because this reactions is extremely selective and fast, particularly in an aqueous environment. The two or three thioether linkages are formed between a single peptide and scaffold comprising the appropriate reactive groups, essentially without any by-products, such as compounds resulting from attachment of two peptides to a single scaffold. This is the result of the exceptional speed of the second and optionally third thioether linkage that is formed between the peptide and scaffold following the formation of the first thioether linkage. The orthogonal ligation reactions performed in the second step of a method of the invention are typically less fast than a thiolate nucleophilic substitution reaction. However, the second coupling reaction (e.g. oxime ligation or alkyne-azide cycloaddition) also runs fast and without any noticeable formation of side products. This is because intramolecular linkage (i.e. linkage between the peptide and scaffold within the same compound, after the two or three thioether linkages are formed) is promoted over intermolecular linkage (i.e. linkage between a peptide and scaffold that have not yet been coupled). Without the presence of the thioether linkages, a relatively high concentration of peptide and scaffold would be required to perform the orthogonal ligation reaction. Due to the presence of the thioether linkages, a lower concentration of peptide and scaffold is sufficient to prepare a compound according to the invention. If the first reaction is a thiolate nucleophilic substitution reaction, the second reaction, e.g. oxime-ligation or alkyne-azide cycloaddition, is concentration independent. A further advantage of the combination of a thiolate nucleophilic substitution reaction and an orthogonal reaction as defined herein as the second reaction is that both reactions can be performed subsequently without the need for purification steps between the first and second reaction.

The peptide and molecular scaffold comprise two or three reactive groups capable of participating in the first coupling reaction and one, two or three reactive groups capable of participating in said second coupling reaction prior to performing said reactions. The peptide and molecular scaffold preferably contains two or three reactive groups capable of participating in the first coupling reaction and one, two or three reactive groups capable of participating in said second coupling reaction prior to performing said reactions. It is further preferred that:

the peptide and scaffold each contain two reactive groups capable of participating in the first reaction and two reactive groups capable of participating in the second reaction if the peptide is attached to the scaffold by four linkages and three peptide loops are formed as a result of these linkages, the peptide and scaffold each contain three reactive groups capable of participating in the first reaction, the peptide contains two reactive groups capable of participating in the second reaction and the scaffold contains three reactive groups capable of participating in the second reaction if the peptide is attached to the scaffold by five linkages and four peptide loops are formed as a result of these linkages, the peptide and scaffold each contain three reactive groups capable of participating in the first reaction if the peptide is attached to the scaffold by six linkages and five peptide loops are formed as a result of these linkages, or the peptide and scaffold each contain two reactive groups capable of participating in the first reaction and one reactive group capable of participating in the second reaction if the peptide is attached to the scaffold by three linkages and two peptide loops are formed as a result of these linkages.

Preferably the two or three reactive groups capable of participating in the first coupling reaction present in the peptide are identical and the two or three reactive groups capable of participating in the first coupling reaction present in the scaffold are also identical. Similarly, the two or three reactive groups capable of participating in the second coupling reaction present in the peptide are identical and the two or three reactive groups capable of participating in the second coupling reaction present in the scaffold are also identical. This way it is more straightforward to obtain the required symmetry in the molecular scaffold. The first and second reactions as such are commonly used in the field of peptide chemistry and a skilled person is well capable of selecting appropriate reactive groups in the peptide and the molecular scaffold, as well as reaction conditions for performing the first and second reactions. Preferred reactive groups are discussed below, but the skilled person will be able to select suitable alternatives.

Preferably, the peptide comprises two or three thiol groups for performing the first reaction. These thiol groups are preferably each present in an amino acid residue of the peptide. This amino acid residue can be any residue comprising a thiol, including natural and non-natural amino acids. Non-limiting examples of suitable amino acids residues are cysteine (Cys), homocysteine, penicillamine, Phe (SH) or (β-mercapto)phenylalanine, Lys(γ-SH) or (gamma-mercapto)lysine, Leu(β-SH) or (β-mercapto)leucine, Pro(3-SH) and Pro(4-SH), and Thr(γ-SH) or (gamma-mercapto) threonine. Preferably the amino acid residue comprising a thiol is selected from a cysteine (Cys), homocysteine and penicillamine. In a particularly preferred embodiment, this amino acid residue is cysteine. It is further preferred that thiol groups capable of participating in the first reaction in the peptide are the same, i.e. are present in the same amino acid residue. This aids in avoiding or limiting the formation of undesired regioisomers of the compound according to the invention. It is further preferred that the peptide does not contain any further thiol groups that could potentially interfere in the first reaction. This can be achieved by using a peptide that only contains the thiols that participate in the first reaction or, if a peptide is used that contains more thiols, by protecting thiol groups that are not intended to participate in the first reaction. Suitable protecting groups for thiols, for instance present in cysteine residues, are well known in the art and include Acm (S-Acetamidomethyl), 9-fluorenylmethoxycarbonyl (Fmoc), SStBu (tert-butylthio), StBu (tert-butyl), STrt (trityl), S-Mbsh (S-4,4-dimethylsulfinylbenzhydryl), SBz (benzyl), STNP (S-thio(3-nitropyridine)), SMob (methoxybenzyl), SDpm (diphenylmethyl) and S-Tmp (S-trimethoxyphenylthio). Hence, if the peptide will be coupled to the scaffold via four linkages (two linkages formed in the first reaction and two linkages formed in the second reaction) the peptide preferably contains two unprotected thiol groups. If the peptide is to be coupled to the scaffold via five or six linkages (three linkages formed in the first reaction and two or three linkages formed in the second reaction) the peptide preferably contains three unprotected thiol groups.

The molecular scaffold preferably comprises two or three leaving groups for performing the first reaction. These leaving groups can be any good leaving group suitable for participating in a nucleophilic substitution reaction. Preferably the two or three reactive groups capable of participating in the first reaction are a halide, in particular chloride, bromide or iodide, preferably bromide or chloride, more preferably bromide. The halides are preferably each attached to an activated methylene group. As used herein, "activated" means that the methylene group has an electropositive polarity. Such activation is caused by the presence of an electrophilic group adjacent to the methylene group. Examples of such electrophilic groups are nitro, cyano, aza, carbonyl, carbamido, carboalkoxy, aryl and carboxy groups. Particularly preferred leaving groups are a halide attached to a methylene, which methylene is in turn attached to an aryl, such as a halide at a benzylic position of an aromatic moiety, or a halide attached to a methylene, which methylene is in turn attached to a carbonyl. As for the peptide, it is further preferred that reactive groups capable of participating in the first reaction in the molecular scaffold, i.e. leaving group as well as activated methylene, are the same as this aids in avoiding or limiting the formation of undesired regioisomers of the compound according to the invention.

The orthogonal reactions that are possible as the second reaction in the methods of the invention are well known in the art. Any amino acid residues comprising a reactive group capable of participating in the second reactions can be used, as well as any amino acid residue of which the side chain is modified to comprise such reactive group.

For instance, in a preferred example if the second reaction is an oxime ligation reaction, both the peptide and the molecular scaffold comprise one, two or three reactive groups capable of participating in the reaction, preferably two or three such reactive groups. The ketone/aldehyde reactive group on the one hand and the aminoxy group on the other hand can be both present in the peptide or in the scaffold. The peptide preferably comprises two or three ketone groups or aminoxy groups. Examples of suitable amino acid derivatives comprising a reactive group capable of participating in an oxime-ligation reaction are shown in FIG. 9. Examples of suitable amino acid derivatives comprising a ketone include para-acetylphenylalanine, meta-acetylphenylalanine, p-benzoylphenylalanine, 4-acetoacetyl-L-phenylalanine, 3-[(6-acetyl-2-naphthalenyl)-amino]-L-alanine, lysine N-substituted derivatives and (S)-2-amino-5-oxohexanoic acid and derivatives thereof. A particularly preferred ketone-containing amino acid residue is para-acetylphenylalanine. Examples of suitable amino acid derivatives comprising an aminoxy include shown in FIG. 9B. It is further possible to use side-chain functionalized amino acids, such as lysine and aspartic acid/glutamic acid, wherein the side chains contains a ketone or aminoxy, see FIG. 9C. The linkages present in a compound of the invention resulting from an oxime-ligation reaction are referred to as oxime bonds.

As another preferred example, if the second reaction is an alkyne-azide cycloaddition, both the peptide and the molecular scaffold comprise two or three reactive groups capable of participating in the reaction. Either two or three alkynes are present in the peptide and two or three azides in the scaffold prior to the reaction or two or three azides are present in the peptide and two or three alkynes in the scaffold. In a particularly preferred embodiment, prior to performing said alkyne-azide cycloaddition, the peptide contains two or three azides and the scaffold contains two or three alkynes. Examples of suitable amino acid derivatives comprising an alkyne or azide are shown in FIG. 8. Suitable examples of molecular scaffolds comprising two or three alkynes are shown in FIGS. 5 and 6. For an alkyne-azide reaction, the reactive groups in the scaffold are preferably chosen from the group consisting of R3C≡CH, R3N₃ and functionalized cyclooctyne, such

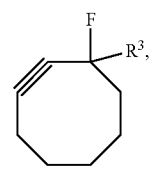

a, wherein R3 is —(C═O)-alkyl- or —(C═O)-aryl-, and R8 is —C═O, wherein 'alkyl' refers to any linear or branched, e.g. C1-4, carbon fragment, and 'aryl' refers to any, e.g. 5- or 6-membered, (optionally substituted) (hetero) aryl linking unit. In a more preferred embodiment, the reactive groups present in the scaffold are either C(=O)—CH$_2$—N$_3$ or

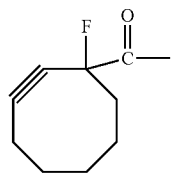

The linkages present in a compound of the invention resulting from an alkyne-azide cycloaddition are referred to as 1,2,3-triazoles.

In a preferred embodiment, a peptide that is used in a method of the invention comprises one, two or three, preferably two or three, of the amino acid residues selected from those depicted in FIGS. 8 and 9. Preferably said two or three amino acid residues selected from FIGS. 8 and 9 are identical.

In one preferred embodiment a method of the invention is for preparing a compound comprising peptide attached to a molecular scaffold, and the method comprises:
1) performing a thiolate nucleophilic substitution reaction between a peptide and a molecular scaffold to form two thioether linkages between said peptide and said molecular scaffold; and
2) performing a reaction between said peptide and said molecular scaffold selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction to form two further linkages between said peptide and said molecular scaffold
thereby forming three or four, preferably three, peptide loops; whereby:
said peptide and said molecular scaffold each comprise two reactive groups capable of participating in said thiolate nucleophilic substitution reaction and two reactive groups capable of participating in said reaction in step 2) prior to performing said reactions, and
said molecular scaffold comprises an aromatic or heteroaromatic cyclic moiety, a 6-membered cycloalkyl or a 6-membered cycloalkylene and possesses twofold symmetry. Further loops may be introduced in the compound by introducing linkages in the peptide subsequent to the first and second reaction, as described herein elsewhere.

In another preferred embodiment a method of the invention is for preparing a compound comprising peptide attached to a molecular scaffold, and the method comprises:
1) performing a thiolate nucleophilic substitution reaction between a peptide and a molecular scaffold to form three thioether linkages between said peptide and said molecular scaffold; and
2) performing a reaction between said peptide and said molecular scaffold selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction to form two further linkages between said peptide and said molecular scaffold thereby forming four or five, preferably four, peptide loops; whereby:
said peptide and said molecular scaffold each comprise three reactive groups capable of participating in said thiolate nucleophilic substitution reaction prior to performing said reactions;
said peptide comprises two reactive groups capable of participating in said reaction in step 2) prior to performing said reactions, and
said molecular scaffold comprises three reactive groups capable of participating in said reaction in step 2) prior to performing said reactions, and
said molecular scaffold comprises an aromatic or heteroaromatic cyclic moiety, a 6-membered cycloalkyl or a 6-membered cycloalkylene and possesses threefold symmetry. Further loops may be introduced in the compound by introducing linkages in the peptide subsequent to the first and second reaction, as described herein elsewhere.

In yet another preferred embodiment a method of the invention is for preparing a compound comprising peptide attached to a molecular scaffold, and the method comprises:
1) performing a thiolate nucleophilic substitution reaction between a peptide and a molecular scaffold to form three thioether linkages between said peptide and said molecular scaffold; and
2) performing a reaction between said peptide and said molecular scaffold selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction to form three further linkages between said peptide and said molecular scaffold thereby forming five or six, preferably five, peptide loops; whereby:
said peptide and said molecular scaffold each comprise three reactive groups capable of participating in said thiolate nucleophilic substitution reaction and three reactive groups capable of participating in said reaction in step 2) prior to performing said reactions, and
said molecular scaffold comprises an aromatic or heteroaromatic cyclic moiety, a 6-membered cycloalkyl or a 6-membered cycloalkylene and possesses threefold symmetry.

In yet another preferred embodiment a method of the invention is for preparing a compound comprising peptide attached to a molecular scaffold, and the method comprises:
1) performing a thiolate nucleophilic substitution reaction between a peptide and a molecular scaffold to form two thioether linkages between said peptide and said molecular scaffold; and
2) performing a reaction between said peptide and said molecular scaffold selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction to form one further linkages between said peptide and said molecular scaffold
thereby forming two or three, preferably two, peptide loops; whereby:
said peptide and said molecular scaffold each comprise two reactive groups capable of participating in said thiolate nucleophilic substitution reaction and one reactive group capable of participating in said reaction in step 2) prior to performing said reactions, and said molecular scaffold comprises an aromatic or heteroaromatic cyclic moiety, a 6-membered cycloalkyl or a 6-membered cycloalkylene and possesses threefold symmetry.

The invention also provides a compound obtainable with a method according to the invention.

Also provided is a compound comprising a peptide and a molecular scaffold, wherein:
i. said peptide is attached to said molecular scaffold by four to six linkages;
ii. said molecular scaffold comprises an aromatic or heteroaromatic cyclic moiety or a 6-membered cycloalkyl or cycloalkylene and possesses twofold or threefold symmetry;
iii. said compound comprises three to six peptide loops formed as a result of attachment of said peptide to said molecular scaffold;
iv. two or three of said linkages are thioether linkages; and
v. two or three of said linkages result from a reaction selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction.

Also provided is a compound comprising a peptide and a molecular scaffold, wherein:
i. said peptide is attached to said molecular scaffold by three linkages;
ii. said molecular scaffold comprises an aromatic or heteroaromatic cyclic moiety or a 6-membered cycloalkyl or cycloalkylene and possesses twofold or threefold symmetry;
iii. said compound comprises two peptide loops formed as a result of attachment of said peptide to said molecular scaffold;
iv. two of said linkages are thioether linkages; and
v. one of said linkages results from a reaction selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction.

The methods of the invention result in the preparation of a compound comprising a peptide attached to a scaffold in essentially a single regioisomeric form, or in essentially two regioisomeric forms, depending on the scaffold that is selected. The term "regioisomers" or "regioisomeric forms" as used herein refer to isomers obtained by coupling of reactive groups in the peptide to different reactive groups on the scaffold. Due to the two subsequent method steps and the structure of the peptide and the scaffold, the compound can only be formed in a single regioisomer, or in one or two regioisomers in a scaffold comprising two reactive groups for both the first and second reaction. Alternatively, the proximity of reactive groups in the peptide and the scaffold is selected such that, after a first thioether linkage is made in the first reaction, the location of the second and optionally third thioether linkage and of the two or three linkages formed in the second reaction is in practice essentially fixed. Hence, in a preferred embodiment, the compound according to the invention is essentially in one or two regioisomeric form, preferably essentially in a single isomeric form. As used herein the term "essentially in one or two regioisomeric form" means that at least 90% of the individual molecules of a compound of the invention is in one or two regioisomeric forms. Preferably at least 95% of the individual molecules of a compound is in one ore two regioisomeric forms, more preferably at least 97%, more preferably at least 98%, more preferably at least 99%. In a particularly preferred embodiment, the compound of the invention is present in one or two regioisomeric forms. As used herein the term "essentially in a single regioisomeric form" means that at least 90% of the individual molecules of a compound of the invention is in the same regioisomeric form. Preferably at least 95% of the individual molecules of a compound is in the same regioisomeric form, more preferably at least 97%, more preferably at least 98%, more preferably at least 99%. In a particularly preferred embodiment, the compound of the invention is present in a single regioisomeric form.

When selecting a scaffold comprising four or six reactive groups whereby two or three of the reactive groups of the same type are on a rotatable position with respect to the cyclic moiety, the compound can be obtained in a single regioisomeric form. The other two or three reactive groups of the same type are directly or indirectly attached to the cyclic moiety. These scaffolds thus comprise a free rotatable bond located between a part of the scaffold that contains the two or three reactive groups capable of participating in the thiolate nucleophilic substitution reaction and a part of the scaffold that contains the two or three reactive groups capable of participating in the reaction in step 2). Such scaffolds are thus particularly preferred when performing a method of the invention and in a compound according to the invention. Hence, in a preferred embodiment, a scaffold according to the invention or used in accordance with the invention, prior to performing said reactions in steps 1) and 2), comprises a free rotatable bond located between a part of the scaffold that comprises two or three reactive groups capable of participating in the thiolate nucleophilic substitution reaction and a part of the scaffold that comprises said two or three reactive groups capable of participating in the reaction in step 2).

In a further preferred embodiment, a scaffold comprises a free rotatable bond located between a part of the scaffold that contains two reactive groups capable of participating in the thiolate nucleophilic substitution reaction and a part of the scaffold that contains two reactive groups capable of participating in the reaction in step 2). Such scaffold is preferred for use in a method of the invention to obtain a compound comprising a peptide that is attached to a scaffold via four linkages, two thioether linkages and two linkages resulting from the reaction in step 2) because the resulting compound is present in pure form, i.e. in a single regioisomeric form. FIG. 5 shows several examples of such scaffolds, scaffolds T4(-≡)$_2$-3 and T4(-≡)$_2$-4 for CLIPS/CLICK reactions and scaffolds T4N-2, T4N-3, T4C-1 and T4C-3 for CLIPS/OXIME reactions. As an example, in scaffold T4(-≡)$_2$-4 the free rotatable bond is located between the two cyclic moieties. Hence, in a further preferred embodiment, a scaffold according to the invention or used in accordance with the invention, prior to performing said reactions in steps 1) and 2), comprises four reactive groups, i.e. two capable participating in the thiolate nucleophilic substitution reaction and two capable participating in the reaction in step 2), and comprises a free rotatable bond located between a part of the scaffold that contains the two reactive groups capable of participating in the thiolate nucleophilic substitution reaction and a part of the scaffold that contains the two reactive groups capable of participating in the reaction in step 2). Said scaffold preferably possesses $C_{2v}$ symmetry.

As used herein, the term "free rotatable bond" refers to a singly bonded pair of atoms other than hydrogen atoms, preferably two carbon atoms or a carbon atom and a nitrogen atom. Preferred examples of such scaffolds comprising a free rotatable bond are scaffolds shown in FIG. 5, i.e. the scaffolds indicated as T4(-≡)$_2$-3, T4(-≡)$_2$-4, T4N-2, T4N-3, T4C-1 and T4C-3. However, based on these examples provided in FIG. 5 and the experimental details on their preparation described herein below, a skilled person is capable of developing and synthesizing other scaffolds comprising such free rotatable bond. A particularly preferred scaffold used in accordance with the invention when the reaction in step 2) is a alkyne-azide cycloaddition is scaffold T4(-≡)$_2$-4 shown in FIG. 5.

In a particularly preferred embodiment a method of the invention is for preparing a compound comprising peptide attached to a molecular scaffold via four bonds, and the method comprises:

1) performing a thiolate nucleophilic substitution reaction between a peptide and a molecular scaffold to form two thioether linkages between said peptide and said molecular scaffold; and 2) performing a reaction between said peptide and said molecular scaffold selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction to form two further linkages between said peptide and said molecular scaffold.

thereby forming three or four, preferably three, peptide loops; whereby:

said peptide and said molecular scaffold each comprise two reactive groups capable of participating in said thiolate nucleophilic substitution reaction and two reactive groups capable of participating in said reaction in step 2) prior to performing said reactions, and said molecular scaffold comprises an aromatic or heteroaromatic cyclic moiety, a 6-membered cycloalkyl or a 6-membered cycloalkylene, possesses twofold symmetry, preferably C$_{2v}$ symmetry, and comprises a free rotatable bond located between a part of the scaffold that contains the two reactive groups capable of participating in the thiolate nucleophilic substitution reaction and a part of the scaffold that contains the two reactive groups capable of participating in the reaction in step 2).

Further loops may be introduced in the compound by introducing linkages in the peptide subsequent to the first and second reaction, as described herein elsewhere, such as by coupling of the N-terminus and the C-terminus of the peptide or formation of a disulfide bridge between two amino acid residues in the peptide. Said reaction in step 2) is preferably an oxime-ligation reaction or an alkyne-azide cycloaddition. In a compound according to the invention, such free rotatable bond is no longer present as a result of fixation of the structure by formation of linkages between peptide and scaffold. However, a preferred compound according to the invention comprises a scaffold that comprises a bond located between a part of the scaffold that contains the two or three, preferably two, reactive groups capable of participating in the thiolate nucleophilic substitution reaction and a part of the scaffold that contains the two or three, preferably two, reactive groups capable of participating in the reaction in step 2) that was a free rotatable bond prior to attached to the peptide. Hence, in such compound a part of the molecular scaffold comprising the two or three thioether linkages and a part of the molecular scaffold comprising the two or three linkages resulting from a reaction selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction are separated by a singly bonded pair of atoms other than hydrogen atoms, preferably two carbon atoms or a carbon atom and a nitrogen atom.

The three to six linkages are preferably covalent linkages. It is further preferred that one, two or three linkages in v. result from a reaction selected from the group consisting of an oxime-ligation reaction, an alkyne-azide cycloaddition and a thiol-ene reaction, preferably an oxime-ligation reaction or an alkyne-azide cycloaddition.

In one preferred embodiment, the compound comprises:

a peptide attached to the scaffold by two thioether linkages and two covalent linkages resulting from a reaction selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction, preferably oxime bonds or 1,2,3-triazole bonds, the scaffold comprises twofold symmetry, preferably C$_{2v}$ symmetry, and the compound comprises three or four, preferably three, peptide loops formed as a result of attachment of the peptide to the scaffold.

In another preferred embodiment, the compound comprises:

a peptide attached to the scaffold by three thioether linkages and two covalent linkages resulting from a reaction selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction, preferably oxime bonds or 1,2,3-triazole bonds, the scaffold comprises threefold symmetry, preferably D$_{3h}$ symmetry, and the compound comprises four or five, preferably four, peptide loops formed as a result of attachment of the peptide to the scaffold.

In another preferred embodiment, the compound comprises:

a peptide attached to the scaffold by three thioether linkages and three covalent linkages resulting from a reaction selected from the group consisting of an oxime-ligation reaction, an alkyne-azide cycloaddition, a thiol-ene reaction, a hydrazone ligation reaction, a Diels Alder type reaction, a disulfide bridge formation and a ring-closing metathesis reaction, preferably oxime bonds or 1,2,3-triazole bonds, the scaffold comprises threefold symmetry, preferably D$_{3h}$ symmetry, and the compound comprises five or six, preferably five, peptide loops formed as a result of attachment of the peptide to the scaffold Each of these compounds may comprise one or more further loops formed as a result of one or more linkages in the peptide, i.e. linkages between two amino acid residues. Preferred examples of such linkages are described herein elsewhere.

Also provided is a library comprising a plurality of compound according to the invention. The term "plurality", as used herein, is defined as two or as more than two. However, a library preferably comprises multiple compounds. Hence, a plurality preferably refers to at least two, three, four, five, ten, one hundred, one thousand, or more, e.g. up to $10^8$, compounds.

Due to the twofold or threefold symmetry of the molecular scaffold as described herein, the reactive groups of the scaffold have a specific position with respect to the aromatic or heteroaromatic cyclic moiety, a 6-membered cycloalkyl or a 6-membered cycloalkylene.

In one preferred embodiment, the scaffold comprises two reactive groups for the first reaction and two reactive groups for the second reaction for attaching a peptide to the scaffold via four linkages or the scaffold is attached to the peptide via four linkages, and the scaffold has twofold symmetry as defined herein, preferably $C_{2v}$ symmetry. The reactive groups or linkages to the peptide can be positioned in the scaffold in any way as long as the symmetry requirements are met. Or put otherwise, any positioning of the reactive groups or linkages is allowed as long as the requirements for the $C_{2v}$ symmetry are met. A skilled person is capable of selecting a suitable position for the reactive groups or linkages. For instance, the scaffold is a 1,3,5-substituted (hetero)aromatic, cycloalkyl or cycloalkylene ring whereby the two reactive groups capable of participating in the second reaction are at the 1st position and the two reactive groups capable of participating in the first, thiolate nucleophilic substitution reaction are either at position 3 and 5. Suitable and preferred positions for the two sets of two reactive groups relative to aromatic or heteroaromatic cyclic moiety, a 6-membered cycloalkyl or a 6-membered cycloalkylene are depicted in FIG. 5.

In such compound wherein the peptide is attached to the scaffold by four linkages, the peptide also comprises two reactive groups capable of participating in the first reaction and two reactive groups capable of participating in the second reaction, or the corresponding linkages after attachment to the scaffold. Preferably the reactive groups or linkages are located in the peptide in such a way that the two reactive groups or linkages of the second reaction, preferably an oxime-ligation or alkyne-azide cycloaddition, are flanked by the two reactive groups or linkages of the first reaction, preferably thiols, or vice versa. Hence, the peptide preferably comprises the sequence A-X-B-X-B-X-A or B-X-A-X-A-B, whereby A is an amino acid residue comprising a reactive group capable of participating in the first reaction or thioether linkage to the scaffold, B is an amino acid residue comprising a reactive group capable of participating in the second reaction or linkage to the scaffold, and X is any number of amino acid residues, preferably at least two amino acid residues. Preferably the peptide has the sequence A-X-B-X-B-X-A. The peptide may further comprises a stretch of one or more amino acid residues attached to one or both of the flanking amino acid residues comprising a reactive group or linkage to the scaffold.

In another preferred embodiment, the scaffold comprises three reactive groups for the first reaction and three reactive groups for the second reaction for attaching a peptide to the scaffold via five or six linkages thereby or the scaffold is attached to the peptide via five or six linkages and the scaffold has threefold symmetry as defined herein, preferably $D_{3h}$ symmetry. The reactive groups or linkages can be positioned in the scaffold in any way as long as the symmetry requirements are met. Or put otherwise, any positioning of the reactive groups is allowed as long as the requirements for the $D_{3h}$ symmetry are met. A skilled person is capable of selecting a suitable position for the reactive groups or linkages. In one embodiment, the reactive groups or linkages for the first and second reaction are alternately attached to the six positions of a 6-membered aromatic, cycloalkyl or cycloalkylene ring. In another embodiment, one reactive group for the first reaction and one reactive group for the second reaction are attached to a freely rotatable substituent at each of the positions 1, 3 and 5 of a 6-membered aromatic ring, cycloalkyl cycloalkylene. Suitable and preferred positions for the two sets of reactive groups relative to aromatic or heteroaromatic cyclic moiety, a 6-membered cycloalkyl or a 6-membered cycloalkylene are depicted in FIG. 5.

In a compound wherein the peptide is attached to the scaffold by five linkages, the peptide prior to attachment comprises three reactive groups capable of participating in the first reaction and two reactive groups capable of participating in the second reaction or two reactive groups capable of participating in the first reaction and three reactive groups capable of participating in the second reaction. Or, subsequent to attachment, the peptide comprises the corresponding linkages. These reactive groups or linkages are preferably present in an alternating manner in the peptide. I.e. the peptide preferably comprises the sequence A-X-B-X-A-X-B-X-A or B-X-A-X-B-X-A-B, whereby A is an amino acid residue comprising a reactive group capable of participating in the first reaction, and B is an amino acid residue comprising a reactive group capable of participating in the second reaction and X is any number of amino acid residues, preferably at least two amino acid residues. It is preferred that the peptide comprises three reactive groups capable of participating in the first reaction and two reactive groups capable of participating in the second reaction. Hence, the peptide preferably comprises the sequence A-X-B-X-A-X-B-X-A. The peptide may further comprises a stretch of one or more amino acid residues attached to one or both of the flanking amino acid residues comprising a reactive group or linkage to the scaffold.

In a compound wherein the peptide is attached to the scaffold by six linkages, the peptide comprises three reactive groups capable of participating in the first reaction and three reactive groups capable of participating in the second reaction. These reactive groups are preferably present in an alternating manner in the peptide. I.e. the, preferably linear peptide, comprises the sequence A-X-B-X-A-X-B-X-A-B or B-X-A-X-B-X-A-B-X-A, whereby A is an amino acid residue comprising a reactive group capable of participating in the first reaction, and B is an amino acid residue comprising a reactive group capable of participating in the second reaction and X is any number of amino acid residues, preferably at least two amino acid residues. The peptide may further comprise a stretch of one or more amino acid residues attached to one or both of the flanking amino acid residues comprising a reactive group or linkage to the scaffold.

Provided is further a compound according to the invention wherein the peptide is a cyclized peptide comprising the sequence c([LRCFRLP[Aha]RQLR[Aha]FRLPCRQ), wherein (Aha) is azidohomoalanine, which peptide is attached to a molecular scaffold by four linkages whereby two of said linkages are thioether linkages, wherein said scaffold comprises an aromatic or heteroaromatic cyclic moiety or a 6-membered cycloalkyl or cycloalkylene, wherein said compound comprises four peptide loops formed as a result of attachment of said peptide to said molecular scaffold and said scaffold possesses twofold symmetry, preferably $C_{2v}$ symmetry. The indication "c([LRCFRLP[Aha]RQLR[Aha]FRLPCRQ)" means that the sequence is cyclic whereby the final amino acid Q is thus attached to the first amino acid L. Said peptide is preferably a cyclized peptide as a result of coupling of N-terminus and C-terminus. Said thioether linkages are formed between the two cysteine residues in said peptide and two reactive groups comprising a leaving group in the molecular scaffold capable of reacting with a cysteine, preferably two halides, more preferably two halide that are each attached to an activated methylene group. Preferably the remaining two of said linkages result from an alkyne-azide cycloaddition and are formed between the two azidohomoalanine residues in the peptide and two reactive groups in the molecular scaffold comprising an alkyne. In a particularly preferred embodiment, the molecular scaffold is T4(-≡)$_2$-3 or T4(-≡)$_2$-4 attached to the peptide, more preferably T4(-≡)$_2$-3. Such compound has been shown to be a potent inhibitor of factor XIIA activity.

Also provided is therefore, a compound according to the invention wherein the peptide is a cyclized peptide comprising the sequence c([LRCFRLP[Aha]RQLR[Aha]FRLPCRQ) for use in therapy. Said peptide is attached to a molecular scaffold by four linkages whereby two of said linkages are thioether linkages, wherein said scaffold comprises an aromatic or heteroaromatic cyclic moiety or a 6-membered cycloalkyl or cycloalkylene, wherein said compound comprises four peptide loops formed as a result of attachment of said peptide to said molecular scaffold and said scaffold possesses twofold symmetry, preferably $C_{2v}$ symmetry. Said peptide is preferably a cyclized peptide as a result of coupling of N-terminus and C-terminus. Said thioether linkages are formed between the two cysteine residues in said peptide and two reactive groups comprising a leaving group in the molecular scaffold capable of reacting with a cysteine, preferably two halides, more preferably two halide that are each attached to an activated methylene group. Preferably the remaining two of said linkages result from an alkyne-azide cycloaddition and are formed between the two azidohomoalanine residues in the peptide and two reactive groups in the molecular scaffold comprising an alkyne. In a particularly preferred embodiment, the molecular scaffold is T4(-≡)$_2$-3 or T4(-≡)$_2$-4 attached to the peptide, more preferably T4(-≡)$_2$-3. Further provided is such compound for use in inhibiting factor XIIA activity, preferably in the treatment of a disorder or condition selected from the group consisting of thrombosis or a thrombotic disease (such as stroke, myocardial infarction or pulmonary embolism), hereditary angioedema and contact activation in extracorporeal circulation. Further provided is the use of such compound in inhibiting factor XIIA activity. Such inhibition can be in vitro inhibition or in vivo inhibition. Also provided is a method inhibiting factor XIIA activity in a patient in need thereof, comprising administering to said patient a therapeutically effective amount of a compound according to the invention wherein the peptide is a cyclized peptide comprising the sequence c([LRCFRLP[Aha]RQLR[Aha]FRLPCRQ). Said method preferably is for treatment of a disorder or condition selected from the group consisting of thrombosis or a thrombotic disease (such as stroke, myocardial infarction or pulmonary embolism) hereditary angioedema and contact activation in extracorporeal circulation.

Both the first and subsequent second reaction run very well and fast in and aqueous environment. Hence, both reactions are preferably performed in an aqueous environment. As used herein, the term "aqueous environment" refers to any solution comprising water. Water must be present in the reaction mixture in an amount sufficient to dissolve the peptide. Typically at least 10% water is sufficient to dissolve the peptide. Hence, preferably water is present in a concentration (v/v %) of at least 10% in the solution in which the methods of the invention are performed. Higher concentrations of water may be preferred if it is desired that the reaction proceeds faster. Hence, preferably water is present at a concentration (v/v %) of at least 20%, more preferably at least 25%, more preferably at least 30%, more preferably at least 35%, more preferably at least 40%, more preferably at least 45%, more preferably at least 50%. The reactions run well in a solution comprising 50% water. For instance, the first and second reactions are performed in a buffer solution, e.g. an ammonium bicarbonate buffer, sodium (bi)carbonate buffer, potassium (bi)carbonate buffer, sodium phosphate buffer or TRIS buffer. The solution or buffer solution may further comprise one or more solvents. Non-limiting examples of solvents that may be present are acetonitrile (ACN), dimethylformamide (DMF), N-Methyl-2-pyrrolidone (NMP), dimethylsulfoxide (DMSO), tetrahydrofuran (THF), tetrafluoroethylene (TFE), dioxane, methanol, ethanol, isopropyl alcohol ((i)-PrOH) and butanol. In a preferred embodiment, the solution in which the first and second reactions are performed comprises a combination of water and acetonitrile, such as 20-90% of a buffer solution, e.g. ammonium bicarbonate buffer, and 10-80% acetonitrile.

The thiolate nucleophilic substitution reaction is preferably performed at basic pH, preferably at slightly basic pH, preferably at pH 7-8.5, more preferably at pH 7.5-8. Depending on the specific reaction that is performed as the second reaction, the pH can be changed following the first reaction.

For instance, an oxime-ligation reaction, although it will take place at a pH slightly above neutral, is preferably carried out at slightly acidic pH, e.g. approximately pH 4.5-6, such as pH 5. Hence, if the second reaction is an oxime-ligation reaction, the pH is preferably brought from slightly basic to slightly acidic between the first and second reaction.

An alkyne-azide cycloaddition is pH independent. Hence, if the second reaction is an alkyne-azide cycloaddition the pH does not need to be changed between the first and second reaction. However, the alkyne-azide cycloaddition is typically performed in the presence of copper, in particular Cu(I). Hence, if the second reaction is an alkyne-azide cycloaddition a Cu(I) is preferably added to the reaction mixture between the first and second reaction.

If the reactive groups in the peptide and/or scaffold capable of participating in the second reaction can interfere with the first reaction, these reactive groups may be protected during the first reaction. A skilled person is able to determine whether the specific second reaction may interfere with the first reaction and, if so, select suitable protecting groups.

For instance, before an oxime-ligation is started as the second reaction, e.g. during the first reaction, the reactive groups capable of participating in the oxime-ligation are preferably protected in order not to interfere with the thiolate nucleophilic substitution reaction. In principle only the reactive groups in the peptide or the reactive groups in the scaffold need to be protected. Preferably, aminoxy reactive groups and aldehyde reactive groups, either present in the scaffold or in the peptide are protected. Examples of protected aminoxy groups are: R3ONHBoc, R3ONHFmoc, R3ONHCbz, R3ONHTrt, R3ONHMmt, or R3ONHMtt, wherein Trt is trityl (1,1,1, triphenylmethyl); Mtt is methoxytrityl ((1 (4 methoxyphenyl) 1,1, diphenylmethyl); Mmt is methyltrityl ((1 (4 methylphenyl)-1,1,-diphenylmethyl); Boc is tert-butoxycarbonyl; Fmoc is 9H-fluoren-9-ylmethoxycarbonyl; and Cbz is carbobenzyloxy. Examples of protected aldehyde groups are R4C(Oalkyl)$_2$, wherein R4 is —(C═O)-alkyl- or —(C═O)-aryl-, wherein 'alkyl' refers to any linear or branched, e.g. C1-4, carbon fragment and 'aryl' refers to any, e.g. 5- or 6-membered, (optionally substituted) (hetero)aryl group. Examples of protected ketone groups are R4C(Oalkyl)$_2$alkyl, R4C(Oalkyl)2aryl, wherein R4 is —(C═O)-alkyl- or —(C═O)-aryl-, wherein 'alkyl' refers to any linear or branched C1-4 carbon fragment and 'aryl' refers to any 5- or 6-membered (substituted) (hetero)aryl linking unit. Hence, if the second reaction is an oxime-ligation reaction, the reactive groups involved therein in the peptide or the scaffold, optionally both, are protected during the first reaction. Protected relevant reactive groups can be deprotected between the first and the second reaction. Procedures for deprotection of the reactive groups are well known in the art. Examples include Boc-deprotection using 6M HCl, acetal-deprotection using dilute acid and phthalimide deprotection using a slight excess of hydrazine hydrate or methyl-hydrazine.

If the second reaction is an alkyne-azide cycloaddition protection of the reactive groups in the peptide and scaffold is not necessary as the second reaction will not interfere with the first reaction.

The method of the invention results in the preparation of a compound comprising two to six, preferably three to five peptide loops as defined herein formed as a result of the linkages between peptide and scaffold. The number of loops depends on the number of reactive groups present in the peptide and scaffold. Additional loops can be formed in the compound by introducing one or more linkages, preferably one, in the peptide. "Linkages in the peptide" as used herein refers to linkages between two functional groups in the peptide, e.g. in a amino acid side chain or in the N- or C-terminus. Hence, in one embodiment a method of the invention further comprises introducing one ore more linkages in the peptide, preferably to form one or more additional loops. Similarly, a compound according to the invention may comprise one or more intrapeptidic linkages. These are thus loops in addition to the two to six peptide loops comprised within a compound prepared by a method of the invention by performing the first and second reactions or present in a compound of the invention. Such one or more linkages in the peptide can either be introduced prior to or subsequent to performing the first and second reaction. It is, however, preferred that the one or more linkages are introduced subsequent to the first and second reaction. Preferred examples of such linkages are disulfide bridges and coupling of the N- and C-terminus. Coupling of the N- and C-terminus is herein also referred to as "head-to-tail cyclization" or "backbone cyclization". Methods for coupling of the N- and C-terminus of a peptide are known in the art. Examples include chemical ligation, for instance in sidechain-protected peptides using benzotriazol-1-yl-oxytripyrrolidino-phosphonium hexafluorophosphate (PyBOP) as described in Timmerman et al. 2009 and enzyme-mediated ligation technologies using e.g. sortase, butelase, peptiligase or omniligase (Schmidt et al 2017). A disulfide bridge can be formed between free thiol groups of for instance cysteine, homocysteine or penicillamine residues. In order to prevent interference with such thiol groups in the first thiolate nucleophilic substitution reaction, the thiol groups that will be used for introducing an additional linkage in the peptide are protected during the first reaction. The location of a disulfide bridge within a peptide is easily regulated by regulating the location of amino acid residues with a free thiol. In a further embodiment, a COOH-side chain of an aspartate or glutamate residue is coupled to the NH$_2$-side chain of a lysine residue. This way an amide bond is formed. Coupling of the N- and C-terminus of the peptide can be achieved in different ways. For instance, amino acid residues are incorporated in the peptide as the N- and C-terminal residue between which a linkage can be formed, such as two cysteines that can be coupled via a disulfide bond. As another example, the N- and C termini may be joined by a peptide bond, i.e. to form an internal bond by coupling the free COOH-end of a peptide to the free NH$_2$-end of the peptide, thereby forming an amide-bond. Yet another example is a Se—Se (diselenium) bond between two selenocysteine residues. Alternative methods for forming an internal bond within an amino acid sequence are available, which methods are known in the art.

In one embodiment a compound according to the invention is combined with a pharmaceutically acceptable carrier, adjuvant, diluent and/or excipient in order to enhance antibody production or a humoral response. Examples of suitable carriers for instance comprise keyhole limpet haemocyanin (KLH), serum albumin (e.g. BSA or RSA) and ovalbumin. Many suitable adjuvants, oil-based and water-based, are known to a person skilled in the art. In one embodiment said adjuvant comprises Specol. In an embodiment, said diluent comprises a solution like for example saline. A pharmaceutical composition comprising a compound according to the invention and a pharmaceutically acceptable excipient, carrier, adjuvant, and/or diluent is therefore also provided. Said pharmaceutical composition preferably is an immunogenic composition, even more preferably a vaccine, capable of inducing a protective immune response. Alternatively, or additionally, a compound according to the invention is used for inducing and/or enhancing an immune response in order to treat a patient suffering from a disease. A compound according to the invention for use as a medicament, pharmaceutical composition, and/or a prophylactic agent is also herewith provided. Preferably, such a medicament, pharmaceutical composition and/or prophylactic agent is a vaccine, capable of inducing a protective immune response. Dose ranges of a compound according to the invention to be used in the prophylactic and/or therapeutic applications as described herein are designed on the basis of rising dose studies in clinical trials, for which rigorous protocol requirements exist. Typically, doses vary between 0.01-1000 µg/kg body weight, particularly about 0.1-100 µg/kg body weight.

The compounds according to the invention can be in any desired form. In one embodiment, the compounds are prepared in solution. I.e. the compounds are not attached to any other structural component. Preparation of compounds in solution is for instance preferred after a desired mimic, e.g. a candidate drug compound, has been identified, for instance in a screening method of the invention. The compounds can then be prepared in solution for their intended application, e.g. as a therapeutic.

In another embodiment, the compound is attached to a solid support, such as an array surface or a resin or carrier material used in for instance chromatographic applications, ELISA-type assays or Biacore technology. For instance, a compound can be attached to the solid support via the N- or C-terminal amino acid residue. As another alternative, the compound, preferably the peptide part of the compound, is attached to the solid support via a linker. Linkers for attachment of a peptide to a solid support are well known in the art. There is no specific order or sequence for attachment to a solid. For instance, the peptide can be coupled to the support prior to attaching it to a scaffold with a method according to the invention. Alternatively, a compound is attached to the solid support subsequent to coupling of a peptide to a scaffold with a method of the invention.

Compounds attached to a solid support are particularly suitable for screening methods wherein a plurality of compounds are screened for binding to a target of interest. In one embodiment therefor is provided a method according to the invention or a compound according to the invention wherein said compound consists of a peptide attached to a molecular scaffold, and is optionally attached to a solid support.

In yet another embodiment, a compound comprises a genetic package displaying said peptide, said genetic package comprising a nucleic acid encoding said peptide. The term "genetic package" as used herein refers a prokaryotic or eukaryotic genetic package, and can be replicable genetic packages including cells, spores, yeasts, bacteria, viruses and bacteriophages, or cell-free display packages such as ribosomes and mRNA packages. Display technologies that can be used for displaying a compound according to the invention are phage display, mRNA display, ribosomal display, DNA display, bacterial display and yeast display. A preferred genetic package is a phage display particle, an mRNA display particle or a ribosomal display particle. The peptides used in the methods of the invention can be displayed on the genetic package, i.e. they are attached to a group or molecule of the genetic package, such as a molecule located at an outer surface of the genetic package. Genetic packages displaying peptides are formed by introducing nucleic acid molecules encoding the peptides to be displayed into the genomes of a replicable genetic packages to form fusion proteins with autologous proteins that are normally expressed at the outer surface of the replicable genetic packages. Alternatively, genetic packages displaying peptides are formed by introducing nucleic acid molecules encoding the peptides to be displayed into the nucleic acid of a cell-free display system. Display technologies are well known in the art and a skilled person is well capable of displaying a peptide used in the methods of the present invention on such display particle. The thiolate nucleophilic substitution reactions for attaching a peptide to a molecular scaffold have been shown to be compatible with sensitive biological systems, like phage-display libraries (e.g. WO 2009/098450). Reference is made to WO 2009/098450 and Heinis et al. 2009 for exemplary procedures. In addition, the orthogonal ligation reactions that are performed as the second reactions in the methods of the invention are in particular compatible with such biological systems. Compounds comprising a genetic package displaying said peptide and a nucleic acid encoding said peptide are particularly suitable for screening methods wherein a plurality of compounds are screened for binding to a target of interest. In one embodiment therefor is provided a method according to the invention or a compound according to the invention wherein said compound comprises a genetic package displaying said peptide and a nucleic acid encoding said peptide.

The peptides used in the methods and compounds of the invention may contain unnatural amino acids, in particular the amino acids comprising reactive groups capable of participating in the reaction in step 2) of the method, such as ketones/aldehydes and aminoxy for oxime ligation reactions and azides and alkynes for alkyne-azide cycloaddition. Peptide-library generating systems which utilize cellular systems, such as bacteria, or cell-free systems, such as free ribosomal systems, for peptide synthesis or expression (e.g. phage display libraries) can be used for incorporating unnatural amino acids into peptides using two methods known in the art.

One method is an auxotroph method, where the bacteria is starved of one amino acid (usually methionine) and another, structurally similar amino acid is presented, and incorporated using the codon which corresponds to the tRNA of the replaced amino acid (usually the methionine codon AUG, and the methionine tRNA, onto which the desired amino acid is loaded by the complementary tRNA synthetase). This method is only applicable for amino acids that are accepted by the replaced amino acids' tRNA synthetase. Methionine can be substituted by, for example, azido-homo-alanine. It is important to note that while using this method, methionine is not incorporated, all methionine residues in other peptides and enzymes are replaced by the new amino acid. The number of diverse amino acids that can be accessed remains 20, as this is a substitution method, not an expansion method.

For incorporation of an unnatural amino acid using the genetic code, a tRNA/codon pair for an unnatural amino acid are selected. The codons with which the amino acid can be incorporated into a peptide are so called 'stop codons' which usually terminate peptide elongation. The Amber (UAG), Ochre (UAA) and Opal (UGA) codons can be used, of which the Amber codon is most commonly used. This method in principle allows multiple amino acid incorporations, as there are three 'stop' codons. A complimentary tRNA of that codon, should be synthesized, onto which the desired amino acid is loaded (either chemically or enzymatically). Examples of amino acids that can be incorporated into a peptide via this method are para-acetyl phenylalanine, and para-azido phenylalanine. This method leaves more versatility to the amino acids that can be incorporated. For cellular systems, such as bacteria, it should be noted that the translation of the stop codon is in competition with peptide termination. This is not the case for cell-free systems, such as free ribosomal systems, where the release factors can be omitted. Recent efforts towards expanding and reprogramming the genetic code, have resulted in the incorporation of several unnatural amino acids into a single peptide, using an mRNA display system. The genetic code methods allow the site-specific incorporation of unnatural amino acids, while all natural amino acids can be accessed, hence it is noted as an expansion method.

As indicated herein before a peptide loop present in a compound according to the invention or prepared with a method of the invention for instance resembles a peptide loop present in a proteinaceous molecule for which the compound is used as a mimic. Said peptide loop preferably resembles a secondary structure within a proteinaceous molecule of interest. A secondary structure within a proteinaceous molecule of interest that is mimicked by a compound according to the invention is for instance a discontinuous epitope, ligand-binding site, receptor-binding site, or catalytic domain of said molecule of interest. The compounds of the invention are particularly useful for mimicking one or more binding sites or epitopes of a protein or proteinaceous molecule, preferably one or more discontinuous binding sites or epitopes. Hence, a compound of the invention preferably is a mimic of a binding site or epitope of a proteinaceous molecule. The presence of multiple loops in compounds of the invention are for instance particularly suitable if the proteinaceous molecule of interest comprises an epitope, catalytic domain, or ligand-binding domain that consists of more than one region of thereof, a so called discontinuous domain. A proteinaceous molecule of interest that is mimicked by, or from which a binding site or epitope is mimicked by a compound of the invention may be any proteinaceous molecule. The discontinuous epitope is for example an immunodominant epitope. Immunodominant epitopes are defined as subunits of an antigenic determinant that are easily recognised by the immune system and thus influence the specificity of the induced antibody. A secondary structure within a proteinaceous molecule of interest that is mimicked by a compound of the invention, however, may also comprise a subdominant epitope. Generally, immunodominant epitopes are, as the name suggests, dominant over most, if not all other epitopes of a given protein or at least part of a given protein. The immune system is thus oblivious for the non-dominant epitopes, also called subdominant epitopes or cryptic epitopes. In another aspect, said secondary structure to be mimicked by a compound according to the invention is a receptor binding site of a ligand, or a ligand binding site of a receptor. A compound according to the invention mimicking a receptor binding site of a ligand can for instance be used to activate (agonist) or block (antagonist) said receptor. With such compound according to the invention it is thus possible to modulate receptor action. A compound according to the invention that resembles a ligand binding site of a receptor for instance binds to the ligand, thereby preferably decreasing the biological activity of said ligand. In yet another aspect, a secondary structure that may be mimicked by compounds according to the invention are for instance catalytic domains of enzymes, such as proteases, nucleases, phophodiesterases, lipases and phosphatases. These can be suitable for use in, for instance, enzyme replacement therapy. As said before, small proteinaceous molecules that closely resemble a native conformation are expected to have less undesired effects, such as induction of immune responses.

Also provided is a method for producing a library comprising a plurality of compounds according to the invention. Such library is especially useful for determining the binding properties and/or immunogenicity of the compounds. Such library is also especially useful for identifying a compound capable of binding to a target of interest, such as a (cell surface) receptor, ligand, antibody, cytokine, hormone. Such library is for instance suitable for screening for a candidate drug compound. The invention therefore also provides a method for identifying a compound capable of binding to a target of interest, comprising contacting a library of compounds according to the invention with the target of interest, determining binding of said compounds to said target and selecting a compound that binds to said target. As used herein "target molecule" or "target of interest" is meant a molecule, preferably a proteinaceous molecule, is intended to be bound by a compound of the invention. Also provided is a use of compound according to invention or a library according to the invention in a method for selecting a candidate drug compound. In addition, the invention provides a method to screen for a binding site capable of interacting with a target molecule, comprising screening a library according to the invention with at least one potential target molecule and detecting binding between a compound of said library and said target molecule.

Methods commonly used in the art for determining binding of a compound to a target can be used in the methods of the invention. For instance, enzyme-linked (ELISA-type) assays are used, because these are typically very sensitive. Screening of such a compound library with any given molecule is simple, fast and straightforward.

A compound or library of compounds according to the invention used in a screening method of the invention is preferably in solution or attached to a solid support, e.g. an array surface, or comprises a genetic package displaying said peptide and a nucleic acid encoding said peptide. Such forms of a compound of the invention allow the easy identification of the amino acid sequence of the peptide present in the compound. For attachment to a solid support this is because the compounds are positionally or spatially addressable, e.g. in an array fashion. For a compound comprising a genetic package displaying said peptide and a nucleic acid encoding said peptide the amino acid sequence is easily identifiable by determining the sequence of the nucleic acid encoding the peptide.

After completion of the selection or the screening process, selected candidate drug compounds can subsequently be synthesized in solution, if desired at a larger scale, according to the same procedure. Thus, according to a method provided it is now possible to synthesize a compound in solution which has essentially the same binding properties as a compound selected in a screening method according to the invention.

A method for selecting a candidate drug compound is also provided, the method comprising
 providing a library of compounds according to the invention,
 contacting said compounds with a target molecule,
 determining the binding of said target molecule to said compounds, and
 selecting at least one compound that shows binding to said target molecule.

In a preferred embodiment, the invention provides a method according to the invention, wherein said binding is determined on a solid phase provided with said library of compounds.

Further detailed procedures for screening a library comprising a plurality of compounds according to the invention are described in WO 2004/077062, which is incorporated herein by reference.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

The invention will be explained in more detail in the following, non-limiting examples.

EXAMPLES

List of Abbreviations

Figure 1:
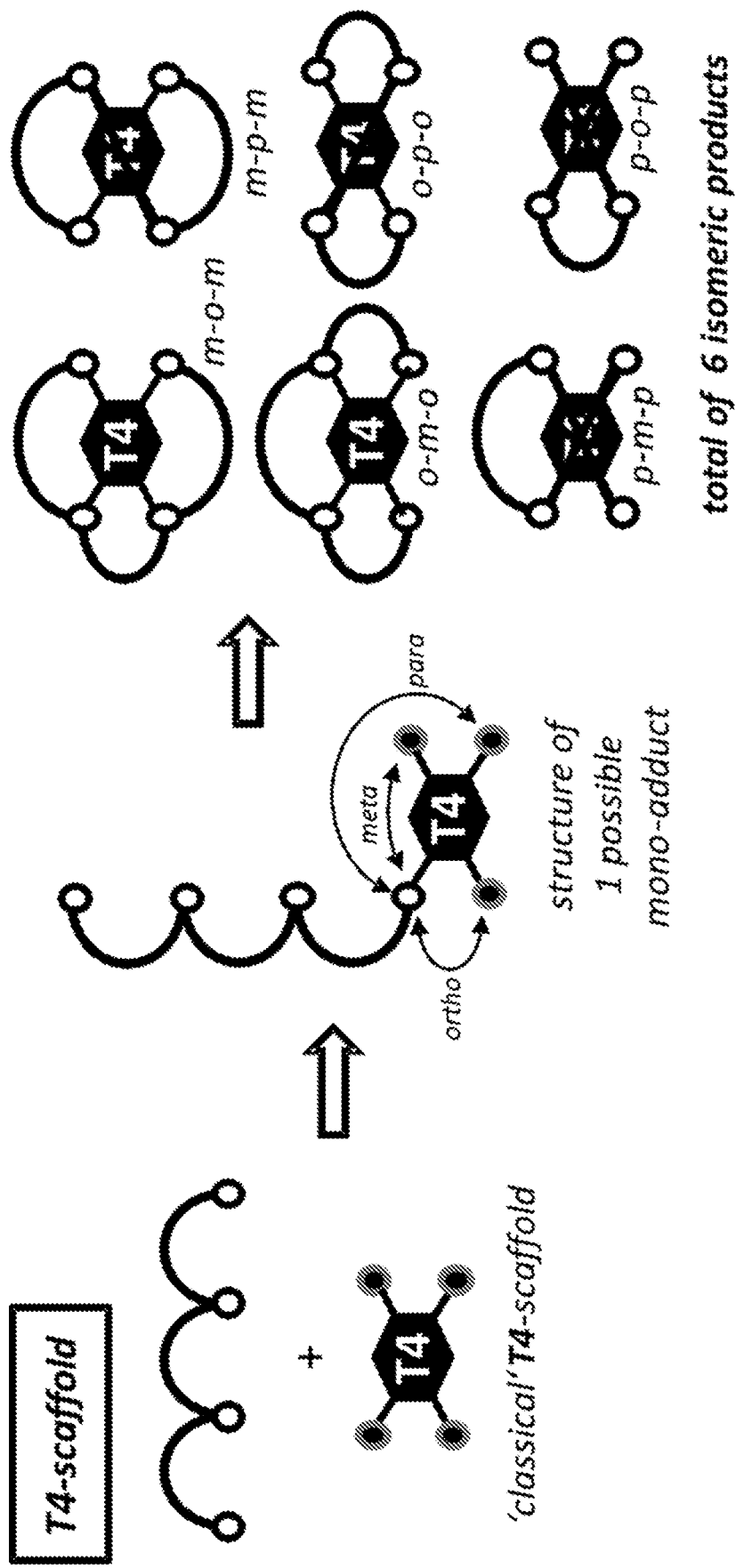
FIG. 1. Attachment of a peptide to a scaffold containing four reactive groups (referred to as T4-scaffold) by four linkages to produce a tricyclic peptide using CLIPS technology as described in Timmerman et al. 2005 results in the formation of a complex mixture of up to six regioisomers.
Figure 2A:
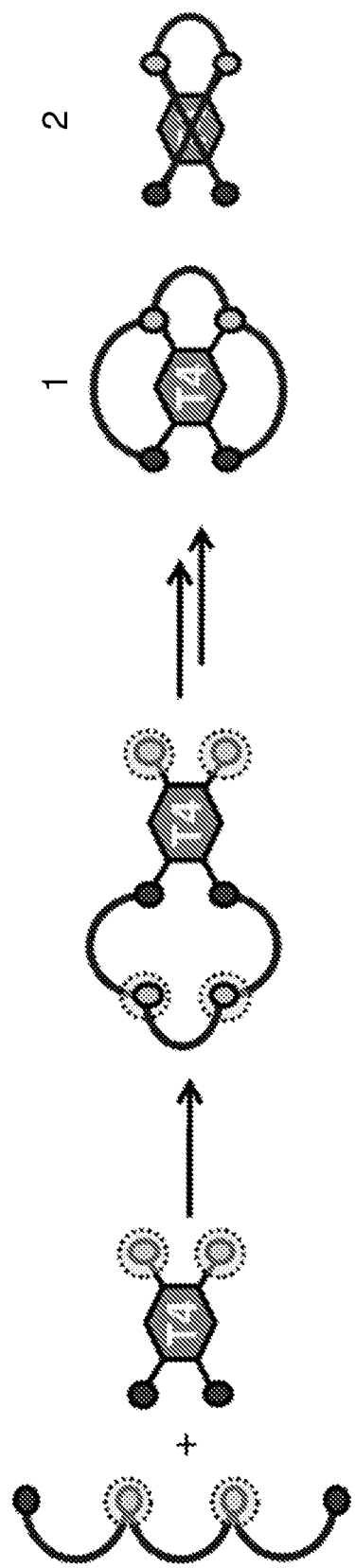
FIG. 2. Schematic representation of coupling of a peptide to a molecular scaffold by four linkages to prepare a compound having three peptide loops (A) Regioisomer 2 only occurs with specific molecular scaffolds. Examples of nucleophilic substitution and alkyne-azide cycloaddition reactions (B) or nucleophilic substitution and oxime ligation reactions (C) to attach a peptide to a scaffold by four linkages.
Figure 2B:
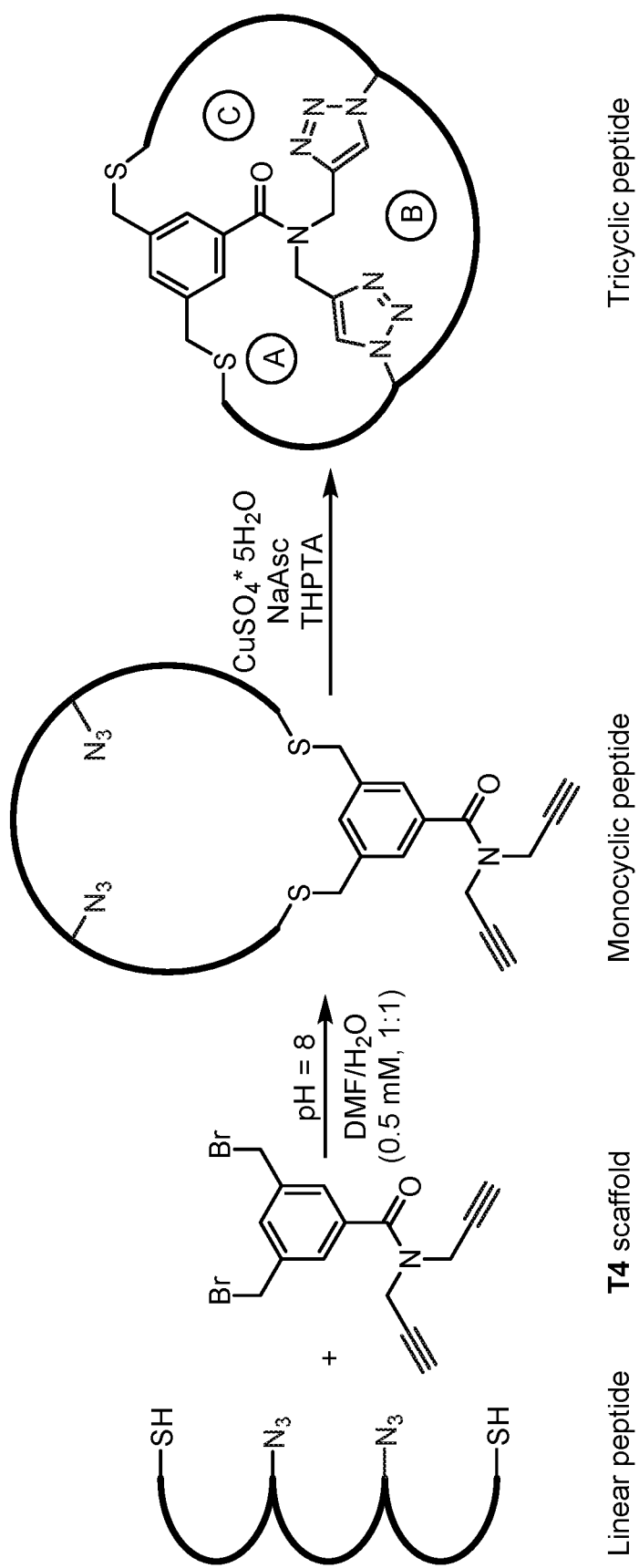
Figure 2C:
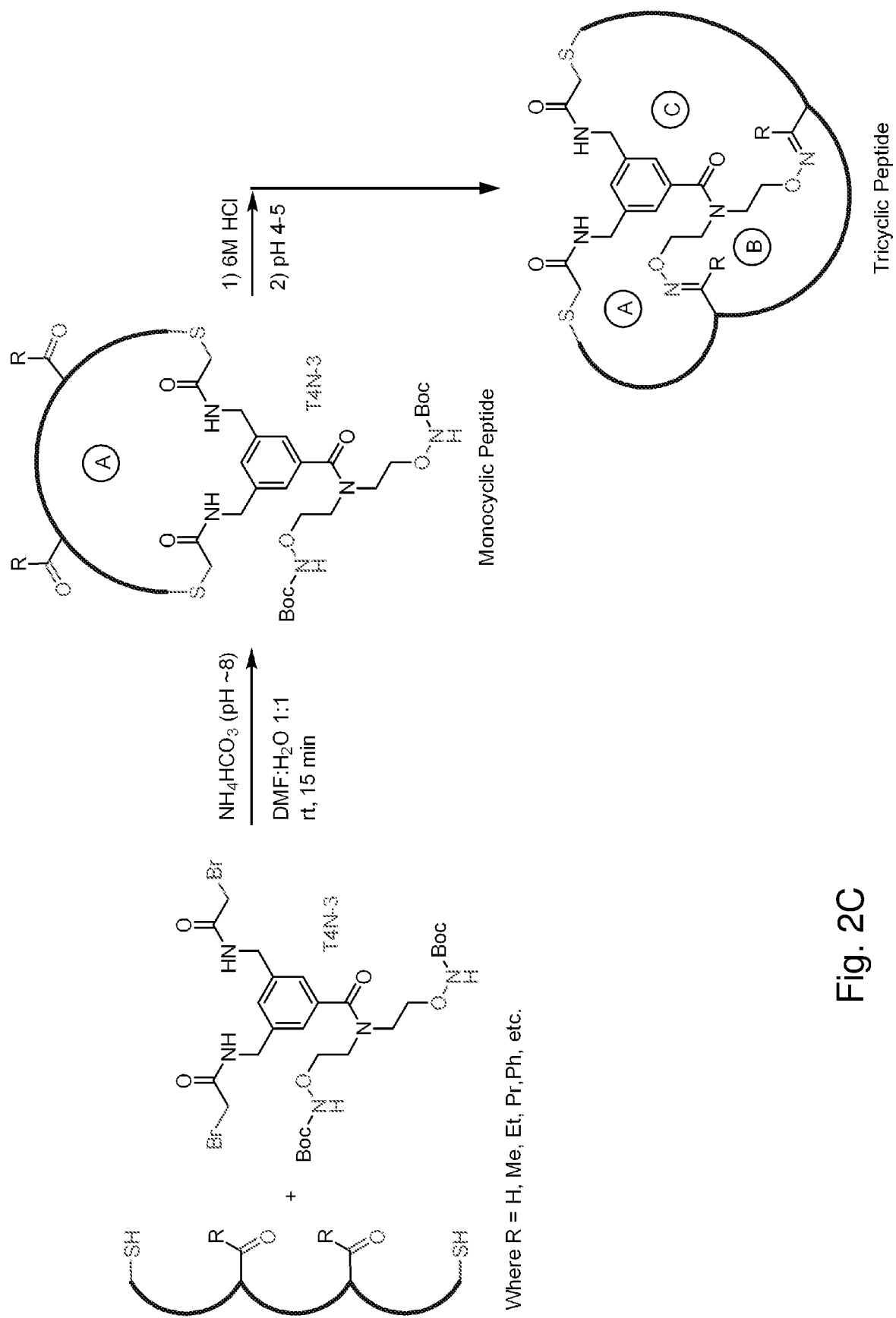
Figure 3A:
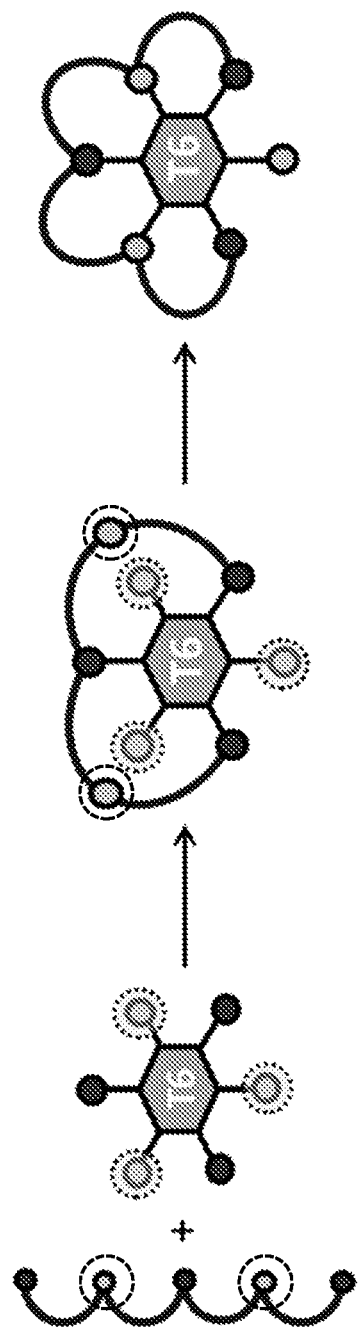
FIG. 3. Schematic representation of coupling of a peptide to a molecular scaffold by five linkages to prepare a compound having four peptide loops (A). Examples of nucleophilic substitution and alkyne-azide cycloaddition reactions (B) or nucleophilic substitution and oxime ligation reactions (C) to attach a peptide to a scaffold by five linkages.
Figure 3B:
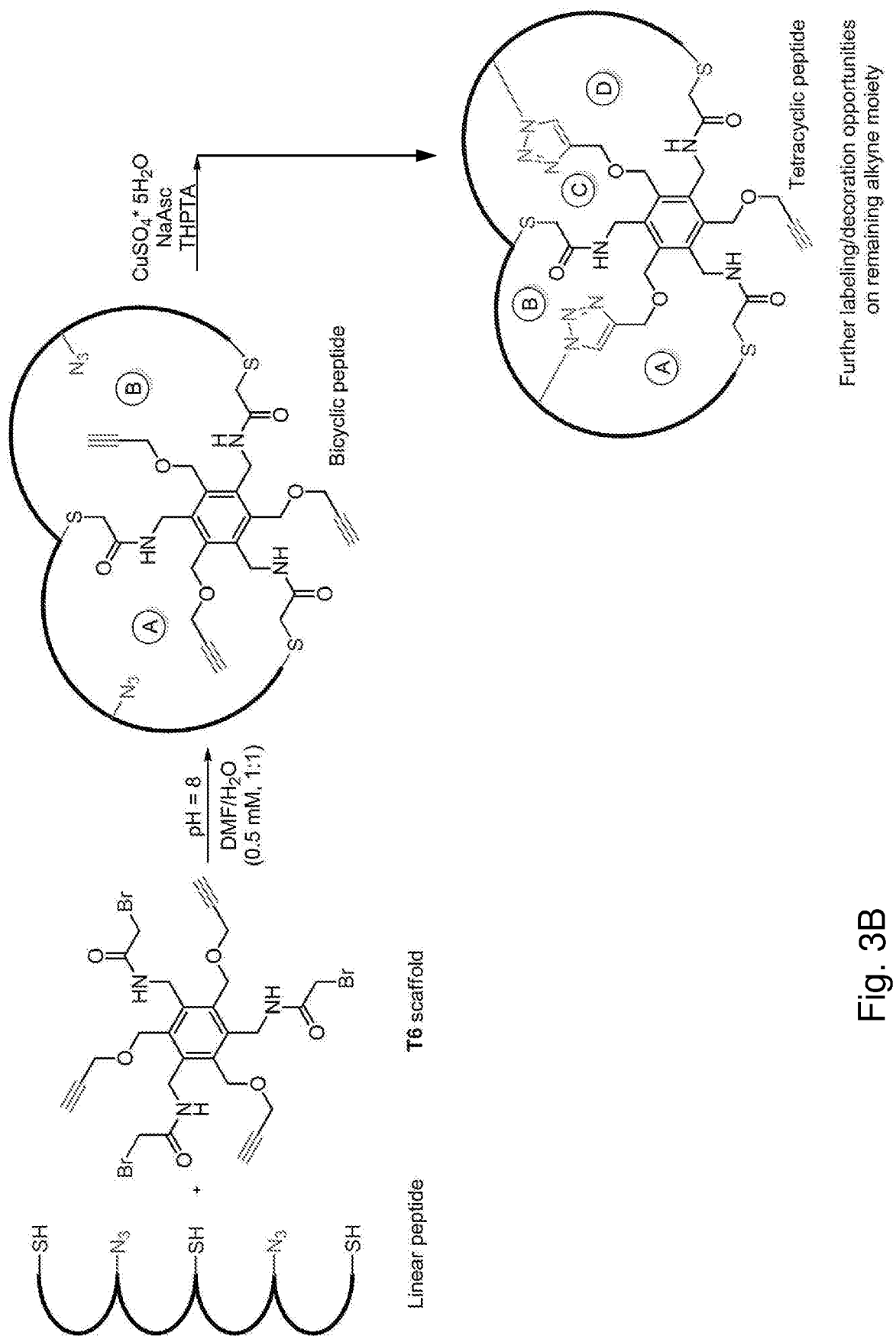
Figure 3C:
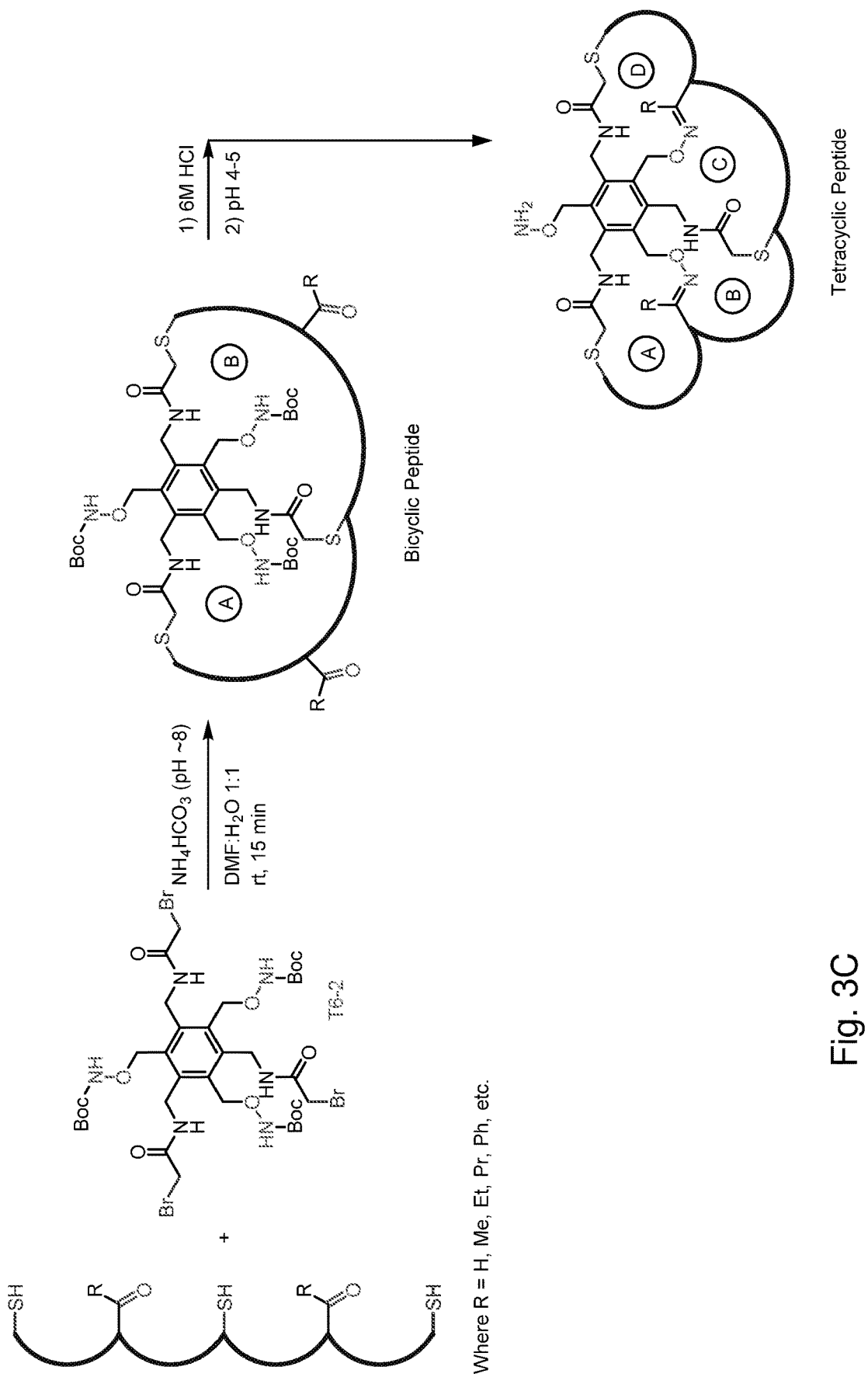
Figure 4A:
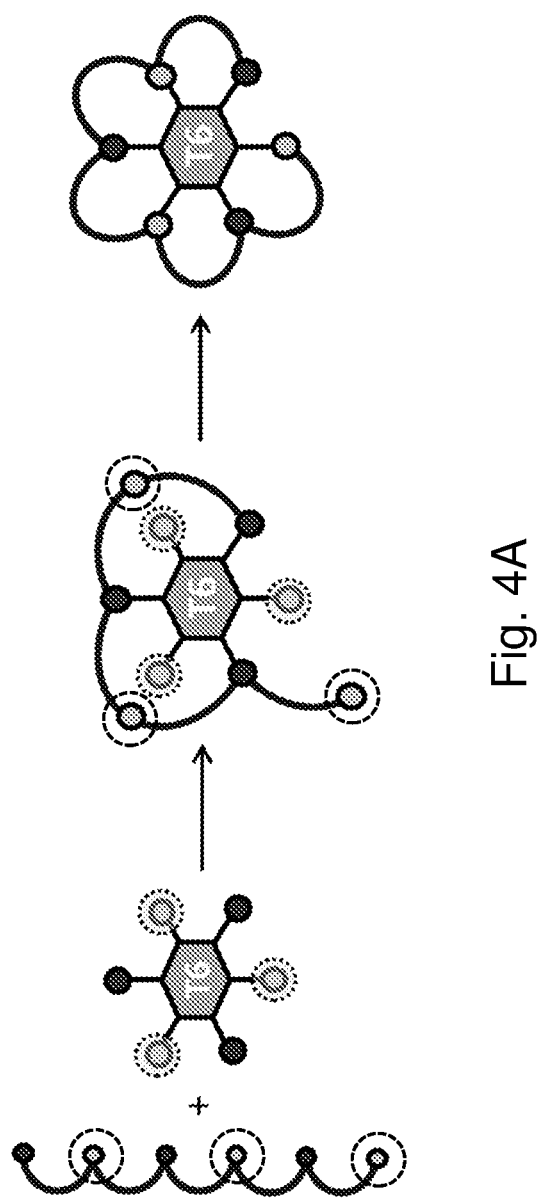
FIG. 4. Schematic representation of coupling of a peptide to a molecular scaffold by six linkages to prepare a compound having five peptide loops (A). Examples of nucleophilic substitution and alkyne-azide cycloaddition reactions (B) or nucleophilic substitution and oxime ligation reactions (C) to attach a peptide to a scaffold by six linkages.
Figure 4B:
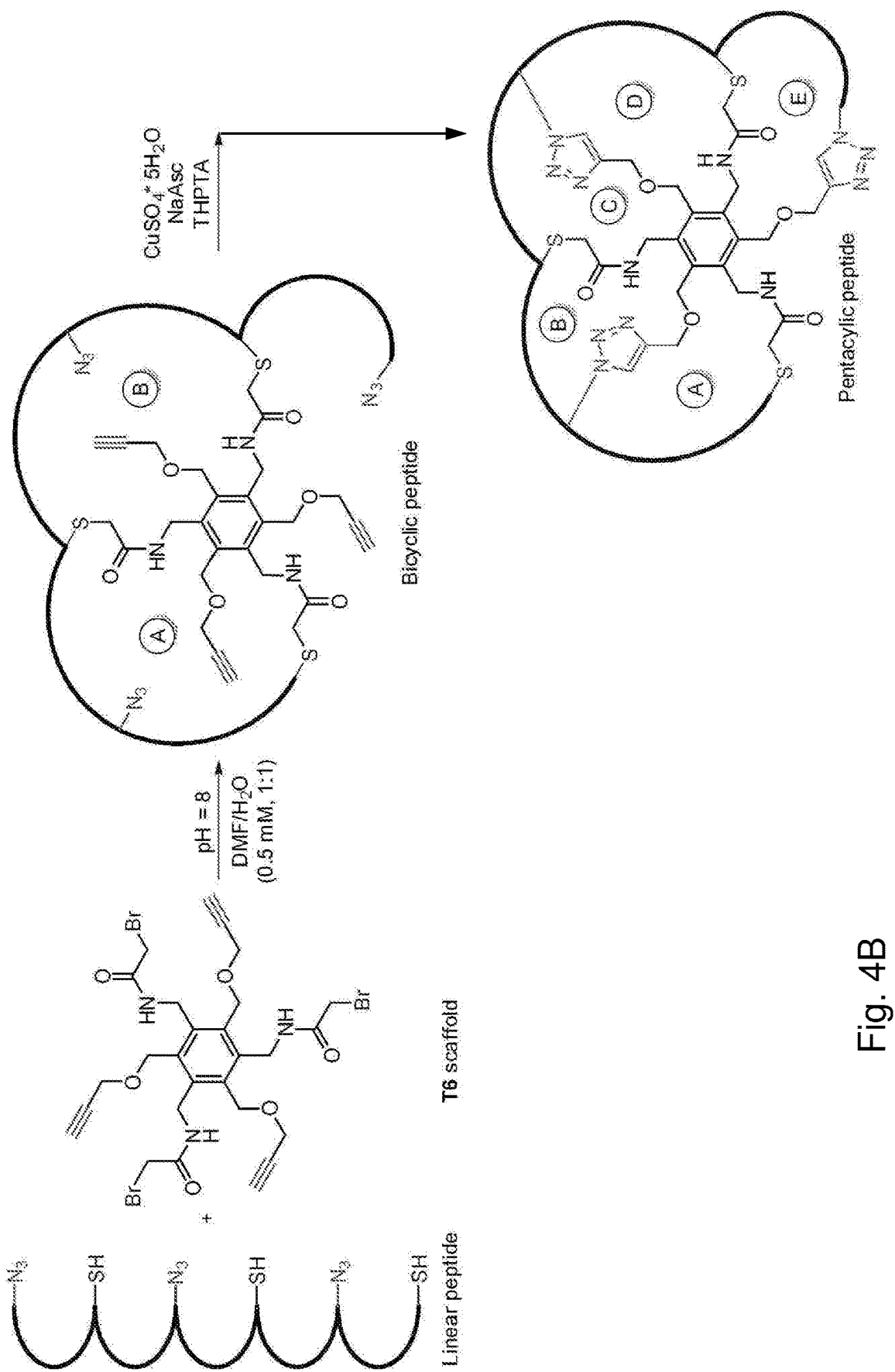
Figure 4C:
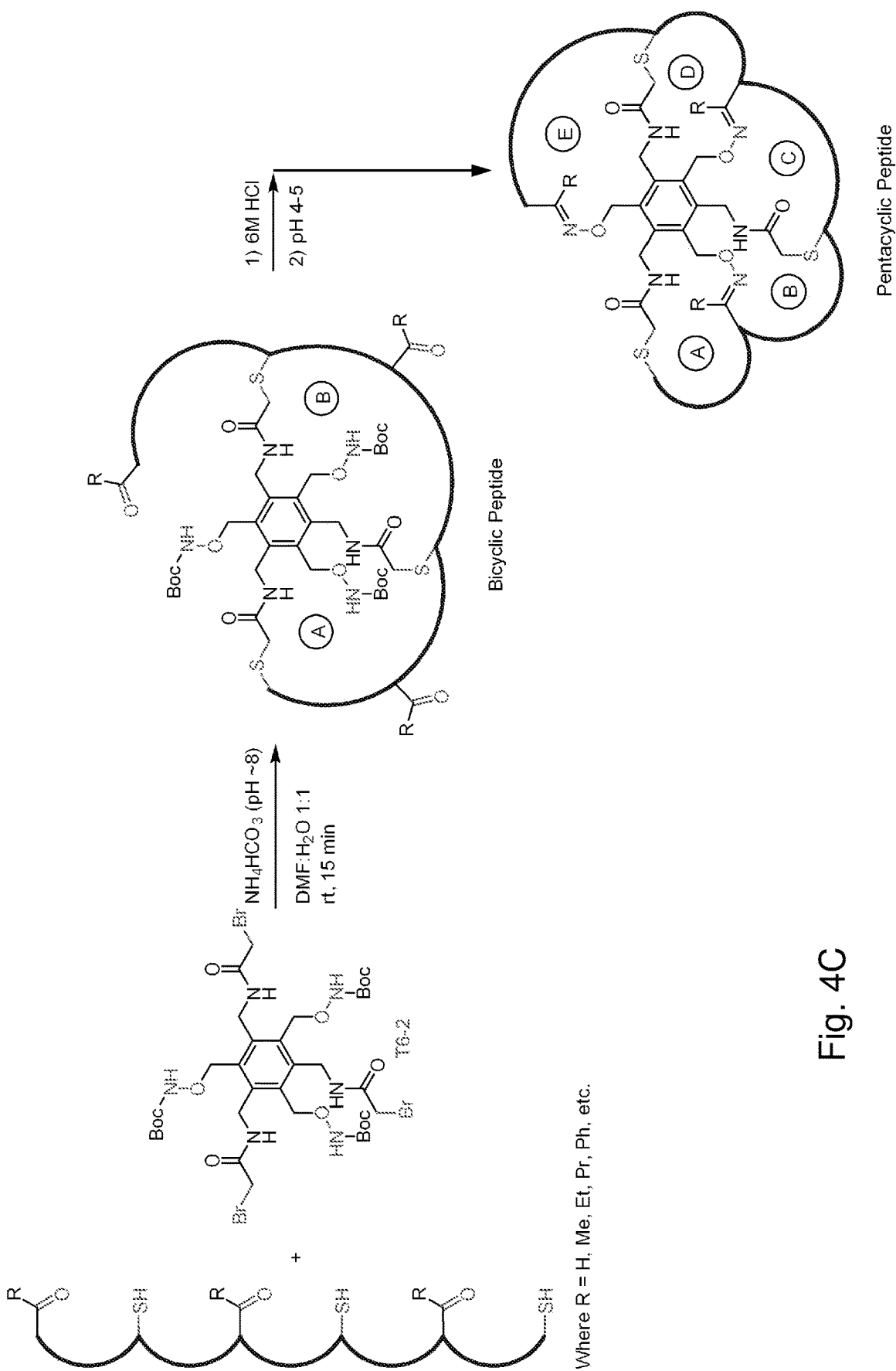
Figure 5:
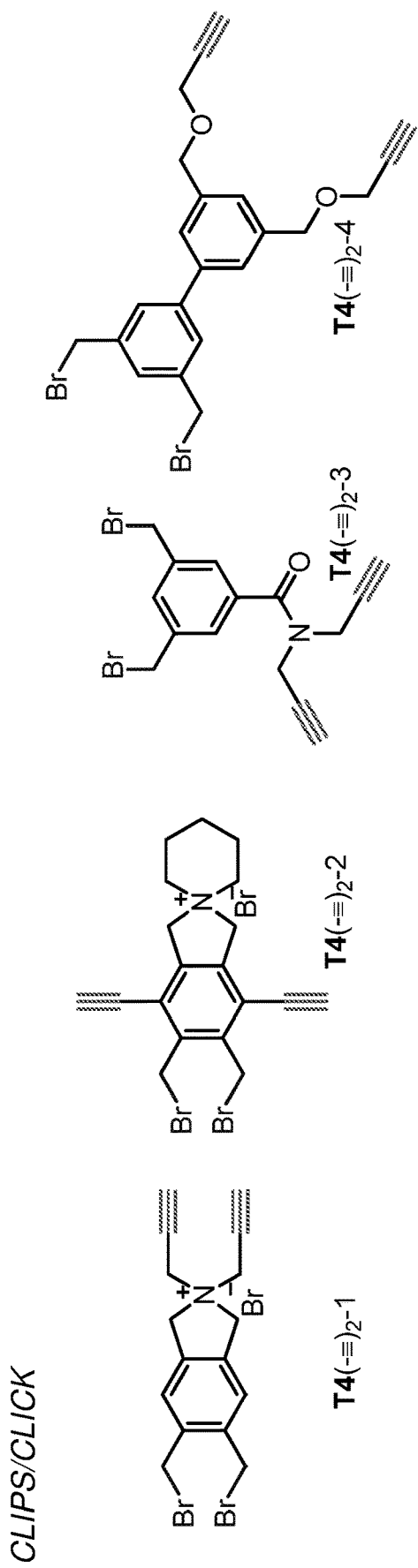
FIG. 5. Examples of molecular scaffolds containing four reactive groups (referred to as T4-scaffolds) that can be used in accordance with the invention for cyclization of peptides. CLIPS/CLICK scaffolds that can be attached to a peptide via thiolate nucleophilic substitution reaction and alkyne-azide cycloaddition. CLIPS/OXIME: scaffolds that can be attached to a peptide via thiolate nucleophilic substitution reaction and oxime ligation reaction.
Figure 6:
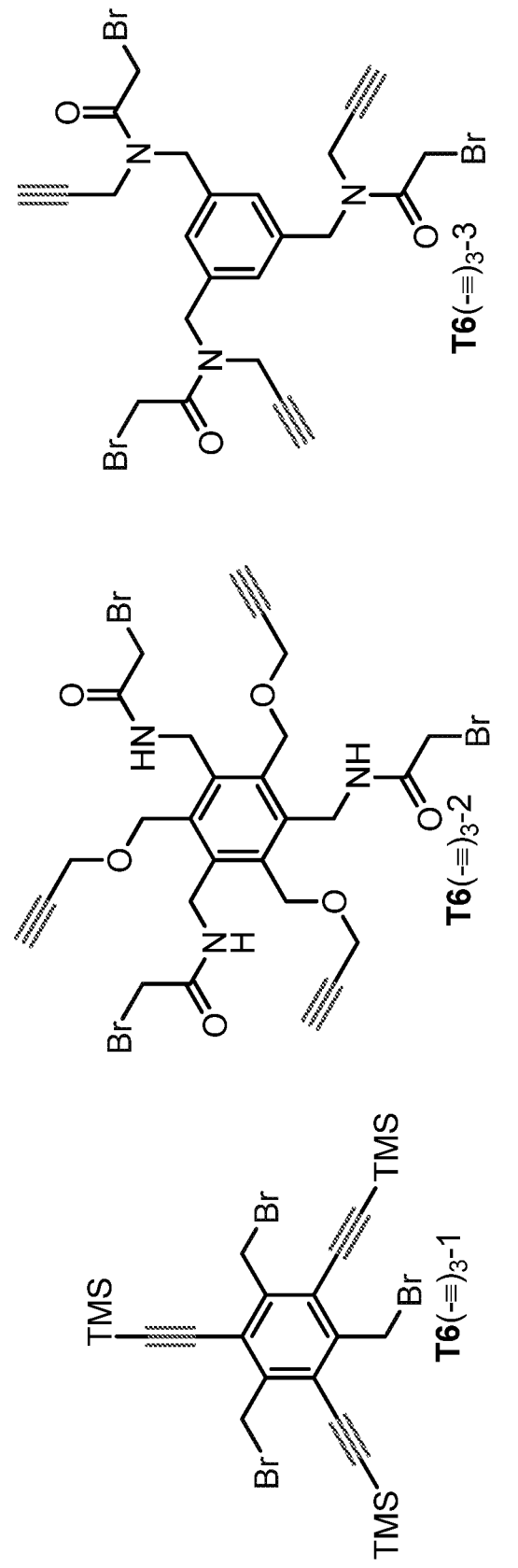
FIG. 6. Examples of molecular scaffolds containing six reactive groups (referred to as T6-scaffolds) that can be used in accordance with the invention for cyclization of peptides. CLIPS/CLICK scaffolds that can be attached to a peptide via nucleophilic substitution reaction and alkyne-azide cycloaddition. CLIPS/OXIME: scaffolds that can be attached to a peptide via nucleophilic substitution reaction and oxime ligation reaction.
Figure 7:
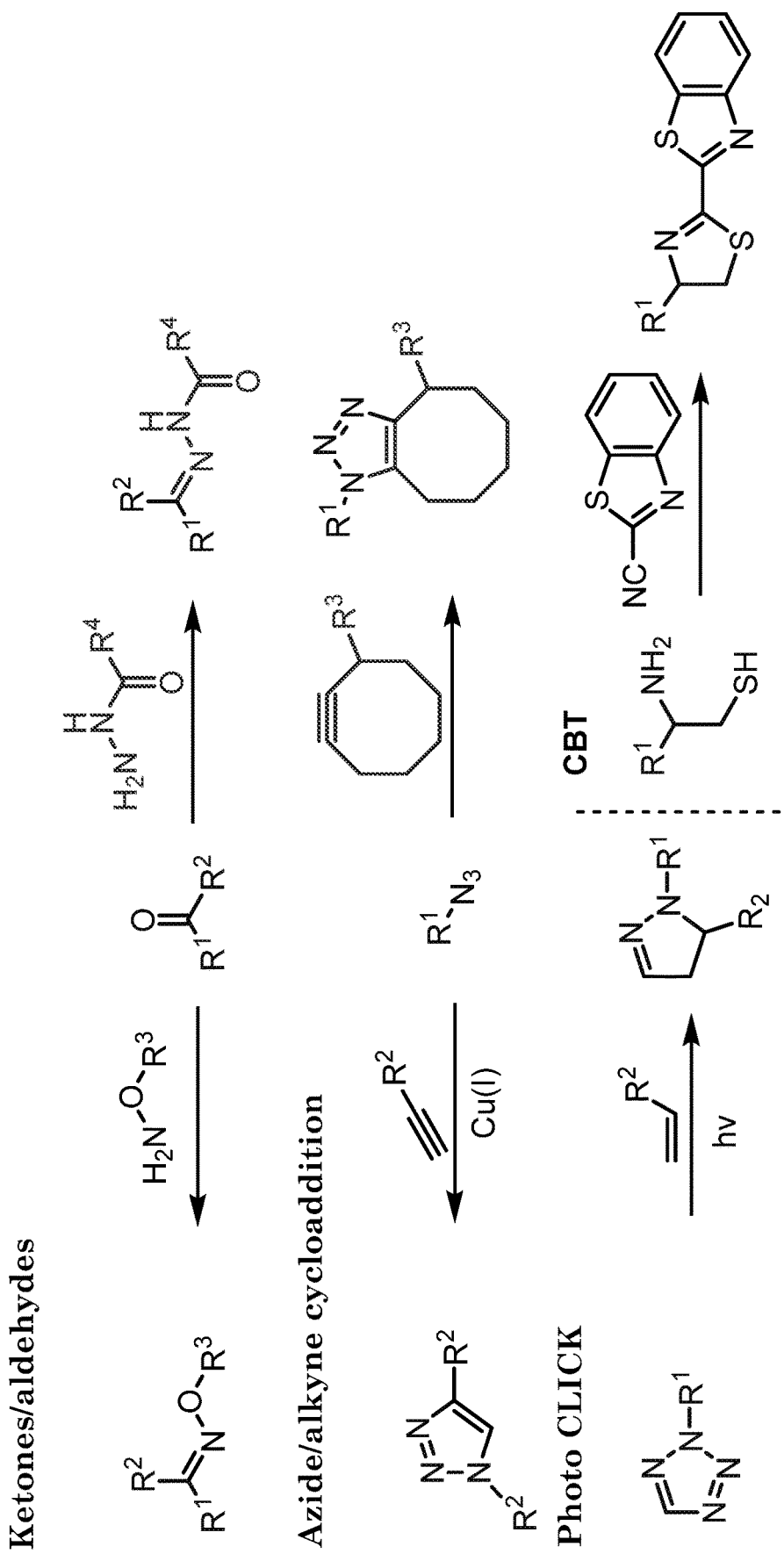
FIG. 7. Schematic examples of "click reactions" that can be used in the methods of the invention.
Figure 8A:
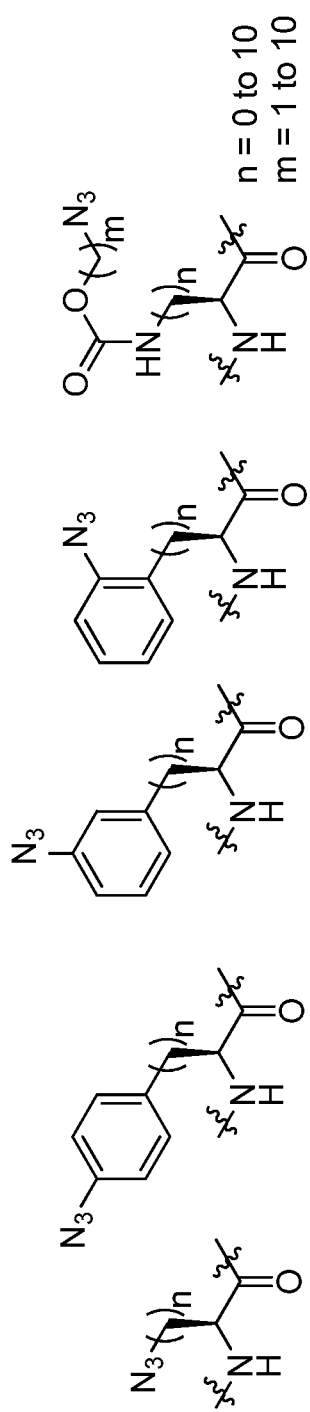
FIG. 8. Examples of amino acid derivative capable of participating in an alkyne-azide cycloaddition reaction. A. azide-containing amino acid residues. B. alkyne-containing amino acid residues.
Figure 8B:
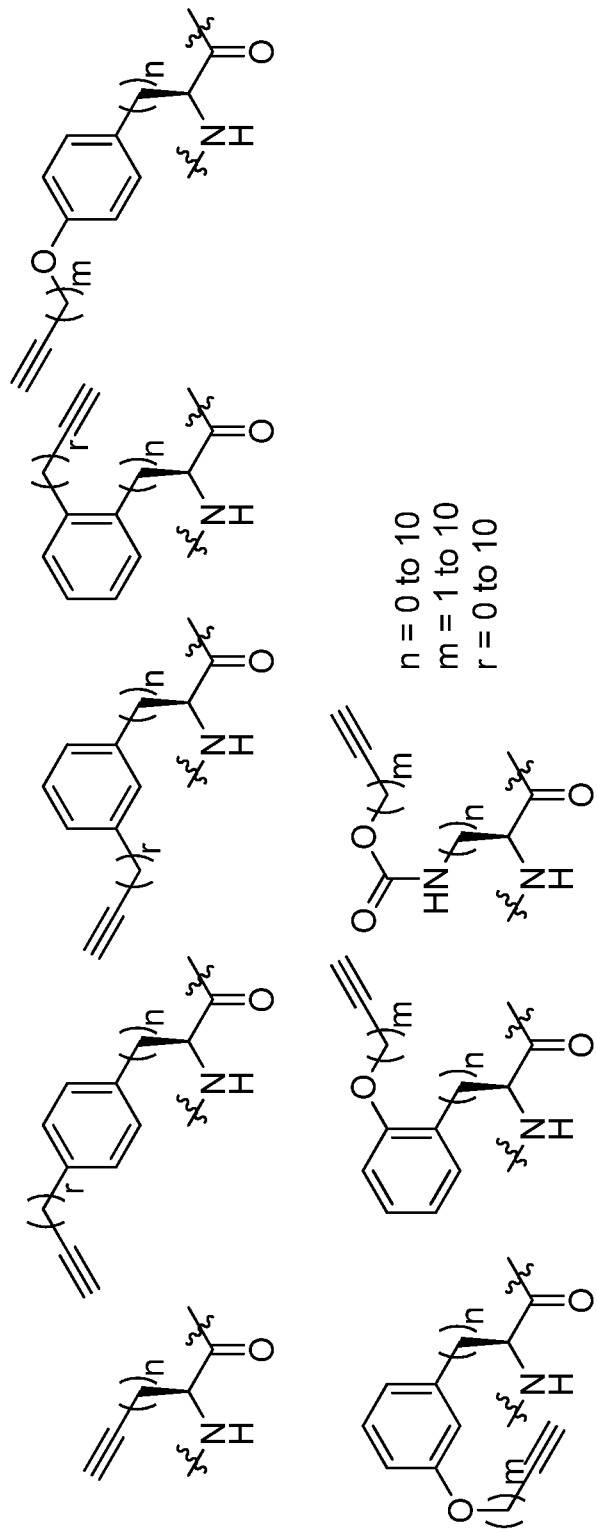
Figure 9A:
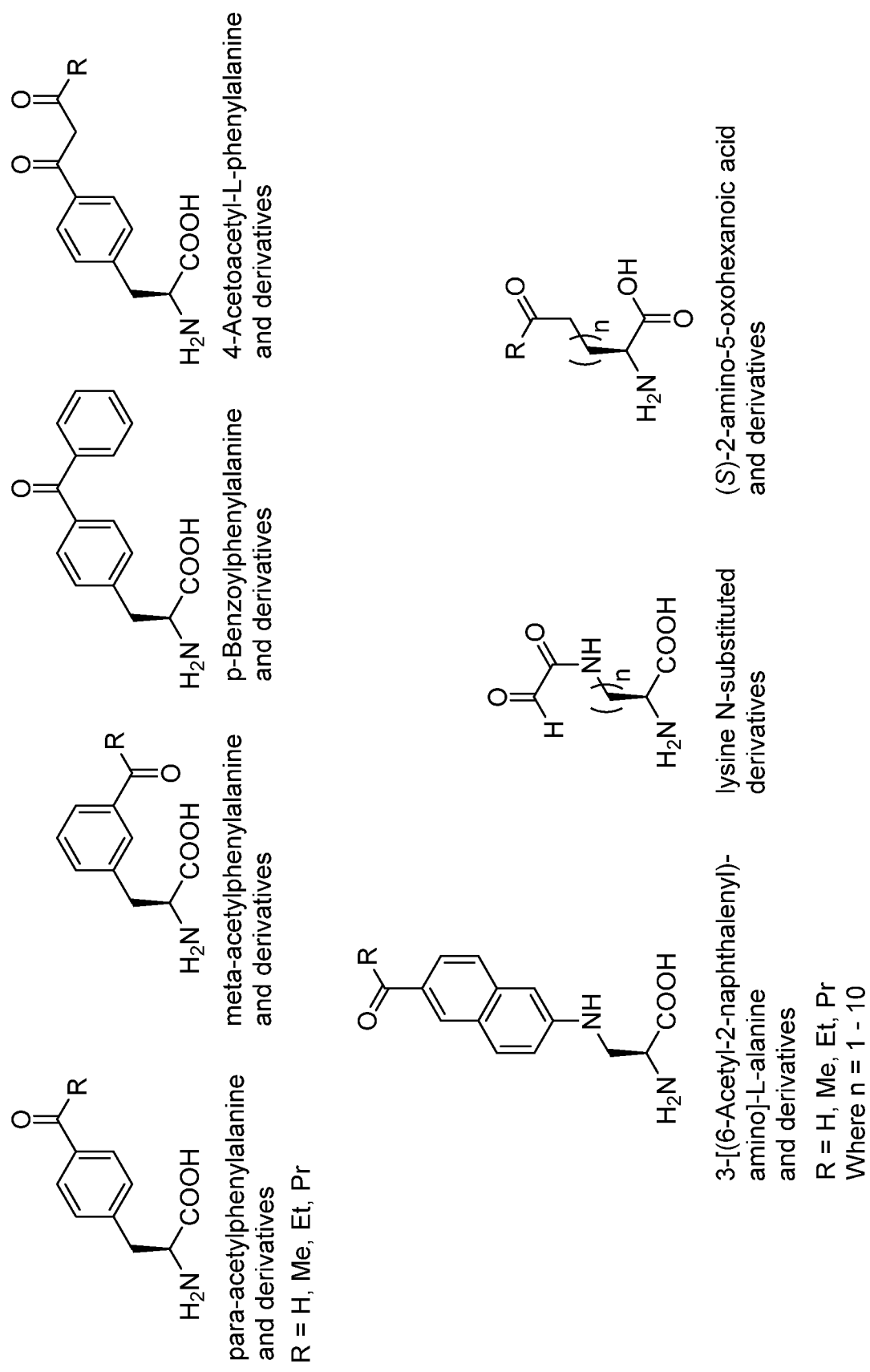
FIG. 9. Examples of amino acid derivative capable of participating in an oxime-ligation reaction. A. ketone-containing amino acid residues. B. aminoxy-containing amino acid residues. C. Side-chain functionalized lysine and aspartic acid/glutamic acid, wherein R contains a ketone or aminoxy.
Figure 9B:
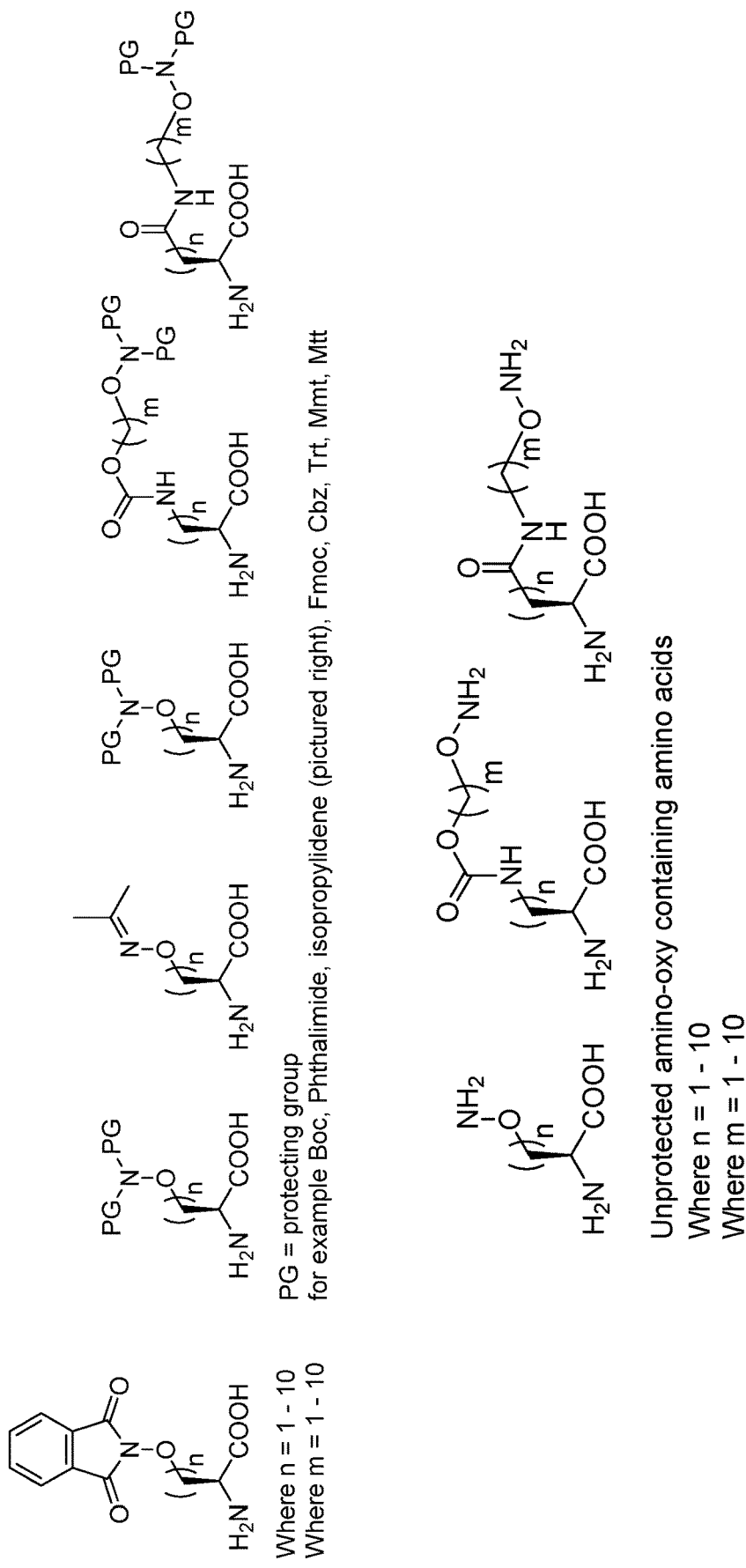
Figure 9C:
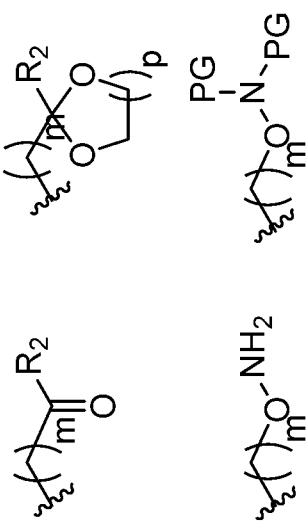
Figure 9C:
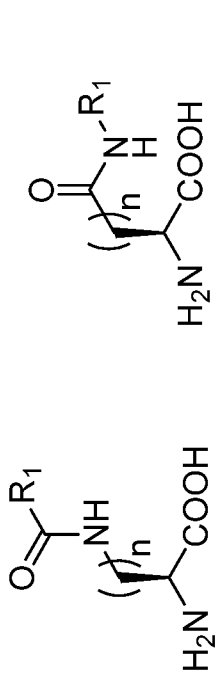

| Boc | tert-Butyloxycarbonyl | Fmoc-OSu | 9-Fluorenylmethyl N-succinimidyl carbonate |
|---|---|---|---|
| Cbz | Carboxybenzyl | HATU | (1-[Bis(dimethylamino)methylene]-1H-1,2,3-triazolo[4,5-b]pyridinium 3-oxid hexafluorophosphate) |
| CBZ-OSu | N-(Benzyloxycarbonyloxy)succinimide | | |
| CLiPS | Chemical Linkage of Peptides onto Scaffolds | | |
| CuAAC | copper-catalyzed alkyne-azide cycloaddition | IBX | 2-Iodoxybenzoic acid |
| | | MeCN | Acetonitrile |

| | | | |
|---|---|---|---|
| DBE | 1,2-Dibromoethane | NBS | N-Bromo succinimide |
| DBU | 1,8-Diazabicycloundec-7-ene | NMP | N-Methyl-2-pyrrolidone |
| DIAD | Diisopropyl azodicarboxylate | pAcF | Para-acetyl Phenylalanine |
| DIPEA | N,N-Diisopropylethylamine | P.E. | Petroleum Ether 40-60 |
| DMAP | 4-Dimethylaminopyridine | Pd/C | Pd on activated carbon |
| DMF | N,N-Dimethylformamide | Phth | Phthalimide |
| DMSO | Dimethylsulfoxide | THF | Tetrahydrofuran |
| ESI | Electron Spray Ionization | THP | Tetrahydropyran |
| EtOAc | Ethyl acetate | THPTA | Tris-hydroxypropyltriazolylmethylamine |
| Fmoc | Fluorenylmethyloxycarbonyl | TLC | Thin Layer Chromatography |
| | | TMS | Trimethylsilyl |

Example 1. Coupling of Peptide and Scaffold Via Thiolate Nucleophilic Substitution Reaction and Oxime Ligation Amino Acids Example of the Synthesis of a Phthalimide Protected Amino-Oxy Containing Amino Acid

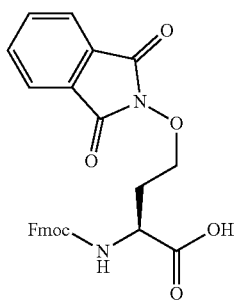

In a flame dried flask, under $N_2$ flow, Fmoc-Asp-OtBu (100 g, 2.41 mmol) was dissolved in 15 ml freshly distilled THF. After cooling the mixture on ice, $BH_3.SMe_2$ (484 µL, 5.10 mmol, 2.1 equiv) was dropwise added. The mixture was warmed to rt. and stirred overnight, after which TLC showed full conversion of the starting material. The reaction mixture was quenched with saturated $NH_4Cl$ solution and extracted with EtOAc. The collected organic phases were washed with brine and dried over $Na_2SO_4$. The volatiles were removed under reduced pressure, yielding a colorless oil. Flash column chromatography (2:2:0.5—$CH_2Cl_2$:P.E.:EtOAc) yielded the homoserine-derived product as a colorless oil (833 mg, 2.10 mmol, 86%). $^1H$ NMR (400 MHz, Chloroform-d) δ 7.79 (d, J=7.5 Hz, 2H), 7.62 (d, J=7.4 Hz, 2H), 7.43 (t, J=7.5 Hz, 2H), 7.35 (t, J=7.3 Hz, 2H), 5.64 (d, J=7.4 Hz, 1H), 4.55-4.36 (m, 3H), 4.25 (t, J=6.9 Hz, 1H), 3.77-3.67 (m, 1H), 3.62 (td, J=11.8, 11.2, 3.2 Hz, 1H), 3.03 (br. s, 1H), 2.19 (ddt, J=14.4, 9.9, 4.7 Hz, 1H), 1.64 (ddd, J=13.7, 7.9, 3.1 Hz, 1H), 1.50 (s, 9H). $^{13}C$ NMR (126 MHz, CDCl3) δ 171.69, 156.92, 143.79, 143.59, 141.29, 127.73, 127.07, 125.06, 125.00, 120.00, 119.97, 82.54, 67.14, 58.30, 51.52, 47.17, 36.05, 27.97.

In a flame dried flask, under $N_2$ flow, the purified Fmoc-protected homoserine (750 mg, 1.89 mmol) was dissolved in 11 ml anhydrous THF. The solution was cooled on an ice bath, and $PPh_3$ (544 mg, 2.08 mmol, 1.1 equiv), N-hydroxyphthalimide (338 mg, 2.08 mmol, 1.1 equiv) were added. DIAD (408 µL, 2.08 mmol, 1.1 equiv) was added dropwise, and the mixture was warmed to rt. After stirring for 5 hours, the volatiles were removed under reduced pressure. The thick orange oil was immobilized on silica, after which flash column chromatography (3:2:0.5—P.E.:$CH_2Cl_2$:EtOAc) yielded the phthalimide-protected homoserine as an off-white solid (793 mg, 1.47 mmol, 78%). $^1H$ NMR (500 MHz, Chloroform-d) δ 7.88 (dd, J=5.0, 3.1 Hz, 3H), 7.83-7.72 (m, 4H), 7.70 (t, J=7.3 Hz, 2H), 7.40 (t, J=7.4 Hz, 2H), 7.36-7.27 (m, 2H), 6.33 (d, J=8.1 Hz, 1H), 4.55 (q, J=5.7 Hz, 1H), 4.49-4.39 (m, 2H), 4.35 (t, J=5.7 Hz, 2H), 4.28 (t, J=7.2 Hz, 1H), 2.36 (d, J=5.6 Hz, 2H), 1.51 (s, 9H). $^{13}C$ NMR (126 MHz, CDCl$_3$) δ 171.70, 156.97, 143.76, 143.55, 141.29, 127.74, 127.07, 125.06, 124.98, 120.01, 119.98, 82.61, 67.15, 58.24, 51.39, 47.15, 36.17, 27.96.

The phthalimide derivative (100 mg, 0.18 mmol) was dissolved in 700 µL freshly distilled $CH_2Cl_2$. HCOOH (1.4 mL) was added and the reaction mixture was stirred overnight at rt. The volatiles were removed under reduced pressure, to yield the tBu-deprotected Fmoc-homoserine derivative (84 mg, 0.17 mmol, 95%) as a colorless foam. $^1H$ NMR (400 MHz, Chloroform-d) δ 7.88 (dd, J=5.3, 3.1 Hz, 2H), 7.79 (dd, J=5.4, 3.1 Hz, 2H), 7.75 (d, J=7.5 Hz, 2H), 7.69 (t, J=6.6 Hz, 2H), 7.39 (t, J=7.5 Hz, 2H), 7.35-7.29 (m, 2H), 6.33 (d, J=8.3 Hz, 1H), 4.57-4.48 (m, 1H), 4.40 (dd, J=7.4, 2.9 Hz, 2H), 4.34 (t, J=6.0 Hz, 2H), 4.27 (t, J=7.2 Hz, 1H), 2.35 (q, J=5.9 Hz, 2H). MS (ESI) [M+H]$^+$ calc 486.48. found 486.7.

Example of the Synthesis of a Boc-Protected Amino-Oxy Containing Amino Acid

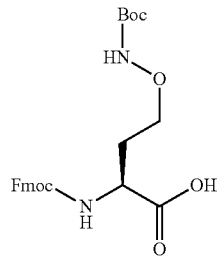

In a flame-dried flask, under Ar-pressure, Fmoc-Asp(OtBu)-OH (43.106 g, 106.12 mmol, 1 equiv) was suspended in 400 ml of anhydrous MeOH. $Cs_2CO_3$ (17.288 g, 53.06 mmol, 0.5 equiv) was added and the mixture immediately becomes a colorless solution, which was subsequently stirred for 45 min. The volatiles were removed under reduced pressure, yielding a while solid. The residue is dissolved in 500 ml anhydrous MeCN and benzyl bromide (37.86 ml, 318.36 mmol, 3 equiv) was added. The mixture was stirred for 3 hours at rt. during which a white precipitate forms. The volatiles were removed and the remaining solid was washed with water and EtOH twice, yielding the desired Fmoc-Asp(OtBu)-OBn as a white solid, in quantitative yield. $^1$H-NMR (400 MHz, Chloroform-d) δ 7.78 (d, J=7.5 Hz, 2H), 7.62 (d, J=6.9 Hz, 2H), 7.42 (t, J=7.4 Hz, 2H), 7.33 (m, J=15.3, 7.5 Hz, 7H), 5.93 (d, J=8.5 Hz, 1H), 5.23 (dd, J=33.0, 12.4 Hz, 1H), 4.70 (dt, J=8.4, 4.1 Hz, 1H), 4.51-4.40 (m, 1H), 4.40-4.30 (m, 1H), 4.26 (t, J=7.1 Hz, 1H), 2.92 (ddd, J=70.8, 17.0, 4.4 Hz, 2H), 1.45 (s, 9H). $^{13}$C NMR (101 MHz, CDCl3) δ 170.70, 169.85, 155.89, 143.81, 143.59, 141.14, 135.15, 128.47, 128.31, 128.13, 127.60, 126.97, 125.08, 125.03, 119.87, 81.74, 67.34, 67.17, 50.55, 46.98, 37.62, 27.89.

Fmoc-Asp(OtBu)-OBn (1.604 g, 3.197 mmol) was dissolved in 15 ml of freshly distilled $CH_2Cl_2$. 15 ml HCOOH is added to the solution and the mixture is stirred overnight at rt, after which TLC showed full conversion of the starting material. The volatiles were removed under reduced pressure and the remnants of HCOOH were removed by co-evaporation with $CH_2Cl_2$, yielding Fmoc-Asp(OH)—OBn as a white solid (1.310 g, 2.94 mmol, 92%). $^1$H NMR (400 MHz, Chloroform-d) δ 11.15 (s, 1H), 7.80 (d, J=7.5 Hz, 2H), 7.66 (d, J=7.4 Hz, 2H), 7.44 (t, J=7.4 Hz, 2H), 7.36 (d, J=7.4 Hz, 7H), 6.16 (d, J=8.5 Hz, 1H), 5.26 (s, 2H), 4.83 (dt, J=8.6, 4.4 Hz, 1H), 4.50 (dd, J=10.4, 7.4 Hz, 1H), 4.46-4.38 (m, 1H), 4.26 (t, J=7.1 Hz, 1H), 3.18 (dd, J=17.4, 4.6 Hz, 1H), 3.01 (dd, J=17.4, 4.2 Hz, 1H)$^{13}$C NMR (101 MHz, CDCl$_3$) δ 175.36, 170.34, 156.04, 143.53, 143.39, 141.02, 134.84, 128.34, 128.20, 127.94, 127.51, 126.87, 124.90, 119.76, 67.44, 67.21, 50.18, 46.79, 36.12.

In a flame-dried flask, under $N_2$ flow, Fmoc-Asp(OH)—OBn (11.11 g, 25 mmol) was dissolved in 175 ml of freshly distilled THF. The reaction mixture is cooled to 0° C., after which $BH_3.SMe_2$ (11.85 ml, 125 mmol, 5 equiv) is added dropwise over 1 hour. The mixture is stirred on ice for 2 h, and subsequently warmed to rt and stirred overnight, after which TLC showed full consumption of the starting material. The mixture was carefully quenched with sat. $NH_4Cl$ solution and extracted with EtOAc (3×). The organic phase was washed with 1M $KHSO_4$, brine and dried over $Na_2SO_4$. The volatiles were removed under reduced pressure, after which Fmoc-homoSer-OBn crystallizes as a white solid (10.74 g, 24.86 mmol, 99%). $^1$H NMR (400 MHz, Chloroform-d) δ 7.79 (d, J=7.4 Hz, 2H), 7.62 (d, J=7.3 Hz, 2H), 7.43 (t, J=7.4 Hz, 3H), 7.40-7.29 (m, 8H), 5.76 (d, J=7.7 Hz, 1H), 5.29-5.11 (m, 2H), 4.68-4.57 (m, 1H), 4.55-4.39 (m, 2H), 4.24 (t, J=6.6 Hz, 1H), 3.79-3.67 (m, 1H), 3.61 (t, J=9.8 Hz, 1H), 2.21 (ddt, J=14.4, 9.4, 4.4 Hz, 1H), 1.75 (ddd, J=14.1, 9.4, 4.4 Hz, 1H).

In a flame-dried flask, under $N_2$, Fmoc-homoSer-OBn (7.01 g, 16.21 mmol) was dissolved in 125 ml of anhydrous THF. Subsequently $Boc_2NOH$ (3.97 g, 17.02 mmol, 1.05 equiv) and $PPh_3$ (4.46 g, 17.02 mmol, 1.05 equiv) were added, and the flask was cooled on an ice bath. DIAD (4.29 ml, 17.02 mmol, 1.05 equiv) was added dropwise via a syringe pump (4.4 ml/h). The mixture was warmed to rt, and stirred overnight. The volatiles were removed under reduced pressure, after which the mixture was immobilized in silica. Column chromatography (6:2:1—P.E.: $CH_2Cl_2$:EtOAc) provided the product as a white solid (7.514 g, 11.60 mmol, 72%). $^1$H NMR (500 MHz, Chloroform-d) δ 7.77 (d, J=7.5 Hz, 2H), 7.67 (d, J=7.3 Hz, 2H), 7.40 (t, J=7.4 Hz, 2H), 7.37-7.33 (m, 2H), 7.33-7.24 (m, 5H), 6.63 (d, J=8.6 Hz, 1H), 5.20 (s, 2H), 4.65 (dt, J=10.3, 5.5 Hz, 1H), 4.42 (dd, J=10.2, 7.5 Hz, 1H), 4.38-4.29 (m, 1H), 4.24 (t, J=7.2 Hz, 1H), 4.16-4.07 (m, 1H), 4.03-3.93 (m, 1H), 2.29 (q, J=10.2, 6.0 Hz, 2H), 2.23 (dd, J=12.8, 8.1 Hz, 1H), 1.55 (s, 18H). $^{13}$C NMR (126 MHz, CDCl$_3$) δ 171.63, 156.42, 150.34, 144.08, 143.95, 141.28, 135.52, 128.54, 128.31, 128.17, 127.66, 127.65, 127.07, 127.06, 125.32, 125.31, 119.92, 84.41, 72.54, 67.18, 67.14, 52.04, 47.21, 29.64, 28.10. HR-MS FD m/z [M$^+$] calcd for $C_{36}H_{42}N_2O_9$: 646.2890. found 646.2866.

Fmoc-homoserine(ONBoc$_2$)-Benzyl-ester (11.32 g, 17.51 mmol) was dissolved in 150 ml of $CH_2Cl_2$. TFA (2.14 ml, 27.94 mmol, 1.6 equiv). It was stirred overnight, after which NMR showed incomplete conversion. 0.9 ml (11.75 mmol, 0.67 equiv) of TFA was added and the reaction mixture was again stirred overnight. The volatiles were removed, after which the mono-Boc compound was purified via column chromatography (6:4:1—P.E.: $CH_2Cl_2$:EtOAc) yielding a white solid 5.17 g (9.22 mmol, 53%). $^1$H NMR (500 MHz, Chloroform-d) δ 7.79 (d, J=7.6 Hz, 2H), 7.69 (d, J=7.5 Hz, 2H), 7.42 (t, J=7.5 Hz, 3H), 7.40-7.27 (m, 9H), 6.57 (s, 1H), 5.22 (s, 2H), 4.64 (q, J=6.5 Hz, 1H), 4.42 (tt, J=17.9, 8.9 Hz, 2H), 4.26 (t, J=7.4 Hz, 1H), 4.01 (ddd, J=11.4, 7.4, 4.3 Hz, 1H), 3.93 (dt, J=10.5, 5.3 Hz, 1H), 2.20 (tq, J=15.4, 9.8, 9.2 Hz, 2H), 1.52 (s, 9H). $^{13}$C NMR (126 MHz, CDCl$_3$) δ 171.96, 157.13, 156.32, 143.98, 143.79, 141.21, 135.33, 128.49, 128.30, 128.19, 127.59, 127.00, 125.21, 119.85, 82.05, 72.89, 67.16, 67.05, 51.81, 47.11, 29.92, 28.14. IR (cm$^{-1}$) 3285, 3065, 2977, 2933, 1702, 1529, 1477, 1449, 1391, 1367, 1337, 1248, 1214, 1159, 1104, 1080, 1057, 1003, 909, 853, 757, 737. HR-MS FD m/z [M+] calcd for $C_{31}H_{34}N_2O7$: 546.2336. found 546.2366. mp 43° C.

In a flame-dried flask, Fmoc-homoserine(ONHBoc)-Benzyl-ester (5.17 g, 9.22 mmol) was dissolved in 200 ml EtOH. The flask was degassed and Pd/C (10 wt % loading, 256 mg) was added. The flask was evacuated and purged with $H_2$ three times and the reaction mixture was stirred under $H_2$ pressure (balloon) for 4 h at rt. TLC showed full conversion of the starting material and the reaction flask was purged with $N_2$. The mixture was filtered over Celite and eluted with EtOH. The volatiles were evaporated under reduced pressure, yielding the desired Fmoc-homoserine(ONHBoc)-OH amino acid as a white solid (4.20 g, 9.21 mmol, 99%). $^1$H NMR (400 MHz, Chloroform-d) δ 7.78 (d, J=7.5 Hz, 2H), 7.67 (d, J=7.3 Hz, 2H), 7.54 (s, 1H), 7.41 (t, J=7.4 Hz, 2H), 7.32 (t, J=7.4 Hz, 2H), 6.66 (s, 1H), 4.63 (q, J=6.1 Hz, 1H), 4.41 (p, J=10.3 Hz, 3H), 4.26 (t, J=7.2 Hz, 2H), 4.11-3.93 (m, 3H), 2.20 (d, J=4.5 Hz, 2H), 1.52 (s, 9H).

Example of the Synthesis of a Ketone-Containing Amino Acid: Synthesis of Para-Acetyl Phenylalanine

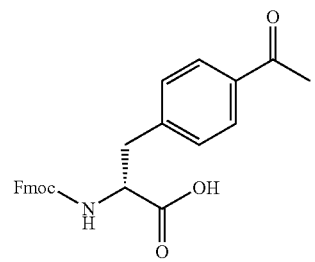

H-Phe-OH (33.073 g, 200 mmol) was added to a flask equipped with a reflux condenser, and suspended in 170 ml EtOH. $Ac_2O$ (52 ml, 540 mmol, 2.7 equiv) was added and the solution was stirred at reflux overnight. The volatiles (acetic acid remnants) were removed under reduced pressure, yielding a yellowish sticky oil. This oil was redissolved in 170 ml of EtOH and concentrated HCl (4 ml, cat) was added. The mixture was heated to reflux and stirred overnight. The volatiles were removed under reduced pressure. The yellow oil was redissolved in EtOAc and washed with a 1M $KHSO_4$ solution, sat. $NaHCO_3$ solution and brine, and subsequently dried over $Na_2SO_4$. The volatiles were removed under reduced pressure, yielding Ac-Phe-OEt as an off-white solid (38.89 g, 165.31 mmol, 82%). $^1$H NMR (500 MHz, Chloroform-d) δ 7.28 (dt, J=15.6, 7.0 Hz, 3H), 7.13 (d, J=6.9 Hz, 2H), 6.16 (d, J=7.2 Hz, 1H), 4.87 (q, J=6.0 Hz, 1H), 4.17 (q, J=7.1 Hz, 2H), 3.12 (tt, J=13.8, 7.0 Hz, 2H), 1.99 (s, 3H), 1.25 (t, J=7.1 Hz, 3H). $^{13}$C NMR (126 MHz, CDCl3) δ 171.69, 169.61, 135.95, 129.26, 128.45, 127.00, 61.43, 53.16, 37.90, 23.04, 14.06. IR (cm$^{-1}$) 3312, 3025, 3002, 2973, 2932, 2908, 1946, 1728, 1641, 1530, 1493, 1480, 1444, 1398, 1374, 1345, 1319, 1259, 1220, 1198, 1156, 1129, 1075, 1033, 1021, 966, 929, 909, 867, 824, 813, 764, 745. mp (° C.) 67.

To a flame-dried flask, under $N_2$ flow and at 0° C., $AlCl_3$ (12.40 g, 93.00 mmol, 5.5 equiv) was added, followed by the dropwise addition of AcCl (7.2 ml, 101.27 mmol, 6.0 equiv). To the chunky suspension, a solution of Ac-Phe-OEt (4.00 g, 17.00 mmol, 1 equiv) in 18 ml of $CH_2Cl_2$ was added dropwise. The dark orange solution was stirred for 30 min on ice, then the mixture was warmed to rt and stirred overnight. The mixture was crashed onto ice with 10% 1M HCl solution. The product was extracted with $CH_2Cl_2$, and the organic phase was washed twice with a sat. $NaHCO_3$ solution and water. After drying over $Na_2SO_4$, the volatiles were removed under reduced pressure to yield a dark brown oil. Flash column chromatography (1:2—P.E.:EtOAc) provided the acylated product as a yellowish oil, which crystallizes upon standing (4.26 g, 15.36 mmol, 90%). $^1$H NMR (400 MHz, Chloroform-d) δ 7.84 (d, J=8.2 Hz, 2H), 7.19 (d, J=8.2 Hz, 2H), 6.17 (d, J=7.5 Hz, 1H), 4.86 (dd, J=19.7, 7.7 Hz, 1H), 4.14 (q, J=6.2 Hz, 2H), 3.19 (dd, J=13.8, 6.1 Hz, 1H), 3.10 (dd, J=13.8, 5.9 Hz, 1H), 2.54 (s, 3H), 1.95 (s, 3H), 1.21 (t, J=7.1 Hz, 3H). $^{13}$C NMR (101 MHz, CDCl3) δ 197.50, 171.19, 169.48, 141.59, 135.78, 129.39, 128.32, 61.51, 52.79, 37.74, 26.38, 22.90, 13.94.

To a flask, equipped with a reflux condenser, the acylated product (7.00 g, 25.24 mmol) was added. A 9M HCl solution was added (100 ml, excess) and the slight orange mixture was heated to 90° C. and stirred for 6 h. The mixture was cooled to rt, yielding a precipitate. This precipitate was filtered and washed with acetone and $Et_2O$ to yield the fully deprotected H-p-AcPhe-OH product as fine, slightly yellow needles (3.769 mg, 15.41 mmol, 61%). The remaining solution was evaporated to dryness, yielding a yellow solid, which was washed with acetone and $Et_2O$. Filtration yielded the second batch of the product as a pale yellow solid (2.316 g, 9.47 mmol, 37%). $^1$H NMR (500 MHz, Deuterium Oxide) δ 7.89 (d, J=8.1 Hz, 2H), 7.36 (d, J=8.1 Hz, 2H), 4.28-4.20 (m, 1H), 3.26 (ddd, J=58.6, 14.5, 6.7 Hz, 2H), 2.55 (s, 3H). $^{13}$C NMR (126 MHz, D2O) δ 203.57, 171.59, 140.59, 135.99, 129.81, 129.29, 54.09, 35.75, 26.31.

The free H-p-AcPhe-OH (1.00 g, 4.09 mmol) was dissolved in 11 ml of 1,4-dioxane, after which 15 ml of an aqueous saturated $NaHCO_3$ solution was added, and the solution was subsequently cooled to 0° C. A solution of Fmoc-OSu (1.45 g, 4.29 mmol, 1.05 equiv) in 10 ml of acetone was added in a dropwise fashion. The flask was warmed to rt, and the solution was stirred overnight. The volatiles were removed under reduced pressure and the remaining solution was diluted with EtOAc. The organic phase was washed with an 1M $KHSO_4$ solution (8 times) followed by brine. After drying over $Na_2SO_4$, the volatiles were vaporized under reduced pressure, yielding Fmoc-pAcF—OH as an off-white solid (1.72 g, 3.99 mmol, 97%). $^1$H NMR (500 MHz, Methanol-d$_4$) δ 7.89 (d, J=8.1 Hz, 2H), 7.78 (d, J=7.5 Hz, 2H), 7.57 (dd, J=11.1, 7.7 Hz, 2H), 7.38 (t, J=6.4 Hz, 4H), 7.28 (q, J=7.0 Hz, 2H), 7.20 (d, J=7.3 Hz, 1H), 4.50 (dd, J=9.6, 4.6 Hz, 1H), 4.30 (dd, J=10.5, 7.2 Hz, 1H), 4.22 (dd, J=10.4, 7.1 Hz, 1H), 4.12 (t, J=6.9 Hz, 1H), 3.31 (d, J=4.5 Hz, 1H), 3.03 (dd, J=13.7, 9.8 Hz, 1H), 2.52 (s, 3H). $^{13}$C NMR (126 MHz, MeOD) δ 198.79, 173.70, 156.85, 143.75, 143.52, 141.09, 135.40, 129.28, 128.16, 127.31, 126.68, 124.83, 124.74, 119.44, 66.49, 55.01, 46.89, 37.15, 25.20. LC-MS (ESI), tr 7.46, ([M+H]$^+$ calc. 429.47. found 429.8).

Peptide Synthesis

Peptides were synthesized on solid phase using a 4-(2', 4'-dimethoxyphenyl-Fmoc-aminomethyl)-phenoxy (RinkAmide) resin (Bachem, Germany), on a Prelude (Protein Technologies Inc., USA) synthesizer. All Fmoc-amino acids were purchased from Biosolve (Netherlands), Bachem (Germany) or Fluorochem Ltd. (UK), with side-chain functionalities protected according to the Fmoc-protocol ((N-tBoc (KW), OtBu (DESTY), N-Trt (HNQ), S-Trt (C) or N-Pbf (R) groups). Canonical amino acids were coupled with a 4-fold excess of HATU: amino acid: DIPEA (1:1:2) in NMP, with a 15 min activation time using double coupling. Unnatural amino acids were coupled with 2-fold excess of HATU: amino acid: DIPEA (1:1:2) in NMP, with a 60 min activation time using double coupling. Fmoc deprotection was performed using a 20% piperidine solution in NMP. Acylation of the N-terminus of the peptide was performed by reacting the resin with NMP:Ac$_2$O:DIPEA (10:1:0.1 v/v/v) for 30 min at rt. The acylated peptide was cleaved from the resin cleavage and coincides with removal of protective groups. The cleavage cocktail (60 ml/mmol resin) which consist of 80 v % TFA, 7.5 wt % phenol, 5 v % thioanisole, 2.5 v % tri-isopropyl silane, 5 v % MilliQ water, and after 2 h stirring at rt, the resin was filtered off and the crude peptide is precipitated with ice-cold ether:pentane— 1:1. The pellet is dissolved in MeCN:H$_2$O (1:1) and lyophilized. Preparative HPLC is performed to further purify the peptide.

Examples of Synthesized Peptides

| Sequence | MW calc. | MW found (ESI) |
|---|---|---|
| Ac-CE(pAcF)A(pAcF)KC-NH$_2$ | 973.15 | 972.5 |
| Ac-CEK(pAcF)AS(pAcF)KDC-NH$_2$ | 1303.49 | 1302.6 |
| Ac-CES(pAcF)AK(pAcF)KAC-NH$_2$ | 1259.48 | 1258.9 |
| Ac-CERKF(pAcF)SGAV(pAcF)KLYSC-NH$_2$ | 2010.68 | 1005.22 [M + 2H]$^{2+}$ |
| Ac-(pAcF)ERKFCSGAVCKLYS(pAcF)-NH$_2$ | 2010.68 | 1005.82 [M + 2H]$^{2+}$ |
| Ac-CEQFhS(ONH$_2$)AKFhS(ONH$_2$)LKNC-NH$_2$ | 1604.18 | 1604.21 |

| Sequence | MW calc. | MW found (ESI) |
|---|---|---|
| Ac-CEWFhS(ONH$_2$)SIKhS(ONH$_2$)LKGC-NH$_2$ | 1587.18 | 1588.60 |
| Ac-CERKFhS(ONH$_2$)SGAVhS(ONH$_2$)KLYSC-NH$_2$ | 1864.35 | 933.97 [M + 2H]$^{2+}$ |
| Ac-hS(ONH$_2$)EQFCAKFCLKNhS(ONH$_2$)-NH$_2$ | 1604.18 | 1604.35 |
| Ac-hS(ONH$_2$)ERKFCSGAVCKLYShS(ONH$_2$)-NH$_2$ | 1864.50 | 932.99 [M + 2H]$^{2+}$ |
| Ac-CEQSK(Aoa)AKFK(Aoa)YKNC-NH$_2$ | 1766.19 | 883.19 [M + 2H]$^{2+}$ |
| Ac-CERKFK(Aoa)SGAVK(Aoa)KLYSC-NH$_2$ | 2034.70 | 1017.81 [M + 2H]$^{2+}$ |
| Ac-K(Aoa)EQFCAKFCLKNK(Aoa)-NH$_2$ | 1774.38 | 887.64 [M + 2H]$^{2+}$ |
| Ac-K(Aoa)ERKFCSGAVCKLYSK(Aoa)-NH$_2$ | 2034.70 | 1017.36 [M + 2H]$^{2+}$ |

T4 Scaffolds

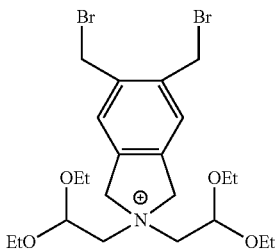

T4C-1

To a flame dried flask, under N$_2$ flow, benzylamine (5 ml, 45.77 mmol) was added, followed by bromoacetaldehyde diethyl acetal (16 ml, 106.36 mmol, 2.3 equiv) and NEt$_3$ (18 ml, 129.05 mmol, 2.8 mmol). The yellowish mixture was stirred at 100° C. for 18 h. The mixture was diluted with EtOAc and washed with H$_2$O and a saturated solution of NaHCO$_3$ and brine, and subsequently dried over Na$_2$SO$_4$. The volatiles were removed under reduced pressure to yield an orange oil. Flash column chromatography (9:1—P.E.: EtOAc) yields the benzyl-protected amine as a pale yellow oil in 31% yield (6.08 g, 17.91 mmol). $^1$H NMR (300 MHz, Chloroform-d) δ 7.30 (ddt, J=21.7, 13.9, 7.0 Hz, 5H), 4.58 (t, J=5.2 Hz, 2H), 3.81 (s, 2H), 3.65 (dq, J=9.2, 7.1 Hz, 4H), 3.51 (dq, J=9.3, 7.0 Hz, 4H), 2.76 (d, J=5.2 Hz, 4H), 1.20 (t, J=7.1 Hz, 12H). $^{13}$C NMR (101 MHz, CDCl$_3$) δ 139.75, 128.68, 127.86, 126.59, 102.25, 61.75, 59.97, 57.21, 15.17. IR (cm$^{-1}$) 3027, 2973, 2928, 2876, 1602, 1494, 1452, 1372, 1345, 1267, 1114, 1056, 1023, 916, 849, 816, 739, 698. HR-MS (FD) 339.23924, (calc. 339.23828)

The benzyl-protected amine (5.008 g, 14.75 mmol) was dissolved in 150 ml EtOH, and the solution was degassed and flushed with N$_2$. Pd/C (10% loading, 256 mg) was added and hydrogen pressure was applied (H$_2$ filled balloon) after evacuation/saturation (3×). The mixture was stirred for 4 h at rt, after TLC indicated full conversion of the starting material. The solution was filtered over a Na$_2$SO$_4$/Celite pad and eluted with EtOH. The volatiles were removed under reduced pressure, yielding the acetal protected amine as a pale yellow oil (3.480 g, 13.98 mmol, 94%). $^1$H NMR (400 MHz, Chloroform-d) δ 4.44 (t, J=5.6 Hz, 2H), 3.60-3.50 (m, 4H), 3.44-3.34 (m, 4H), 2.59 (d, J=5.6 Hz, 4H), 1.06 (t, J=7.1 Hz, 12H). $^{13}$C NMR (101 MHz, CDCl$_3$) δ 101.70, 61.98, 51.62, 14.99. IR (cm$^{-1}$) 2974, 2876, 1455, 1372, 1346, 1282, 1223, 1118, 1056, 1021, 944, 854, 813, 603, 504. HR-MS (FD) 249.19077 (calc. 249.19401)

In a flame-dried flask, under N$_2$ flow, 1,2,4,5-tetrakis (bromomethyl)benzene (2.50 g, 5.55 mmol, 3 equiv) was dissolved in 200 ml of freshly distilled MeCN and DIPEA (650 μL, 6.77 mmol, 1.2 equiv) was added. The secondary amine product (461 mg, 1.85 mmol, 1 equiv) was dissolved in 30 ml MeCN, and added dropwise to the durene solution. After stirring overnight, the reaction mixture was concentrated, and immobilized on silica, after which the scaffold was obtained via flash column chromatography (2:1—CH$_2$Cl$_2$: EtOAc to 15% MeOH in CH$_2$Cl$_2$), as a bright orange waxy solid (468 mg, 0.87 mmol, 47%). $^1$H NMR (400 MHz, DMSO-d$_6$) δ 7.58 (s, 2H), 5.06 (s, 4H), 4.87 (s, 4H), 3.80 (d, J=4.8 Hz, 4H), 3.66-3.53 (m, 4H), 3.44-3.36 (m, 4H), 3.16 (dt, J=7.4, 3.7 Hz, 2H), 1.32-1.22 (m, 12H). LC-MS (ESI) tr 6.76 min, [M]$^+$ calc. 538.34. found 538.2.

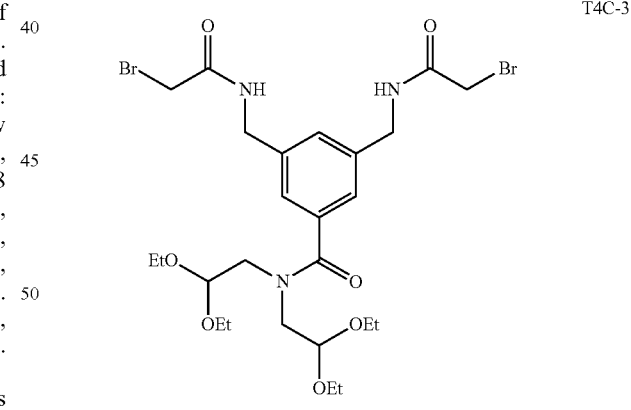

T4C-3

In a flame-dried flask, under N$_2$ flow, tert-butyl 3,5-bis (bromomethyl)benzoate (500 mg, 1.37 mmol) was dissolved in 27 ml anhydrous DMF. KPhth (1015 mg, 5.48 mmol, 4 equiv) was added next, and the mixture was heated to 125° and stirred overnight. The suspension was cooled to rt and the mixture was evaporated to dryness. The mixture was dissolved in CH$_2$Cl$_2$ and washed with water, 1M KHSO$_4$, saturated aqueous NaHCO$_3$ and water. After drying over Na$_2$SO$_4$ the volatiles were removed under reduced pressure. The phthalimide remnants were removed via flash column chromatography (3:1—P.E:EtOAc to remove first spot, then increased to 4:1—EtOAc:P.E.), yielding the phthalimide product as a white solid (533 mg, 1.07 mmol, 78%). $^1$H NMR (300 MHz, Chloroform-d) δ 7.90 (d, J=1.4 Hz, 2H), 7.85 (dd, J=5.4, 3.1 Hz, 4H), 7.72 (dd, J=5.4, 3.1 Hz, 4H), 7.64 (s, 1H), 4.87 (s, 4H), 1.56 (s, 9H). $^{13}$C NMR (75 MHz, CDCl$_3$) δ 167.88, 164.97, 137.03, 134.06, 133.01, 132.31, 132.02, 128.57, 123.46, 81.35, 41.10, 28.11. IR (cm$^{-1}$) 2975, 2938, 1769, 1706, 1607, 1554, 1536, 1466, 1427, 1391, 1367, 1342, 1310, 1257, 1231, 1155, 1122, 1099, 1086, 973, 957, 918, 896, 845, 794, 774, 726, 710, 695. HR-MS FD m/z [M$^+$] calcd for C$_{29}$H$_{24}$N$_2$O$_6$: 496.1634. found 496.1634. mp 212° C.

The phthalimide compound (468 mg, 0.94 mmol) was dissolved in 5 ml freshly distilled CH$_2$Cl$_2$ and HCOOH was added (10 ml, excess). The mixture was stirred overnight at rt, during which a precipitate forms. The solids were filtered off, and dried. The liberated acid was obtained as an off-white powder (398 mg, 0.91 mmol, 96%), which was used without further purification. $^1$H NMR (400 MHz, DMSO-d$_6$) δ 13.10 (s, 1H), 7.88 (q, J=4.4 Hz, 8H), 7.76 (s, 2H), 7.53 (s, 1H), 4.82 (s, 4H). $^{13}$C NMR (126 MHz, CDCl$_3$) δ 167.61, 166.70, 137.65, 134.61, 131.43, 130.93, 127.27, 123.26, 40.44. IR (cm$^{-1}$) 3064, 1771, 1704, 1604, 1466, 1428, 1393, 1359, 1343, 1311, 1261, 1240, 1190, 1170, 1112, 1102, 1086, 1071, 980, 960, 914, 885, 834, 792, 773, 746, 725, 710. mp 228° C. (sublimates), 351° C. melts. HRMS FD m/z [M$^+$] calcd for C$_{25}$H$_{16}$N$_2$O$_6$: 440.1008. found 440.1004.

In a flame-dried flask, under N$_2$ flow, the Phth-acid (1000 mg, 2.27 mmol), was suspended in 15 ml of anhydrous DMF. HATU (949 mg, 2.497 mmol, 1.1 equiv) and DIPEA (1 ml, 5.74 mmol, 2.5 equiv) were added, yielding a clear solution. The mixture was stirred for 30 min, after which the acetal protected amine (594 mg, 2.38 mmol, 1.05 equiv) was added. The mixture was stirred overnight, after which it was diluted with EtOAc and washed with H$_2$O and brine. After drying over Na$_2$SO$_4$, filtration and evaporation of the volatiles, the phthalimide-amide is obtained as a pale brown solid, which is used without further purification. (1540 mg, 2.27 mmol, quant). $^1$H NMR (500 MHz, Chloroform-d) δ 7.82 (dd, J=5.3, 3.1 Hz, 4H), 7.70 (dd, J=5.4, 3.0 Hz, 4H), 7.54 (s, 1H), 7.33 (s, 2H), 4.82 (s, 4H), 4.77 (t, J=4.8 Hz, 1H), 4.33 (t, J=4.7 Hz, 1H), 3.80-3.68 (m, 2H), 3.63 (d, J=4.9 Hz, 2H), 3.57 (dt, J=15.5, 6.7 Hz, 3H), 3.44 (dt, J=14.8, 7.0 Hz, 3H), 3.38 (d, J=4.8 Hz, 2H), 3.25 (p, J=7.1 Hz, 2H), 1.20 (t, J=6.6 Hz, 8H), 1.02 (t, J=6.8 Hz, 6H). $^{13}$C NMR (126 MHz, CDCl$_3$) δ 171.76, 167.76, 137.71, 137.21, 134.03, 132.05, 129.72, 126.25, 123.39, 101.49, 100.98, 63.56, 63.26, 52.70, 49.26, 41.12, 15.42, 15.20. IR cm$^{-1}$ 2974, 2929, 2877, 1765, 1702, 1635, 1605, 1468, 1445, 1421, 1394, 1348, 1329, 1313, 1260, 1233, 1173, 1119, 1103, 1054, 1016, 958, 960, 938, 914, 886, 846, 799, 733, 712 HR-MS FD m/z [M$^+$] calcd for C$_{37}$H$_{41}$N$_3$O$_9$: 671.2843. found 671.2842 mp 161-164° C.

The phthalimide amide (1530 mg, 2.27 mmol) was suspended in 20 ml of Toluene/EtOH (1:2). Hydrazine hydrate (51% solution in water, 1.42 ml, 22.77 mmol, 10 equiv) was added and the mixture was stirred at reflux for 2 hours, during which a thick precipitate has formed. The mixture was cooled to rt after which the solids were filtered off, and washed with CH$_2$Cl$_2$. The volatiles were removed under reduced pressure, yielding the crude diamine in quantitative yield, which was used without further purification. $^1$H NMR (400 MHz, DMSO-d6) δ 7.33 (s, 1H), 7.14 (s, 2H), 5.76 (s, 2H), 4.73 (s, 1H), 4.54 (s, 1H), 3.73 (s, 4H), 3.71-3.63 (m, 2H), 3.62-3.55 (m, 3H), 3.55-3.40 (m, 5H), 3.35 (d, J=12.5 Hz, 4H), 1.16 (t, J=6.3 Hz, 8H), 1.08-0.95 (m, 6H).

The crude diamine (contains water, 1190 mg, est. 2.27 equiv) was dissolved in 55 ml CH$_2$Cl$_2$ with 5 ml EtOH added. Then NaHCO$_3$(1334 mg, 15.89 mmol, 7 equiv) and Bromoacetic acid N-hydroxysuccinimide ester (1768 mg, 7.49 mmol, 3.3 equiv) were added and the mixture was stirred for 1 hour, after which TLC analysis showed full conversion. The reaction mixture was diluted with water and extracted with CH$_2$Cl$_2$. The organic phase was subsequently washed with water, brine and a sat. solution of NaHCO$_3$. After drying over Na$_2$SO$_4$, filtration and evaporation of the volatiles under reduced pressure, the crude product was obtained, which was purified by column chromatography (7:1—EtOAc:P.E.), yielding the desired scaffold as a fluffy white solid (950 mg, 1.54 mmol, 64% overall). $^1$H NMR (500 MHz, Chloroform-d) δ 7.20 (t, J=5.9 Hz, 2H), 7.18 (s, 2H), 7.13 (s, 1H), 4.79 (t, J=4.9 Hz, 1H), 4.46 (t, J=4.8 Hz, 1H), 4.36 (d, J=5.9 Hz, 4H), 3.88 (s, 4H), 3.75 (p, J=7.2 Hz, 2H), 3.66 (d, J=4.9 Hz, 2H), 3.58 (dq, J=14.1, 6.9 Hz, 5H), 3.43 (d, J=4.8 Hz, 2H), 3.37 (dt, J=15.5, 7.2 Hz, 2H), 1.22 (t, J=6.9 Hz, 6H), 1.13 (t, J=6.9 Hz, 6H). $^{13}$C NMR (126 MHz, CDCl$_3$) δ 172.11, 165.89, 138.56, 137.35, 127.32, 125.09, 101.14, 100.80, 63.33, 52.68, 48.78, 43.40, 28.86, 15.28. IR (cm$^{-1}$) 3262, 3067, 2971, 2873, 1678, 1665, 1599, 1480, 1424, 1373, 1341, 1297, 1266, 1248, 1227, 1209, 1177, 1120, 1063, 1027, 933, 905, 858, 830, 799, 763, 723, 708. HR-MS FD m/z [M$^+$] calcd for C$_{25}$H$_{39}$Br$_2$N$_3$O$_7$: 651.1155. found 651.1136. mp 74° C.

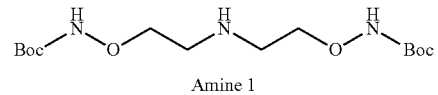 [SMILES: CC(C)(C)OC(=O)NOCCNCCONC(=O)OC(C)(C)C]

Amine 1

The synthesis of Bis-Boc hydroxylamine. To a flame-dried flask, under N$_2$ flow, N-Benzylhydroxylamine hydrochloride (3.794 g, 23.77 mmol) was suspended in 30 ml of freshly distilled MeCN. NEt$_3$ (3.65 ml, 26.15 mmol, 1.1 equiv) was added and the mixture was stirred for 2 h at rt. The solids were filtered off, and washed with 30 ml of MeCN. The remaining liquid was cooled to 0° C. and a solution of Boc$_2$O (5.931 g, 27.19 mmol, 1.14 equiv) in 30 ml of MeCN was added dropwise. The solution was subsequently warmed to rt and stirred overnight. A second portion of Boc$_2$O (8.300 g, 38.03 mmol, 1.6 equiv) in 30 ml of MeCN was added, together with DMAP (290 mg, 2.38 mmol, 0.1 equiv). The solution was warmed to 40° C. and stirred for 6 h, after which it was cooled to rt. The volatiles were removed under reduced pressure, yielding a white waxy solid. The residue was dissolved in EtOAc and washed with a 1M sodium phosphate buffer (pH 7), followed by brine and the organic phase was dried over Na$_2$SO$_4$. The volatiles were removed via rotary evaporation, yielding the N,N-bis-Boc protected N-Benzylhydroxylamine as a colorless oil, which solidified to a waxy solid upon standing (7.424 g, 22.96 mmol, 96%).

All of the previously obtained product was dissolved in 35 ml of EtOH. The solvent was deoxygenated and flushed with N$_2$. Pd/C (5 wt % loading, 436 mg, 5 mol %) was added and 112 pressure was added via a balloon. After three cycles of evacuation/saturation, the mixture was stirred at rt for 16 h, when TLC showed no starting material. The reaction mixture was filtered over a Celite pad and was eluted with EtOH. The volatiles were removed via rotary evaporation, and the resulting oil was redissolved in EtOAc. It was washed with a 1M NaOH solution trice, after which the aqueous phase was carefully neutralized to pH 7 with a 1M KHSO$_4$ solution. Then, the product was extracted with EtOAc, and the collected organic phases were washed with brine and dried over Na$_2$SO$_4$. The volatiles were removed under reduced pressure, yielding a sticky oil, which crystallized upon standing, yielding bis-Boc hydroxylamine as a white crystalline solid (4.586 g, 19.66 mmol, 85%). *Analytical data are in accordance with those reported in literature* (Jayasekara, P. S.; Jacobson. 2014).

To a flask, diethanolamine (4.8 ml, 50 mmol) was added and dissolved in 170 ml of dioxane and 100 ml of sat. NaHCO$_3$ solution (aq). Then, a solution of Cbz-OSu (13.09 g, 52.5 mmol, 1.05 equiv) in 125 ml of acetone was added to the mixture in a dropwise fashion. The mixture was stirred overnight at rt, after which the volatiles were removed under reduced pressure. The resulting slurry was redissolved in EtOAc and washed alternatingly with water and a 1M KHSO$_4$ solution (aq) (6×) and brine. After drying over Na$_2$SO$_4$, the volatiles were removed under reduced pressure, yielding the Cbz-protected diethanolamine product colorless oil (10.065 g, 42.06 mmol, 84%). $^1$H NMR (400 MHz, Chloroform-d) δ 7.43-7.31 (m, 5H), 5.15 (s, 2H), 3.85 (s, 3H), 3.78 (s, 2H), 3.50 (p, J=4.6 Hz, 4H). $^{13}$C NMR (75 MHz, CDCl$_3$) δ 156.24, 135.93, 128.04, 127.59, 127.30, 66.81, 60.82, 60.43, 51.78, 51.20. IR (cm$^{-1}$) 3368, 3064, 3032, 3942, 2879, 1671, 1496, 1473, 1455, 1415, 1363, 1262, 1217, 1130, 1046, 989, 906, 858, 768, 734, 696.

In a flame-dried flask, under N$_2$ flow, Cbz-protected diethanolamine (10.0 g, 41.79 mmol) was dissolved in 230 ml of freshly distilled THF. PPh$_3$ (23.02 g, 87.76 mmol, 2.1 equiv) and Boc$_2$N—OH (20.47 g, 87.76 mmol, 2.1 equiv) were added, and the solution was cooled to 0° C. DIAD (17.3 ml, 87.76 mmol, 2.1 equiv) was added dropwise via a syringe pump (5 ml/h). The mixture was warmed to rt and stirred overnight. The volatiles were removed under reduced pressure, providing a yellow oil. Flash column chromatography (3:2:0.5—P.E.:CH$_2$Cl$_2$:EtOAc) yielded the protected amino-oxy compound as a colorless oil (21.39 g, 31.94 mmol, 76%). $^1$H NMR (400 MHz, Chloroform-d) δ 7.39-7.30 (m, 5H), 5.14 (s, 2H), 4.10 (t, J=5.0 Hz, 2H), 4.04 (t, J=5.5 Hz, 2H), 3.67 (q, J=5.2 Hz, 4H), 1.53 (s, 18H), 1.51 (s, 18H). $^{13}$C NMR (101 MHz, CDCl3) δ 155.73, 149.88, 136.43, 128.49, 128.03, 127.93, 83.72, 83.68, 75.00, 74.90, 67.21, 47.26, 46.68, 28.01. IR (cm$^{-1}$) 2979, 2936, 1792, 1751, 1703, 1475, 1457, 1412, 1393, 1368, 1344, 1271, 1247, 1140, 1109, 1092, 1038, 1004, 912, 890, 848, 794, 768, 751, 735, 697.

The protected amino-oxy compound (840 mg, 1.2 mmol, 1 equiv) was dissolved in 20 ml of CH$_2$Cl$_2$. TFA (368 μL, 4.8 mmol, 4 equiv) was added dropwise, after which the mixture was stirred for 16 h at rt. TLC and NMR analysis showed the mono-deprotection. The volatiles were removed under reduced pressure. To remove the Cbz-group, the oily residue was redissolved in 25 ml of EtOH. The solution was evacuated, and purged with N$_2$. Pd/C (10 wt %, 75 mg) was added. H$_2$ pressure was applied via a balloon. The solution was thrice evacuated and saturated with H$_2$. The solution was stirred for 3 h at rt, after which it was filtered over a Celite pad. After elution with EtOH the volatiles were removed under reduced pressure, yielding an opaque oil. Further purification via flash column chromatography (EtOAc:EtOH—5:1) yielded the deprotected amine 1 as a very sticky foam (363 mg, 1.08 mmol, 90%). $^1$H NMR (400 MHz, Chloroform-d) δ 4.26-4.13 (m, 4H), 3.40-3.18 (m, 4H), 1.50 (s, 18H). $^{13}$C NMR (126 MHz, CDCl$_3$) δ 158.30, 82.98, 71.54, 45.93, 28.17. IR (cm$^{-1}$) 3198, 2981, 2938, 1672, 1446, 1395, 1369, 1287, 1253, 1201, 1161, 1112, 1051, 1011, 925, 837, 799, 774, 721.

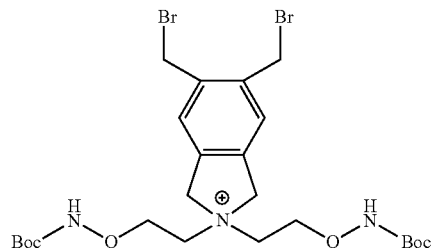

T4N-1

In a flame-dried flask, under N$_2$-flow, 1,2,4,5-tetrakis (bromomethyl)benzene (1.350 g, 3 mmol, 3 equiv) was dissolved in 175 ml of freshly distilled MeCN. DIPEA (348 μL, 2 mmol, 2 equiv) was added and the mixture was stirred until all solids had dissolved. A solution of the deprotected amine 1 (335 mg, 1 mmol, 1 equiv) in 20 ml of MeCN was added to the durene solution in dropwise fashion over the course of an hour, and the mixture was stirred overnight. Full consumption of the starting material was shown via LC-MS analysis. Flash column chromatography (EtOAc, then 5:1 up to 2:1 EtOAc:EtOH) yielded T4N-1 as a yellow foam (400 mg, 0.64 mmol, 64%). $^1$H NMR (400 MHz, CH$_3$CN+D$_2$O) δ 7.47 (s, 2H), 5.05 (s, 4H), 4.74 (s, 4H), 4.18 (s, 4H), 3.95-3.88 (m, 411), 1.43 (s, 18H). $^{13}$C NMR (101 MHz, CH$_3$CN+D$_2$O) δ 157.78, 138.90, 134.88, 126.62, 82.51, 70.58, 69.38, 60.80, 30.16, 28.10. LC-MS [M]$^+$ calc. 624.39. found 624.4.

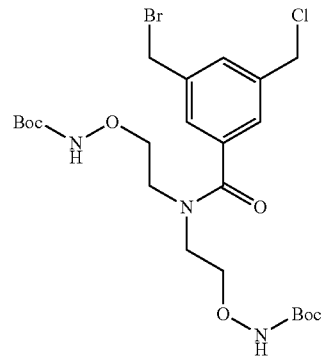

T4N-2 approx. 30 Br=Cl

In a flame-dried flask, under N$_2$ flow, 3,5-dimethyl benzoic acid (2.00 g, 13.31 mmol) was suspended in 1.6 ml of toluene. Thionyl chloride (2 ml, 27.6 mmol, 2.06 equiv) was added and the mixture was warmed to a gentle reflux and stirred for 4 hours. The volatiles were removed under reduced pressure, after which the oily residue was diluted with 4 ml of freshly distilled CH$_2$Cl$_2$. t-BuOH (2.05 ml, 21.31 mmol, 1.6 equiv) was added followed by pyridine (1.13 ml, 13.98 mmol, 1.05 equiv). The mixture was stirred for 12 hours, after which the solids are removed by filtration and washed with CH$_2$Cl$_2$. The organic phase was washed with 4M HCl, water, 2M NaOH and water. After drying over K$_2$CO$_3$, the volatiles are removed, yielding the OtBu-ester as a colorless oil (2.48 g, 12.03 mmol, 90%). $^1$H NMR (400 MHz, Chloroform-d) δ 7.63 (s, 2H), 7.17 (s, 1H), 2.38 (s, 6H), 1.62 (s, 9H). $^{13}$C NMR (101 MHz, CDCl$_3$) δ 166.12, 137.75, 133.99, 127.09, 80.70, 28.18, 21.13.

In a flame-dried flask, under N₂ flow, the OtBu-ester (13.95 g, 67.64 mol) was dissolved in freshly distilled CH₂Cl₂ (250 ml). NBS (25.28 g, 142.04 mmol, 2.1 equiv) was added and the mixture was degassed and flushed with N₂. The flask was irradiated with a commercially available halogen construction lamp (500 W), heating the mixture to a gentle reflux. The mixture was stirred for 1.5 hours, after which ¹H-NMR showed the reaction completed*. The mixture was diluted with CH₂Cl₂ and washed with water. After drying over Na₂SO₄, the volatiles were removed under reduced pressure, yielding a colorless oil. The mixture was crystallized from hexane, providing the brominated product as a white solid (7.56 g, 20.77 mmol, 31%). A second crystallization yielded another 1.71 g (4.70 mmol, 7%). *The mixture contains both doubly-brominated product (<15%), as well as <15% incompletely brominated starting material. ¹H NMR (400 MHz, Chloroform-d) δ 7.94 (s, 2H), 7.60 (s, 1H), 4.51 (s, 4H), 1.61 (s, ¹³C NMR (101 MHz, CDCl₃) δ 164.31, 138.54, 133.28, 133.10, 129.69, 81.56, 31.94, 28.01. IR (cm⁻¹) 3013, 2982, 2969, 2932, 1790, 1714, 1604, 1472, 1449, 1390, 1369, 1319, 1236, 1213, 1154, 1110, 1060, 999, 973, 953, 918, 893, 846, 794, 771, 753, 734, 692. mp 52° C.

The brominated product (5.00 g, 13.73 mmol) was dissolved in freshly distilled CH₂Cl₂ (50 ml). HCOOH was added and the solution was stirred overnight at rt, after which ¹H-NMR showed completion of the reaction. The volatiles were removed under reduced pressure and co-evaporation with CH₂Cl₂ (3×) yielded the acid product as a white solid (3.98 g, 12.92 mmol, 94%) which was used without further purification. ¹H NMR (400 MHz, Chloroform-d) δ 8.10 (s, 2H), 7.71 (s, 1H), 4.55 (s, 4H). ¹³C NMR (101 MHz, CDCl₃) δ 170.03, 139.08, 134.64, 130.45, 130.31, 31.53. IR (cm⁻¹) 2971, 2821, 2710, 2604, 2539, 1686, 1603, 1460, 1437, 1420, 1308, 1278, 1248, 1211, 1162, 1111, 1056, 998, 938, 927, 904, 855, 771, 728, 691, 662. mp 123° C. (sublimates), 142° C. (melts).

To a flame-dried flask, under N₂ flow, the acid product (2.00 g, 6.49 mmol) was added and suspended in SOCl₂ (9 ml, excess). The mixture was warmed to reflux and the orange solution was stirred for 4 hours. Then, the temperature was lowered to 50° C., and the mixture was stirred overnight. Remnants of SOCl₂ were removed under reduced pressure, and were co-evaporated with toluene twice. The resulting orange oil was dissolved in 50 ml of freshly distilled CH₂Cl₂ and DMAP (50 mg, 6 mol %) was added. A solution of amine 1 (1.94 g, 5.78 mmol, 0.9 equiv) and DIPEA (1.13 ml, 6.49 mmol, 1 equiv) in 10 ml of CH₂Cl₂ was added dropwise to the acid chloride solution. After 2 h, the reaction shows complete conversion. The mixture is transferred to a separator funnel and washed with a 1M KHSO₄ solution (aq) and brine, end dried over Na₂SO₄. The volatiles were removed under reduced pressure, providing an orange oil. Flash column chromatography (3:1-2:1-4:3-pentane:EtOAc) yields the product as a yellowish sticky solid. Via ¹H-NMR, ¹³C-NMR and LC-MS, it was determined that the product contains not 2 bromides, but halogen exchange had taken place, and some fraction of the product contained Cl instead of Br. Based on NMR data, this accounts for 30% of the mass. The follow-up chemistry is not subject to adverse effects. Therefore the molecular weight of the compound is now 612.02 instead of 625.36, yielding the T4N-2 scaffold in 21% yield (763 mg, 1.24 mmol). ¹H NMR (400 MHz, Chloroform-d) δ 8.37 (s, 1H), 7.95 (s, 1H), 7.38 (s, 1H), 7.34 (s, 1H), 4.50(s,1H), 4.39 (s, 3H), 4.01 (s, 2H), 3.87 (s, 2H), 3.79 (s, 2H), 3.49 (s, 2H), 1.39 (d, J=7.0 Hz, 18H). ¹³C NMR (75 MHz, CDCl₃) δ 171.60, 156.97, 156.71, 138.90, 138.57, 137.23, 137.18, 130.45, 129.98, 127.42, 126.90, 81.68, 81.38, 74.31, 73.53, 48.09, 45.10, 43.97, 32.06, 28.23. (underlined are the peaks belonging to the Chloride substituent). LC-MS shows 2 peaks, 1) tr 8.11, (minor) where 1×Cl, 1×Br, [M+H]⁺ calc. 581.91. found 581.91, as well as m/z 604.2 (Na⁺), m/z 482.0 (—Boc+H⁺) and m/z 382.2 (−2Boc+2H⁺). 2) tr 8.18 (major) where 2× Br, [M+H]⁺ calc. 626.38. found 625.8, as well as m/z 648.1 (Na⁺), m/z 525.9 (—Boc+H⁺) and m/z 426.1 (−2Boc+2H⁺).

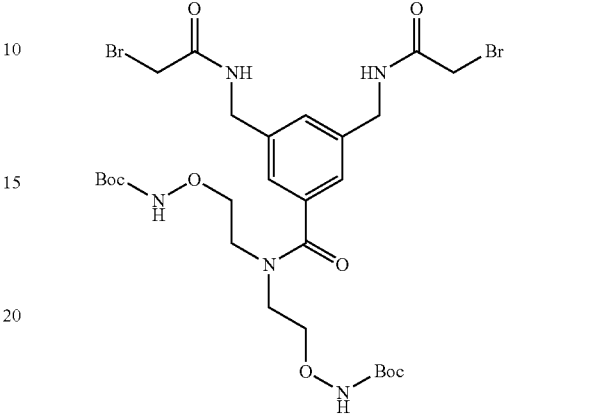

T4N-3

In a flame-dried flask, under N₂ flow, tert-butyl 3,5-bis(bromomethyl)benzoate (500 mg, 1.37 mmol) was dissolved in 27 ml anhydrous DMF. KPhth (1015 mg, 5.48 mmol, 4 equiv) was added next, and the mixture was heated to 125° and stirred overnight. The suspension was cooled to rt and the mixture was evaporated to dryness. The mixture was dissolved in CH₂Cl₂ and washed with water, 1M KHSO₄, saturated aqueous NaHCO₃ and water. After drying over Na₂SO₄ the volatiles were removed under reduced pressure. The phthalimide remnants were removed via flash column chromatography (3:1—P.E:EtOAc to remove first spot, then increased to 4:1—EtOAc:P.E.), yielding the phthalimide product as a white solid (533 mg, 1.07 mmol, 78%). ¹H NMR (300 MHz, Chloroform-d) δ 7.90 (d, J=1.4 Hz, 2H), 7.85 (dd, J=5.4, 3.1 Hz, 4H), 7.72 (dd, J=5.4, 3.1 Hz, 4H), 7.64 (s, 1H), 4.87 (s, 4H), 1.56 (s, 9H). ¹³C NMR (75 MHz, CDCl₃) δ 167.88, 164.97, 137.03, 134.06, 133.01, 132.31, 132.02, 128.57, 123.46, 81.35, 41.10, 28.11. IR (cm⁻¹) 2975, 2938, 1769, 1706, 1607, 1554, 1536, 1466, 1427, 1391, 1367, 1342, 1310, 1257, 1231, 1155, 1122, 1099, 1086, 973, 957, 918, 896, 845, 794, 774, 726, 710, 695. mp 212° C.

The phthalimide compound (468 mg, 0.94 mmol) was dissolved in 5 ml freshly distilled CH₂Cl₂ and HCOOH was added (10 ml, excess). The mixture was stirred overnight at rt, during which a precipitate forms. The solids were filtered off, and dried. The liberated acid was obtained as an off-white powder (398 mg, 0.91 mmol, 96%), which was used without further purification. ¹H NMR (400 MHz, DMSO-d₆) δ 13.10 (s, 1H), 7.88 (q, J=4.4 Hz, 8H), 7.76 (s, 2H), 7.53 (s, 1H), 4.82 (s, 4H). ¹³C NMR (126 MHz, CDCl₃) δ 167.61, 166.70, 137.65, 134.61, 131.43, 130.93, 127.27, 123.26, 40.44.

The crude acid (298 mg, 0.68 mmol) was suspended in 3 ml of DMF. HATU (283 mg, 0.74 mmol, 1.1 equiv) was added, followed by DIPEA (235 μL, 1.35 mmol, 2 equiv). The mixture was stirred for 15 min, after which amine 1 (283 mg, 0.74 mmol, 1.1 equiv) was dissolved in 4 ml DMF, and added dropwise to the reaction mixture. After 4 h, full conversion is observed via LC-MS analysis. The mixture was concentrated under reduced pressure, and the residue was dissolved in EtOAc and washed with water (5×) followed by brine. After drying over Na₂SO₄, the volatiles were removed under reduced pressure, and the product was purified via flash column chromatography (1:1—P.E.:EtOAc) yielding the amide as a white foam (375 mg, 0.50 mmol, 73%). ¹H NMR (300 MHz, Chloroform-d) δ 8.42 (s, 1H), 8.08 (s, 1H), 7.68 (dd, J=5.3, 3.1 Hz, 4H), 7.58 (dd, J=5.4, 3.1 Hz, 4H), 7.43 (s, 1H), 7.28 (s, 2H), 4.71 (s, 4H), 3.97 (s, 2H), 3.85 (s, 2H), 3.75 (s, 2H), 3.42 (s, 2H), 1.33 (s, 18H). ¹³C NMR (75 MHz, CDCl₃) δ 171.87, 167.75, 156.88, 156.63, 137.24, 137.06, 134.10, 131.77, 129.64, 126.22, 123.33, 81.39, 81.07, 74.27, 73.41, 47.96, 43.87, 40.98, 28.17. IR (cm⁻¹) 3266, 2976, 2934, 1770, 1707, 1624, 1468, 1426, 1391, 1366, 1344, 1248, 1161, 1108, 1050, 1012, 955, 728, 711. mp 78° C.

The amide compound (1866 mg, 2.36 mmol) was added to a flask, and dissolved in EtOH:Toluene—2:1 (31 ml). Hydrazine hydrate (50% solution in water, 1.6 ml, 23.6 mml, 10 equiv) was added and the mixture was heated to reflux, where a solid starts to precipitate after 30 min. The mixture was stirred at reflux overnight, after which the yellow suspension was cooled to rt. The solids were filtered off and washed with CH₂Cl₂ (3×). The volatiles were removed under reduced pressure, yielding the bis-amine as a white solid (1084 mg, 2.18 mmol, 92%), which was used in the next reaction step without further purification. ¹H NMR (500 MHz, Chloroform-d) δ 8.51 (s, 1H), 8.21 (s, 1H), 7.33 (s, 2H), 7.31 (s, 1H), 4.11 (s, 2H), 4.00 (s, 2H), 3.92 (s, 4H), 3.87 (s, 2H), 3.59 (s, 2H), 1.49 (s, 18H). ¹³C NMR (126 MHz, CDCl₃) δ 173.28, 157.34, 156.60, 143.71, 136.76, 127.11, 124.05, 81.65, 81.48, 74.01, 73.35, 48.03, 45.97, 43.39, 38.62, 28.26.

The bis-amine (688 mg, 1.38 mmol) was dissolved in 36 ml of freshly distilled CH₂Cl₂, and 7 ml of EtOH was added to dissolve the amine fully. NaHCO₃(s) (381 mg, 4.53 mmol, 3.3 equiv) was added. Bromoacetic acid N-hydroxy succinimide ester (1071 mg, 4.54 mmol, 3.3 equiv) was added and the reaction mixture was stirred at rt for 30 min, after which LC-MS analysis showed full conversion. The volatiles were removed under reduced pressure, after which the residue was dissolved in CH₂Cl₂, and washed with 1M KHSO₄, water, brine and dried over Na₂SO₄, and the solvent was again removed. Flash column chromatography (7:1—EtOAc:P.E.) yielded the T4N-3 scaffold as a white foam (635 ngm 0.86 mmol, 62%). ¹H NMR (500 MHz, Chloroform-d) δ 8.30 (d, J=15.0 Hz, 2H), 7.62 (t, J=5.9 Hz, 2H), 7.21 (s, 2H), 7.16 (s, 1H), 4.32 (d, J=5.9 Hz, 4H), 4.02 (s, 2H), 3.92 (s, 2H), 3.84 (s, 4H), 3.77 (s, 2H), 3.46 (s, 2H), 1.44 (s, 18H). ¹³C NMR (126 MHz, CDCl₃, rt) δ 172.47, 166.58, 157.14, 156.76, 138.92, 136.62, 128.38, 127.39, 125.56, 124.58, 81.80, 81.66, 73.71, 73.61, 73.20, 72.99, 48.22, 44.09, 43.72, 43.35, 42.97, 29.64, 29.50, 28.86, 28.74, 28.23, 27.85, 26.96.

T6 Scaffolds

Benzene-1,3,5-triyltrimethanol (400 mg, 2.38 mmol) was suspended in 8 ml of tBuOH, and IBX (4.00 g, 14.27 mmol, 6 equiv) was added. The mixture was heated to reflux and stirred for 5 h. The suspension was cooled to rt and the solids were filtered off, and subsequently washed with CH₂Cl₂. The clear liquid was evaporated to dryness, yielding the tri-aldehyde as white powder (385 mg, 2.38 mmol, quant). ¹H NMR (500 MHz, Chloroform-d) δ 10.21 (s, 3H), 8.64 (s, 3H). ¹³C NMR (126 MHz, CDCl3) δ 189.78, 137.80, 134.76.

In a flame-dried flask, under N₂, the tri-aldehyde (162 mg, 1.00 mmol) was dissolved in 6 ml of 1:1 CHCl₃:MeOH. Then 2,2-diethoxyethanamine (653 μL, 4.5 mmol, 4.5 equiv) was added in a dropwise fashion. The mixture was stirred for 1 h at rt. after which the volatiles were removed under reduced pressure to yield the imine as an orange oil (499 mg, 0.98 mmol, 98%). The residue (458 mg, 0.90 mmol) was dissolved in 4 ml of MeOH and cooled to 0° C. NaBH₄ (204 mg, 5.42 mmol, 6 equiv) was added and the mixture was stirred for 1 hour, after which TLC showed full completion. The reaction mixture was quenched with sat. NH₄Cl solution and extracted with CH₂Cl₂. The combined organic phases were washed with sat. NaHCO₃ solution and brine, and subsequently dried over Na₂SO₄. The volatiles were removed under reduced pressure to yield the tri-amine as a pale yellow oil (457 mg, 0.88 mmol, 98%), which was used as the crude, without further purification. ¹H NMR ¹H NMR (500 MHz, Chloroform-d) δ 7.12 (s, 3H), 4.58 (t, J=5.5 Hz, 3H), 3.74 (s, 6H), 3.63 (dt, J=14.2, 7.0 Hz, 6H), 3.53-3.42 (m, 6H), 2.70 (d, J=5.5 Hz, 6H), 1.15 (t, J=7.1 Hz, 15H). ¹³C NMR ¹³C NMR (126 MHz, CDCl₃) 140.22, 126.42, 101.91, 62.10, 53.58, 51.46, 15.18.

The tri-amine (457 mg, 0.89 mmol, 1 equiv) was dissolved in 7.5 ml of CH₂Cl₂, after which 13 ml of a sat. NaHCO₃ solution was added. The mixture was cooled to 0° C. and a solution of bromoacetyl bromide (227 μL, 2.70 mmol, 4.5 equiv) in 6 ml of CH₂Cl₂ was added in a dropwise fashion. The biphasic solution was warmed to rt and stirred for 2 h, after which TLC showed full conversion. The product was extracted with CH₂Cl₂ and the organic phase was washed with sat. NaHCO₃ solution and dried over Na₂SO₄. The volatiles were removed under reduced pressure, yielding an orange oil. Flash column chromatography (1:1—P.E.:EtOAc) provided the T6C-2 scaffold as a pale orange oil (318 mg, 0.36 mmol, 41%). ¹H NMR (500 MHz, Chloroform-d) δ 7.06-6.81 (m, 3H), 4.69 (d, J=6.3 Hz, 3H), 4.60 (d, J=8.2 Hz, 4H), 4.44 (dt, J=18.1, 4.5 Hz, 2H), 4.07 (t. J=11.0 Hz, 4H), 3.78 (s, 2H), 3.75-3.62 (m, 6H), 3.59-3.48 (m, 2H), 3.44 (dt, J=15.3, 7.4 Hz, 4H), 3.36 (s, 6H), 1.20-1.12 (m, 18H). ¹³C NMR (126 MHz, CDCl3) δ 168.38, 168.29, 168.20, 167.41, 167.38, 138.89, 138.42, 138.31, 138.05, 137.89, 137.56, 126.16, 126.01, 124.34, 123.57, 100.83, 100.79, 100.73, 64.11, 64.03, 63.85, 63.81, 53.12, 53.09, 51.01, 50.96, 49.74, 49.65, 49.55, 49.38, 49.31, 49.21, 27.03, 26.74, 26.46, 26.30, 26.14, 25.92, 15.34, 15.25.

T6C-2

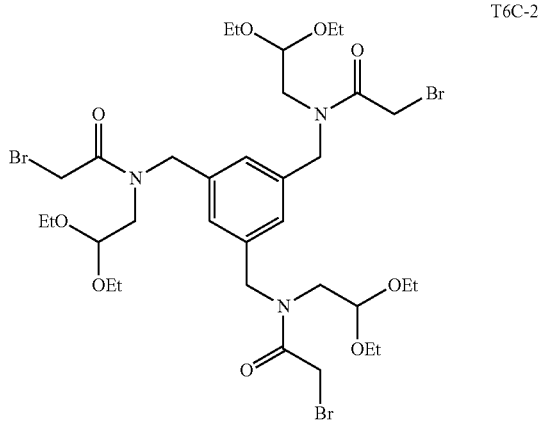 [SMILES: CCOC(CN(Cc1cc(CN(CC(OCC)OCC)C(=O)CBr)cc(CN(CC(OCC)OCC)C(=O)CBr)c1)C(=O)CBr)OCC]

T6N-1

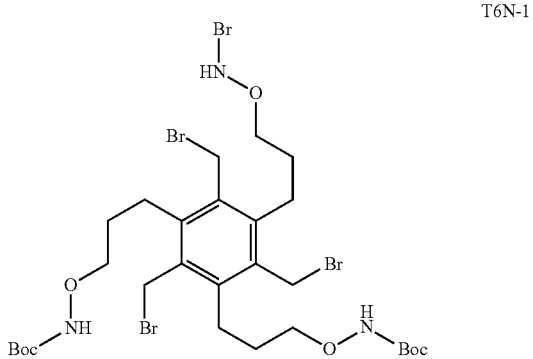 [SMILES: CC(C)(C)OC(=O)NOCCCc1c(CBr)c(CCCONBr)c(CBr)c(CCCONC(=O)OC(C)(C)C)c1CBr]

To a flame-dried flask, under Ar pressure (balloon), iodobenzene (28 ml, 250 mmol) was added, followed by TFA (100 ml) and CHCl$_3$ (240 ml). Oxone (116 g, 377 mmol, 1.5 equiv) was added under vigorous stirring. Five minutes after the addition of all the oxone, the mixture was put on ice for 30 min, due to heat evolution. The ice bath was removed and the mixture was stirred for 2 days at rt. The solids were suspended in CHCl$_3$ and filtered. The collected filtrate was evaporated to dryness under reduced pressure, yielding the bis-trifluoroacetoxy iodobenzene as an off-white solid (89.3 g, 208 mmol, 83%). $^1$H NMR (300 MHz, Chloroform-d) δ 8.20 (d, J=7.8 Hz, 2H), 7.74 (t, J=7.4 Hz, 1H), 7.62 (t, J=7.8 Hz, 2H).

In a flame-dried flask, under N$_2$ flow, iodine (102 g, 40 mmol, 6 equiv) was dissolved in 120 ml of CCl$_4$. Mesitylene was added, followed by bis-trifluoroacetoxy-iodobenzene (50 g, 116.3 mmol, 1.7 equiv). The bright purple solution was stirred overnight, during which a white-ish cake was formed on the side. The solids were filtered off, resulting in a yellowish solid, containing I$_2$ crystals. The cake was washed with acetone until the cake no longer gives off an orange color. The tris-iodinated product was isolated as an off-white solid (25.74 g, 51.70 mmol, 76%). $^1$H NMR (400 MHz, Chloroform-d) δ 3.01 (s, 9H).

A solution was made of Ac$_2$O (470 ml), AcOH (235 ml) and H$_2$SO$_4$ (47 ml), to which 1,3,5-triiodo-2,4,6-trimethylbenzene was added (25 g, 50.2 mmol), yielding a milky pink suspension. KMnO$_4$ (31.82 g, 301.3 mmol, 4.1 equiv) was added in small portions over 3 hours, due to the heat evolution after every step. The yellow suspension was stirred over the weekend. The solution was concentrated, after which water was added. The aqueous phase was extracted with CH$_2$Cl$_2$ (6×), and the collected organic phases were washed with brine, and dried over Na$_2$SO$_4$. After concentration, the product was precipitated from acetone. The precipitate was filtered, washed with acetone and dried under reduced pressure, yielding the tri-acetate compound as a fine, off-white powder (14.78 g, 22.0 mmol, 44%). $^1$H NMR (400 MHz, Chloroform-d) δ 5.72 (s, 6H), 2.13 (s, 9H).

Synthesis of tert-butyl (prop-2-yn-1-yloxy)carbamate: To a flame-dried flask, under N$_2$ flow, propargyl bromide (80% wt. solution in toluene, 10 ml, 89.76 mmol), was dissolved in 266 ml of freshly distilled MeCN and the solution was cooled to 0° C. Tert-butyl hydroxycarbamate (13.75 g, 116.7 mmol, 1.15 equiv) was added, followed by DBU (17.45 ml, 116.7 mmol, 1.3 equiv). The mixture was stirred for 30 min at 0° C., after which the mixture was warmed to rt and stirred for another hour. The volatiles were removed under reduced pressure and the residue was suspended in CH$_2$Cl$_2$. A saturated solution of NaHCO$_3$ was added and the organic phase was washed twice, followed by brine. After drying over Na$_2$SO$_4$, the residue was concentrated. Flash column purification (10:1—P.E.:EtOAc) yielded the acetylene-product as a colorless oil (1.28 g, 59.65 mmol, 66%). $^1$H NMR (400 MHz, Chloroform-d) δ 7.36 (s, 1H), 4.50 (d, J=2.3 Hz, 2H), 2.52 (t, J=2.3 Hz, 1H), 1.51 (s, 9H).

To a flame-dried high pressure tube, under Ar flow, the tri-acetoxy compound (100 mg, 0.149 mmol), PdCl$_2$(PPh$_3$)$_2$ (7.0 mg, 8.9 μmol 6 mol %) and CuI (1.3 mg, 6.6 μmol, 4.5 mol %) were added and suspended in 1.2 ml of NEt$_3$. To the yellow suspension, tert-butyl (prop-2-yn-1-yloxy)carbamate (112 mg, 0.54 mmol, 3.6 equiv) was added. The Lube was sealed and heated to 50° C. and the mixture was stirred overnight. The resulting brown suspension was filtered over Celite and eluted with CH$_2$Cl$_2$. The volatiles were removed under reduced pressure. Flash column purification (2:1 to 1:1—P.E.:EtOAc) yielded the tri-alkyne product as a yellowish foam (75 mg, 0.094 mmol, 62%). $^1$H NMR (500 MHz, Chloroform-d) δ 7.99 (s, 3H), 5.50 (s, 6H), 4.74 (s, 6H), 2.12 (s, 9H), 1.51 (s, 27H). $^{13}$C NMR (126 MHz, CDCl3) δ 171.25, 156.43, 139.06, 126.23, 95.14, 81.95, 80.92, 64.14, 63.18, 28.15, 20.76.

In a flame-dried flask under N$_2$ flow, the tri alkyne (2.19 g, 2.73 mmol, 1 equiv) was dissolved in 100 ml EtOH. The solution was degassed and purged with N$_2$. NEt$_3$ was added (5% v/v, 5.2 ml,) and the solution was degassed and purged with N$_2$. Pd/C (10% wt. loading, 500 mg, 20 mol %) was added and the solution was degassed. H$_2$ pressure was applied (balloon) and the reaction vessel was degassed and purged with H$_2$ (3×) to saturate the flask with H$_2$. The mixture was stirred overnight under H$_2$ pressure, after which TLC analysis and $^1$H-NMR showed full consumption of the starting material. The reaction mixture was filtered over Celite and eluted with CH$_2$Cl$_2$. The volatiles were removed under reduced pressure. Flash column chromatography (2:1 to 1:1—P.E.:EtOAc) yielded tri-alkene the product as a yellow foam (1.86 g, 2.298 mmol, 84%). $^1$H NMR (400 MHz, Chloroform-d) δ 7.76 (d, J=13.0 Hz, 3H), 6.59 (dt, J=33.3, 14.4 Hz, 3H), 6.05 (dt, J=11.8, 6.6 Hz, 3H), 4.90 (d, J=56.2 Hz, 6H), 4.02 (s, 6H), 1.93 (s, 9H), 1.35 (s, 27H). $^{13}$C NMR (101 MHz, CDCl$_3$) δ 170.34, 156.65, 139.58, 139.49 (broad peak), 131.16, 130.79, 129.59, 129.38, 81.34, 72.54, 62.19, 27.94, 20.50.

The tri-alkene product (163 mg, 0.201 mmol) was dissolved in 9 ml EtOH. K$_2$CO$_3$ (5 mg, cat.) was added and the opaque solution was stirred overnight. The volatiles were removed under reduced pressure. The residue was dissolved in CH$_2$Cl$_2$ and washed with brine. The aqueous phase was twice more extracted with CH$_2$Cl$_2$ and dried over Na$_2$SO$_4$. The volatiles were removed under reduced pressure, yielding the alkene alcohol a pale yellow foam. $^1$H NMR (300 MHz, Chloroform-d) δ 7.71 (s, 2H), 7.03-6.86 (m, 3H), 6.30-6.08 (m, 3H), 4.54 (s, 6H), 4.25 (d, J=8.4 Hz, 6H), 2.80 (t, J=6.5 Hz, 2H), 1.45 (s, 27H).

The alkene alcohol residue was dissolved in 7 ml EtOH. The solution was degassed and purged with N$_2$. Pd/C (10 wt % loading, 32 mg, 10%) was added and the solution was degassed. H$_2$ pressure was applied (balloon) and the reaction vessel was degassed and purged with H$_2$ (3×) to saturate the flask with H$_2$. The mixture was stirred overnight under H$_2$ pressure, after which TLC analysis and $^1$H-NMR showed full conversion of the starting material. The mixture was filtered over Celite and eluted with EtOH. The volatiles were removed under reduced pressure, yielding the desired alkane product as a colorless foam (131 mg, 0.190 mmol, 94%). $^1$H NMR (500 MHz, Chloroform-d) δ 8.14 (s, 3H), 4.65 (s, 6H), 3.92 (s, 6H), 3.49 (br s, 3H), 3.02-2.85 (m, 6H), 1.82 (s, 6H), 1.50 (s, 27H). $^{13}$C NMR (126 MHz, CDCl$_3$) δ 157.23, 141.79, 135.33, 81.51, 76.29, 58.40, 30.76, 28.29, 26.08. (IR cm$^{-1}$) 3433 (br), 3263 (br), 2973, 2926, 1710, 1477, 1455, 1392, 1366, 1276, 1250, 1162, 1110, 1003, 754. mp (° C.) 68

In a flame-dried flask, under Ar flow, the alkane product (50 mg, 72.6 µmol) was dissolved in 2.5 ml freshly distilled CH$_2$Cl$_2$ and cooled to 0° C. Pyridine (26 µl, 0.33 mmol, 4.5 equiv) was added, followed by dropwise addition of PBr$_3$ (24 µL, 0.25 mmol, 3.5 equiv). After 1 h on ice, the solution was warmed to rt. and becomes opaque. LC-MS analysis showed full conversion to the desired product. The reaction mixture was diluted with EtOAc and quenched with NaHCO$_3$. After neutralization with KHSO$_4$, the product was extracted with EtOAc (3×). The collected organic phases were washed with brine and dried over Na$_2$SO$_4$. After filtration, the volatiles were removed under reduced pressure, yielding T6N-1 as a colorless foam (20 mg, 22.8 µmot 31%). $^1$H NMR (500 MHz, Chloroform-d) δ 7.22 (s, 3H), 4.60 (s, 6H), 4.03 (t, J=5.8 Hz, 6H), 3.01 (t, J=9.5, 8.2 Hz, 9H), 1.99 (d, J=12.9 Hz, 6H), 1.51 (s, 27H). $^{13}$C NMR (126 MHz, CDCl$_3$) δ 157.08, 142.83, 133.61, 81.90, 76.26, 29.60, 28.75, 28.25, 26.48. IR (cm$^{-1}$) 3275, 2925, 2854, 1712, 1476, 1454, 1366, 1248, 1161, 1107, 773, 517. mp (° C.) 56-57

T6N-2

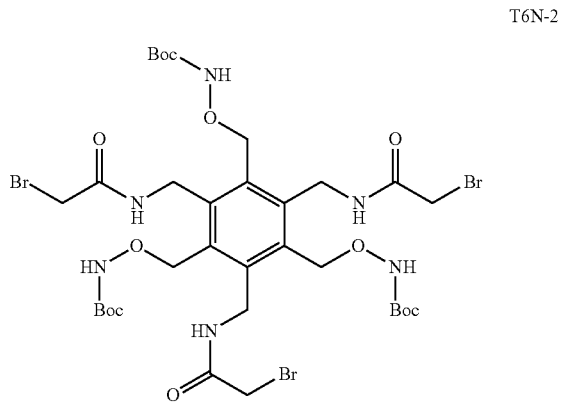 [SMILES: CC(C)(C)OC(=O)NOCc1c(CNC(=O)CBr)c(CONC(=O)OC(C)(C)C)c(CNC(=O)CBr)c(CONC(=O)OC(C)(C)C)c1CNC(=O)CBr]

To a flame-dried flask, under N$_2$, mesitylene (0.7 ml, 5 mmol) was added, followed by acetic acid (2.6 ml) and HBr in AcOH (33% wt solution) (3.5 ml). Then para-formaldehyde (570 mg, 18.8 mmol, 3.7 equiv) was added. The solution was stirred for at 95° C. After 3 h solids started to develop. The mixture was stirred for another 9 h, after which het mixture was cooled to rt. After crashing the mixture onto ice, the solids were filtered and dried. The solid was recrystallized from CH$_2$Cl$_2$: P.E. to yield the desired bromomethylated product as white needles (1.99 g, 5 mmol, 99%). $^1$H NMR (500 MHz, Chloroform-d) δ 4.61 (s, 6H), 2.50 (s, 9H). $^{13}$C NMR (126 MHz, CDCl$_3$) δ 137.84, 133.18, 29.93, 15.38.

In a flame-dried flask, under N$_2$, tris(bromomethyl)mesitylene (5.012 g, 12.53 mmol) was suspended in 200 ml of anhydrous DMF. Potassium Phthalimide (KPhth, 14.00 g, 75.58 mmol, 6 equiv) was added and the slurry was vigorously stirred for 18 h at 125° C. The white solid was filtered off, and washed twice with DMF, water and acetone. The white amorphous solid was dried on high vacuum, yielding the phthalimide derivative in 78% (5.846 g, 9.78 mmol). $^1$H NMR (400 MHz, Chloroform-d) δ 7.80 (dd, J=5.4, 3.0 Hz, 6H), 7.70 (dd, J=5.4, 3.1 Hz, 6H), 4.97 (s, 6H), 2.52 (s, 9H).

In a flame-dried flask, under N$_2$ flow, the phthalimide derivative (2.50 g, 4.18 mmol) was suspended in 30 ml of DBE. Br$_2$ (711 µL, 13.80 mmol, 33 equiv) was added and the mixture was heated to reflux, while irradiated with a commercially available 500 W halogen lamp. After two hours, the solution had become light orange, after which $^1$H-NMR showed the reaction had not reached full conversion. A second portion of Br$_2$ (400 µL, 7.76 mmol, 1.86 equiv) was added and reflux and irradiation was continued for two more hours, after which $^1$H-NMR showed full conversion. The reaction mixture was quenched with a 0.5M Na$_2$S$_2$O$_3$ solution, and extracted with CH$_2$Cl$_2$. A sticky yellow solid was obtained after removal of the volatiles under reduced pressure. Flash column chromatography (3:1 to 1:1—P.E.: EtOAc) provided the brominated product as a white solid (3.09 g, 3.71, 88%). *Analytical data is in concurrence with those reported in literature* (Roelens et al. 2009).

In a flame-dried flask, under N$_2$ flow, the brominated compound (2.50 g, 3 mmol), was suspended in 42 ml of freshly distilled MeCN, and the mixture was cooled to 0° C. N-Boc hydroxylamine (1.80 g, 13.5 mmol, 4.5 equiv), was added after which DBU (1.80 ml, 12 mmol, 4 equiv) was added dropwise. The suspension turned to a clear yellowish solution after 10 min. The mixture was warmed to rt and stirred overnight. The volatiles were removed under reduced pressure. The residue was dissolved in CH$_2$Cl$_2$ and washed with a sat. NaHCO$_3$ solution and brine followed by drying over Na$_2$SO$_4$. After filtration and removal of the volatiles under reduced pressure, the crude product was obtained as a bright yellow foam. Flash column purification (2.5:1—P.E.:EtOAc) yielded the amino-oxy functionalized product as a bright yellow solid (1.43 g, 1.44 mmol, 48%). $^1$H NMR (500 MHz, Chloroform-d) δ 7.80 (dd, J=5.4, 3.0 Hz, 6H), 7.70 (dd, J=5.4, 3.1 Hz, 6H), 7.26 (s, 3H), 5.45 (s, 6H), 5.39 (s, 6H), 1.42 (s, 27H). $^{13}$C NMR (126 MHz, CDCl$_3$) δ 168.25, 156.16, 139.09, 135.69, 133.95, 131.95, 123.20, 81.60, 72.47, 36.81, 28.15.

The amino-oxy functionalized product (200 mg, 0.202 mmol) was suspended in 3.5 ml of EtOH:toluene (2:1), after which hydrazine-hydrate (50% sol. in water, µL, mmol, equiv) was added. The suspension was heated to reflux. When the mixture has reached 70° C., it becomes a colorless solution. After stirring for 20 minutes at reflux, a white solid starts to precipitate. Reflux was continued for 12 hours, after which the solids were filtered off and the residue was evaporated to dryness, yielding the tris-amine as an off-white solid (118 mg, 0.198 mmol, 98%), which was used without further purification in the next step. $^1$H NMR (500 MHz, Chloroform-d) δ 5.16 (s, 6H), 4.12 (s, 6H), 1.53 (s, 27H). $^{13}$C NMR (126 MHz, CDCl$_3$) δ 157.25, 145.71, 131.96, 81.51, 72.04, 39.78, 28.33.

The tris-amine was suspended in 7 ml CHCl$_3$ and the suspension was cooled to 0° C. 7 ml of a sat. solution NaHCO$_3$ is added. Bromoacetyl bromide (70 µL, 0.786 mmol, 4 equiv) was added dropwise and the solution was warmed to rt and stirred for 3 hours. LC-MS confirmed the absence of s.m. and the product was extracted with CH$_2$Cl$_2$. The organic phase was washed with brine and dried over Na$_2$SO$_4$ and the volatiles were removed under reduced pressure. The product was purified via flash column chromatography (1:1—P.E.:EtOAc), yielding the scaffold T6N-2 as a colorless solid (120 mg, 0.125 mmol, 63%). $^1$H NMR (500 MHz, Chloroform-d) δ 8.81 (s, 3H), 8.13 (s, 3H), 5.31 (s, 6H), 4.79 (d, J=6.2 Hz, 6H), 3.85 (s, 6H), 1.47 (s, 27H). $^{13}$C NMR (126 MHz, CDCl3) δ 166.73, 157.56, 141.69, 133.99, 82.53, 71.98, 37.72, 28.98, 28.24. MS (ESI⁺) calc. 964.5. found 964.8.

Peptide Cyclization Experiments
For Ketone in the Peptide, Amino-Oxy in the Scaffold
CLiPS Reaction For a typical CLIPS experiment, the peptide is dissolved in a 3:2 DMF:MilliQ solution (max. 0.25 mM). Then the scaffold is added (0.9 equiv), as a solution in MeCN or MeCN:H$_2$O (depending on the scaffold). The resulting peptide solution is adjusted to pH 7.8-8, by addition of an NH$_4$HCO$_3$ solution in water. The progress of the reaction is monitored via reversed phase LC-MS or UPLC-MS. Once the reaction is complete (typically 15-30 min), deprotection of the amino-oxy protecting group can commence.

Liberation of the Amino-Oxy Grout) and Oxime Ligation

To the CLiPS reaction mixture, an equal volume of 6M HCl (aq) is added, to initiate Boc-deprotection. The reaction mixture is stirred typically for 1 hour, to ensure full liberation of all amino-oxy moieties, which can be confirmed via reversed phase LC-MS or UPLC-MS. It is important to note that oxime ligation already occurs during these conditions, but full conversion to the twice oximed peptide construct is not reached. The pH of the reaction mixture is adjusted to approximately pH ~4, using a 5.5M NaOH (aq) solution (typically 95 vol % of the added HCl solution). The reaction mixture is then left for 1 to 16 hours, until full conversion is reached, as judged by reversed phase LC-MS or UPLC-MS.

Examples of Peptide Cyclization Reactions

Example A: T4N-3 Cyclization with a Small Peptide

Figure 10:
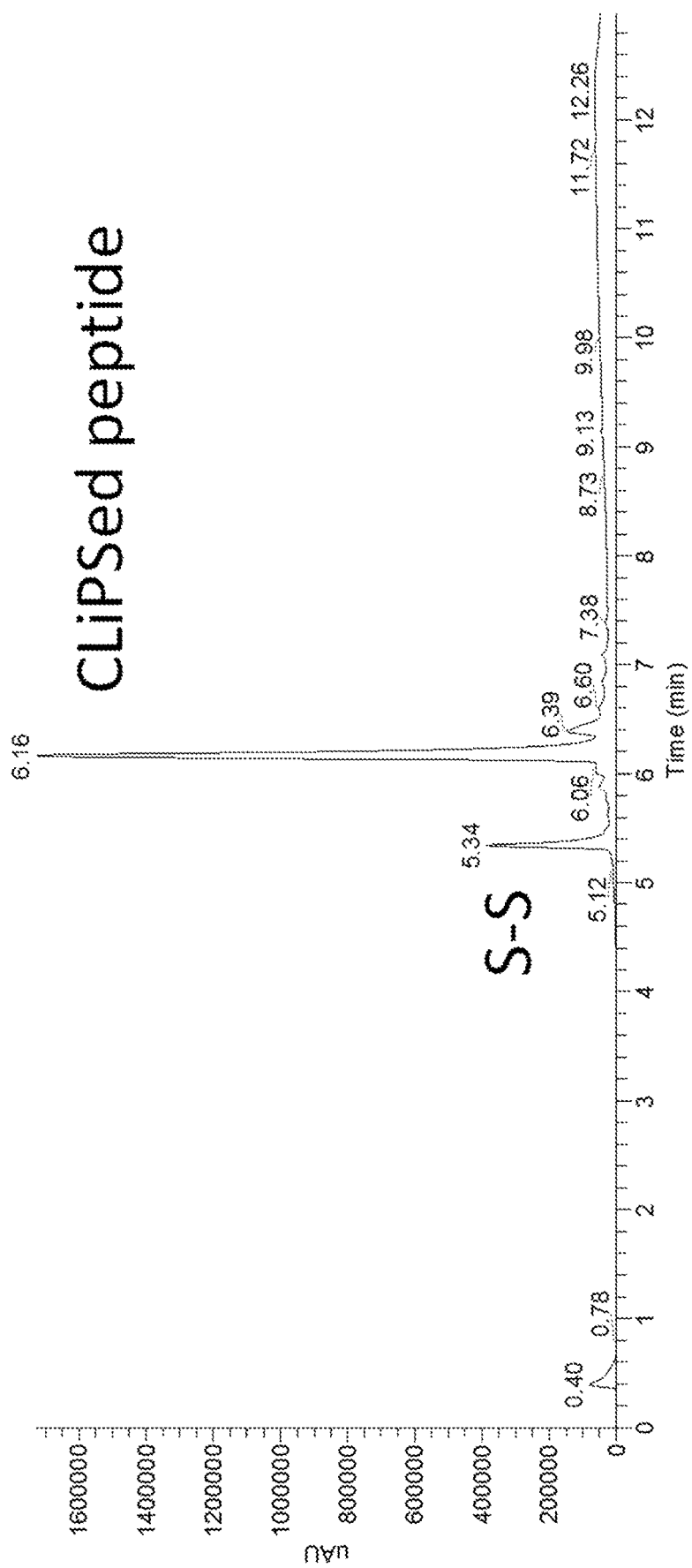
FIG. 10. LC-MS chromatogram of peptide Ac—CE(pAcF)A(pAcF)KC—NH$_2$ attached to scaffold T4N-3 via CLiPS reaction.

Peptide Ac—CE(pAcF)A(pAcF)KC—NH$_2$ (1.10 mg, 1.13 µmol) was dissolved in 1 ml 3:2 DMF:H$_2$O (1.13 mM). Scaffold T4N-3 (6.10 mg in 500 µl MeCN stock, used 65 µl, 0.8 equiv) was added followed by 50 µl of a 1M NH$_4$HCO$_3$ solution, to reach pH 8.5. FIG. 10 shows the LC-MS chromatogram after 30 min reaction time. At R$_t$ 6.16 min, the UV trace is seen of the CLiPSed peptide, with m/z 1549.6 (calc 1549.6), corresponding to the [M+H]$^+$ and 775.3 (calc 775.3) for the [M+2H]$^{2+}$. At R$_t$ 5.34 min, trace of the peptide-disulfide is seen.

Figure 11:
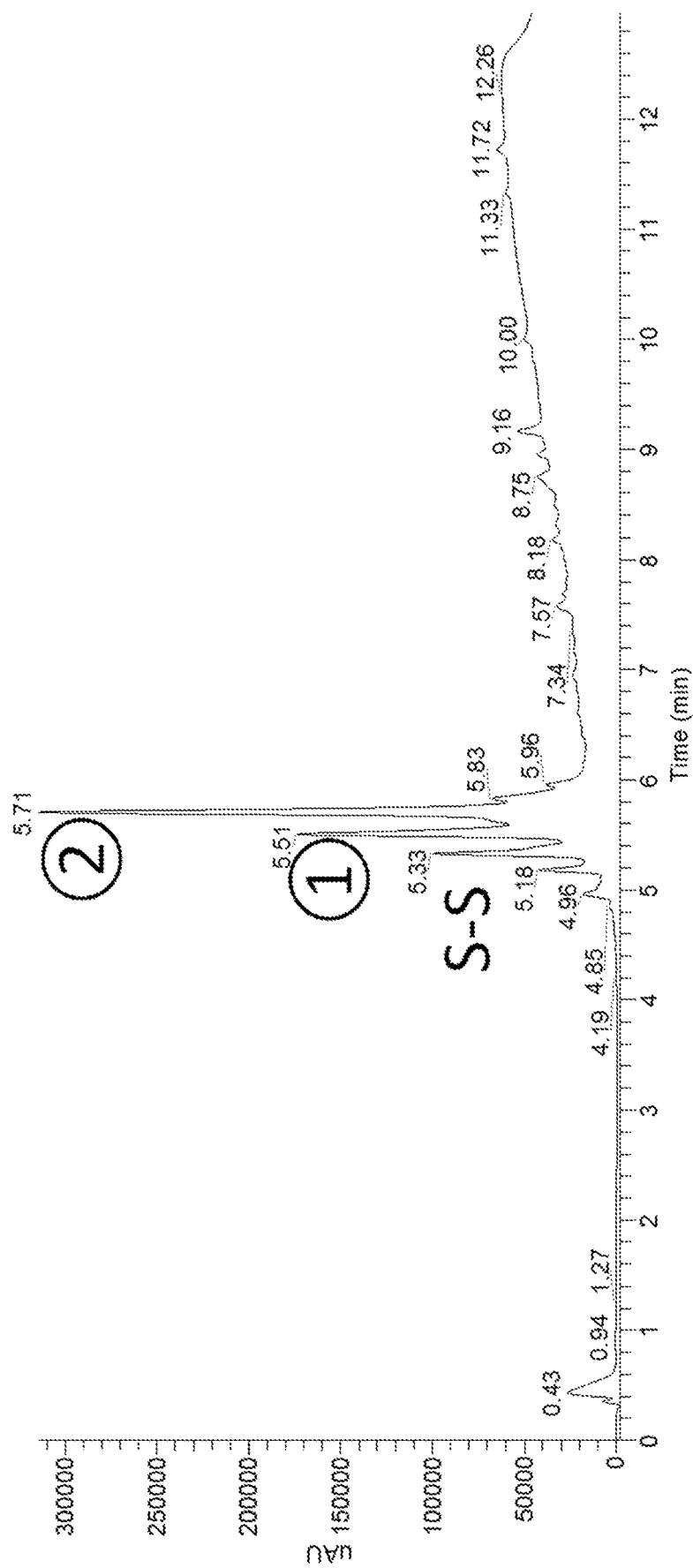
FIG. 11. LC-MS chromatogram of peptide Ac—CE(pAcF)A(pAcF)KC—NH$_2$ attached to scaffold T4N-3 after CLiPS and oxime reaction.

The reaction mixture is acidified using 1 ml of 6M HCl solution, for Boc-deprotection. The reaction mixture is stirred at rt for 1 h, after which the pH is corrected to pH4 using 810 µl of a 5.5M NaOH (aq) solution. The reaction mixture was stirred overnight at rt. FIG. 11 shows the LC-MS chromatogram. At R$_t$ 5.51 min, peak 1 is seen, and at R$_t$ 5.71 min peak 2. Both 1 and 2 show similar mass spectra, which correspond to the 2×CLiPSed, 2×OXIMed peptide construct with for ①  m/z 1314.6 (calc 1314.5), corresponding to the [M+H]$^+$ and 657.6 (calc 657.7) for the [M+2H]$^{2+}$. And for ②  m/z 1313.7 (calc 1314.5), corresponding to the [M+H]+ and 657.6 (calc 657.7) for the [M+2H]$^{2+}$. Different peaks are seen, most likely different conformations of one and the same molecule. At R$_t$ 5.34 min, trace of the peptide-disulfide is seen.

Example B: T4N-3 Cyclization with a Larger Peptide

Figure 12:
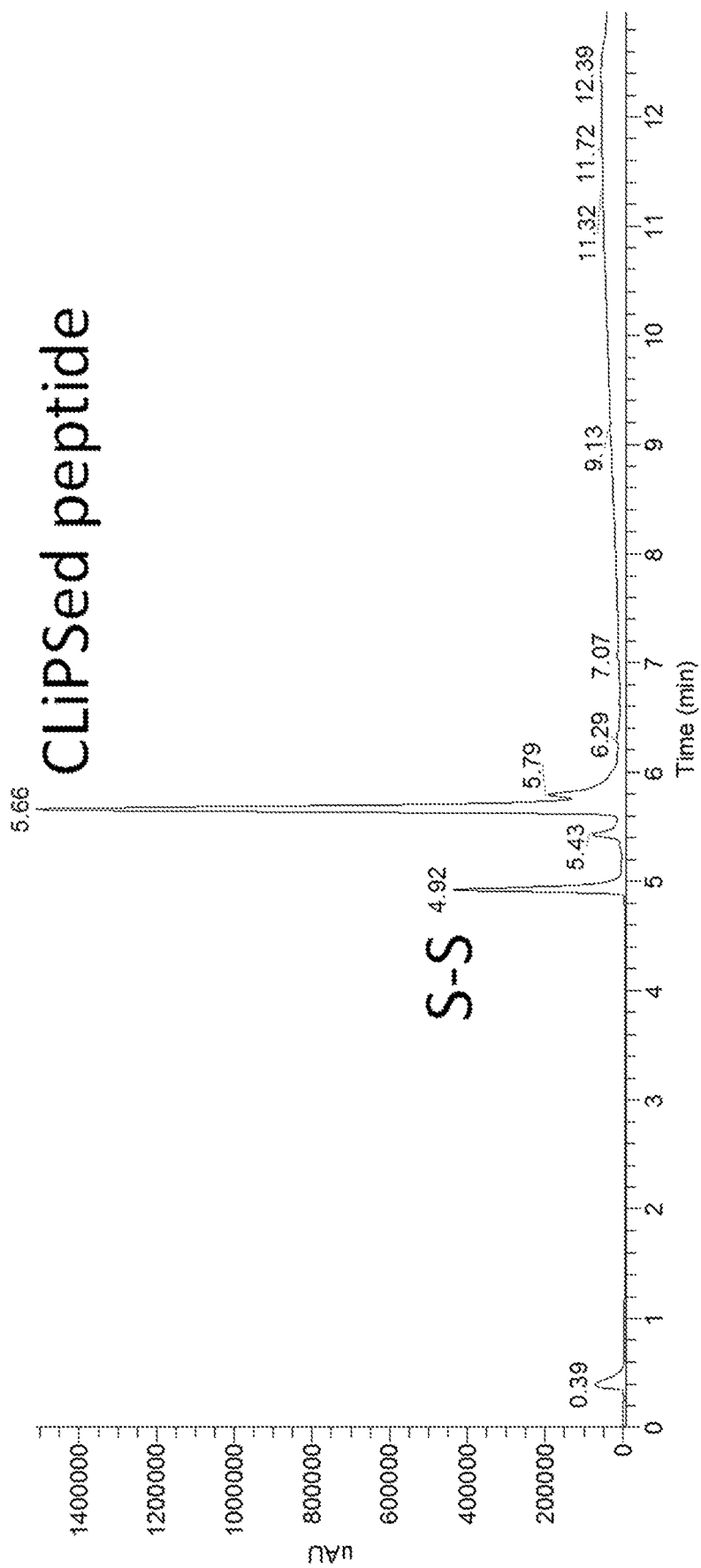
FIG. 12. LC-MS chromatogram of peptide Ac—CEK(pAcF)AS(pAcF)KDC—NH$_2$ attached to scaffold T4N-3 via CLiPS reaction.

Peptide Ac—CEK(pAcF)AS(pAcF)KDC—NH$_2$ (1.30 mg, 0.99 µlnca) was dissolved in 1 ml 3:2 DMF:H$_2$O (1.13 mM). Scaffold T4N-3 (6.10 mg in 500 µl MeCN stock, used 57 µl, 0.7 equiv) was added followed by 50 µl of a 1M NH$_4$HCO$_3$ solution, to reach pH 8.5. FIG. 12 shows the LC-MS chromatogram after 30 min reaction time. At R$_t$ 5.66 min, the UV trace is seen of the CLiPSed peptide, with m/z 1880.8 (calc 1879.8), corresponding to the [M+H]$^+$ and 940.7 (calc 940.4) for the [M+2H]$^{2+}$. At R$_t$ 4.92 min, trace of the peptide-disulfide is seen.

Figure 13:
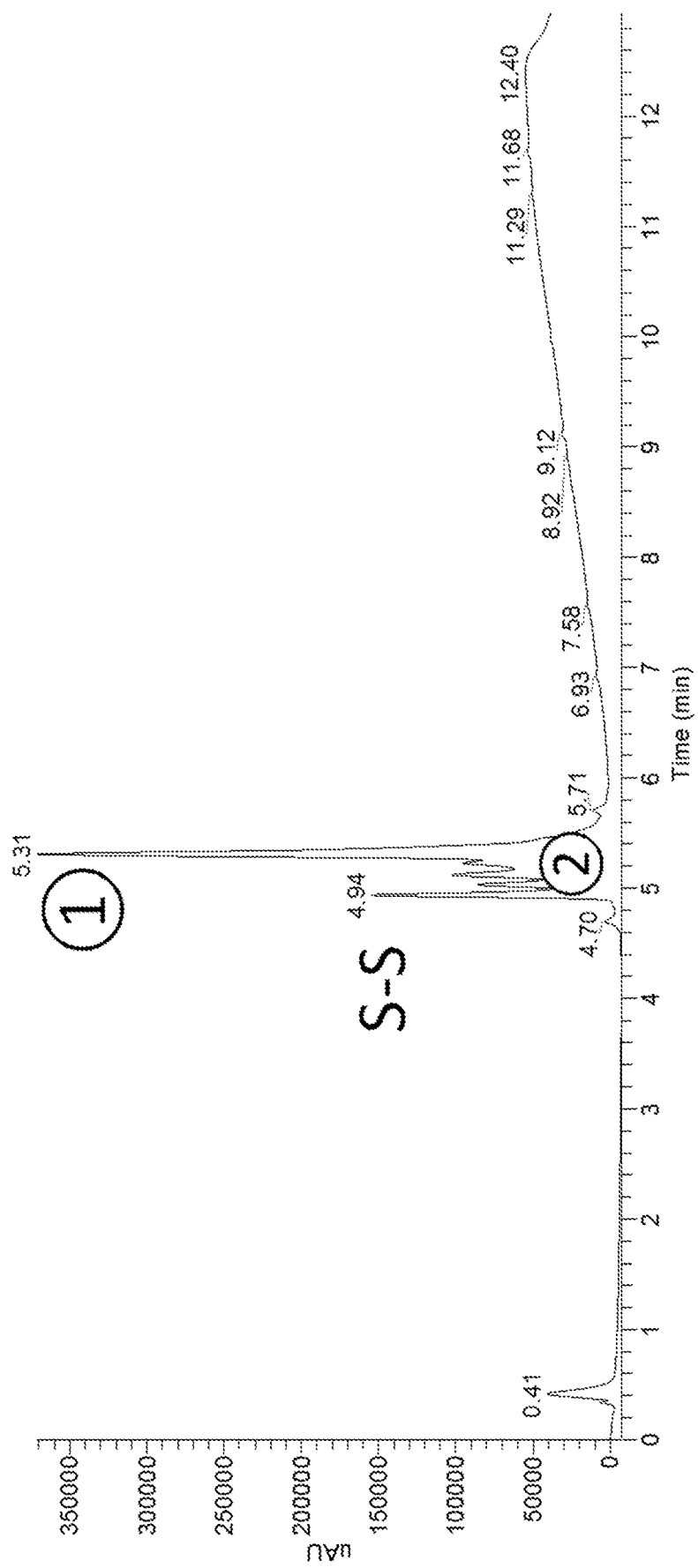
FIG. 13. LC-MS chromatogram of peptide Ac—CEK(pAcF)AS(pAcF)KDC—NH$_2$ attached to scaffold T4N-3 via CLiPS and oxime reaction.

The reaction mixture is acidified using 1 ml of 6M HCl solution, for Boc-deprotection. The reaction mixture is stirred at rt for 1 h, after which the pH is corrected to pH4 using 790 µl of a 5.5M NaOH (aq) solution. The reaction mixture was stirred overnight at rt. FIG. 13 shows the LC-MS chromatogram. At R$_t$ 5.31 min peak 1 is seen, and at R$_t$ 5.03-5.20 min 3 small peaks close together are shown, as part of 2. Both 1 and 2 show similar mass spectra, which correspond to the 2×CLiPSed, 2×OXIMed peptide construct with for ①  m/z 1644.7 (calc 1644.8), corresponding to the [M+H]$^+$ and 822.7 (calc 822.9) for the [M+2H]$^{2+}$. And for ②  m/z 1644.7 (calc 1644.8) corresponding to the [M+H]$^+$ and 822.7 (calc 822.9) for the [M+2H]$^{2+}$. One conformer is generally favored, as there is a major peak at R$_t$=5.31 min. The other conformers are in peak 2. At 5.34 min, trace of the peptide-disulfide is seen.

General Procedure for T4C-3 Cyclization Experiments with a Peptide Containing an Amino-Oxy Residue:

The peptide is dissolved in 1:1 DMSO:H$_2$O to a final concentration of 50 mM, then scaffold is added (0.63 equiv, from stock solution). The reaction mixture is basified to pH >8 by adding 1M NH$_4$HCO$_3$. General scale is 0.3 mg of peptide, which calls for 30 µL of 1M NH$_4$HCO$_3$-solution. After UPLC shows the CLIPS reaction has reached full conversion (generally within 30 min.), the reaction is acidified using 15% TFA solution. An equal volume to the base is added (generally 30 uL). The solution is left overnight, yielding the oxime product in quantitative yield.

Example C: T4C-3 Cyclization with Medium-Sized Peptide

Figure 14:
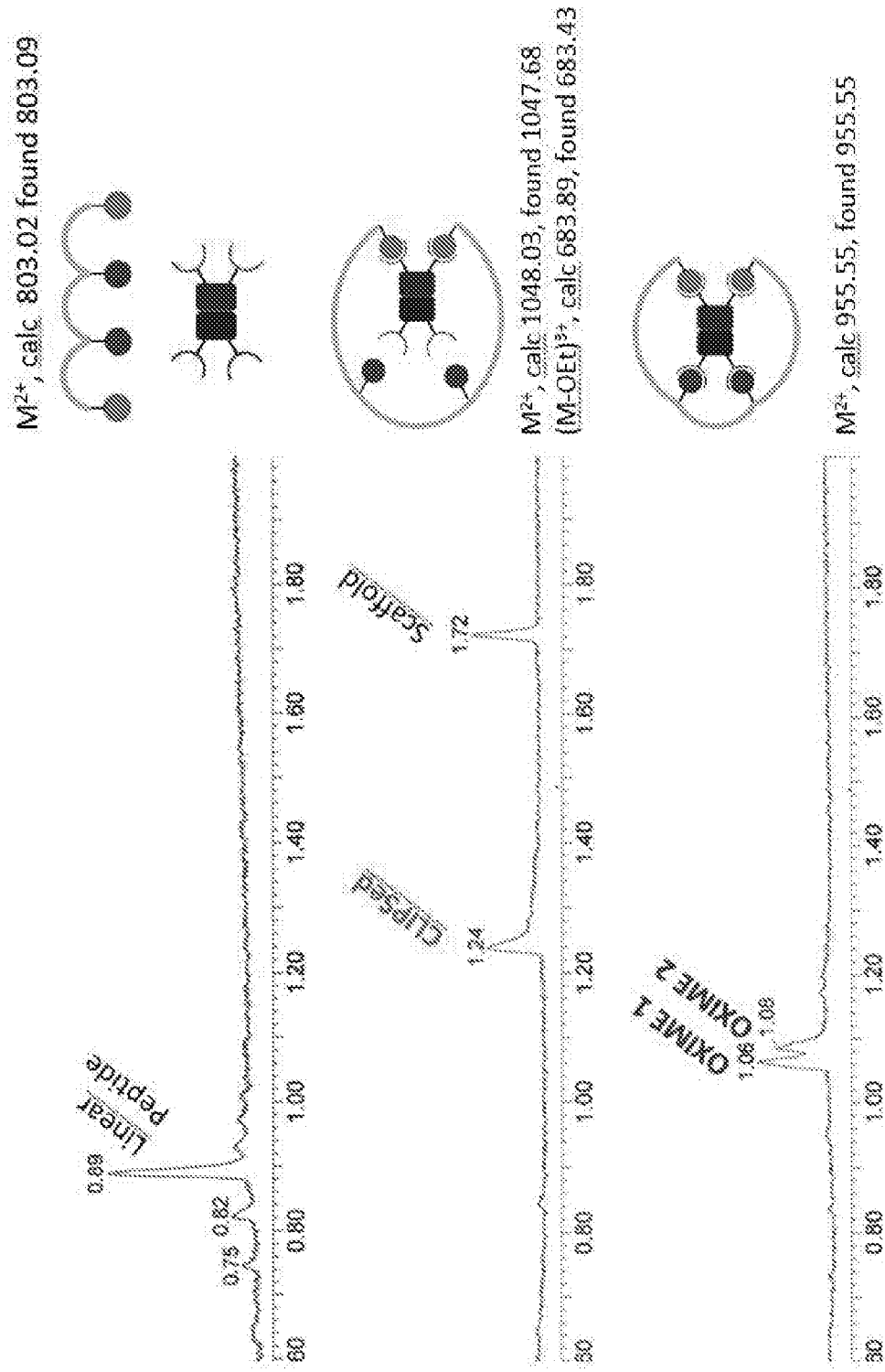
FIG. 14. UPLC-MS chromatogram of peptide Ac—CEQFhS(ONH$_2$)AKFhS(ONH$_2$)LKNC—NH$_2$ attached to scaffold T4C-3 via CLiPS and oxime reaction.

Peptide Ac—CEQF hS(ONH$_2$)AKF hS(ONH$_2$)LKNC—NH$_2$ (0.22 mg) is dissolved in 274 µL DMSO:H$_2$O (1:1). Scaffold T4C-3 is added (2.31 mg in 200 µL MeCN, 4.27 µL was added). Then 30 µL of a 1M solution NH$_4$HCO$_3$ is added, after which CLIPS takes place within 20 min. FIG. 14 shows the R$_t$ shift from 0.89 min of the linear peptide, to 1.24 min of the CLIPSed peptide. The mass corresponds to the desired product. 35 µL of a 15% TFA solution is added, yielding the double oxime product after 16 h at rt. Two products are found, with R$_t$ 1.06 and 1.08 min respectively. The mass spectra are in concurrence with the double oxime product. Two peaks are visible, which most likely represent different conformations of one and the same molecule.

Example D: T4C-3 Cyclization with Medium-Sized Peptide

Figure 15:
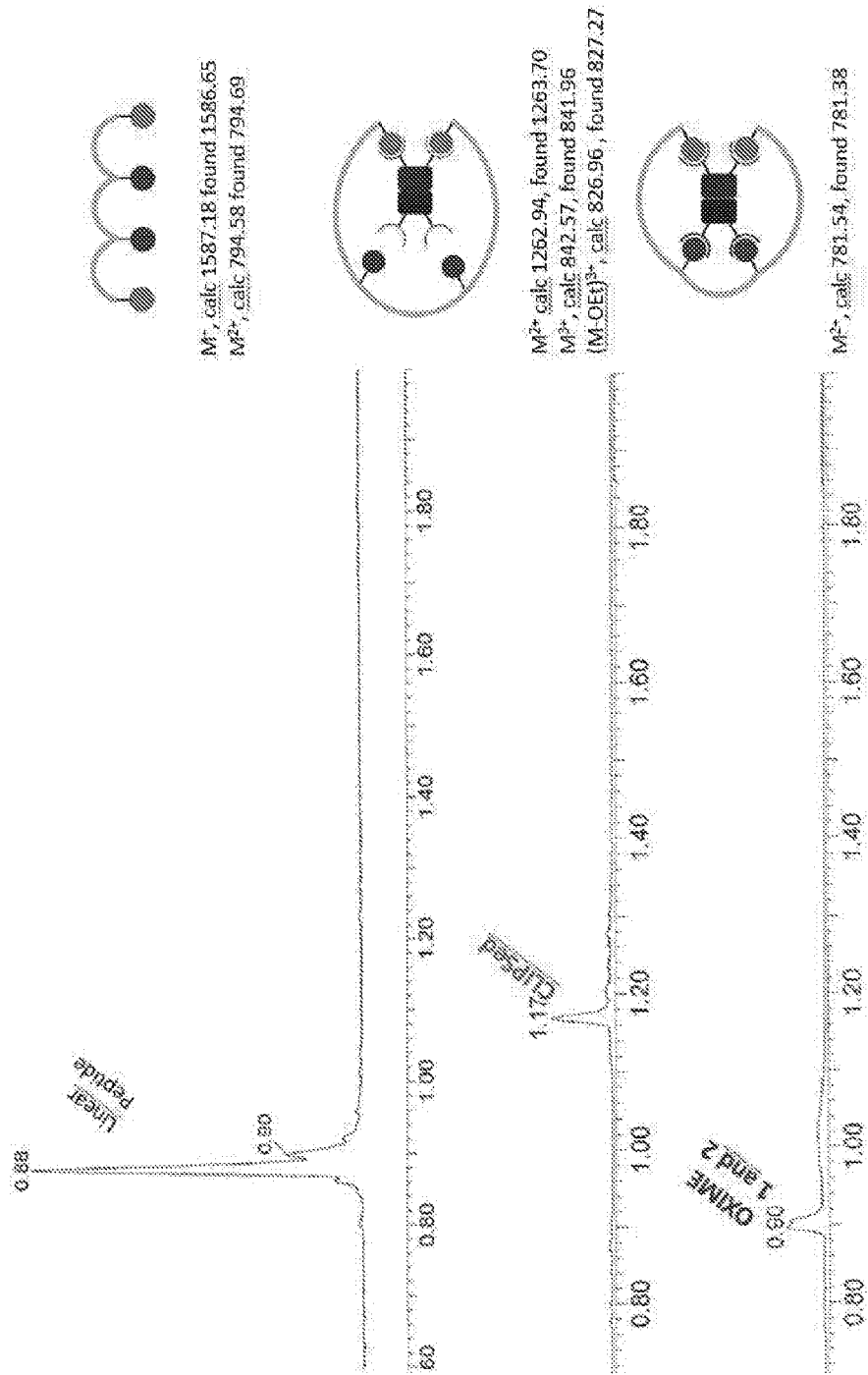
FIG. 15. UPLC-MS chromatogram of peptide Ac—CERKFK(Aoa)SGAVK(Aoa)KLYSC—NH$_2$ attached to scaffold T4C-3 via CLiPS and oxime reaction.

Peptide Ac—CERKFK(Aoa)SGAVK(Aoa)KLYSC—NH$_2$ (0.26 mg) is dissolved in 254 µL DMSO:H$_2$O (1:1). Scaffold T4C-3 is added (0.93 mg in 100 µL MeCN, 5.66 µL was added). Then 30 µL of a 1M solution NH$_4$HCO$_3$ is added, after which CLIPS takes place within 20 min. FIG. 15 shows the R$_t$ shift from 0.88 min of the linear peptide, to 1.17 min of the CLIPSed peptide. The mass corresponds to the desired product. 30 µL of a 15% TFA solution is added, yielding the double oxime product after 16 h at rt. Two products are found, with R$_t$=0.90 min. The product peaks are very close together. The mass spectra are in concurrence with the double oxime product.

Example E: T4C-3 Cyclization with Medium-Sized Peptide—Aminooxy at Termini

Figure 16:
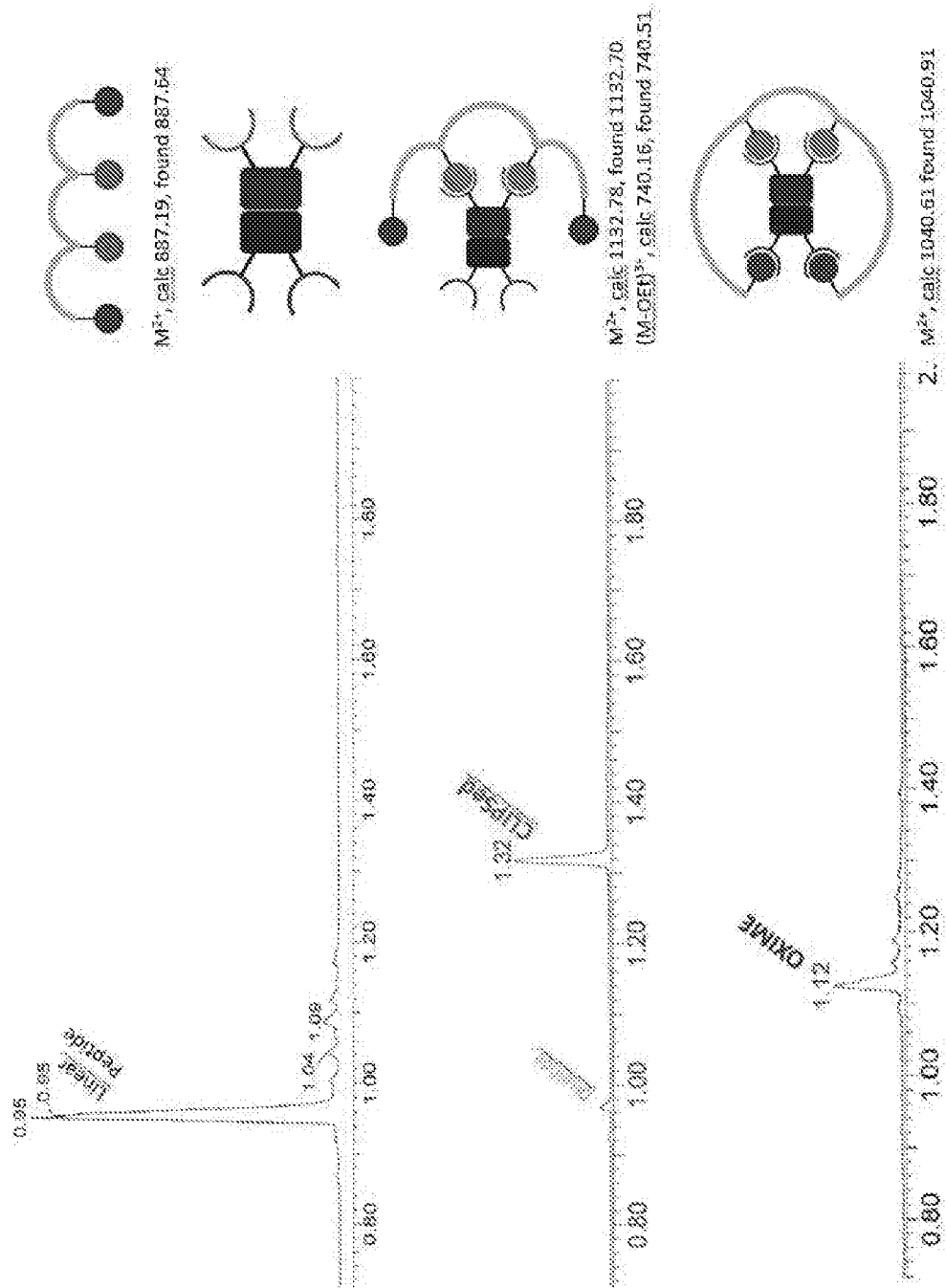
FIG. 16. UPLC-MS chromatogram of peptide Ac—K(Aoa)EQFCAKFCLKNK(Aoa)-NH$_2$ attached to scaffold T4C-3 via CLAPS and oxime reaction.

Peptide Ac—K(Aoa)EQFCAKFCLKNK(Aoa)-NH$_2$ (0.41 mg) is dissolved in 460 µL DMSO:H$_2$O (1:1). Scaffold T4C-3 is added (0.78 mg in 100 μL MeCN, 12.19 μL was added). Then 40 μL of a 1M solution NH$_4$HCO$_3$ is added, after which CLIPS takes place within 20 min. FIG. 16 shows the R$_t$ shift from 0.95 min of the linear peptide, to 1.32 min of the CLIPSed peptide. The mass corresponds to the desired product. 50 μL of a 15% TFA solution is added, yielding the double oxime product after 16 h at rt. A single peak is found, with R$_t$ 1.12 min. and the mass spectrum corresponds to the desired product.

Example E: T4C-3 Cyclization with Medium-Sized Peptide—Aminooxy at Termini

Figure 17:
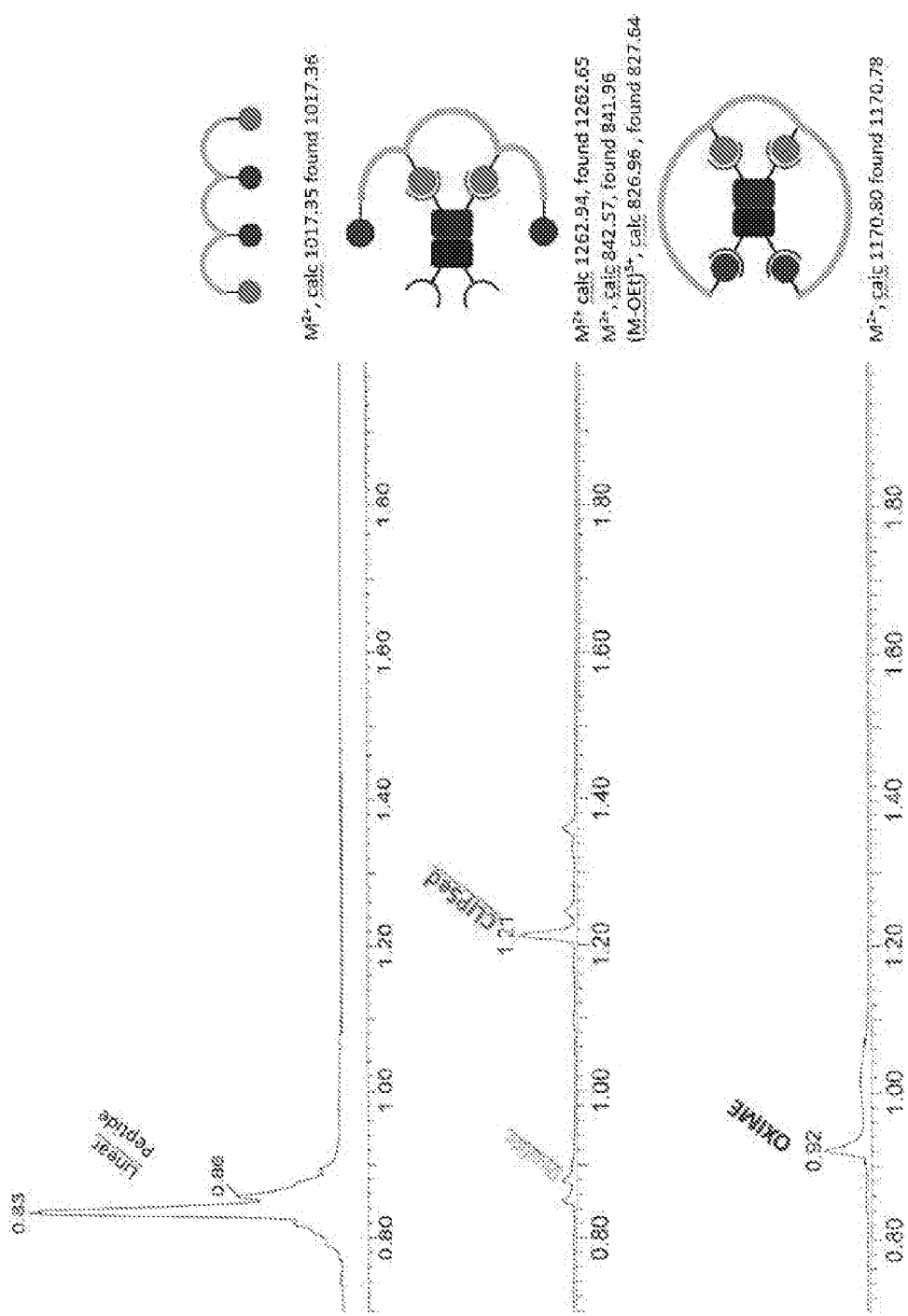
FIG. 17. UPLC-MS chromatogram of peptide Ac—K(Aoa)ERKFCSGAVCKLYSK(Aoa)-NH$_2$ attached to scaffold T4C-3 via CLiPS and oxime reaction.

Peptide Ac—K(Aoa)ERKFCSGAVCKLYSK(Aoa)-NH$_2$ (0.23 mg) is dissolved in 226 μL DMSO:H$_2$O (1:1). Scaffold T4C-3 is added (0.93 mg in 100 μL MeCN, 5.00 μL was added). Then 30 μL of a 1M solution NH$_4$HCO$_3$ is added, after which CLIPS takes place within 20 min. FIG. 17 shows the R$_t$ shift from 0.83 min of the linear peptide, to 1.21 min of the CLIPSed peptide. The mass corresponds to the desired product. 30 μL of a 15% TFA solution is added, yielding the double oxime product after 16 h at rt. A single peak is found, with R$_t$=0.92 min., and the mass spectrum corresponds to the desired product.

Example 2. Coupling of Peptide and Scaffold Via Thiolate Nucleophilic Substitution Reaction and Alkyne-Azide Cycloaddition 1. Synthesis Routes for T4(-≡)$_2$-Scaffolds The synthesis routes for different T4(-≡)$_2$-scaffolds is shown in scheme 1.

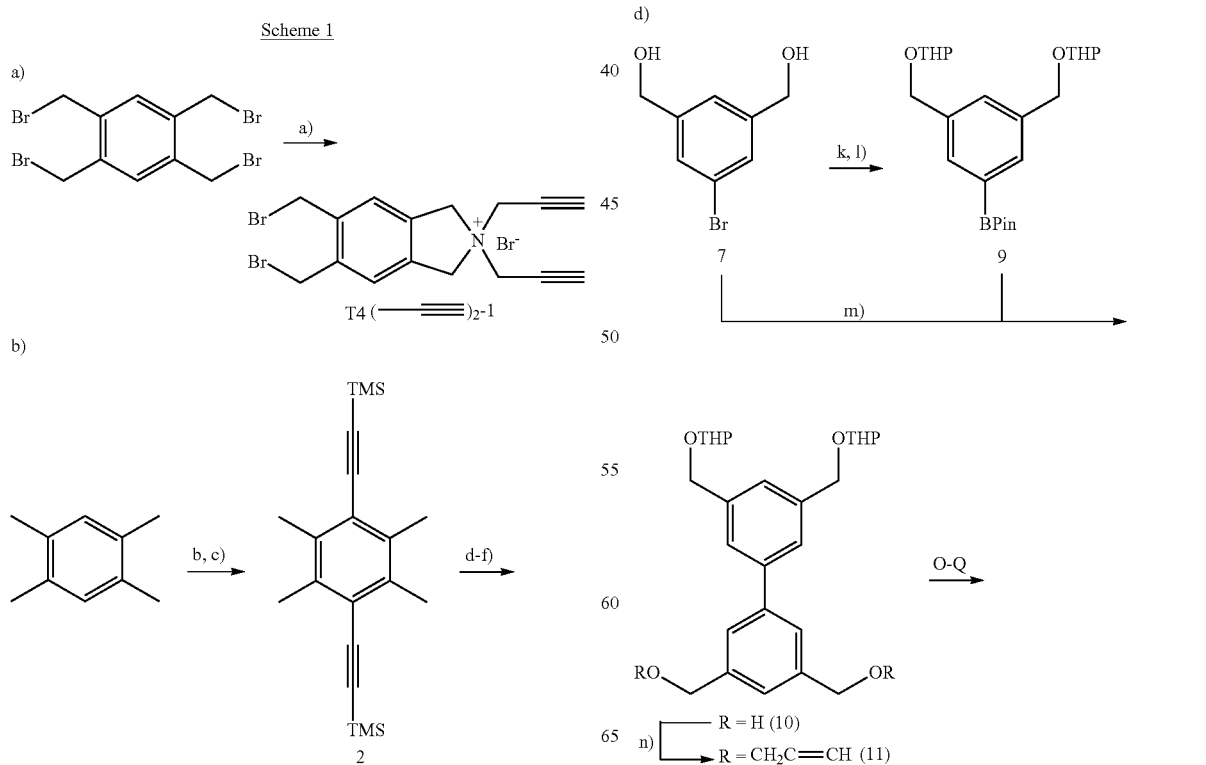

-continued

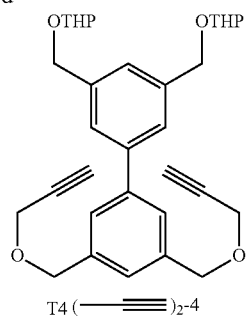

T4 (—≡≡≡—)₂-4

Scheme 1. a) Synthesis of T4 (- ≡≡≡ )₂-1 scaffold: a) dipropargylamine, DIPEA, CH₃CN, RT (quant. [contains DIPEA salt]); b) Synthesis of T4 (- ≡≡≡ )₂-2 scaffold: b) [bis(trifluoroacetoxy)iodo]benzene, I₂, CCl₄, RT (74%): c) ethynyltrimethylsiland CuI, Pd(PPh₃)₂Cl₂, Et₂NH, RT (82%);
d) NBS, dibenzoylperoxide, CCl₄, Δ (10%); e) K₂CO₃, CH₃OH, 0° C. (90%); f) piperidine, DIPEA, CH₂Cl₂/CH₃CN (71%); c) Synthesis of T4(- ≡≡≡ )₂-3 scaffold: g) SOCl₂, toluene Δ; then tert-BuOH, pyridine, CH₂Cl₂, RT (51% over two steps); h) NBS, hv, CH₂Cl₂, Δ (42%); i) HCOOH, CH₂Cl₂, RT (97%): j) SOCl₂, Δ; then DIPEA, DMAP, dipropargylamine, CH₂Cl₂, 0° C. to RT, (48% over two steps); d) Synthesis of T4(- ≡≡≡ )₂-4 scaffold: k) 3, 4-dihydro-2H-pyran, PPTS, THF, RT (86%O; l) B₂Pin₂, NaOAc, Pd(dba)₂, DPEPhos, toluene, Δ (87%); m) Pd(dppf)Cl₂, K₂CO₃, dioxane/H₂O (2:1), 60° C. (86%); N)NaH, propargIbromide, THF, RT (70%); o) PPTS, EtOH, 55° C (98%); p) MsCl, Et₃N, THF, Rt (95%); q) LiBr, THF, RT (80%); dba = dibenzylidene acetone, DIPEA = N,N-diisopropylethylamine, DMAP = 4-dimethylaminopyridine, DPEPhos = bis[(2-diphenylphosphine)phenyl] ehter, dppf = diphenylphosphino)ferrocene, NBS = N-bromosucinimide, PPTS = pyridinium p-toluenesulfonat.

2. Experimental Procedures and Spectroscopic Data of Compounds

General Section

Unless stated otherwise, reactions were performed without special precautions like drying or $N_2$/Argon atmosphere. Dried $CH_2Cl_2$ and $CH_3CN$ were obtained by distilling these solvents with $CaH_2$ as drying agent. Dried THF was obtained by distillation with sodium. All dried solvents were stored under $N_2$ atmosphere. Dry DMF and DMSO on 4 Å molecular sieves were obtained from Sigma-Aldrich and stored under $N_2$ atmosphere. Reagents were purchased with the highest purity (usually >98%) from Sigma Aldrich and Fluorochem and used as received. Reactions were monitored with thin layer chromatography (TLC) carried out on 0.25 mm E. Merck silica gel plates (60E-254). SilaFlash® P60 (particle size 40-63 µm) was used for silica column chromatography. NMR spectra were recorded on Bruker DRX-300, 400 and 500 MHz instruments and calibrated on residual undeuterated solvent signals as internal standard. The ¹H-NMR multiplicities were abbreviated as followed: s=singlet, d=doublet, t=triplet, q=quartet, quint=quintet, m=multiplet. High resolution mass spectra (HRMS) were recorded on an AccuTOF GC v 4 g, JMS-T100GCV Mass spectrometer (JEOL, Japan). FD/FI probe equipped with FD Emitter, Carbotec or Linden (Germany), FD 10 µm. Current rate 51.2 mA/min over 1.2 min machine using field desorption (FD) as ionization method. Melting points were recorded on a Wagner & Munz Polytherm A melting point apparatus and are uncorrected. IR spectra were recorded on a Bruker Alpha FTIR machine.

T4 Scaffolds

Scaffold T4(-≡)₂-1

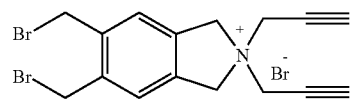

To a stirred solution of 1,2,4,5-tetrakis(bromomethyl)benzene (8.13 mmol, 3.85 g, 3 equiv) and DIPEA (5.42 mmol, 0.9 mL, 2 equiv) in dry $CH_3CN$ (550 mL) was added dropwise dipropargylamine (2.709 mmol, 263 mg, 1 equiv) in dry $CH_3CN$ (30 mL). After consumption of the amine (2 h), the solvent was evaporated in vacuo, $Et_2O$ (100 mL) was added and the mixture was stirred for 30 min. The precipitate was isolated and filtered over a silica plug (100% $CH_2Cl_2$ to $CH_2Cl_2$/MeOH 9:1). The solvents were evaporated and the product was lyophilized to obtain the scaffold T4(-≡)₂-1 (quantitative, containing DIPEA salt) as a grey powder. The scaffold was used as such. ¹H NMR (400 MHz, $D_2O$/$CD_3CN$ 9:1) δ 7.74 (s, 4H), 5.28 (s, 4H), 4.97 (s, 4H), 4.76 (d, 4H), 3.56 (t, 2H). ¹³C NMR (400 MHz, $D_2O$/$CD_3CN$ 9:1) S 140.9, 136.0, 129.0, 85.8, 73.7, 68.9, 54.7, 45.5, 32.9. IR v 2978, 2932, 2663, 2617, 2121, 1426, 1391, 1182, 1135 cm⁻¹. HRMS (EI⁺) m/z calculated for $C_{16}H_{16}Br_2N$, 379.9649. found 379.9676.

Scaffold T4(-≡)₂-2

Diiodoarene 1

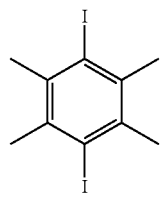

Durene (114 mmol, 15.3 g, 1 equiv.) and [bis(trifluoroacetoxy)iodo]benzene (145 mmol, 62.4 g, 1.3 equiv.) were added and the mixture was stirred at rt overnight. The solvent was evaporated and 0.1 M NaOH-solution (100 mL) was added. The product was extracted with $CH_2Cl_2$ (3×75 mL), followed by washing of the organic layer with $H_2O$ (1×100 mL) and brine (1×100 mL). The organic layer was dried over $MgSO_4$, filtered and concentrated in vacuo. The crude product was triturated in MeOH and 1 was collected via vacuum filtration (74%). ¹H NMR (400 MHz, $CDCl_3$) δ 2.63 (s, 12H). ¹³C NMR (400 MHz, $CDCl_3$) δ 138.0, 112.4, 30.0. IR v 1396, 1160, 971, 673 cm⁻¹. HRMS (EI⁺) m/z calculated for $C_{10}H_{12}I_2$ 385.9028. found 385.8989. Spectral data in agreement with reported data (Zhdankin et al, 2017).

TMS-Acetylene 2

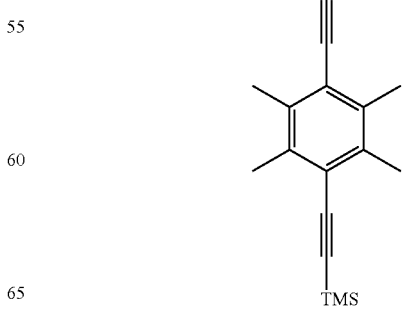

To a solution of 1 (3.02 g, 7.82 mmol, 1 equiv), Pd(PPh$_3$)$_2$Cl$_2$ (0.380 g, 0.541 mmol, 0.07 equiv) and CuI (0.101 g, 0.530 mmol, 0.07 equiv) in Et$_2$NH was added ethynyltrimethylsilane (2.45 mL, 17.3 mmol, 2.2 equiv) and the reaction was stirred at RT overnight. The solvent was evaporated followed by extraction with CH$_2$Cl$_2$ (3×100 mL) and washing of the organic layer with H$_2$O (2×200 mL) and brine (250 mL). The combined organic layers were dried over MgSO$_4$ and concentrated in vacuo. The product was purified via column chromatography (PE) leading to 2 as off-white crystals (82%). $^1$H NMR (400 MHz, CDCl$_3$) δ 2.38 (s, 12H), 0.27 (s, 18H). $^{13}$C NMR (400 MHz, CDCl$_3$) δ 136.0, 123.4, 104.2, 103.2, 18.5, 0.27. IR ν 2957, 2138, 1270, 1073, 863 cm$^{-1}$. HRMS (EI$^+$) m/z calculated for C$_{20}$H$_{30}$Si$_2$ 326.1886. found 326.1870.

Tetrakis(Bromomethyl)Arene 3

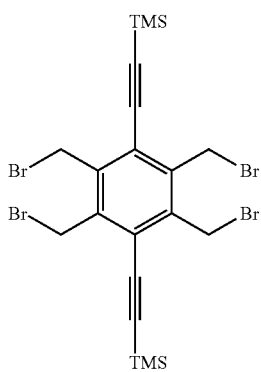 [SMILES: C[Si](C)(C)C#Cc1c(CBr)c(CBr)c(C#C[Si](C)(C)C)c(CBr)c1CBr]

2 (2.30 g, 7.06 mmol, 1 equiv) was dissolved in CCl$_4$ (50 mL). NBS (6.1 g, 34.3, 5 equiv) and dibenzoylperoxide (452 mg, 1.88 mmol, 0.3 equiv) were added and the mixture was refluxed overnight. The solvents were evaporated and the crude product was purified with column chromatography (100% PE to PE/EtOAc 9:1). Subsequent recrystallization from PE gave 3 as a white powder in 10% yield. $^1$H NMR (400 MHz, CDCl$_3$) δ 4.83 (s, 4H), 0.34 (s, 9H). $^{13}$C NMR (400 MHz, CDCl$_3$) δ 139.6, 125.6, 109.8, 98.5, 27.8, 0.24. IR ν 2957, 2154, 1420, 1283, 1247, 1200, 957, 837 cm$^{-1}$. HRMS (FD$^+$) m/z calculated for C$_{20}$H$_{26}$Br$_4$Si$_2$ 641.8266. found 641.8285.

Scaffold T4(-≡)$_2$-2

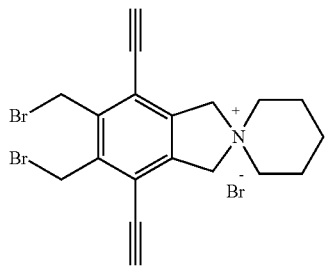

Compound 3 (300 mg, 0.480 mmol, 1 equiv) was suspended in dry MeOH (24 mL) and cooled to 0° C. K$_2$CO$_3$ (13.0 mg, 0.104 mmol, 0.2 equiv) was added and the mixture was stirred for 30 min. The solvent was removed in vacuo, and CH$_2$Cl$_2$ was added followed by washings with H$_2$O (2×15 mL) and brine (20 mL). The organic layer was dried over MgSO$_4$, filtered and concentrated. The crude product (0.482 mmol, 240 mg, 3 equiv.) and DIPEA (0.321 mmol, 56 μL, 2 equiv.) were dissolved in dry CH$_2$Cl$_2$/CH$_3$CN (3/1:40 mL) under argon atmosphere. The mixture was heated slightly with a heat gun to ensure complete solvation. Piperidine (0.161 mmol, 16 μL, 1 equiv.) in CH$_3$CN (2 mL) was added dropwise at a rate of 0.1 mL/h. The reaction mixture was stirred overnight, followed by concentration of the mixture. Column chromatography was carried out to isolate the product T4(-≡)$_2$-2 as a colorless oil. The product was then lyophilized to obtain a white solid (71%). $^1$H NMR (400 mHz, CD$_3$OD) δ 5.09 (s, 4H), 4.92 (s, 4H), 4.59 (s, 2H), 3.67-3.70 (t, 4H), 2.00-2.05 (q, 4H), 1.76-1.81 (q, 4H). $^{13}$C NMR (300 MHz, CD$_3$OD) δ 141.88, 137.66, 120.52, 92.61, 77.49, 69.36, 63.55, 27.03, 22.43, 21.92. IR ν 943.54, 1033.55, 1061.91, 1078.57, 1114.23, 1160.01, 1172.68, 1209.72, 1270.77, 1323.98, 1444.45, 1719.71, 2871.49, 3175.00, 3251.47, 3360.79. HRMS (ESI$^+$) m/z calculated for C$_{19}$H$_{20}$Br$_2$N$^+$ 419.9962. found 421.9943. According to LCMS, an amount of Br—Cl exchange was observed which could have happened after the washings with brine in the previous step. However, this did not cause a problem in the follow-up CLIPS reactions.

Scaffold T4(-≡)$_2$-3

Tert-Butyl Ester 4

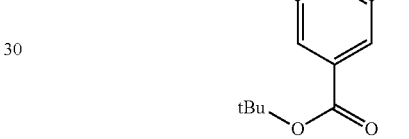

3,5-dimethylbenzoic acid (10.0 gram, 66.6 mmol, 1 equiv) was dissolved in toluene (8 mL) under nitrogen atmosphere. SOCl$_2$ (10.0 mL, 137 mmol, 2.06 equiv) was added and the mixture was refluxed for 2.5 h. The temperature was decreased to RT and the mixture was stirred overnight. After evaporation of the solvents, CH$_2$Cl$_2$ (20 mL) was added followed by tert-butanol (8.01 gram, 108 mmol, 1.6 equiv) and pyridine (5.53 g, 69.9 mmol, 1.05 equiv) and the mixture was stirred overnight. The mixture was filtered and the mother layer was concentrated in vacuo. The crude product was purified via column filtration (EtOAc) yielding ester 4 as a colorless oil (51%). $^1$H NMR (400 MHz, CDCl$_3$) δ 7.61 (s, 2H), 7.15 (s, 1H), 2.35 (s, 6H), 1.60 (s, 9H). $^{13}$C NMR (400 MHz, CDCl$_3$) δ 166.2, 137.9, 134.1, 132.0, 127.2, 80.8, 28.3, 21.3. IR ν 3006, 1711, 1315, 1231, 1159 cm$^{-1}$. HRMS (EI$^+$) m/z calculated for C$_{13}$H$_{18}$O$_2$ 206.1307. found 206.1297.

Bis(Bromomethyl)-Tert-Butyl Ester 5

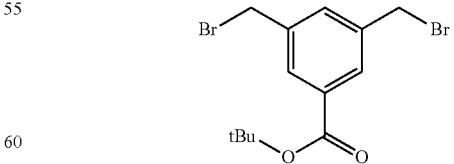

Compound 4 (6.79 g, 32.9 mmol, 1 equiv) was dissolved in CH$_2$Cl$_2$ (130 mL) under inert atmosphere. N-bromosuccinimide (12.2 g, 68.5 mmol, 2.1 equiv) was added and the mixture was irradiated with a lamp (hv). The lamp was removed after 1 h and the mixture was stirred overnight.

H₂O (100 mL) was added to the mixture and the layers were separated. The organic layer was washed with H₂O (3×100 mL) and brine (1×200 mL). The organic layer was dried over MgSO₄, filtered and concentrated in vacuo resulting in a colorless oil. The purified product was obtained via recrystallization from hexanes yielding 5 as a white solid in 42% yield. $^1$H NMR (400 MHz, CDCl₃) δ 7.92 (s, 2H), 7.59 (s, 1H), 4.50 (s, 4H), 1.60 (s, 9H). $^{13}$C NMR (400 MHz, CDCl₃) δ 164.7, 138.6, 133.6, 131.3, 130.0, 81.9, 32.2, 28.3. IR ν 2977, 1713, 1241, 1160 cm⁻¹. HRMS (EI⁺) m/z calculated for C₁₃H₁₆Br₂O₂ 361.9517. found 361.9503.

Benzoic Acid 6

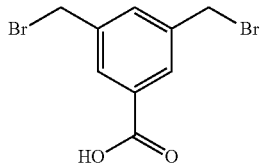 [SMILES: O=C(O)c1cc(CBr)cc(CBr)c1]

Compound 5 (4.90 g, 13.5 mmol, 1 equiv) was dissolved in dry CH₂Cl₂ (under inert atmosphere. Formic acid (54 mL of a 0.25M solution) was added and the mixture was stirred overnight. Solvents were evaporated yielding product 6 as a white powder in a yield of 97% with no need for further purification. $^1$H NMR (400 MHz, CDCl₃) δ 8.08 (s, 2H), 7.69 (s, 1H), 4.52 (s, 4H). $^{13}$C NMR (400 MHz, CDCl₃) δ 170.8, 139.3, 135.0, 130.7, 130.6, 31.8. IR ν 2972, 1694, 1254 cm⁻¹. HRMS (EI⁺) m/z calculated for C₉H₈Br₂O₂ 305.8891. found 305.8889.

Scaffold T4(-≡)₂-3

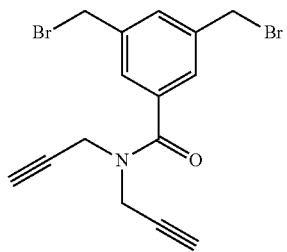 [SMILES: C#CCN(CC#C)C(=O)c1cc(CBr)cc(CBr)c1]

Compound 6 (3.92 g, 12.7 mmol, 1 equiv) was dissolved in SOCl₂ (15 mL) and refluxed overnight at room temperature. After evaporation of the volatiles, the acyl chloride was dissolved in dry CH₂Cl₂ (130 mL). DMAP (37 mg, 0.30 mmol, 0.02 equiv) was added to the mixture, followed by dropwise addition of dipropargylamine (1.42 mL, 1.23 mmol, 1.05 equiv) in CH₂Cl₂ (13 mL) at 0° C. The temperature was increased to room temperature, and after completion of the reaction H₂O (100 mL) and CH₂Cl₂ (50 mL) were added. The layers were separated and the organic layer was washed with H₂O (2×200 mL) and brine (1×250 mL). The organic layer was dried over MgSO₄, filtered and concentrated in vamp. Column purification of the crude product yielded the desired scaffold T4(-≡)₂-3 as a white powder in a yield of 48%. $^1$H NMR (400 MHz, CDCl₃, measured at −50° C.) δ 7.55-7.51 (m, 3H), 4.47 (s, 4H), 4.46 (d, 2H, part of AB), 4.15 (d, 2H, part of AB), 2.44 (t, 1H, part of AB), 2.31 (t, 1H, part of AB). $^{13}$C NMR (400 MHz, CDCl₃, measured at −50° C.) δ 169.6, 139.0, 135.4, 131.8, 127.9, 74.0, 72.8, 38.5 (rotamer signal A), 33.9 (rotamer signal B), 32.2. IR ν 3277, 1644, 1599, 1452, 1219 cm⁻¹. HRMS (EI⁺) m/z calculated for C₁₅H₁₃Br₂NO 380.9364. found 380.9345.

Scaffold T4(-≡)₂-4

Bisalcohol 7

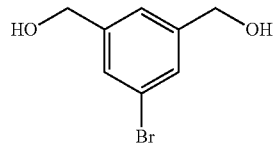 [SMILES: OCc1cc(Br)cc(CO)c1]

5-bromoisophtalic acid (25.0 gram, 0.102 mol, 1 equiv) was acid (25.0 gram, 0.102 mol, 1 equiv) was dissolved in dry THF (500 mL) at 0° C. under argon atmosphere. 10M Borane dimethylsulfide complex (50 mL, 0.50 mmol, 5 equiv) was added and the mixture was stirred at room temperature overnight. H₂O (1000 mL) was added carefully to the mixture followed by addition of EtOAc (1000 mL). After separation of the layers, the organic layer was washed with H₂O (3×750 mL) and brine (1000 mL). The organic layer was dried over MgSO₄, filtered and concentrated in vacuo yielding alcohol 7 as a white powder in 85% yield with no need for further purification. $^1$H NMR (400 MHz, DMSO) δ 7.36 (s, 2H), 7.25 (s, 1H), 5.30 (t, 2H), 4.48 (d, 4H). $^{13}$C NMR (400 MHz, DMSO) δ 145.2, 127.1, 123.1, 121.3, 62.1. IR ν 3210, 2851, 1602, 1419 cm⁻¹. HRMS (FD⁺) m/z calculated for C₈H₉BrO₂ 215.9786, found 215.9798. Spectral data in agreement with reported data (Wytko and Weiss, 1994).

THP-Ether 8

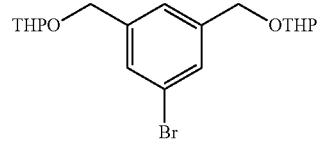

7 (4.18 g, 19.2 mmol, 1 equiv) was dissolved in dry THF (9 mL) under nitrogen atmosphere. 3,4-Dihydro-2H-pyran (5.3 mL, 58 mmol, 3 equiv) and PPTS (417 mg, 1.66 mmol, 0.09 equiv) were added and the mixture was stirred 48 h. H₂O (50 mL) was added and the product was extracted with EtOAc (3×50 mL). The combined organic layers were washed with brine (1×50 mL) and dried over MgSO₄. After filtration and concentration in vacuo, the product was filtered over a plug of silica leading to 8 as a colorless oil in a yield of 90%. $^1$H NMR (400 MHz, CDCl₃) δ 7.44 (s, 2H), 7.25 (s, 1H), 4.75 (d 2H, part of AB), 4.70 (t, 2H), 4.46 (d, 2H, part of AB), 3.92-3.87 (m, 2H), 3.58-3.52 (m, 2H), 1.87-1.52 (m, 12H). $^{13}$C NMR (400 MHz, CDCl₃) δ 140.8, 129.8, 125.5, 122.7, 98.1, 68.1, 62.3, 30.6, 25.6, 19.4. IR ν 2940, 2869, 1574, 1386, 1119, 1024 cm⁻¹. HRMS (FD⁺) m/z calculated for C₁₈H₂₅BrO₄ 384.0936. found 384.0950. Spectral data in agreement with reported data.[1]

Boronic Ester 9

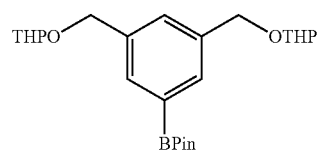

8 (10.4 g, 27.0 mmol, 1 equiv), B$_2$Pin$_2$ (8.41 g, 32.8 mmol, 1.2 equiv), Pd(dba)$_2$ (158 mg, 0.275 mmol, 0.01 equiv), DPEPhos (146 mg, 0.271 mmol, 0.01 equiv) and sodium acetate (4.50 g, 55 mmol, 2 equiv) were combined in dry toluene (35 mL) under nitrogen atmosphere. The mixture was heated to reflux and stirred over weekend. H$_2$O (50 mL) was added, layers were separated and the organic layer was washed with H$_2$O (3×50 mL) and brine (1×250 mL). Drying with MgSO$_4$, filtration and concentration followed by purification via column chromatography (PE/EtOAc: 9:1 to 6:1) yielded compound 9 as a colorless oil in a yield of 86%. $^1$H NMR (400 MHz, CDCl$_3$) δ 7.71 (s, 2H), 7.52 (s, 1H), 4.79 (d, 2H, part of AB), 4.71 (t, 2H), 4.50 (d, 2H, part of AB), 3.95-3.90 (m, 2H), 3.56-3.53 (m, 2H), 1.90-1.50 (m, 12H), 1.34 (s, 12H). $^{13}$C NMR (400 MHz, CDCl$_3$) δ 137.9, 133.8, 130.7, 98.0, 84.0, 69.0, 62.2, 30.7, 25.6, 25.0, 19.5. IR ν 2975, 2870, 1606, 1372, 1344, 1122, 1034 cm$^{-1}$. HRMS (FD$^+$) m/z calculated for C$_{24}$H$_{37}$BO$_6$ 431.2719. found 431.2655.

THP-Biaryl 10

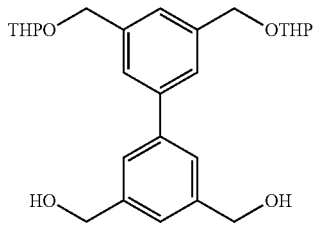

9 (7.36 g, 17.0 mmol, 1.05 equiv) and 7 (3.52 g, 16.2 mmol, 6, 17.0 mmol, 1.05 equiv) and 7 (3.52 g, 16.2 mmol, 1 equiv) were added in dioxane/H$_2$O (2:1, 85 mL) under nitrogen atmosphere. Potassium carbonate (6.70 g, 48.6 mmol, 3 equiv) and Pd(dppf)Cl$_2$ (1.21 g, 1.64 mmol, 0.1 equiv) were added and the mixture was stirred overnight at 60° C. The mixture was poured in H$_2$O (500 mL) and the mixture was extracted with EtOAc (3×400 mL). The combined organic layers were washed with brine (1×1000 mL) and dried over MgSO$_4$, filtered and concentrated in vacuo. Purification via column chromatography (PE/EtOAc 1:1 to 1:3) yielded 10 as a colorless oil in a yield of 86%. $^1$H NMR (400 MHz, CDCl$_3$) δ 7.48 (s, 2H), 7.46 (s, 2H), 7.35 (s, 1H), 7.28 (s, 1H), 4.81 (d, 2H, part of AB), 4.73 (t, 2H), 4.65 (s, 4H), 4.53 (d, 2H, part of AB), 3.96-3.91 (m, 2H), 3.59-3.53 (m, 2H), 3.11 (br s, 2H), 1.90-1.52 (m, 12H). $^{13}$C NMR (400 MHz, CDCl$_3$) δ 141.9, 141.4, 141.2, 138.9, 126.6, 126.1, 124.9, 124.5, 98.0, 68.9, 65.0, 62.4, 30.6, 25.5, 19.5. IR ν 3395, 2940, 2868, 1601, 1119, 1025 cm$^{-1}$. HRMS (FD$^+$) m/z calculated for C$_{26}$H$_{34}$O$_6$ 442.2355. found 442.2347.

Propargylic Ether 11

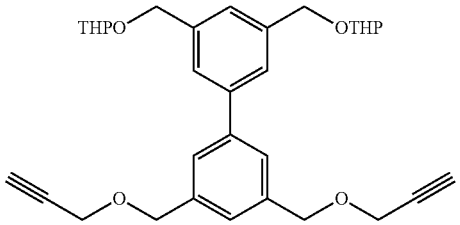

10 (3.42 g, 7.75 mmol, 1 equiv) was added to a suspension of NaH (691 mg, 17.3 mmol, 2.2 equiv) in THF (45 mL) at 0° C. After stirring for 1 h, propargyl bromide (1.3 mL, 17.3 mmol, 2.2 equiv) was added dropwise and the mixture was stirred overnight at rt. H$_2$O (500 mL) was added and the product was extracted with EtOAc (4×300 mL). The combined organic layers were washed with brine (1000 mL), dried over MgSO$_4$ and concentrated in vacuo. Purification by column chromatography (PE/EtOAc 4:1) furnished 11 as a colorless oil (70%). $^1$H NMR (400 MHz, CDCl$_3$) δ 7.54 (s, 2H), 7.52 (s, 2H), 7.37 (s, 1H), 7.34 (s, 1H), 4.85 (d, 2H, part of AB), 4.74 (t, 2H), 4.68 (s, 4H), 4.57 (d, 2H, part of AB), 4.22 (d, 4H), 3.97-3.92 (m, 2H), 3.59-3.52 (m, 2H), 2.49 (t, 2H), 1.92-1.50 (m, 12H). $^{13}$C NMR (400 MHz, CDCl$_3$) δ 141.7, 141.1, 139.1, 138.2, 126.8, 126.7, 126.6, 126.1, 98.0, 79.7, 74.9, 71.5, 68.9, 62.4, 57.4, 30.7, 25.6, 19.5. IR ν 3285, 2941, 2868, 1601, 1385, 1118, 1078, 1034 cm$^{-1}$. HRMS (FD$^+$) m/z calculated for C$_{32}$H$_{38}$O$_6$ 518.2668. found 518.2675.

Bisalcohol 12

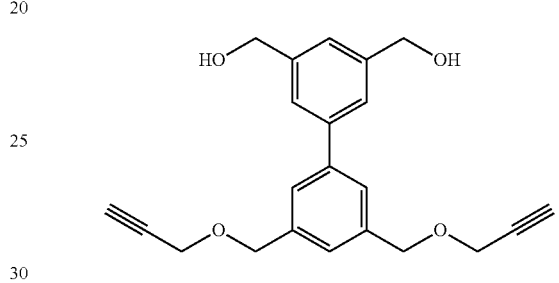

11 (2.78 g, 5.37 mmol, 1 equiv) was dissolved in EtOH (30 mL) and PPTS (4.02 g, 15.8 mmol, 2.9 equiv) was added. The mixture was stirred for 2 h at 55° C., followed by addition of 1420 (50 mL) and extraction with EtOAc (3×100 mL). The combined organic layers were dried over MgSO$_4$ and concentrated in vacuo. Column chromatography (PE/EtOAC 2:1 to 1:2) afforded the 12 in 98% as a colorless oil. $^1$H NMR (400 MHz, CDCl$_3$) δ 7.47 (s, 2H), 7.41 (s, 2H), 7.30 (s, 1H), 7.23 (s, 1H), 4.61 (s, 4H), 4.57 (s, 4H), 4.20 (d, 4H), 3.72 (s, 2H), 2.52 (t, 2H). $^{13}$C NMR (400 MHz, CDCl$_3$) δ 141.8, 141.2, 140.7, 138.1, 126.7, 126.3, 124.7, 124.5, 79.6, 75.1, 71.4, 64.6, 57.4. IR ν 3287, 2860, 1601, 1445, 1350, 1254, 1162, 1071 cm$^{-1}$. HRMS (FD$^+$) m/z calculated for C$_{22}$H$_{22}$O$_4$ 350.1518. found 350.1515.

Scaffold T4(-≡)$_2$-4

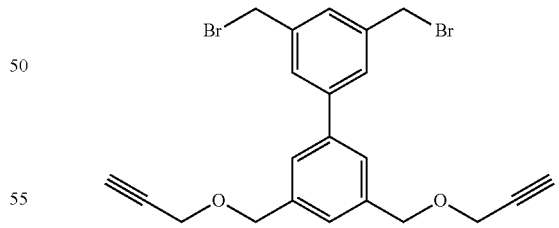

Compound 12 (861 mg, 2.46 mmol, 1 equiv) and Et$_3$N (860 μL, 6.15 mmol, 2.5 equiv) was dissolved in dry THF (25 mL) at 0° C. followed by the dropwise addition of MsCl (761 μL, 9.84 mmol, 4 equiv). The mixture was stirred at RT overnight and subsequently quenched with H$_2$O (100 mL) for 1 h. The product was extracted with EtOAc (3×150 mL) and washed with sat. NaBr-solution (300 mL). The organic layer was dried over MgSO$_4$ and concentrated in vacuo. The resulting colorless oil was dissolved in dry THF (20 mL), LiBr (855 mg, 9.84 mmol, 4 equiv) was added and the mixture was stirred for 2 h. H₂O (100 mL) was added followed by extraction with EtOAc (3×200 mL). The combined organic layers were washed with sat. NaBr-solution (500 mL), dried over MgSO₄ and concentrated in vacuo. Purification by column chromatography (PE/EtOAc 5:1 to 3:1) yielded scaffold T4(-≡)₂-4 as a white powder (80%). $^1$H NMR (400 MHz, CDCl₃) δ 7.55 (s, 2H), 7.52 (s, 2H), 7.41 (s, 1H), 7.37 (s, 1H), 4.68 (s, 4H), 4.53 (s, 4H), 4.24 (d, 4H), 2.50 (t, 2H). $^{13}$C NMR (400 MHz, CDCl₃) δ 142.1, 140.5, 139.1, 138.5, 128.7, 128.1, 127.1, 126.4, 79.6, 75.0, 71.4, 57.6, 32.9, 29.8. IR ν 3289, 2924, 2853, 1601, 1448, 1352, 1214, 1082 cm$^{-1}$. HRMS (EI$^+$) m/z calculated for C₂₂H₂₀Br₂O₂ 473.9830. found 473.9840.

Scaffold T6(E)₃-1

Phthalimide 13

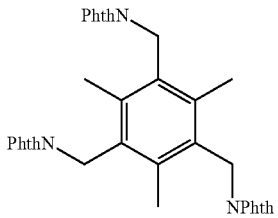

1,3,5-tris(bromomethyl)mesitylene (19.8 mmol, 7.88 g, 1 equiv.) was dissolved in anhydrous DMF (300 mL) under inert atmosphere. Phthalimide potassium salt (120 mmol, 22.2 g, 6 equiv.) was added and the mixture was refluxed overnight. After cooling down to room temperature, the mixture was filtered and successively washed with DMF (2×50 mL), H₂O (2×100 mL) and acetone (100 mL). After drying of the residue in vacuo, product 13 was isolated as a white solid (16.8 mmol, 85%). Spectral data was in agreement with reported data (Roelens et al. 2009).

Bromide 14

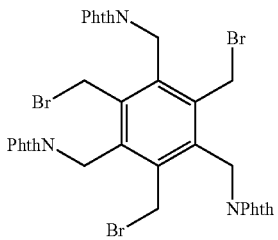

Phthalimide 13 (18.1 mmol, 10.8 g, 1 equiv.) was suspended in 1,2-dibromoethane (120 mL) and bromine (60.2 mmol, 3.1 mL, 3.3 equiv.) was added. The mixture was stirred and irradiated at 120° C. for 25 min and afterwards additionally irradiated without heating for 2.5 h. The excess of bromine was quenched by adding an aqueous solution of thiosulfate ( . . . M) and the product was extracted with dibromoethane (2×50 mL). The combined organic layers were washed with saturated NaHCO₃-solution (100 mL), brine (150 mL) and dried over MgSO₄, filtered and concentrated in vacuo. Purification by column chromatography (CH₂Cl₂) yielded 14 as a yellow solid (9.11 mmol, 51%). Spectral data was in agreement with reported data (Roelens et al. 2009).

Propargylic Ether 15

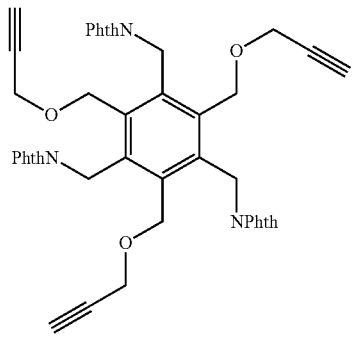

14 (8.45 mmol, 7.05 g, 1 equiv, prepared according to literature procedure) was suspended in DMSO (85 mL) and silver triflate (28.6 mmol, 7.34 g, 3.4 equiv.) was added. The mixture was stirred vigorously under darkness for 1 h followed by addition of DIPEA (42.3 mmol, 7.4 mL, 5 equiv.) and stirring for 1 h. Water (50 mL) was added and the mixture was filtered, followed by extraction with CH₂Cl₂ (4×100 mL). The combined organic layers were washed with 2M HCl (2×75 mL) and water (100 mL) and dried over MgSO₄, filtered and concentrated. The crude yellow solid (7.40 mmol, 88%) was dissolved in dry CH₂Cl₂ (170 mL) under inert atmosphere. In situ generated trimethyl(2-propyn-1-yloxy)silane (3.5 equiv.) and triethylsilane (22.6 mmol, 3.4 mL, 3.4 equiv.) were added and the mixture was cooled to −60° C. TMSOTf (3.42 mmol, 620 μL, 0.5 equiv.) was added and the mixture was stirred overnight at rt. After dilution with DCM (200 mL), the mixture was washed with H₂O (200 mL), brine (250 mL) and dried over MgSO₄. Filtration, concentration and purification by column chromatography (CH₂Cl₂/EtOAc 95:5) yielded 15 as a white solid (3.987 mmol, 59%). $^1$H NMR (400 MHz, CDCl₃) δ 7.79-7.65 (dq, 12H), 5.08 (s, 6H), 4.96 (s, 6H), 3.97 (d, 6H), 2.22 (t, 3H). $^{13}$C NMR (400 MHz, CDCl₃) δ 168.17, 137.76, 132.25, 133.90, 132.23, 123.34, 79.47, 74.69, 66.40, 57.80, 37.00. IR ν 1770, 1391, 1058, 712 cm$^{-1}$. HRMS (FD$^+$) m/z calculated for C₄₅H₃₃N₃O₉ 759.2217. found 759.2191.

Scaffold T6(-≡)₃-1

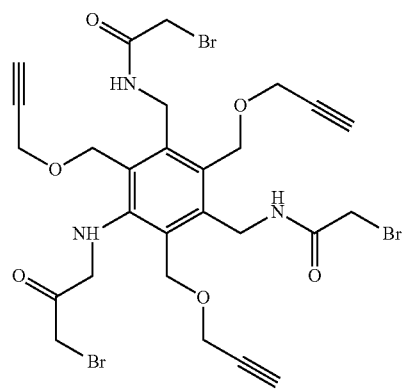 [SMILES: C#CCOCc1c(CNC(=O)CBr)c(COCC#C)c(NCC(=O)CBr)c(COCC#C)c1CNC(=O)CBr]

To a suspension of propargylic ether 15 (0.341 mmol, 259 mg, 1 equiv.) in EtOH/toluene (3:1, 3.5 mL) under inert atmosphere was added methylhydrazine (2.09 mmol, 110 μL, 6.1 equiv.). The mixture was stirred overnight at 90° C. After completion, the mixture was poured into a 40% KOH-solution (25 mL) and extracted with CH₂Cl₂ (3×25 mL). The combined organic layers were dried over MgSO4, filtered and concentrated. The crude white solid (0.252 mmol, 74%) was used in the follow-up reaction without further purification. Bromoacetylbromide (23.0 mmol, 2 mL, 17 equiv.) was added in dry CH$_2$Cl$_2$ (15 mL) and the mixture was cooled to 0° C. Triamine X (1.35 mmol, 497 mg, 1 equiv.) in CH$_2$Cl$_2$ (15 mL) was added dropwise to the mixture. After completion, the mixture was quenched with saturated NaHCO$_3$-solution (25 mL) and extracted with CH$_2$Cl$_2$ (3×30 mL). The combined organic layers were washed with H$_2$O (50 mL), brine (35 mL) and dried over MgSO$_4$. Concentration and purification with column chromatography (PE/EtOAc 2:1 to 5:1) yielded the desired T6(-≡)$_3$-1 scaffold (0.739 mmol, 55%) as a white powder. $^1$H NMR (400 MHz, CDCl$_3$) δ 7.16 (t, 3H), 4.82 (s, 6H), 4.72 (d, 6H), 4.36 (d, 6H), 3.86 (s, 6H), 2.58 (t, 3H). $^{13}$C NMR (400 MHz, CDCl$_3$) δ 164.85, 139.08, 136.91, 78.80, 76.22, 65.91, 58.51, 38.37, 29.09. IR v 3277, 1641, 1537, 1070 cm$^{-1}$. HRMS (FD$^+$) m/z calculated for C$_{27}$H$_{30}$Br$_3$, N$_3$O$_6$ 731.9791. found 731.9744.

3. Solid-Phase Peptide Synthesis (SPPS)

General Section:

Amino acids are indicated by single-letter codes; peptides are acetylated at the N-terminus and amidated at the C-terminus. Unnatural amino acid azidohomoalanine is abbreviated as [Aha].

General Procedure for Fmoc-Synthesis of Peptides:

Peptides were synthesized on solid-phase using a 4-(2', 4'-dimethoxyphenyl-Fmoc-aminomethyl)-phenoxy (RinkAmide) resin (BACHEM, Germany) on a Prelude (Protein Technologies Incl., USA), Symfony (Protein Technologies Inc., USA), Syro(I) (MultiSyntech, Germany) synthesizer. All Fmoc-amino acids were purchased from Biosolve (Netherlands) or Bachem GmbH (Germany) with appropriate side-chain functionalities protected as N-t-Boc (amino acids KW), O-t-Bu (DESTY), N-Trt (HNQ), S-Trt (C) or N-Pbf (R) groups. All solvents used in peptide synthesis (piperidine, trifluoroacetic acid, NMP and DMF were bought from Biosolve (Netherlands) in peptide grade quality. Fmoc-azidohomoalanine-OH (Fmoc-Aha-OH) was synthesized according to a literature procedure described by Spring et al. in 2011. Amino acids were dissolved in DMF (200 mM) and used as such. Piperidine was used as a 20% stock solution in NMP, HATU as an 0.4M stock solution in DMF, and DIPEA as a 2M stock solution in NMP. Standard amino acids, including [Aha] were coupled via a single-coupling protocol (5-fold excess of HATU/amino acid and 10-fold excess of DIPEA) with a reaction time of 1 hour. In case of difficult amino acid couplings, e.g. R, K and C, the double-coupling protocol (10-fold excess of HATU/amino acid and 20-fold excess of DIPEA) with a reaction time of 2×15 min was used. Acetylation (Ac) of the N-terminus of the peptide was performed by reacting the resin with NMP/Ac$_2$O/DIPEA (10:1:0.1) for 30 minutes at room temperature. The acetylated peptide was cleaved from the resin by reaction with a cocktail of TFA/MiliQ/thioanisole/DODT/TIS (90:5:2.5:5:2.5) for 2 hours at room temperature. Precipitation of the peptide with Et$_2$O/pentane (1:1) followed by lyophilization of the precipitated peptide afforded the crude peptide. Purification of the crude peptide was performed by reversed-phase HPLC (mobile phase consists of gradient mixture of eluent-A(milliQ-H$_2$O containing 0.05% TFA) and eluent-B (ACN containing 0.05% TFA).

4. CLIPS/CuAAC Ligation-Cyclization

Cyclizations with T4 Scaffolds

General Information

Ligation-cyclization reactions were measured on a UPLC-ESMS system (3 min, 5-80% B, Acquity UPLC Peptide BEH C18 Column, 130 Å, 1.7 µm, 2.1×50 mm with UV detection (λ=215 nm) and positive ion current for MS analysis, unless stated otherwise. Linear peptides are described with a number (#) followed by in subscript the loop length (y), e.g. #$_{333}$ (for a certain peptide with 3×3×3 peptide loops). Monocyclic CLIPS-peptides are described with covalent attachment to the T4(-≡)$_2$-@ (where @ is the scaffold number which is 1,2,3 or 4), e.g. [#$_{333}$-T4(-≡)$_2$-@]. Tricyclic CLIPS/CuAAC peptides are described with a Roman Number instead of an Arabic number, e.g. the product of tricyclization of peptide 1$_{333}$ with scaffold T4(-≡)$_2$-4 will be described as [I$_{333}$-T4(-≡)$_2$-4].

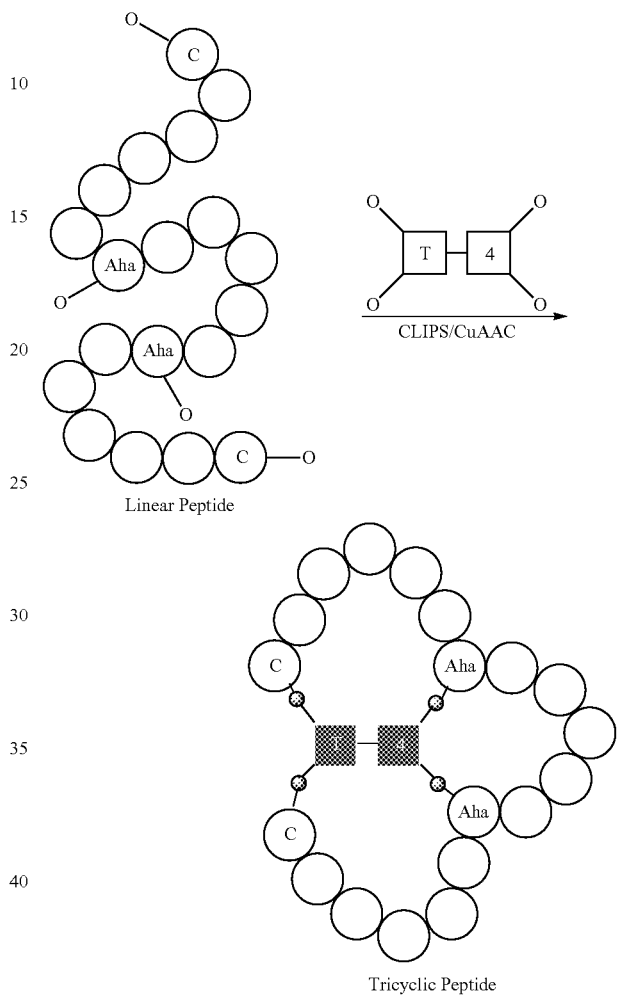

General Procedures for the One-Pot CLIPS/CuAAC Ligation-Cyclization

Linear peptide (1.0 equiv) was dissolved in DMF/H$_2$O (2:1, 0.5 mM) and 0.8 equiv of a 10 mM stock solution of T4(-≡)$_2$-scaffold (in DMF) was added to the mixture. The pH of the solution was adjusted to 8 by adding NH$_4$HCO$_3$-solution (1M) in order to start the CLIPS reaction. After complete consumption of the linear peptide, a pre-incubated cocktail of CuSO$_4$ (2 equiv), THPTA-ligand (2 equiv) and sodium ascorbate (10 equiv) in H$_2$O was added to the reaction mixture. After completion, 0.1M EDTA-solution (5 equiv) was added to the mixture to quench the reaction, followed by immediate reversed phase HPLC purification or lyophilization.

CuAAC-Reaction Completion Check: Staudinger Reduction

To check whether CuAAC reaction was completed, to a 70 uL UPLC sample was added 20 uL 1M TCEP. The mixture was incubated for 24 h and analyzed with UPLC. Both CLIPS/CuAAC and CuAAC/CLIPS were carried out. When CuAAC was carried out first, the free thiols of cysteine residues were prone to oxidation along with severe coordination towards copper(I) leading to formation of S—S oxidized peptide. Furthermore, CLIPS reactions can be performed under micromolar concentrations thereby limiting the oligomerization of the peptide-scaffold constructs. For these reasons it is recommended to always start with CLIPS prior to CuAAC.

Figure 18A:
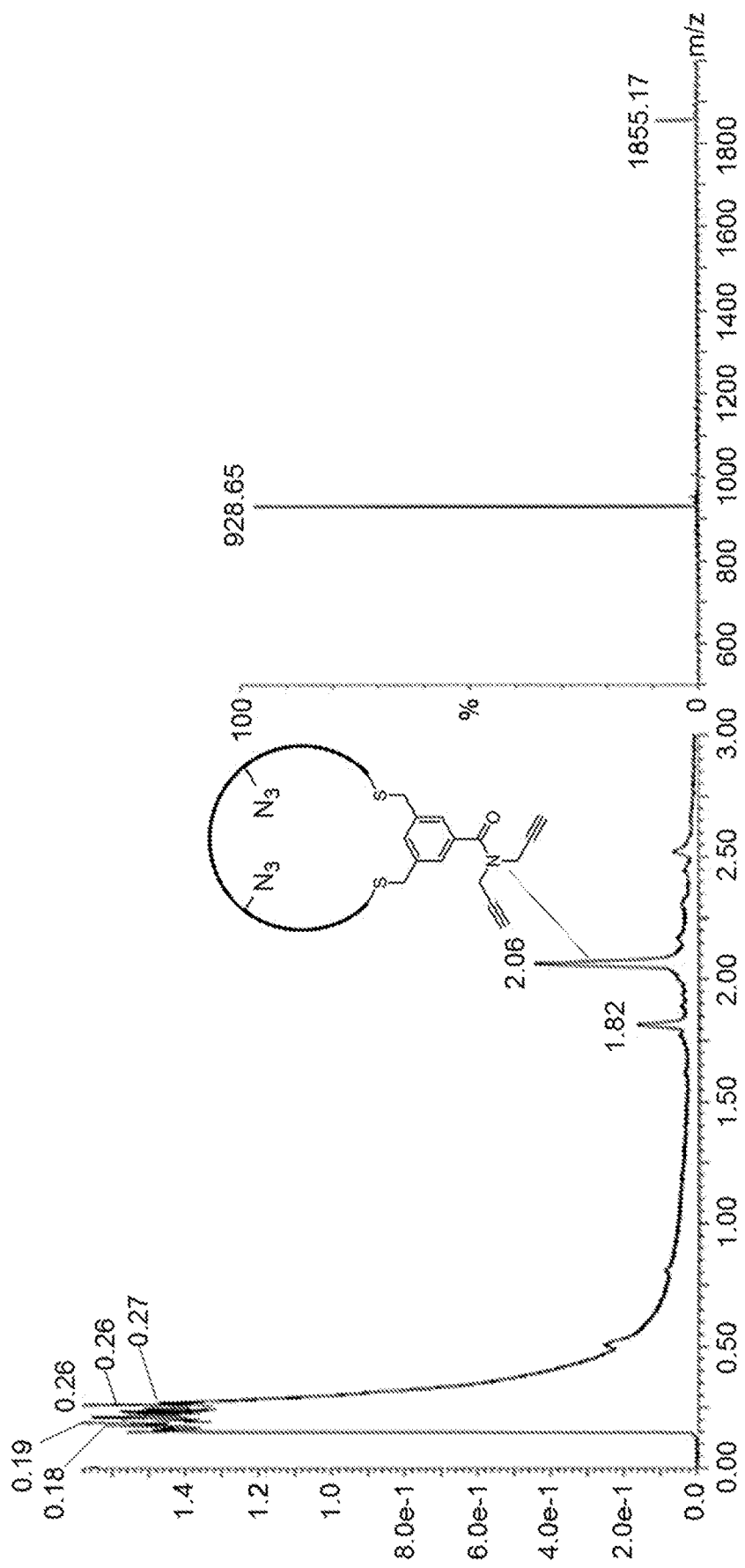
FIG. 18. A. The UPLC-MS chromatogram of a CLIPS reaction where $R_t$=2.06 min. corresponds to the CLIPSed peptide. B. UPLC-MS chromatogram one minute after the addition of the copper/ligand/ascorbate mix (CLICK) which proves complete conversion as $R_t$=1.64 min. The small peak with $R_t$=1.82 min. corresponds to a small amount of S—S oxidized peptide.
Figure 18B:
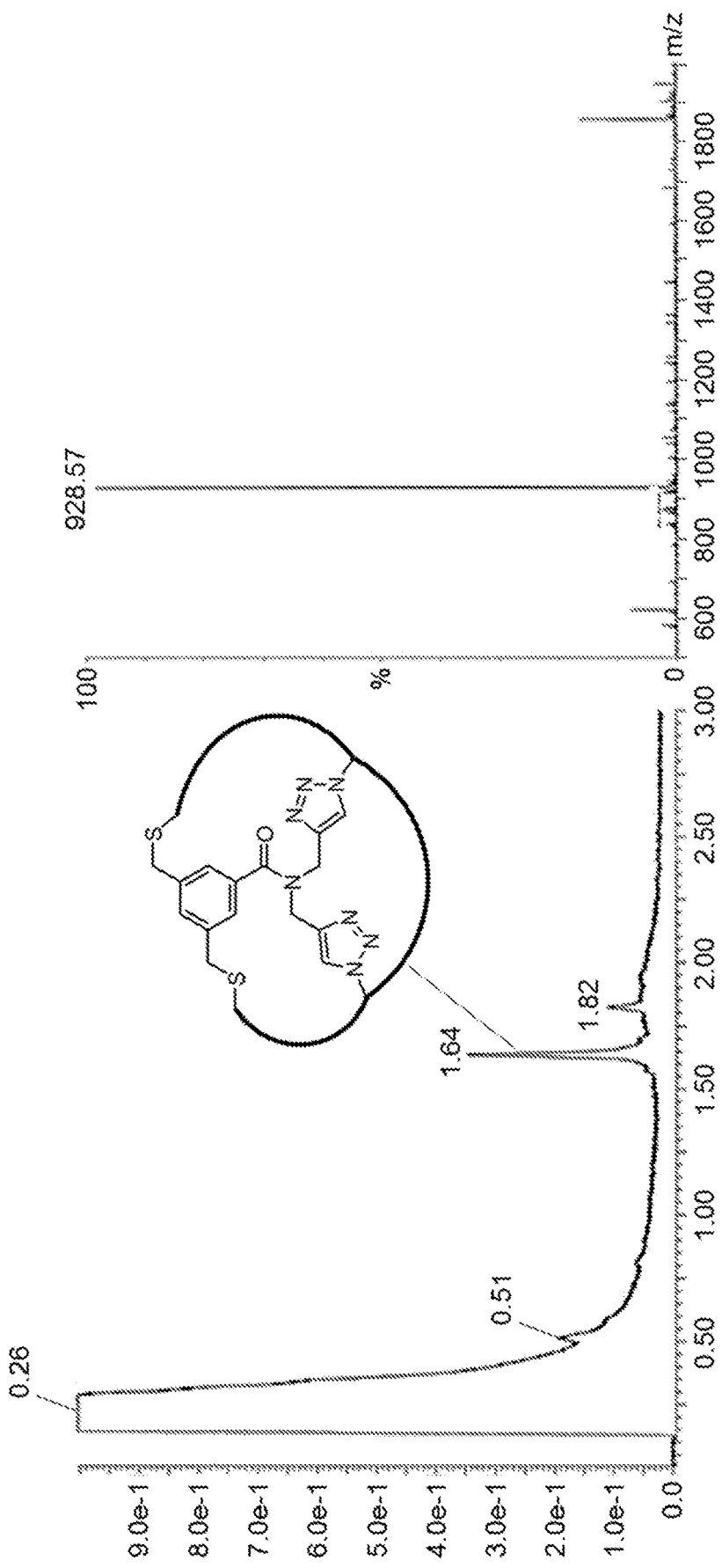

Full Experimental Procedure for CLIPS/CLICK Cyclization of Peptide Ac—CQWG[Aha]KSR[Aha]FIIC—NH$_2$ on Scaffold T4(-≡)$_2$-3 tion, followed by direct analysis with UPLC/UV and ESI-MS. Therefore, a 50 µL sample of the reaction mixture was mixed with 20 µL of a 0.1 M EDTA-solution (pH=7.8) in order to complex all added Cu(I) ions and thus quench the CLICK-reaction. After 1 minute, the reaction was essentially complete according to UPLC-MS (FIG. 18B).

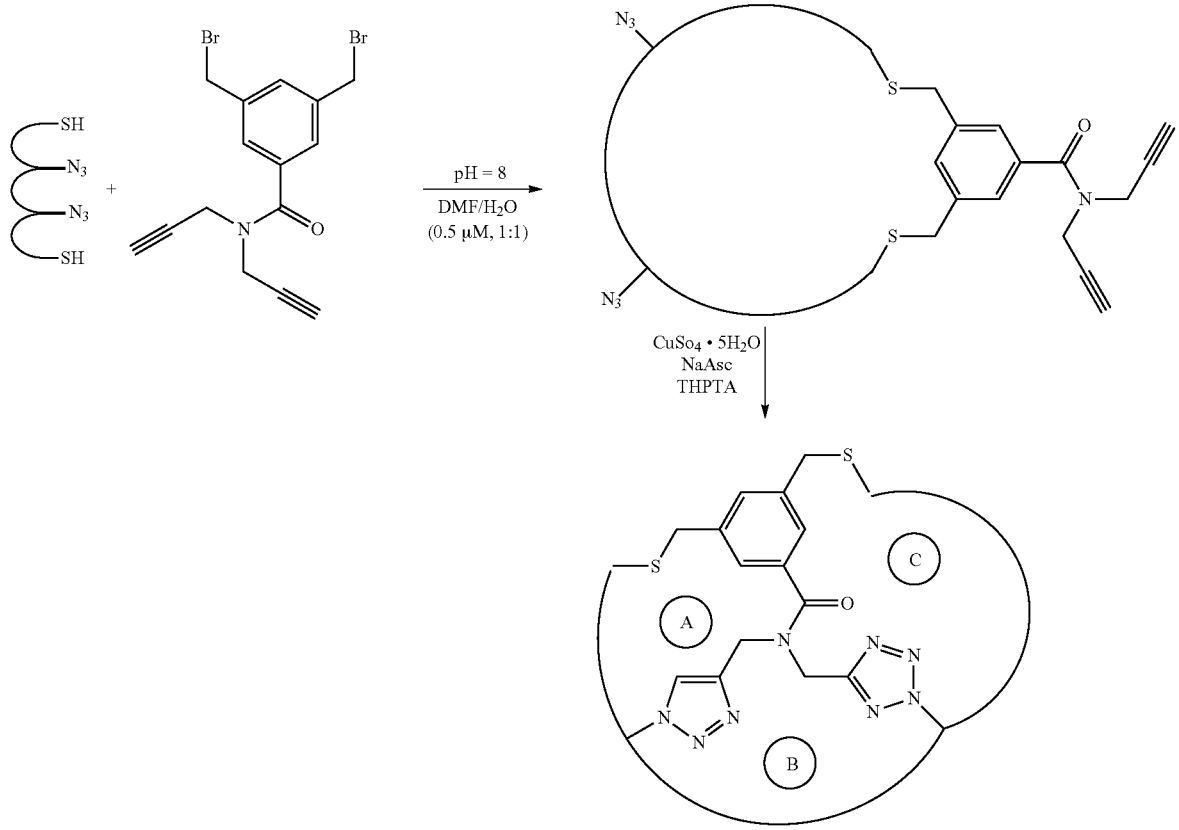

CLIPS: Peptide Ac—CQWG[Aha]KSR[Aha]FIIC—NH$_2$ (1.00 mg, 0.612 µmol, 1 equiv.) was dissolved in DMF/H$_2$O (2:1, 1.2 mL) to give a 0.5 mM solution. Then, scaffold T4(-≡)$_2$-3 (1.71 mg, 4.45 µmol) was dissolved in DMF (445 µL) to give a 10 mM solution and 49 µL (0.8 equiv.) of this solution was added to the peptide solution. Subsequently, 10 µL of an NH$_4$HCO$_3$-solution (1M) was added to reach pH=8 in order to start the reaction. Complete consumption of the peptide and formation of the monocyclic peptide was confirmed by UPLC/UV in combination with ESI-MS analysis (FIG. 18A), which took less than 30 minutes in this particular case.

CLICK: A 10 mM stock solution of copper(II) sulfate pentahydrate in H$_2$O was prepared by dissolving copper(II) sulfate pentahydrate (5.0 mg, 20 µmol) in 500 µL H$_2$O. A 10 mM stock solution of THPTA ligand in H$_2$O was prepared by dissolving THPTA (5.0 mg, 12 µmol) in 1.2 mL H$_2$O. Both compounds were added in twofold molar excess with respect to the peptide. 122 µL of a 10 mM copper(II)sulfate stock solution and 122 µL of a 10 mM THPTA stock solution were combined in a separated vial, followed by the addition of 5 equiv. of sodium ascorbate (1.2 mg, 6.06 µmol). Eventual equivalents compared to peptide are 2/2/10 for copper/ligand/ascorbate, respectively). Subsequently, the Cu(I)/THPTA/ascorbate mix was added to the peptide solu- Full Experimental Procedure for CLIPS/CuAAC Cyclization of Peptide Ac—CQWG[Aha]KAS[Aha]FSEC—NH$_2$ on Scaffold T4(-≡)$_2$-3

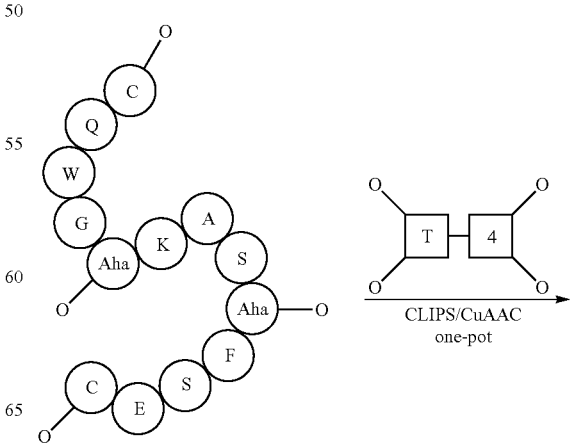

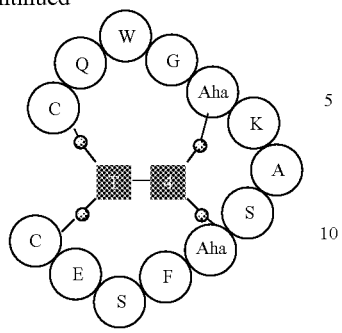

CLIPS: peptide Ac—CQWG[Aha]KAS[Aha]FSEC—NH$_2$ (5.30 mg, 3.44 μmol, 1 equiv) was dissolved in DMF/H$_2$O (2:1, 6.9 mL) to give a 0.5 mM solution. Then, scaffold T4(—≡)$_2$-3 (0.275 μL, 2.75 μmol, 0.8 equiv from a 10 mM solution in DMF) was added. Subsequently, 20 μL of an NH$_4$HCO$_3$-solution (200 mM) was added to reach pH=8 in order to start the reaction.

CuAAC: a pre-incubated mix of CuSO$_4$/THPTA/Asc (2:2:10 equiv compared to linear peptide) in H$_2$O was added to the CLIPS-mixture in order to start the CuAAC-reactions.

Figure 19:
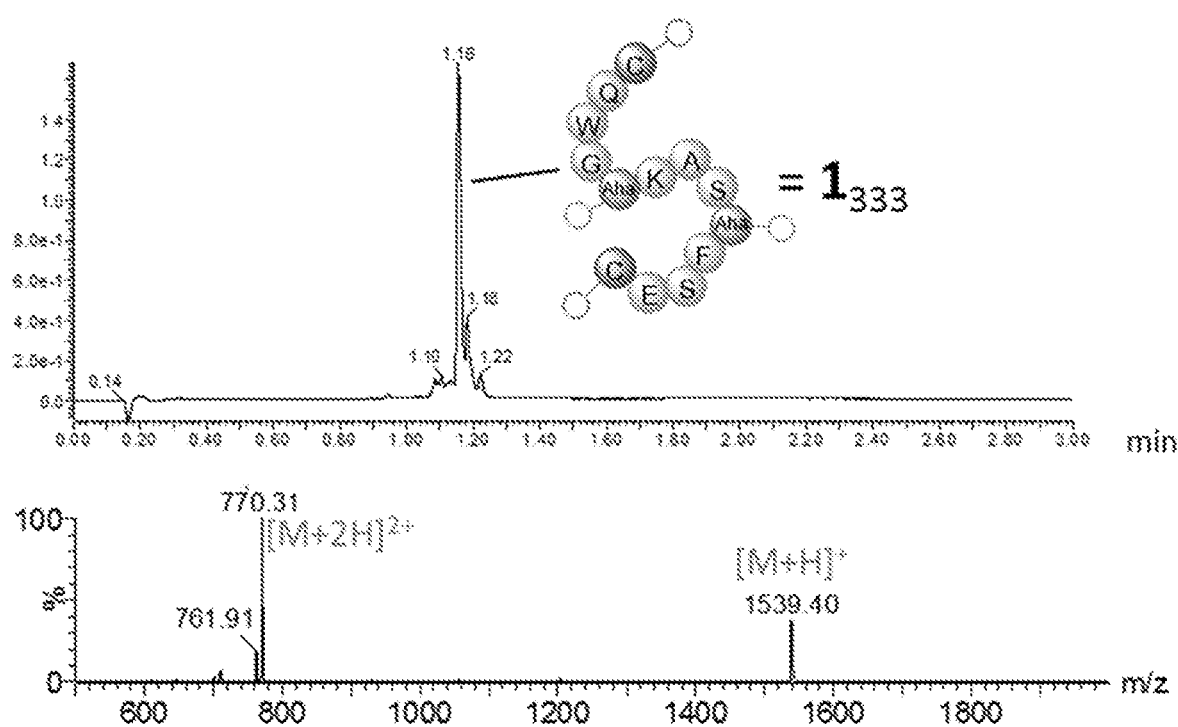
FIG. 19. UPLC-MS chromatogram of linear peptide Ac—CQWG[Aha]KAS[Aha]FSEC—NH$_2$ ($1_{333}$).
Figure 20:
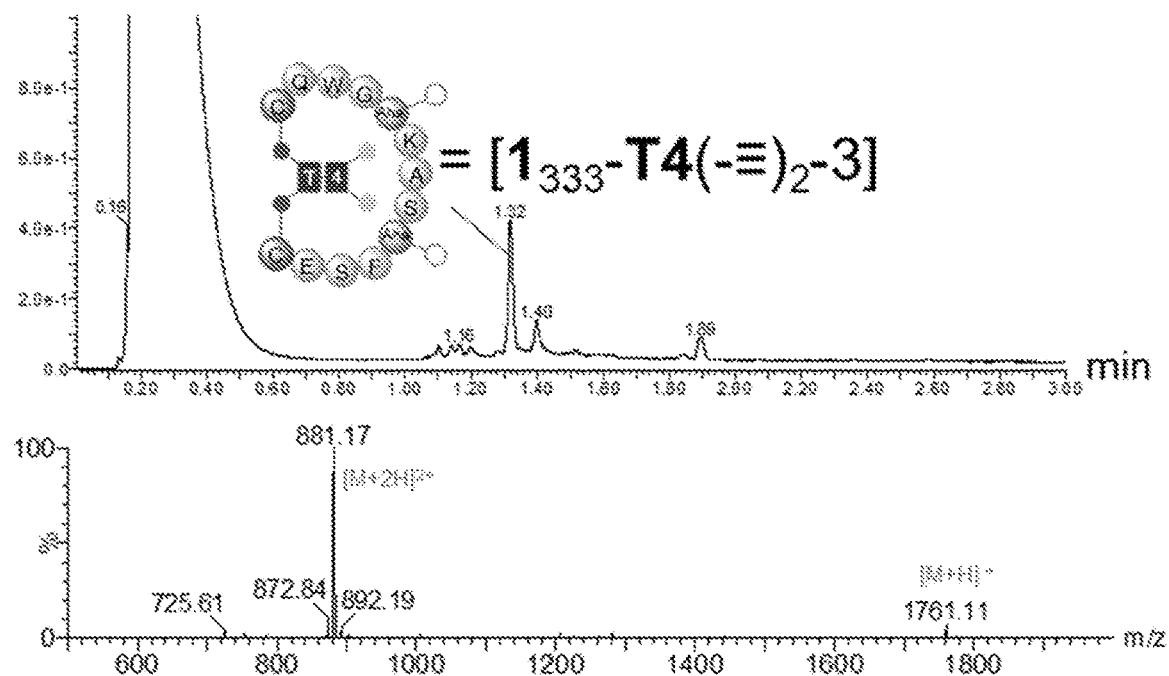
FIG. 20. UPLC-MS chromatogram of one-pot CLIPS/CuAAC reaction. A. Monocyclic CLIPS peptide [$1_{333}$-T4(-≡)$_2$-3]. B. Tricyclic CLIPS/CuAAC peptide [$I_{333}$-T4(—≡)$_2$-3]. C. Isolated tricycle after HPLC purification (CQWG[Aha]KAS[Aha]FSEC on scaffold T4(-≡)$_2$-3).
Figure 20:
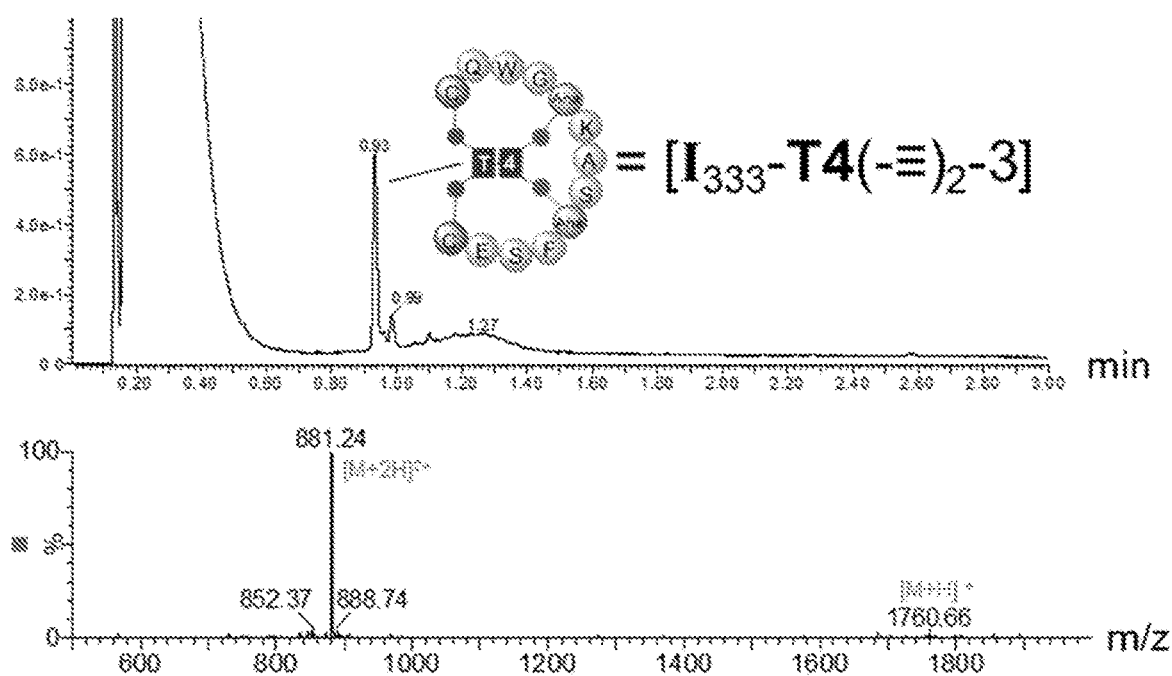
Figure 20:
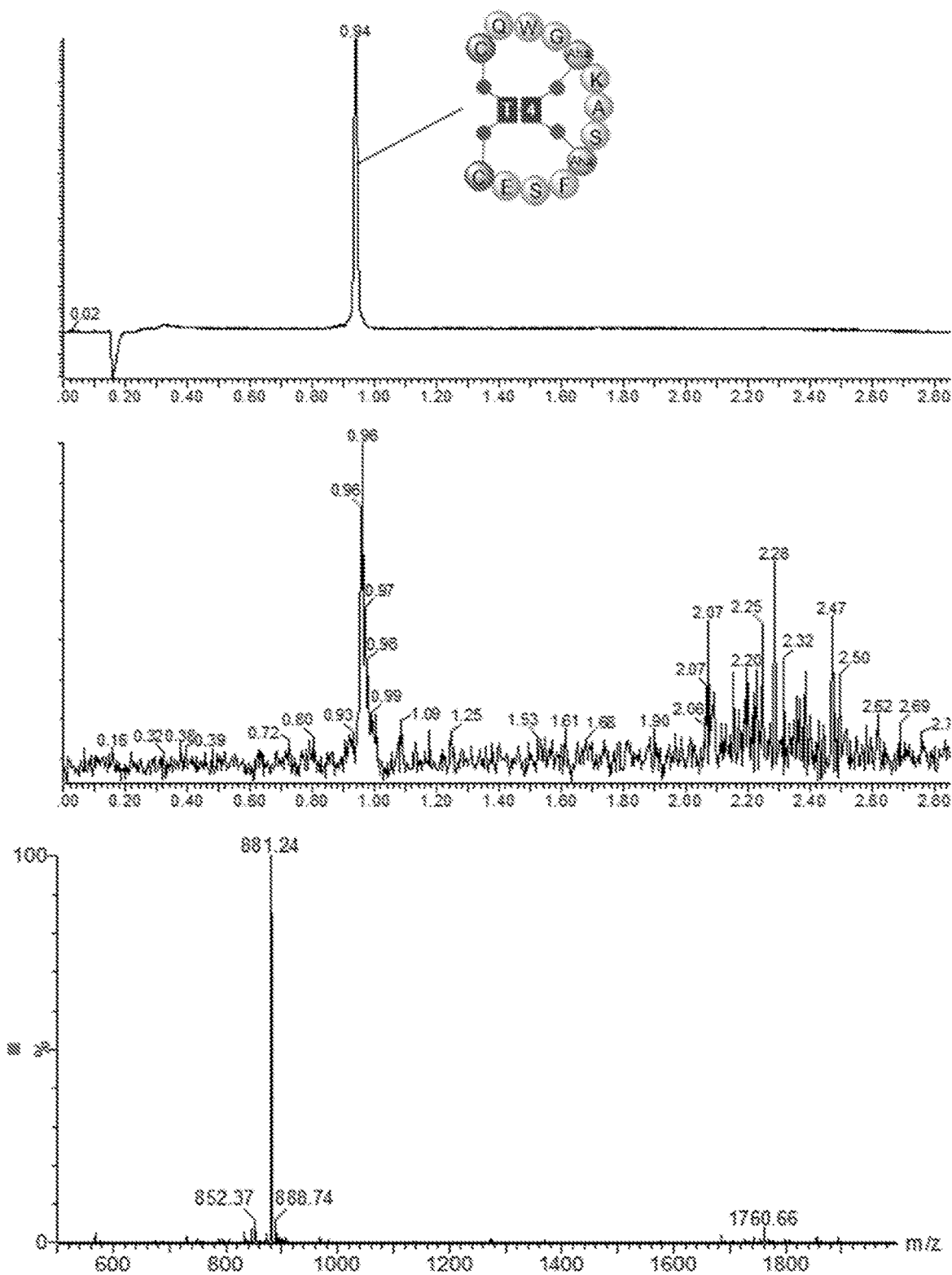

FIG. 19 shows the UPLC-MS chromatogram of the peptide (peptide I$_{333}$). FIG. 20 shown the UPLC-MS chromatogram of the CLIPS (FIG. 20A) and CuAAC (FIG. 20B) reaction of peptide I$_{333}$ coupled to scaffold T4(-≡)$_2$-3.

After completion, the reaction was quenched by adding 0.1M EDTA-solution and directly purified on RP-HPLC yielding the tricyclic peptide in 18% yield (FIG. 20C).

Full Experimental Procedure for CLIPS/CuAAC Cyclization of Peptide Ac—CQWG[Aha]KAS[Aha]FSEC—NH$_2$ on Scaffold T4(-≡)$_2$-4

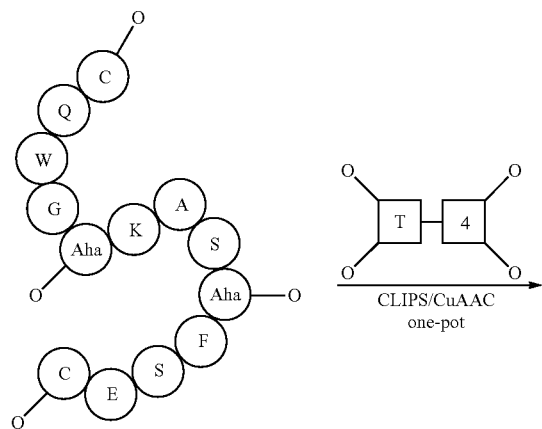

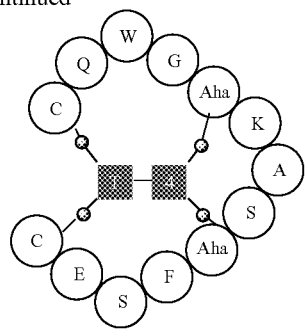

CLIPS: peptide Ac—CQWG[Aha]KAS[Aha]FSEC—NH$_2$ (9.64 mg, 6.26 μmol, 1 equiv) was dissolved in DMF/H$_2$O (2:1, 12.6 mL) to give a 0.5 mM solution. Then, scaffold T4(—≡)$_2$-4 (0.501 μL, 5.01 μmol, 0.8 equiv from a 10 mM solution in DMF) was added. Subsequently, 504 of an NH$_4$HCO$_3$-solution (200 mM) was added to reach pH=8 in order to start the reaction.

CuAAC: a pre-incubated mix of CuSO$_4$/THPTA/Asc (2:2:10 equiv compared to linear peptide) in H$_2$O was added to the CLIPS-mixture in order to start the CuAAC-reactions.

Figure 21:
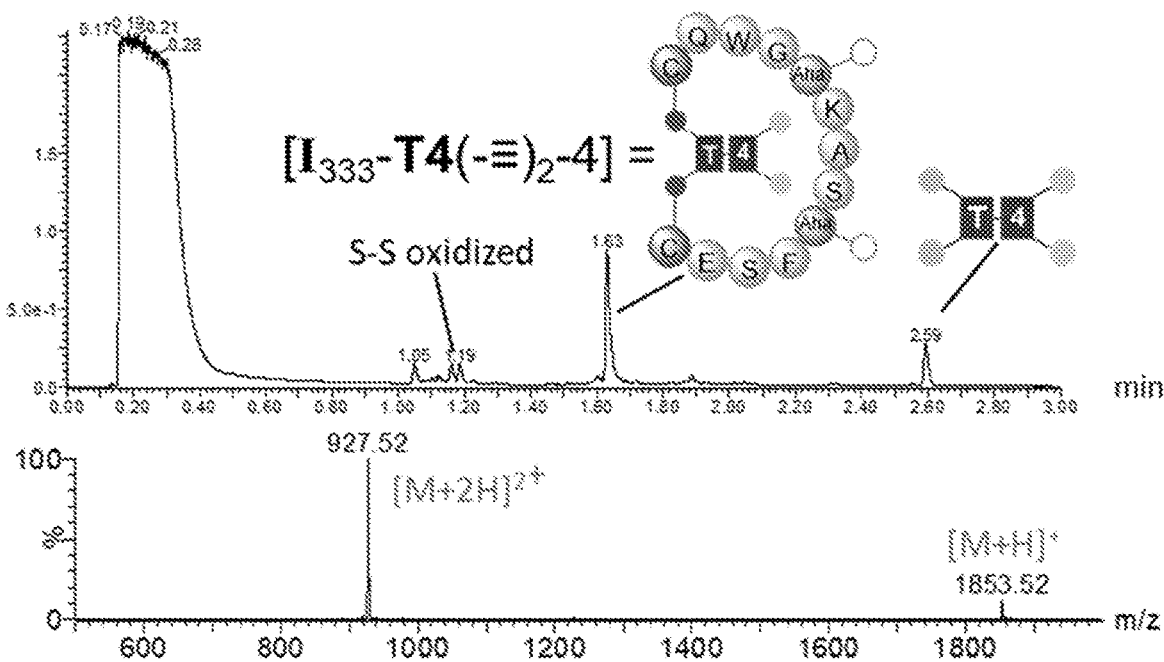
FIG. 21. UPLC-MS chromatogram of one-pot CLIPS/CuAAC reaction. A Monocyclic CLIPS peptide [$1_{333}$-T4(-≡)$_2$-4]. B. Tricyclic CLIPS/CuAAC peptide [$I_{333}$-T4(—≡)$_2$-4]. C. Isolated tricycle after HPLC purification (CQWG[Aha]KAS[Aha]FSEC on scaffold T4(-≡)$_2$-4).
Figure 21:
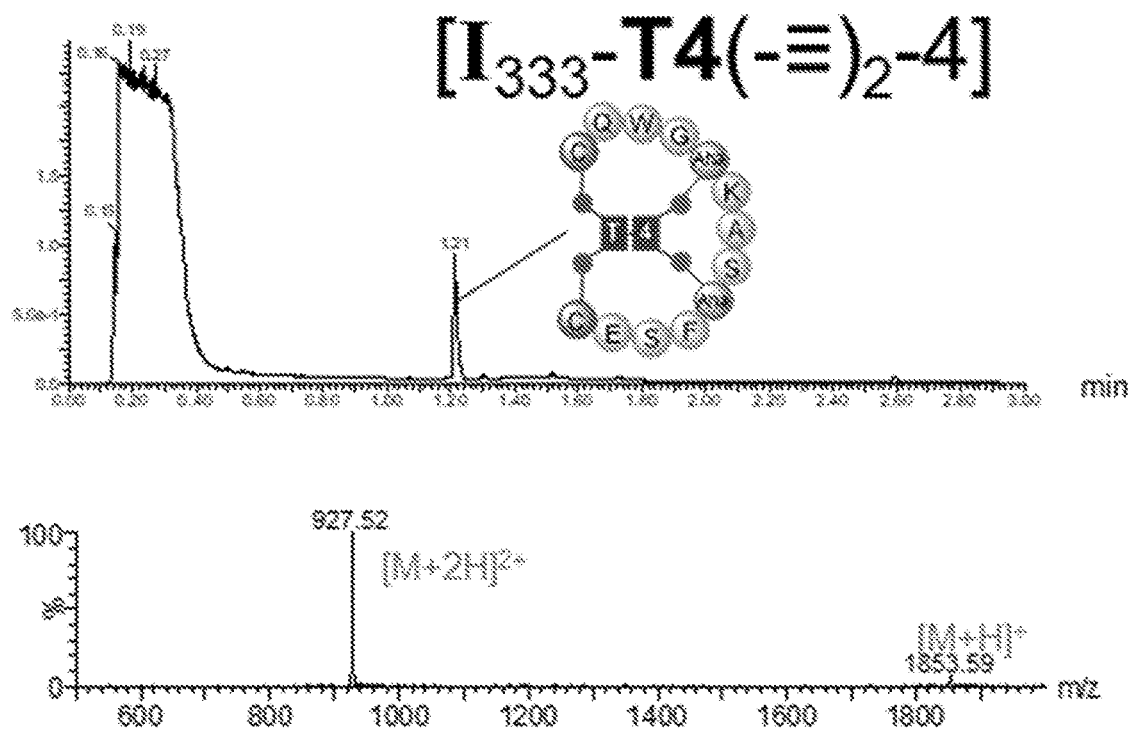
Figure 21:
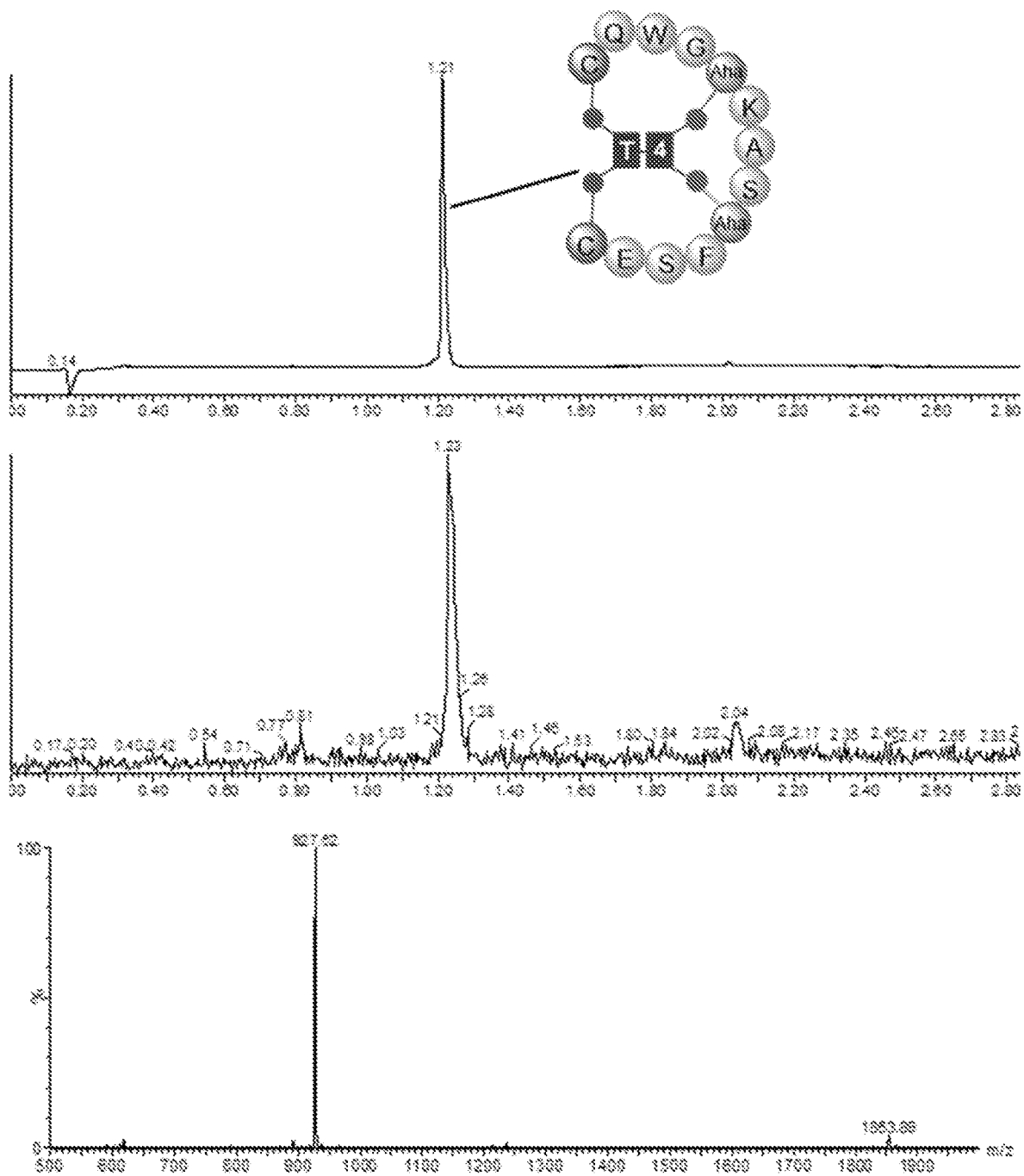
Figure 22:
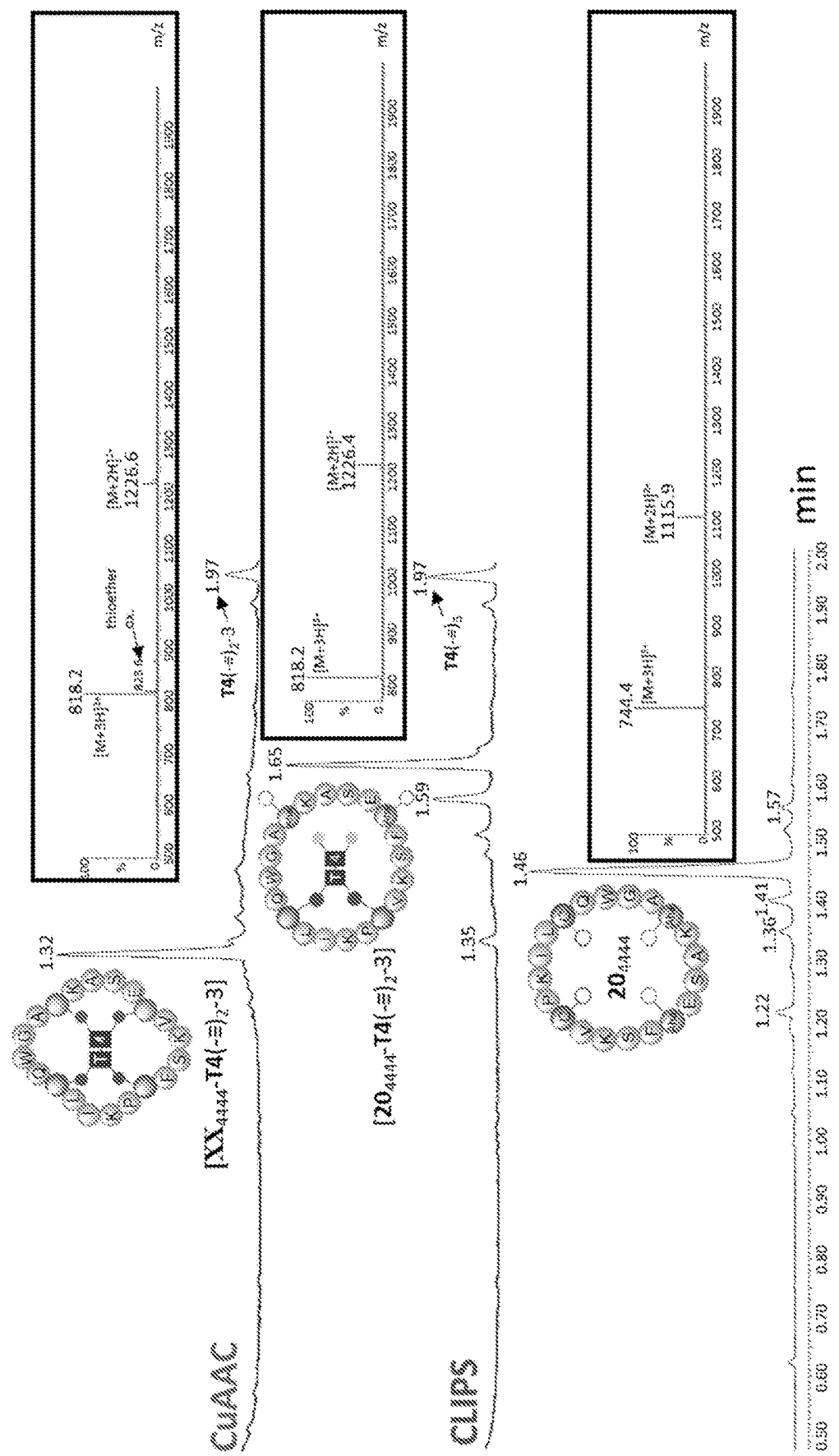
FIG. 22. UPLC-MS chromatogram of one-pot CLIPS/CuAAC reaction of ILCQWGA[Aha]KASE[Aha]FSKVCPK: $20_{4444}$+T4(-≡)$_2$-3.
Figure 23:
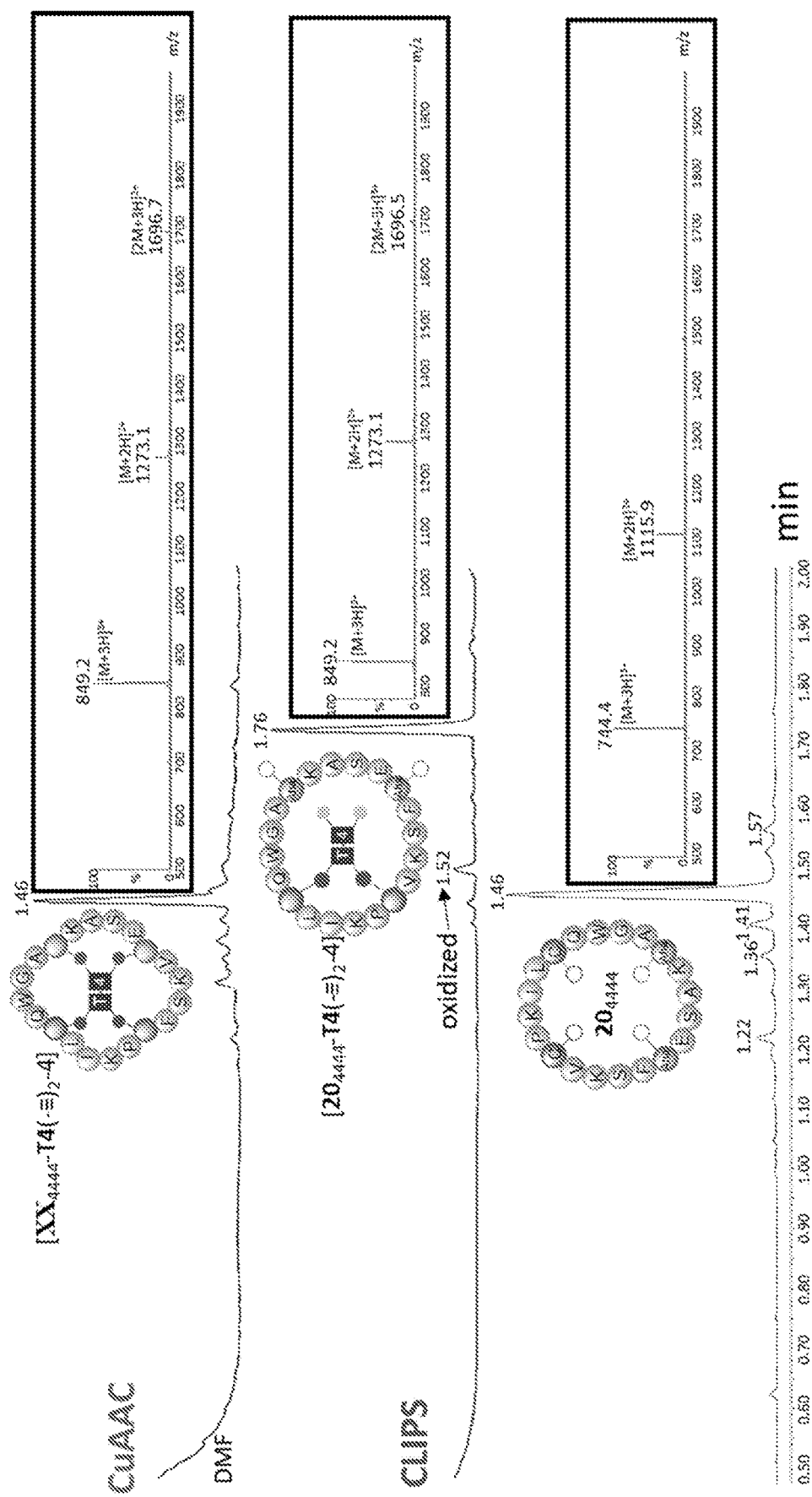
FIG. 23. UPLC-MS chromatogram of one-pot CLIPS/CuAAC reaction of ILCQWGA[Aha]KASE[Aha]FSKVCPK: $20_{4444}$+T4(-≡)$_2$-4.
Figure 24:
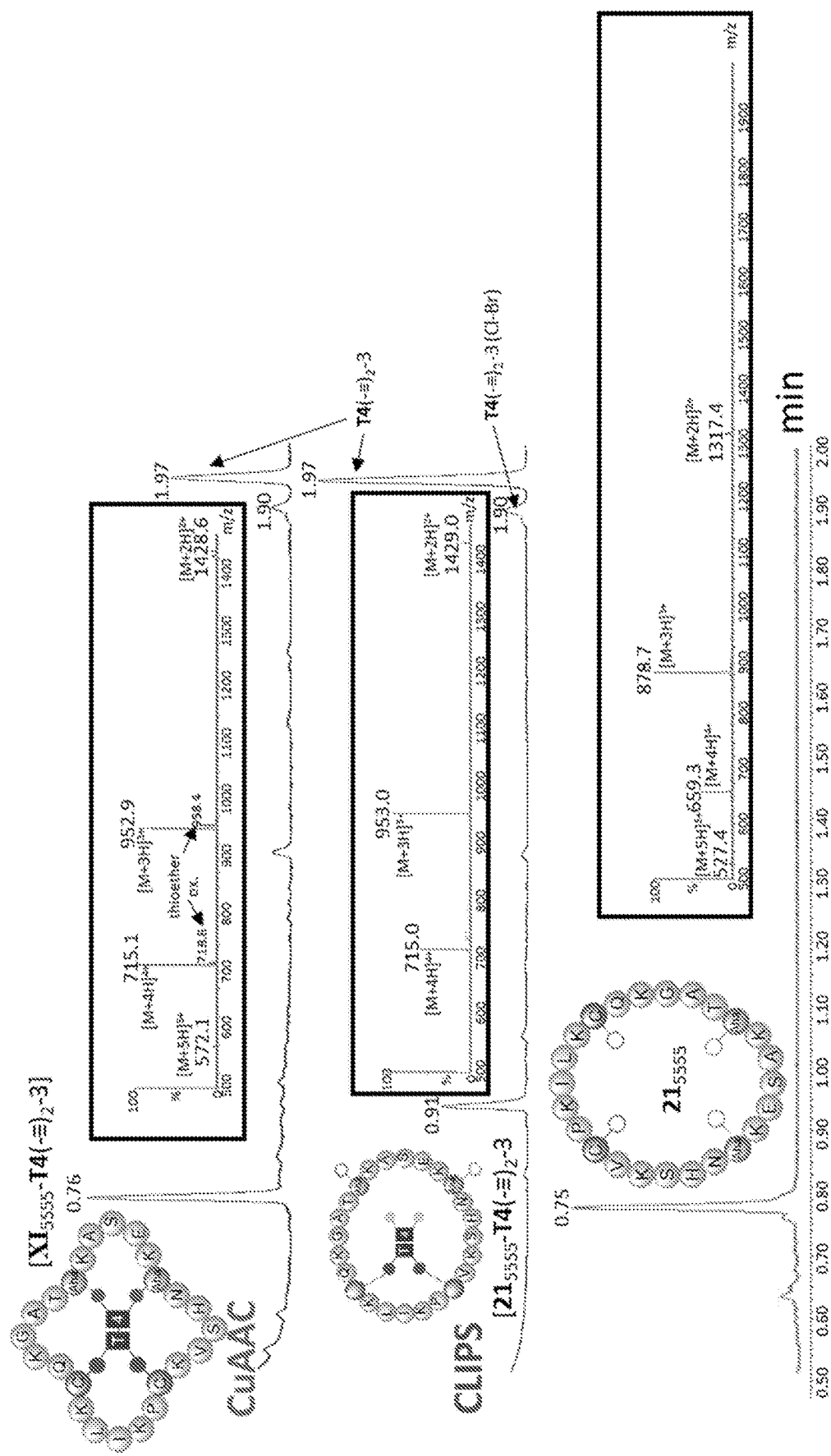
FIG. 24. UPLC-MS chromatogram of one-pot CLIPS/CuAAC reaction of ILKCQKGAT[Aha]KASEK[Aha]NHS-KVCPK $21_{5555}$+T4(-≡)$_2$-3.

FIG. 19 shows the UPLC-MS chromatogram of the peptide (peptide I$_{333}$). FIG. 21 shows the UPLC-MS chromatogram of the CLIPS (FIG. 21A) and CuAAC (FIG. 21B) reaction of peptide I$_{333}$ coupled to scaffold T4(-≡)$_2$-4.

After completion, the reaction was quenched by adding 0.1M EDTA-solution and directly purified on RP-HPLC yielding the tricyclic peptide in 28% yield (FIG. 21C).

Further CLIPS/CuAAC Reactions

CLIPS/CuAAC cyclizations were carried out with 19 different peptides and scaffolds T4(-≡)$_2$-1, T4(-≡)$_2$-42, T4(-≡)$_2$-3 and T4(-≡)$_2$-4 as described above in the general procedures for the one-pot CLIPS/CuAAC ligation-cyclization described above and in analogy with the full experimental procedures for CLIPS/CLICK cyclizations described above. The results (including retention times, MW$_{calc/found}$ for linear peptides, monocyclic CLIPS-peptides and tricyclic CLIPS/CuAAC-peptides) of all reactions are shown in table 1.

TABLE 1

Rt given in min, MW given in Da, N-termini were acetylated, C-terminal amide, positive ion mode (For T4(-≡)$_2$-1 scaffold reactions, the mass-Br$^-$ is reported), samples were measured on a UPLC-ESMS system (3 min, 5-80%B, Acquity UPLC Peptide BEH C18 Column, 130Å, 1.7 gm, 2.1x50 mm with UV detection (λ = 215 nm) and positive ion current for MS analysis.

| Peptide | Code | Sequence | R$_t$ linear [MW$_{calc}$/found] | R$_t$ T4(-≡)$_2$-3 CLIPS [MW$_{calc}$/found] | R$_t$ T4(-≡)$_2$-1 CLIPS [MW$_{calc}$/found] | R$_t$ T4(-≡)$_2$-1 CLIPS/CuAAC [MW$_{calc}$/found] | R$_t$ T4(-≡)$_2$-2 CLIPS [MW$_{calc}$/found] | R$_t$ T4(-≡)$_2$-2 CLIPS/CuAAC [MW$_{calc}$/found] |
|---|---|---|---|---|---|---|---|---|
| 1 | 1$_{333}$ | CQWG[Aha]KAS[Aha]FSEC | 1.16 [1538.7/1538.5] | | 1.08 [1758.0/1757.5] | 0.85 [1758.0/1758.1] and 0.86 [1758.0/1758.1] | n.d. | n.d. |
| 2 | 2$_{333}$ | CNSN[Aha]SKE[Aha]TWNC | 0.87 [1578.7/1579.1] | | n.d. | n.d. | n.d. | n.d. |
| 3 | 3$_{333}$ | CQYR[Aha]KIL[Aha]KGRC | 0.85 [1661.0/1661.2] | | n.d. | n.d. | n.d. | n.d. |
| 4 | 4$_{333}$ | CAIP[Aha]RYR[Aha]NVTC | 1.03 [1588.8/1589.6] | | n.d. | n.d. | n.d. | n.d. |
| 5 | 5$_{333}$ | CTHW[Aha]QEK[Aha]SGNC | 0.85 [1585.7/1586.5] | | n.d. | n.d. | n.d. | n.d. |
| 6 | 6$_{333}$ | CHPY[Aha]RQV[Aha]TVDC | 0.92 [1613.8/1613.4] | | n.d. | n.d. | n.d. | n.d. |
| 7 | 7$_{333}$ | CDHV[Aha]KFY[Aha]RHDC | 0.85 [1715.9/1716.7] | | n.d. | n.d. | n.d. | n.d. |
| 8 | 8$_{333}$ | CNEG[Aha]SHN[Aha]GIKC | 0.72 [1454.6/1454.2] | | n.d. | n.d. | n.d. | n.d. |
| 9 | 9$_{333}$ | CQLQ[Aha]GSY[Aha]RFIC | 1.40 [1610.8/1611.2] | | n.d. | n.d. | n.d. | n.d. |
| 10 | 10$_{222}$ | CQW[Aha]KA[Aha]FSC | 1.45 [1265.4/1265.7] | 1.26 [1484.7/1484.1] | | 0.84/0.91 [1484.7/1484.9] | n.d. | n.d. |

| Peptide | Code | Sequence | R$_t$ T4(-≡)$_2$-3 CLIPS [MW$_{calc}$/found] | R$_t$ T4(-≡)$_2$-3 CLIPS/CuAAC [MW$_{calc}$/found] | R$_t$ T4(-≡)$_2$-4 CLIPS [MW$_{calc}$/found] | R$_t$ T4(-≡)$_2$-4 CLIPS/CuAAC [MW$_{calc}$/found] |
|---|---|---|---|---|---|---|
| 1 | 1$_{333}$ | CQWG[Aha]KAS[Aha]FSEC | 1.34 [1759.9/1759.4] | 0.94 [1759.9/1759.7] | 1.63 [1853.1/1852.7] | 1.21 [1853.1/1852.8] |
| 2 | 2$_{333}$ | CNSN[Aha]SKE[Aha]TWNC | 1.10 [1800.0/1800.7] | 0.82 [1800.0/1800.3] | 1.42 [1893.1/1894.6] | 1.08 [1893.1/1893.4] |

TABLE 1-continued

Rt given in min, MW given in Da, N-termini were acetylated, C-terminal amide, positive ion mode (For T4(-≡)$_2$-1 scaffold reactions, the mass-Br$^-$ is reported), samples were measured on a UPLC-ESMS system (3 min, 5-80%B, Acquity UPLC Peptide BEH C18 Column, 130Å, 1.7 gm, 2.1x50 mm with UV detection (λ = 215 nm) and positive ion current for MS analysis.

| | | Sequence | R$_t$ linear [MW$_{calc}$/found] | R$_t$ T4(-≡)$_2$-1 CLIPS [MW$_{calc}$/found] | R$_t$ T4(-≡)$_2$-1 CLIPS/CuAAC [MW$_{calc}$/found] |
|---|---|---|---|---|---|
| 3 | 3$_{333}$ | CQYR[Aha]KIL[Aha]KGRC | 0.99 [1882.3/1882.7] | 0.79 [1882.3/1882.6] | 1.20 [1975.4/1975.6] |
| 4 | 4$_{333}$ | CAIP[Aha]RYR[Aha]NVTC | 1.21 [1810.1/1810.4] | 0.93 [1810.1/1809.7] | 1.49 [1903.2/1903.5] |
| 5 | 5$_{333}$ | CTHW[Aha]QEK[Aha]SGNC | 1.03 [1807.0/1807.3] | 0.75 [1807.0/1806.7] | 1.32 [1900.1/1901.3] |
| 6 | 6$_{333}$ | CHPY[Aha]RQV[Aha]TVDC | n.d. | n.d. | 1.43 [1928.2/1927.9] |
| 7 | 7$_{333}$ | CDHV[Aha]KFY[Aha]RHDC | n.d. | n.d. | 1.23 [2030.3/2030.7] |
| 8 | 8$_{333}$ | CNEG[Aha]SHN[Aha]GIKC | n.d. | n.d. | 1.30 [1769.0/1769.3] |
| 9 | 9$_{333}$ | CQLQ[Aha]GSY[Aha]RFIC | 1.60 [1486.7/1486.4] | n.d. | 1.85 [1925.2/1925.5] |
| 10 | 10$_{222}$ | CQW[Aha]KA[Aha]FSC | | 1.00 [1486.7/1485.9] and 1.03 [1486.7/1485.5] | 1.86 [1579.8/1580.2] |

| Peptide | Code | Sequence | R$_t$ linear [MW$_{calc}$/found] | R$_t$ T4(-≡)$_2$-1 CLIPS [MW$_{calc}$/found] | R$_t$ T4(-≡)$_2$-1 CLIPS/CuAAC [MW$_{calc}$/found] | R$_t$ T4(-≡)$_2$-2 CLIPS [MW$_{calc}$/found] | R$_t$ T4(-≡)$_2$-2 CLIPS/CuAAC [MW$_{calc}$/found] |
|---|---|---|---|---|---|---|---|
| 11 | 11$_{222}$ | CES[Aha]FA[Aha]KKC | 1.11 [1208.4/1208.6] | 1.17 [1427.7/1427.1] | 0.94/0.96 [1427.7/1426.0] | 0.91 +1467.7/1467.6+ | — |
| 12 | 12$_{222}$ | ACGS[Aha]FE[Aha]KNCG | 0.96 [1308.4/1308.7] | 1.20 [1527.7/1527.3] | 0.82/0.94 [1527.7/1526.4] | 0.95 +1567.8/1567.4+ | — |
| 13 | 13$_{222}$ | NACEE[Aha]FK[Aha]KSC | 0.97 [1451.6/1451.5] | 1.15 [1670.9/1670.2] | — | 0.89 [1711.0/1710.9] | n.d. |
| 14 | 14$_{111}$ | CQ[Aha]K[Aha]FC | 0.92 [921.1/921.7] | 1.05 [1140.4/1409.3] | 0.68/0.70 [1140.4/1139.3] | n.d. | n.d. |
| 15 | 15$_{111}$ | CE[Aha]F[Aha]KC | 1.11 [922.1/921.9] | 1.14 [1141.4/1141.5] | 0.63 (br) [1141.4/1142.1] | n.d. | n.d. |
| 16 | 16$_{444}$ | CQWGA[Aha]KASE[Aha]FSEKC | 1.10 [1867.1/1867.3] | 1.00 [2086.4/2086.4] and 0.81 [2086.4/2086.0] | 0.79 [2086.4/2087.2] | n.d. | n.d. |

TABLE 1-continued

Rt given in min, MW given in Da, N-termini were acetylated, C-terminal amide, positive ion mode (For T4(-≡)$_2$-1 scaffold reactions, the mass-Br$^-$ is reported), samples were measured on a UPLC-ESMS system (3 min, 5-80%B, Acquity UPLC Peptide BEH C18 Column, 130Å, 1.7 gm, 2.1x50 mm with UV detection (λ = 215 nm) and positive ion current for MS analysis.

| | | | R$_t$ T4(-≡)$_2$-3 CLIPS [MW$_{calc}$/found] | | | |
|---|---|---|---|---|---|---|
| 17 | 17$_{555}$ | CQWGAS[Aha]KASEV[Aha]FSEKGC | 1.10 [2110.3/2110.0] | n.d. | n.d. | n.d. |
| 18 | 18$_{333}$ | [Aha]QWGCKASCFSE[Aha] | 1.14 [1538.7/1538.5] | 1.12 [1758.0/1758.4] and 0.87 [1758.0/1757.7] | 0.84 [1758.0/1758.2] | n.d. |
| 19 | 19$_{111}$ | [Aha]QCKCF[Aha] | 0.99 [921.1/921.8] | 0.96 [1140.4/1140.5] and 0.68 [1140.4/1140.3] | 0.641 [1140.4/1140.1] | n.d. |

| Peptide | Code | Sequence | R$_t$ T4(-≡)$_2$-3 CLIPS [MW$_{calc}$/found] | R$_t$ T4(-≡)$_2$-3 CLIPS/CuAAC [MW$_{calc}$/found] | R$_t$ T4(-≡)$_2$-4 CLIPS [MW$_{calc}$/found] | R$_t$ T4(-≡)$_2$-4 CLIPS/CuAAC [MW$_{calc}$/found] |
|---|---|---|---|---|---|---|
| 11 | 11$_{222}$ | CES[Aha]FA[Aha]KKC | 1.12 [1429.6/1429.9] | 0.68 [1429.6/1476.9] and 0.72 [1429.6/1429.3] | 1.45 [1522.8/1522.6] | 1.09 [1522.8/1522.5] |
| 12 | 12$_{222}$ | ACGS[Aha]FE[Aha]KNCG | 1.16 [1529.7/1529.6] | 0.71 (br) [1529.7/1529.6] | 1.48 [1622.8/1622.9] | 1.07 [1622.8/1623.0] |
| 13 | 13$_{222}$ | NACEE[Aha]FK[Aha]KSC | 1.15 [1672.9/1672.7] | 0.64 [1672.9/1672.2] and 0.72 [1672.9/1672.4] | 1.48 [1766.0/1765.6] | 0.99 [1766.0/1766.2] |
| 14 | 14$_{111}$ | CQ[Aha]K[Aha]FC | 1.35 [1142.3/1141.4] | 0.79 [1142.3/1142.7] and 0.82 [1142.3/1142.7] | 1.68 [1235.5/1235.8] | 1.12 [1235.5/1235.0] and 1.18 [1235.5/1235.3] |

TABLE 1-continued

Rt given in min, MW given in Da, N-termini were acetylated, C-terminal amide, positive ion mode (For T4(-≡-)$_2$-1 scaffold reactions, the mass-Br$^-$ is reported), samples were measured on a UPLC-ESMS system (3 min, 5-80%B, Acquity UPLC Peptide BEH C18 Column, 130Å, 1.7 gm, 2.1x50 mm with UV detection (λ = 215 nm) and positive ion current for MS analysis.

| | | | | | |
|---|---|---|---|---|---|
| 15 | 15$_{111}$ | CE[Aha]F[Aha]KC | 1.47 [1143.3/1143.2] | 0.83 (br) [1143.3/1143.3] and 1.10 [1236.4/1237.2] | 1.81 [1236.4/126.3] | 1.04 [1236.4/1236.8] |
| 16 | 16$_{444}$ | CQWGA[Aha]KASE[Aha]FSEKC | 1.22 [2088.3/2088.2] | 0.91 [2088.3/2088.2] | 1.46 [2181.4/2181.1] | 1.08 [2181.4/2180.7] |
| 17 | 17$_{555}$ | CQWGAS[Aha]KASEV[Aha]FSEKGC | 1.21 [2331.6/2330.8] | 0.92 [2331.6/2330.9] | 1.45 [2424.7/2425.9] | 1.09 [2424.7/2424.5] |
| 18 | 18$_{333}$ | [Aha]QWGCKASCFSE[Aha] | 1.38 [1759.9/1759.4] | 1.00 [1759.9/1759.8] | 1.66 [1853.1/1851.1] | 1.20 [1853.1/1853.0] |
| 19 | 19$_{111}$ | [Aha]QCKCF[Aha] | 1.37 [1142.3/1142.1] | 0.82 [1142.3/1142.7] | 1.76 [1235.5/1235.6] | 1.21 [1235.5/1235.9] |

General Procedure for T4 Cyclizations of Monocycles to Generate Tetracyclic Peptides:

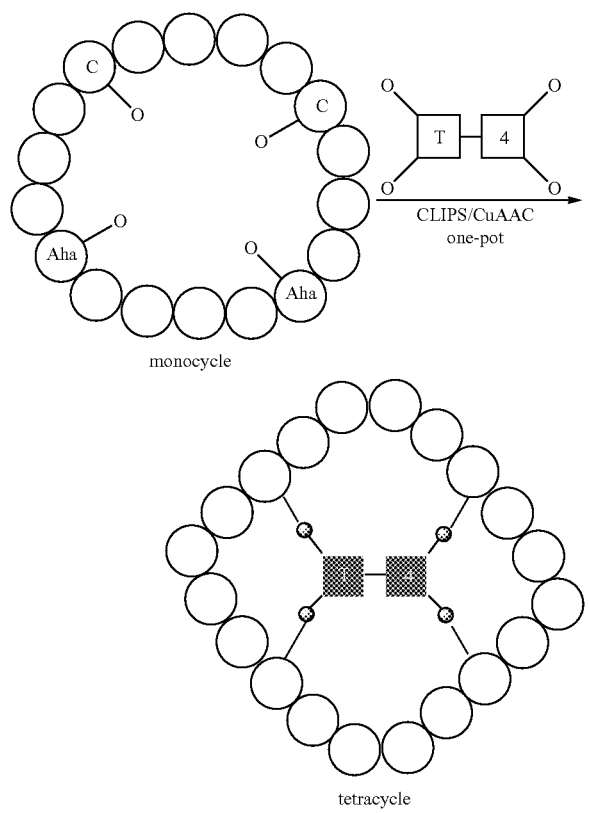

monocycle tetracycle

Monocyclic peptides can be created via various methods for head-to-tail cyclizations (e.g. Schmidt et al. 2017 and Timmerman et al. 2009)

CLIPS: monocyclic peptide $20_{4444}$ (0.52, 0.233 µmol, 1 equiv) was dissolved in 480 µL DMF/H$_2$O (2:1) to give a 0.5 mM solution. Then, scaffold T4(-≡)$_2$-4 (19 µL, 0.186 mol, 0.8 equiv from a 10 mM stock solution in DMF) was added. Subsequently, 40 µL of an aqueous NH$_4$HCO$_3$-solution (200 mM) was added to reach pH=8 in order to start the reaction.

CuAAC: a pre-incubated mix of CuSO$_4$/THPTA/Asc (2:2:10 equiv compared to linear peptide) in H$_2$O was added to the CLIPS-mixture in order to start the CuAAC-reactions.

Figure 25:
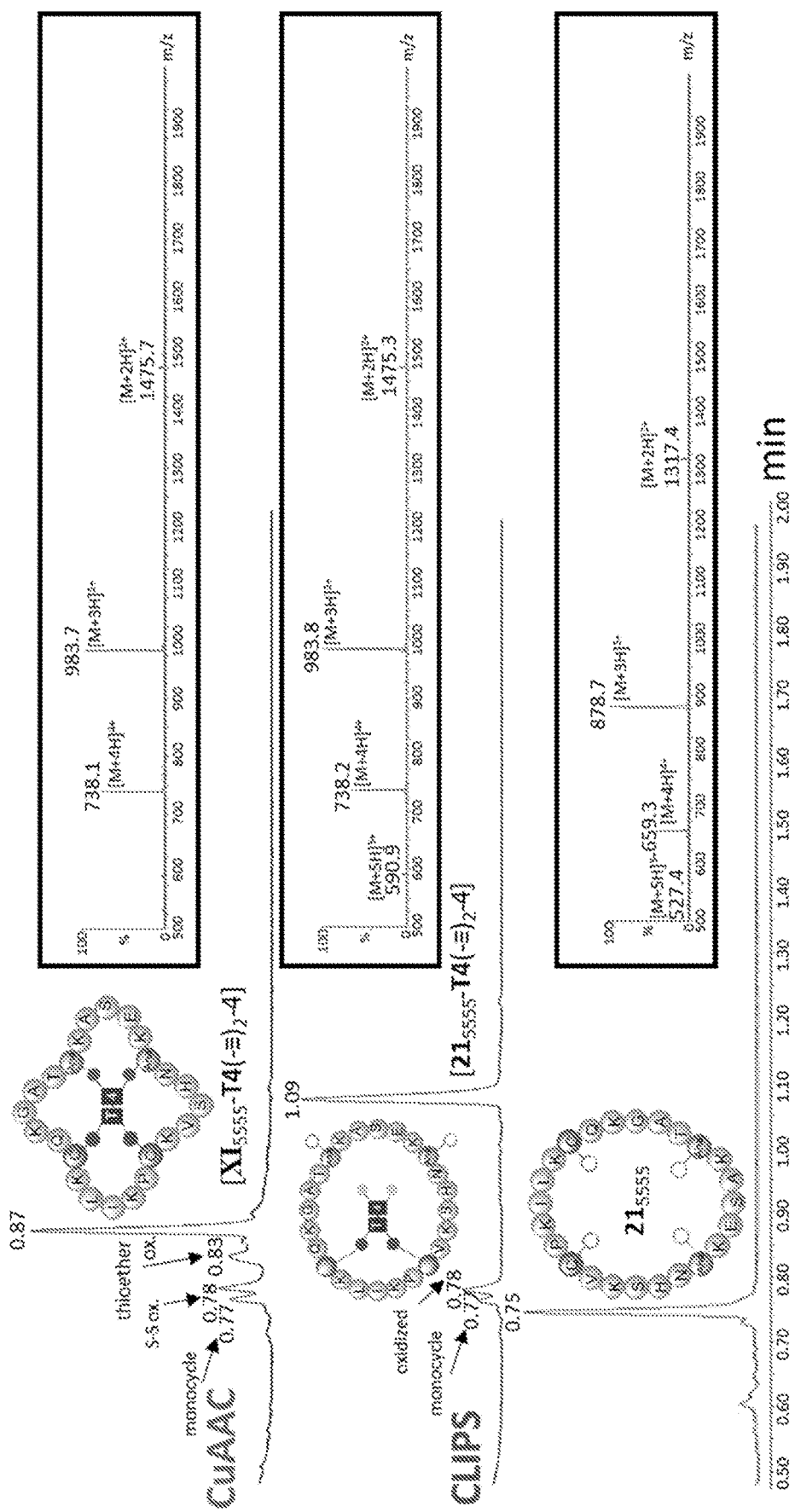
FIG. 25. UPLC-MS chromatogram of one-pot CLIPS/CuAAC reaction of ILKCQKGAT[Aha]KASEK[Aha]NHS-KVCPK 215555+T4(-≡)$_2$-4.

Two head-to-tail cyclized peptides were further cyclized using different T4 scaffolds to yield tetracyclic peptides. The UPLC-MS chromatogram of head-to-tail cyclized peptides, bicyclic CLIPS peptide and tetracyclic CLIPS/CuAAC peptides are shown in FIGS. 21-24 as follows:

ILCQWGA[Aha]KASE[Aha]FSKVCPK:
$20_{4444}$ + T4(-≡)$_2$-3 (FIG. 22),

ILCQWGA[Aha]KASE[Aha]FSKVCPK:
$20_{4444}$ + T4(-≡)$_2$-4 (FIG. 23),

ILKCQKGAT[Aha]KASEK[Aha]NHSKVCPK
$21_{5555}$ + T4 (-≡)$_2$-3 (FIG. 24), and ILKCQKGAT[Aha]KASEK[Aha]NHSKVCPK
$21_{5555}$ + T4(-≡)$_2$-4 (FIG. 25).

Cyclizations with T6 Scaffolds
General Procedure T6 Cyclizations for Generation of Pentacyclic Peptides CLIPS: Linear peptide $22_{11111}$ (0.72 mg, 0.533 mol, 1 equiv) was dissolved in DMF/H$_2$O (1:1) to give a 0.5 mM solution. Then, scaffold T6(-≡)$_3$.1 (43 µL, 0.426 µmol, 0.8 equiv from a 10 mM stock solution in DMF) was added. Subsequently, 40 µL of an aqueous NH$_4$HCO$_3$-solution (200 mM) was added to reach pH=8 in order to start the reaction.

Figure 26:
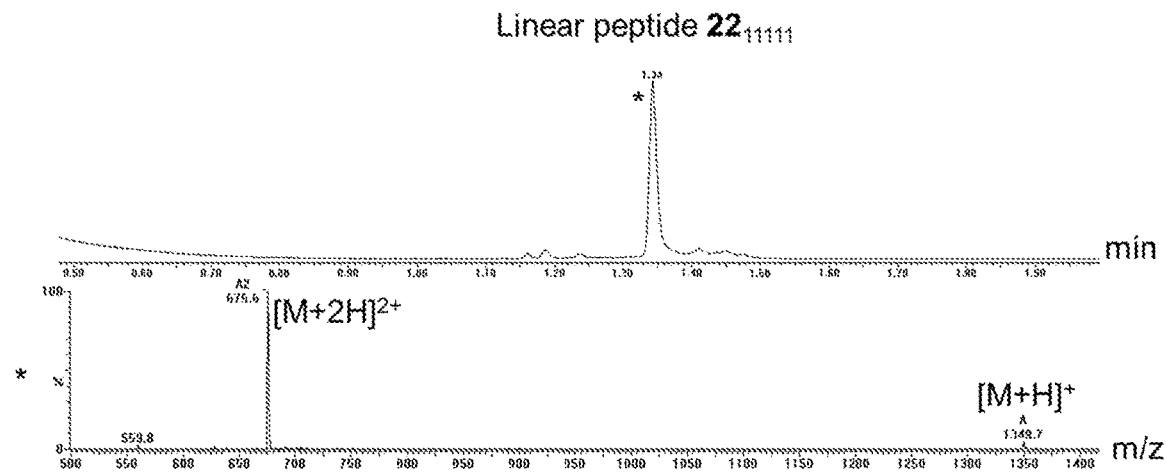
FIG. 26. UPLC-MS chromatogram of one-pot CLIPS/CuAAC reaction of Ac—CQ[Aha]KCF[Aha]ACK[Aha]-NH$_2$: $22_{11111}$+T6(-≡)$_3$-1.
Figure 26:
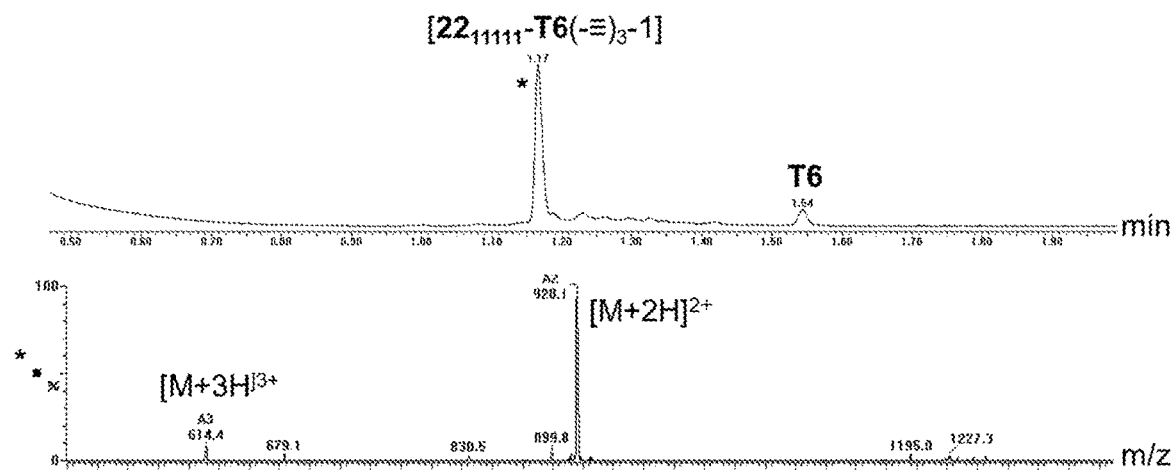
Figure 26:
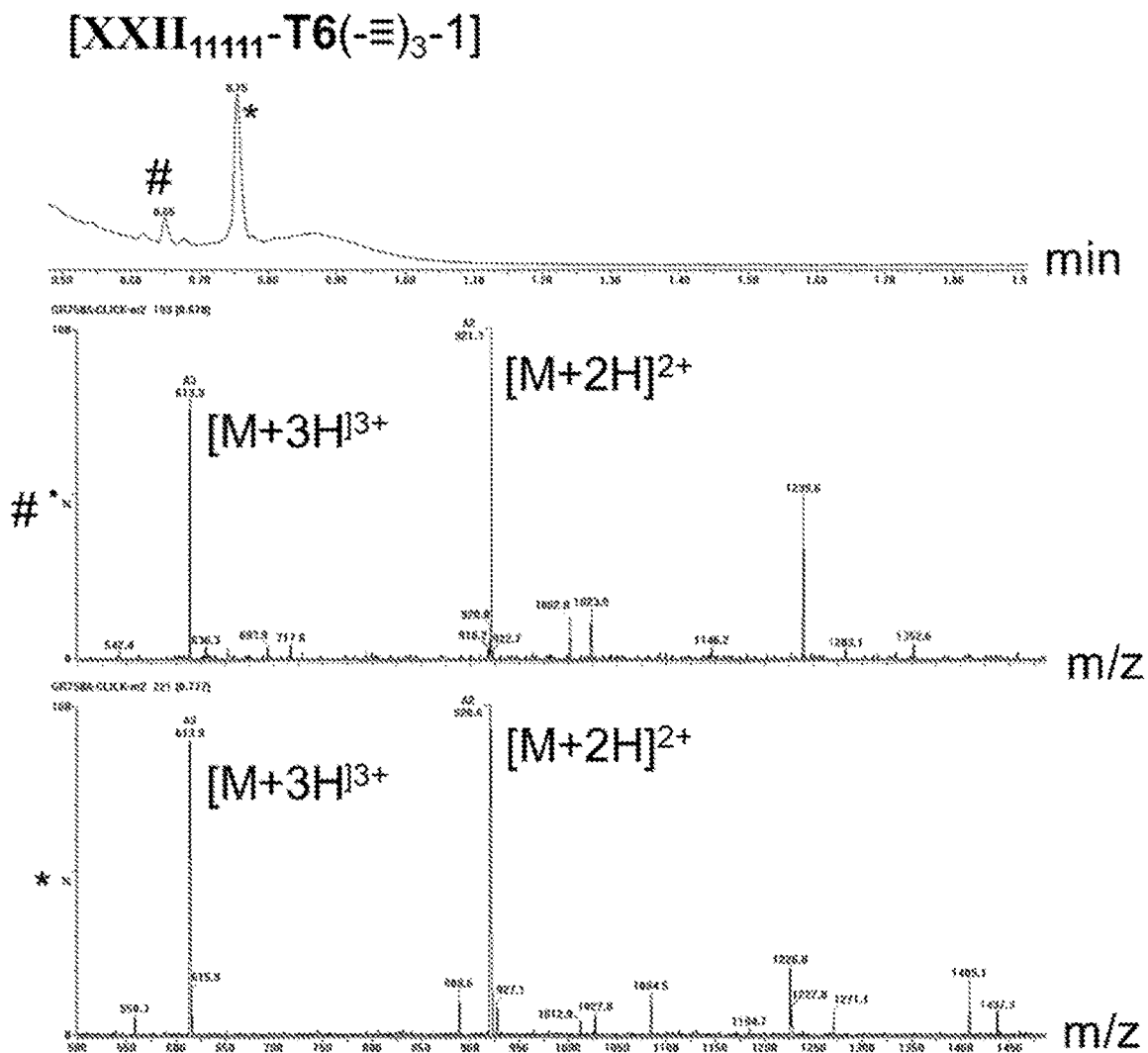
Figure 27:
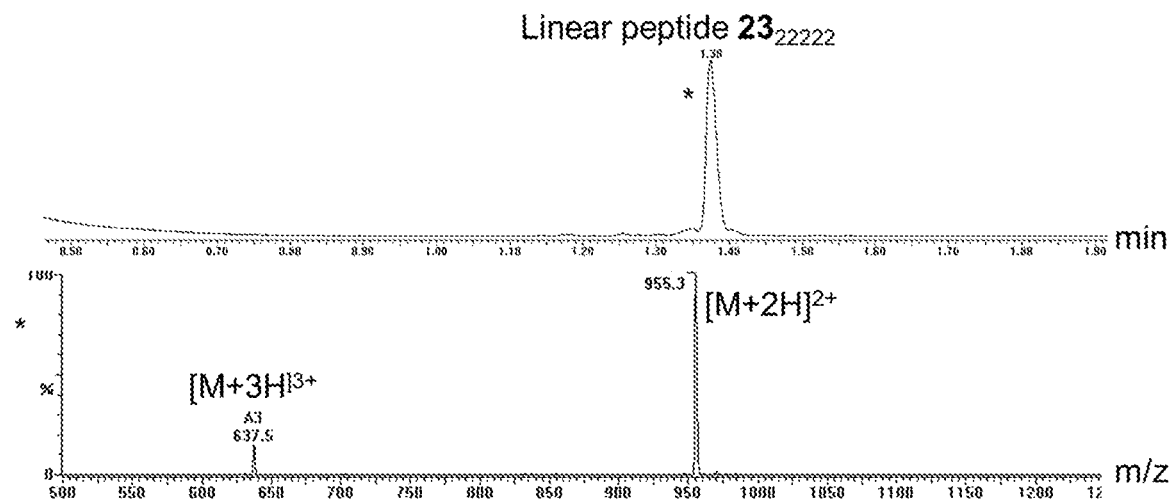
FIG. 27. UPLC-MS chromatogram of one-pot CLIPS/CuAAC reaction of Ac—CQW[Aha]KACFS[Aha]ATCKN[Aha]-NH$_2$: $23_{22222}$+T6-(-≡)$_3$-1.
Figure 27:
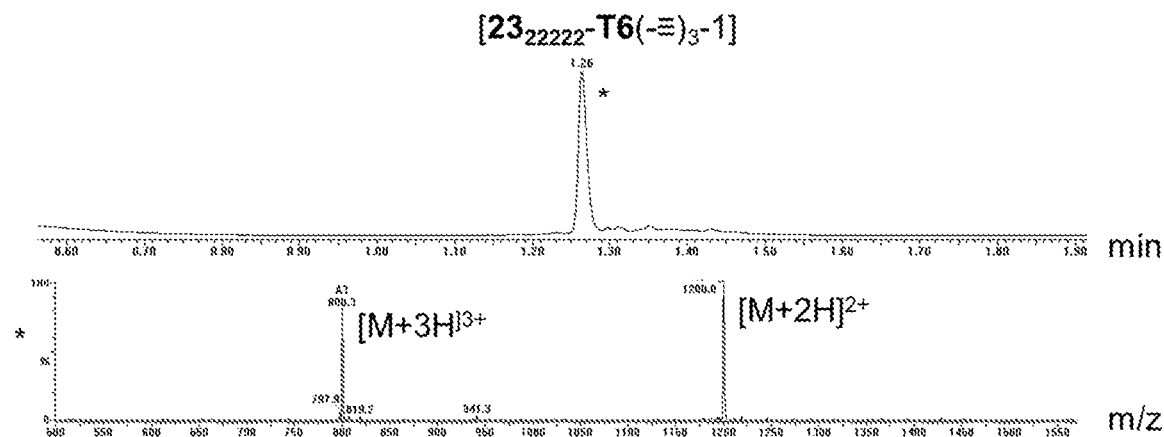
Figure 27:
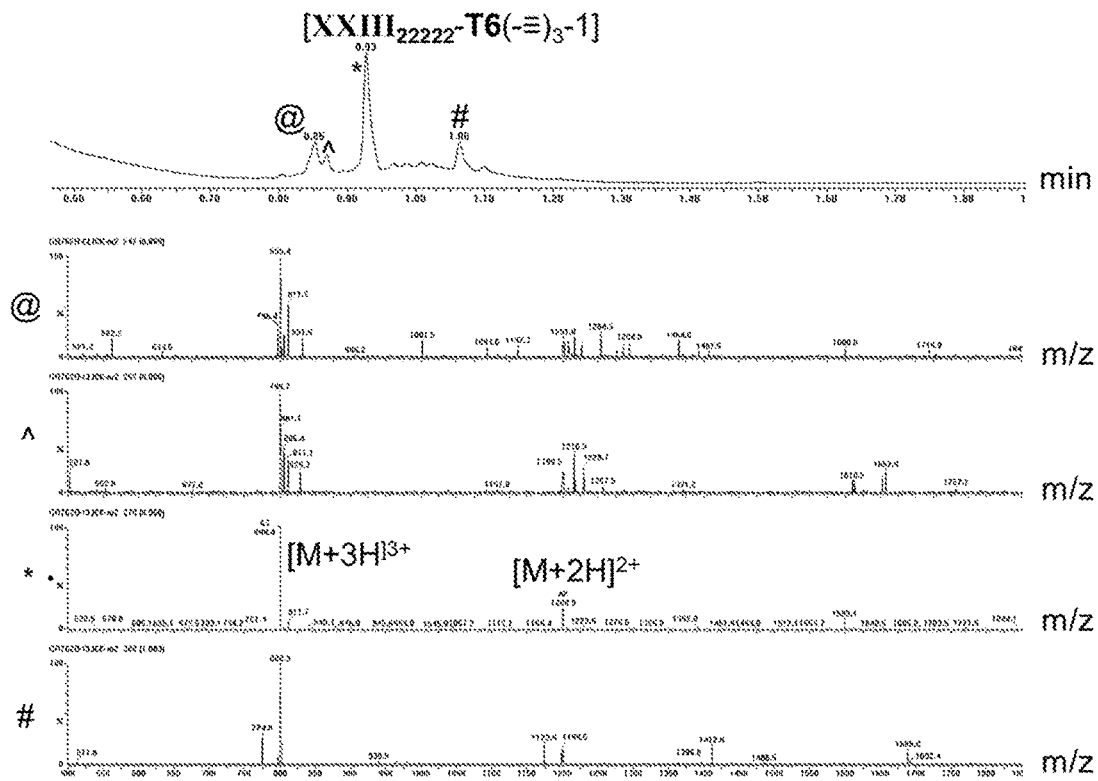
Figure 28:
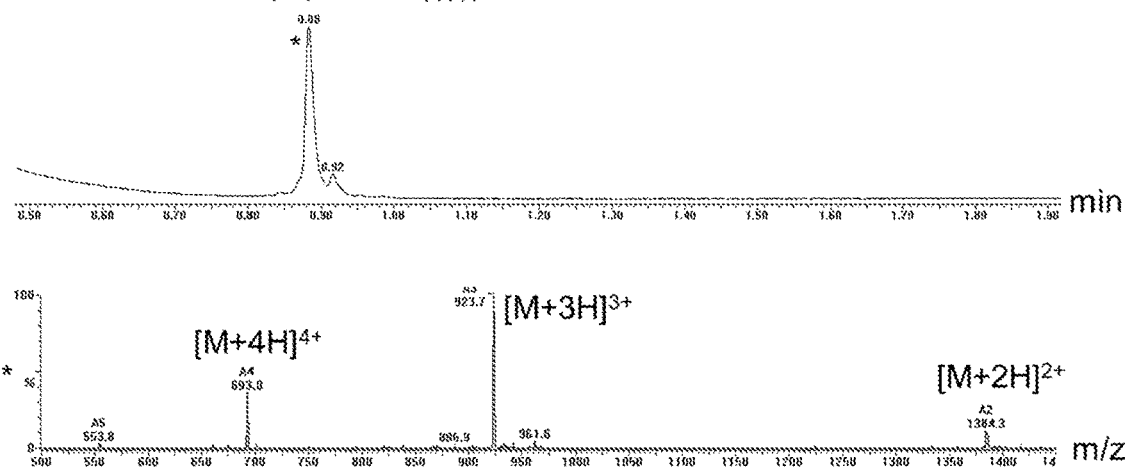
FIG. 28. UPLC-MS chromatogram of one-pot CLIPS/CuAAC reaction of H-CQWGA[Aha]KASECFSEK[Aha]ATKGCGNKG[Aha]-NH$_2$: $24_{44444}$+T6-(≡)$_3$-1.
Figure 28:
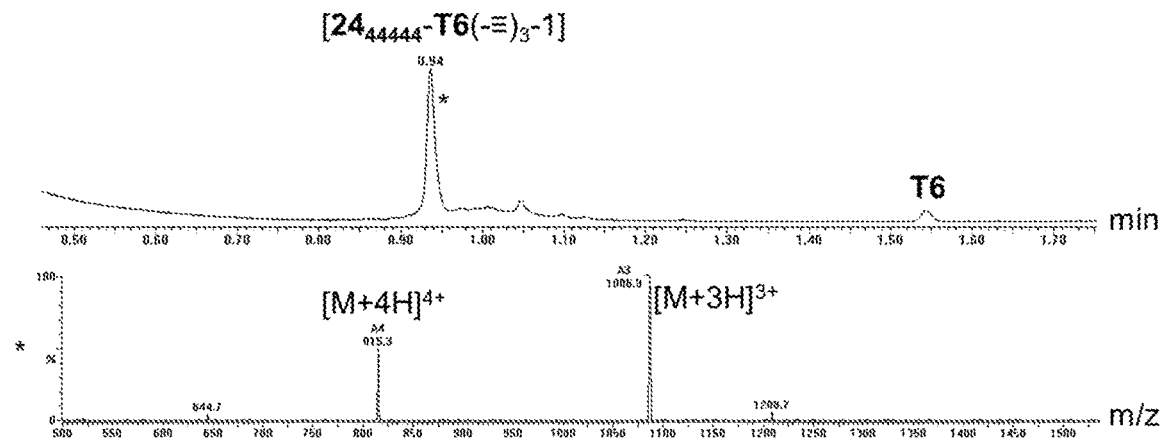
Figure 28:
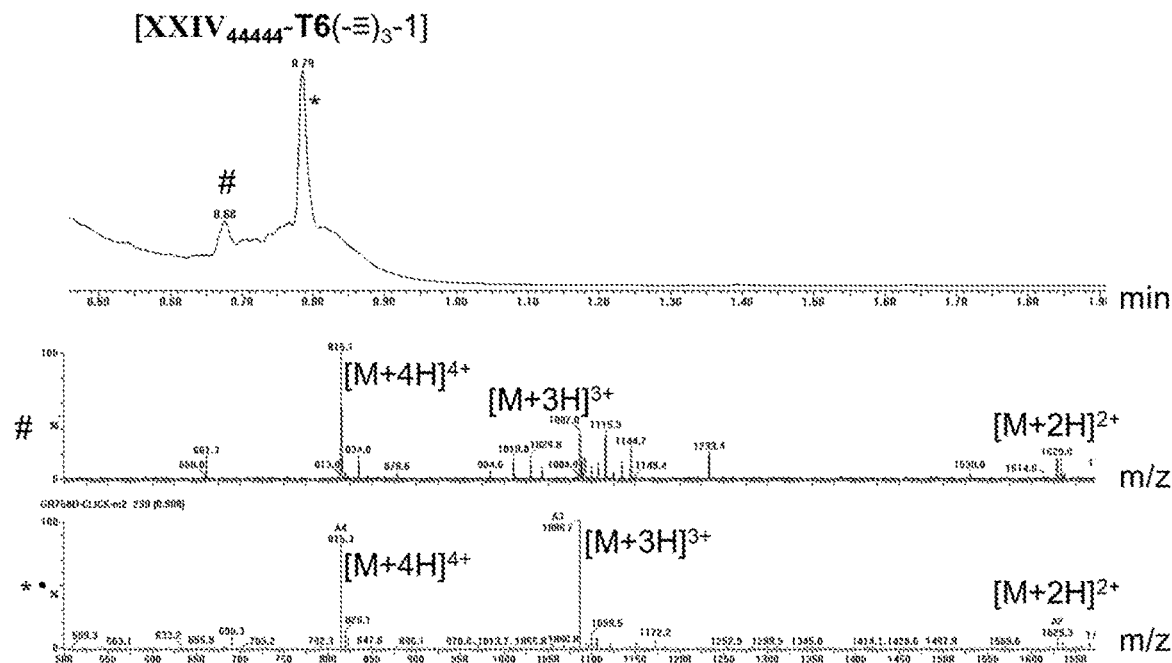
Figure 29:
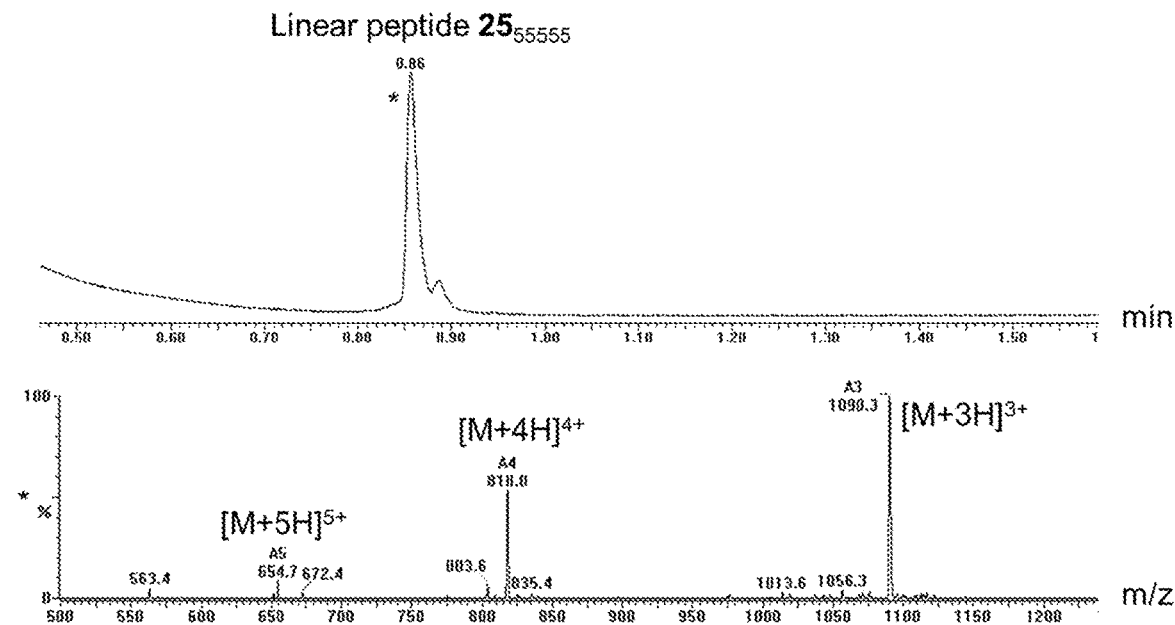
FIG. 29. UPLC-MS chromatogram of one-pot CLIPS/CuAAC reaction of H-CQWGAS[Aha]KASEVCFSEKG[Aha]ATKGKCGNKGE[Aha]-NH$_2$: $25_{55555}$+T6-(≡)$_3$-1.
Figure 29:
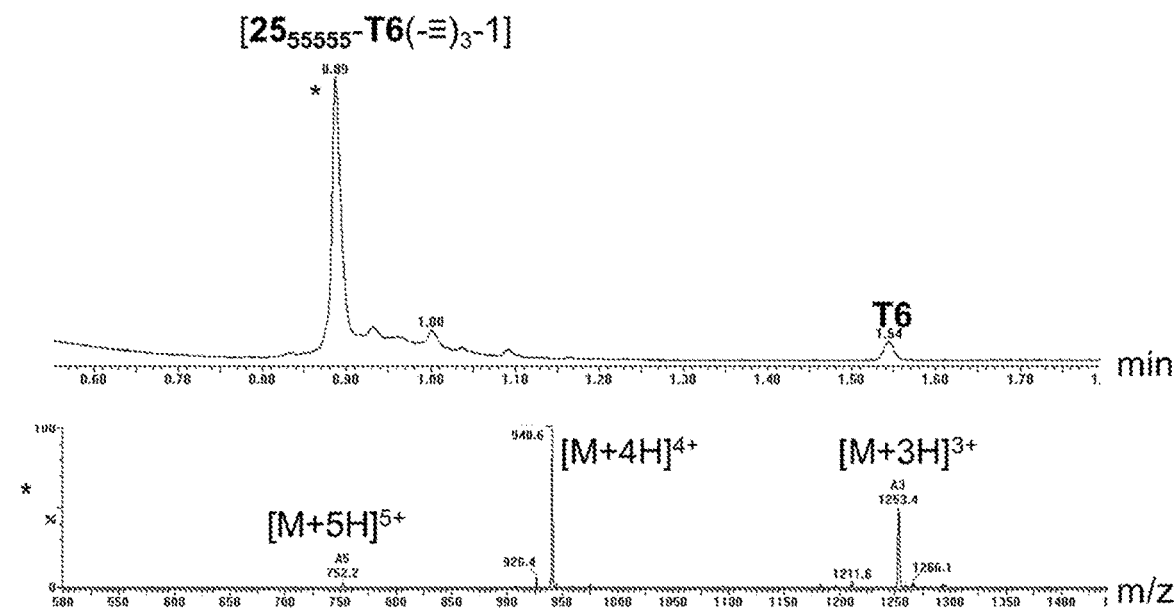
Figure 29:
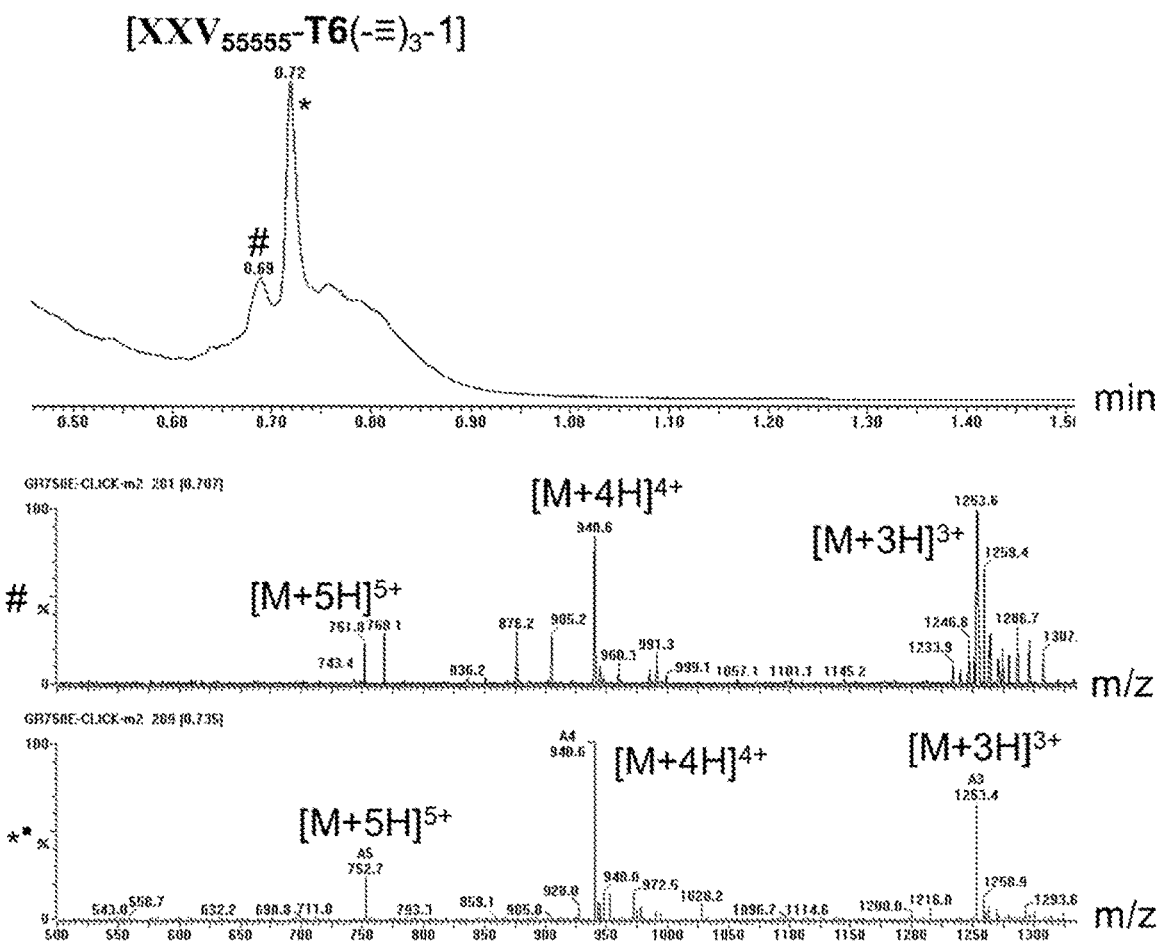

CuAAC: a pre-incubated mix of CuSO$_4$/THPTA/Asc (2:2:10 equiv compared to linear peptide) in H$_2$O was added to the CLIPS-mixture in order to start the CuAAC-reactions.

peptides were cyclized using different T4 scaffolds to yield tetracyclic peptides. The UPLC-MS chromatogram of head-to-tail cyclized peptides, bicyclic CLIPS peptide and tetracyclic CLIPS/CuAAC peptides are shown in FIGS. 21-24 as follows:

Ac-CQ[Aha]KCF[Aha]ACK[Aha]-NH$_2$:
$22_{11111}$ + T6(-≡)$_3$-1 (FIG. 26),

Ac-CQW[Aha]KACFS[Aha]ATCKN[Aha]-NH$_2$:
$23_{22222}$ + T6-(≡)$_3$-1 (FIG. 27),

H-CQWGA[Aha]KASECFSEK[Aha]ATKGCGNKG[Aha]-NH$_2$:
$24_{44444}$ + T6-(≡)$_3$-1 (FIG. 28), and H-CQWGAS[Aha]KASEVCFSEKG[Aha]ATKGKCGNKGE[Aha]-NH$_2$:
$25_{55555}$ + T6-(≡)$_3$-1 (FIG. 29).

Example 3. Identification of Biologically Active Tetracycle

Figure 30:
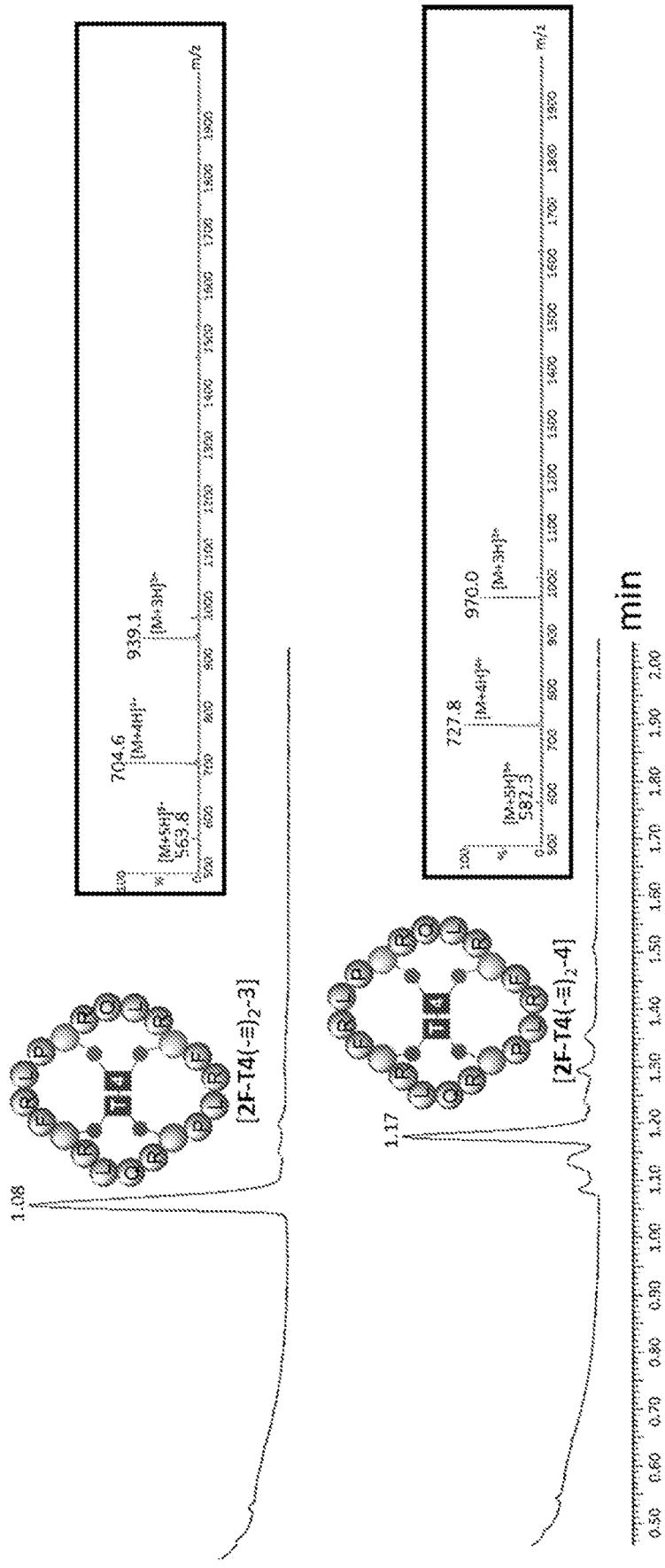
FIG. 30. A. UPLC-MS chromatogram of one-pot CLIPS/CuAAC reaction of c(LRCFRLP[Aha]RQLR[Aha]FRLPCRQ) with scaffolds T4(-≡)$_2$-3 and T4(-≡)$_2$-4. B. Functional activity against Factor XIIA of tetracyclic peptides and a control bicyclic peptide.
Figure 30:
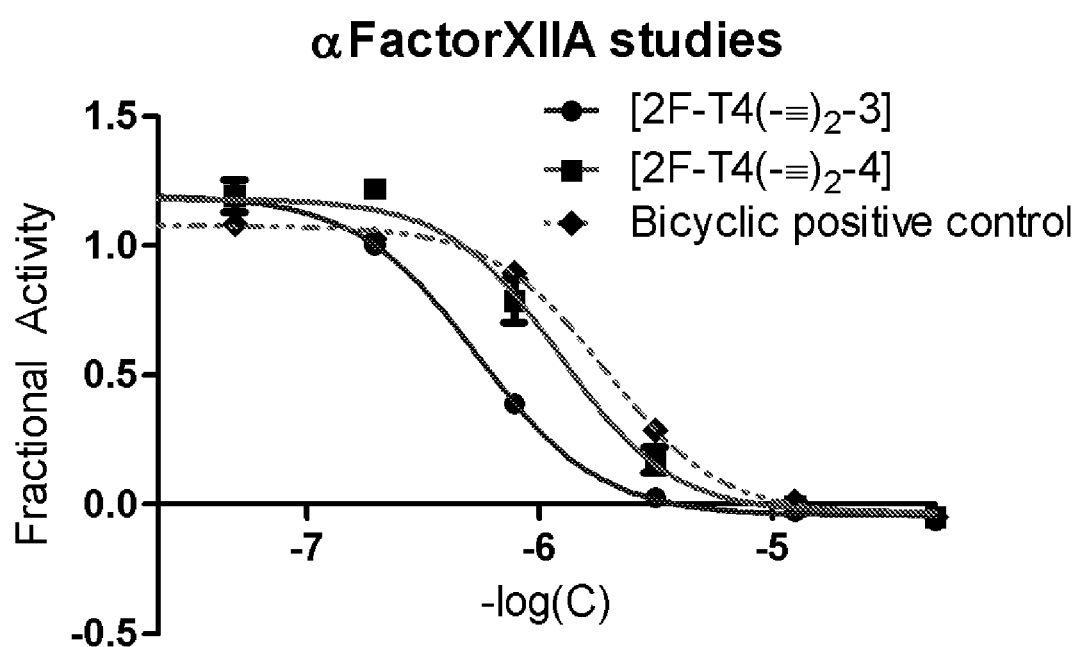

A peptide with sequence R[Aha]FRLPCRQLRCFRLP[Aha]RQL-OcamL (wherein OcamL is the recognition site of omnilase-1 enzyme) was enzymatically head-to-tail cyclized using omniligase-1 as described in Schmidt et al. 2017. This peptide was subsequently coupled to two different T4 scaffolds, T4(-≡)$_2$-3 and T4(-≡)$_2$-4, yielding tetracyclic peptides. FIG. 30A shows the UPLC-MS chromatogram of the CLIPS- and CLICK reaction mixtures leading to tetracyclic peptides.

Biological activity against coagulation factor XIIA, expressed as half maximal inhibitory concentration (IC50), was determined by a residual fluorescence assay as described in Baeriswyl et al 2015, Middendorp et al. 2017 and Heinis et al 2009. In brief, soluble recombinant human factor XIIA (Baeriswyl et al. 2015) was incubated with several dilutions of tetracyclic or bicyclic peptide (7 dilutions from 50 µM to 12 nM). After 15 min, a tripeptide with a cleavable fluorescent AMC group on the C-terminus (hence called as "substrate") was added to the mixture. The enzyme factor XIIA is known to cleave the AMC group when no enzyme inhibitors are present leading to increased fluorescent signal. However, binding between the tetracyclic or bicyclic peptide will hinder the cleavage of the fluorescent label of the substrate by the enzyme, therefore leading to less fluorescent signal. Via non-linear regression an IC$_{50}$ can be determined (which was carried out by the software GraphPath). A variant of a known bicyclic peptide inhibitor of coagulation factor XIIA (FXIIA618, Baeriswyl et al. 2015) having the same peptide sequence but attached to scaffold 1,3,5-tris-(bromomethyl)benzene (TBMB) instead of TATA was used for comparison of biological activity.

As shown in FIG. 30B, the tetracyclic peptides show an excellent biological activity against FXIIA, with an IC50 of 0.54 μM ([2F-T4(-≡)$_2$-3]) and 1.2 μM ([2F-T4(-≡)$_2$-4]), compared to an IC$_{50}$ of 1.9 μM for the bicyclic peptide.

REFERENCES

Advanced Organic Chemistry, J. March, 4th edition
Baeriswyl, V. et al. *ACS Chem. Biol.* 10, 1861-1870 (2015).
Bashiruddin N K, Nagano M, Suga H. Bioorg Chem. 2015 August; 61:45-50.
Blaskovich, M. A., Lin, Q., Delarue, F. L., Sun, J., Park, H. S., Coppola, D., Hamilton, A. D., and Sebti, S. M. (2000) Nat. Biotechnol. 18, 1065-1070
Bock V., Hiemstra H., van Maarseveen, J H., Eur. J. Org. Chem. 2006, 51-68
Chua K, Fung E, Micewicz E D, Ganz T, Nemeth E, Ruchala P. Bioorg Med Chem Lett. 2015 Nov. 1; 25(21):4961-9.
Devaraj N K. Weissleder R. Hilderbrand S A. Bioconjugate chemistry. 2008; 19(12):2297-2299. doi:10.1021/be8004446
Dondoni et al. Chem. Eur. J. 2009, 15, 14444-9
Hamura Y, Calama M C, Park H S & Hamilton A D, A 'calixarene with four peptide loops: an antibody mimic for recognition of protein surfaces', Angew. Chem. Int. Ed. 1997, 36, 2680-2683
Heinis, C., Rutherford, T., Freund, S. & Winter, G. Nat. Chem. Biol. 5, 502-507 (2009).
Jayasekara, P. S.; Jacobson, K. A. Synthetic Commun. 2014, 44, 2344-2347.
Kolb H C, Finn M G, Sharpless K B. Angew Chem Int Ed Engl. 2001 Jun. 1; 40(11):2004-2021
Lau, Y. H.; Spring, D. R. *Synlett*, 2011, 13, 1917-1919.
Roelens, S.; Vacca, A.; Francesconi, O.; Venturi, C. Chem. Eur. J. 2009, 15, 8296-8302. Smeenk L E, Dailly N, Hiemstra H, van Maarseveen J H, Timmerman P. Org Lett. 2012; 14(5):1194-7.
Middendorp, S. J. et al. *J. Med. Chem.* 60, 1151-1158 (2017)
Schmidt, M. et al. *Adv. Synth. Catal.* 359, 2050-2055 (2017).
Smeenk et al. Organic Letters. 14(5), 1194-1197 (2012).
Smeenk L E, Timmers-Parohi D, Benschop J J, Puijk W C, Hiemstra H, van Maarseveen J H, Timmerman P. Chembiochem. 2015; 16(1):91-9.
Sun, J., Blaskovich, M. A., Jain, R. K., Delarue, F., Paris, D., Brem, S., Wotoczek-Obadia, M., Lin, Q., Coppola, D., Choi, K., Mullan, M., Hamilton, A. D., and Sebti, S. M. (2004) Cancer Res. 64, 3586-3592
Ten Brink H T, Rijkers D T S, Liskamp R M J, J. Org. Chem. 2006, 71, 1817.1824
Timmerman P et al. ChemBioChem. 2005 May; 6(5):821.4.
Timmerman P et al. J Biol Chem. 2009, 284(49): 34126-34134
White C J, Yudin, A. K. Nature Chem., 2011, 3(7), 509-524. DOI: 10.1038/NCHEM.1062
Wytko J. A., Weiss J, *J. Incl. Phenom. Mol. Recognit. Chem.* 1994, 19, 207-225.
Zhdankin et al. *Chem. Eur. Joc.* 2017, 23, 691-695.

The invention claimed is:

1. A method for preparing a compound comprising a peptide attached to a molecular scaffold, the method comprising:
   1) performing a thiolate nucleophilic substitution reaction between a peptide and a molecular scaffold to form two or three thioether linkages between said peptide and said molecular scaffold; and
   2) performing a subsequent reaction between said peptide and said molecular scaffold selected from the group consisting of an oxime-ligation reaction, an alkyne-azide cycloaddition, a thiol-ene reaction, a hydrazone ligation reaction, a Diels Alder reaction, a tetrazine ligation reaction, a disulfide bridge formation and a ring-closing metathesis reaction to form two or three further linkages between said peptide and said molecular scaffold, thereby forming three to six peptide loops resulting from the formation of two or three thioether linkages between said peptide and said molecular scaffold in step 1 and two or three further linkages between said peptide and said molecular scaffold in step 2; whereby:
   said peptide and said molecular scaffold comprise two or three reactive groups capable of participating in said thiolate nucleophilic substitution reaction and two or three reactive groups capable of participating in said reaction in step 2) prior to performing said reactions, and
   said molecular scaffold comprises an aromatic or heteroaromatic cyclic moiety, a 6-membered cycloalkyl or a 6-membered cycloalkylene and possesses twofold or threefold symmetry.

2. The method according to claim 1 wherein said reaction in step 2) is selected from the group consisting of an oxime-ligation reaction, an alkyne-azide cycloaddition and a thiol-ene reaction.

3. The method according to claim 1 wherein said molecular scaffold prior to performing said reactions in steps 1) and 2) comprises:
   two reactive groups capable of participating in said thiolate nucleophilic substitution reaction and two reactive groups capable of participating in said reaction in step 2), or
   three reactive groups capable of participating in said thiolate nucleophilic substitution reaction and three reactive groups capable of participating in said reaction in step 2).

4. The method according to claim 1 wherein said peptide, prior to performing said reactions in steps 1) and 2), comprises two or three thiol groups and said molecular scaffold, prior to performing said reactions in steps 1) and 2), comprises two or three halides attached to activated methylene groups.

5. The method according to claim 1 wherein said peptide is a linear peptide prior to performing said reactions in steps 1) and 2).

6. The method according to claim 1 further comprising introducing one or more linkages in said peptide.

7. The method according to claim 1 wherein said scaffold, prior to performing said reactions in steps 1) and 2), comprises a free rotatable bond located between a part of the scaffold that comprises two or three reactive groups capable of participating in said thiolate nucleophilic substitution reaction and a part of the scaffold that comprises said two or three reactive groups capable of participating in said reaction in step 2).

8. The method according to claim 1 wherein:
   said peptide and said molecular scaffold, prior to performing said reactions in steps 1) and 2), comprise two reactive groups capable of participating in said thiolate nucleophilic substitution reaction and two reactive groups capable of participating in said reaction in step 2),
   said molecular scaffold possesses C2 symmetry, and
   said molecular scaffold, prior to performing said reactions in steps 1) and 2), comprises a free rotatable bond located between a part of the scaffold that comprises said two reactive groups capable of participating in the thiolate nucleophilic substitution reaction and a part of the scaffold that comprises said two reactive groups capable of participating in the reaction in step 2).

9. A compound comprising a peptide attached to a molecular scaffold, wherein:
   i. said peptide is attached to said molecular scaffold by four to six linkages;
   ii. said molecular scaffold comprises an aromatic or heteroaromatic cyclic moiety or a 6-membered cycloalkyl or cycloalkylene and possesses twofold or threefold symmetry;
   iii. said compound comprises three to six peptide loops formed as a result of attachment of said peptide to said molecular scaffold by said four to six linkages;
   iv. two or three of said linkages are thioether linkages; and
   v. two or three of said linkages result from a reaction selected from the group consisting of an oxime-ligation reaction, an alkyne-azide cycloaddition, a thiol-ene reaction, a hydrazone ligation reaction, a Diels Alder reaction, a tetrazine ligation reaction, a disulfide bridge formation and a ring-closing metathesis reaction.

10. The compound according to claim 9 wherein said compound is essentially in one or two regioisomeric forms.

11. The compound according to claim 9 wherein said peptide comprises an intra-peptide linkage.

12. The compound according to claim 9 wherein a part of said molecular scaffold comprising said two or three thioether linkages and a part of said molecular scaffold comprising said two or three linkages resulting from a reaction selected from the group consisting of an oxime-ligation reaction, an alkyne-azide cycloaddition, a thiol ene reaction, a hydrazone ligation reaction, a Diels Alder reaction, a tetrazine ligation reaction, a disulfide bridge formation and a ring-closing metathesis reaction are separated by a singly bonded pair of atoms other than hydrogen atoms.

13. The compound according to claim 9, wherein said compound comprises a genetic package displaying said peptide and comprising a nucleic acid encoding said peptide.

14. A library comprising a plurality of compounds according to claim 9.

15. A method for identifying a compound capable of binding to a target of interest, comprising contacting a library of compounds according to claim 14 with the target of interest, determining binding of said compounds to said target and selecting a compound that binds to said target.

16. The method according to claim 15, wherein said target of interest is a receptor, a ligand, an antibody, a cytokine, or a hormone.

* * * * *